(12) United States Patent
Alam et al.

(10) Patent No.: US 10,870,653 B2
(45) Date of Patent: Dec. 22, 2020

(54) WNT PATHWAY MODULATORS

(71) Applicant: Agency for Science, Technology and Research, Singapore (SG)

(72) Inventors: Jenefer Alam, Singapore (SG); Soo Yei Ho, Singapore (SG); Wei Ling Wang, Singapore (SG); Athisayamani Jeyaraj Duraiswamy, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 0 days.

(21) Appl. No.: 16/226,398

(22) Filed: Dec. 19, 2018

(65) Prior Publication Data
US 2019/0185478 A1 Jun. 20, 2019

Related U.S. Application Data

(62) Division of application No. 15/105,224, filed as application No. PCT/SG2014/000602 on Dec. 17, 2014, now Pat. No. 10,189,842.

(30) Foreign Application Priority Data

Dec. 17, 2013 (GB) .................................. 1322333.4

(51) Int. Cl.
| A61K 31/519 | (2006.01) |
| A61P 35/04 | (2006.01) |
| A61P 35/00 | (2006.01) |
| C07D 487/04 | (2006.01) |

(52) U.S. Cl.
CPC .......... *C07D 487/04* (2013.01); *A61K 31/519* (2013.01); *A61P 35/00* (2018.01); *A61P 35/04* (2018.01)

(58) Field of Classification Search
CPC .......................... C07D 487/04; A61K 31/519
See application file for complete search history.

(56) References Cited

U.S. PATENT DOCUMENTS

| 10,189,842 B2 | 1/2019 | Alam et al. |
| 2007/0219183 A1 | 9/2007 | Levin et al. |

FOREIGN PATENT DOCUMENTS

| CN | 101535313 A | 9/2009 |
| CN | 101906105 A | 12/2010 |
| WO | WO 2008/052964 A1 | 5/2008 |
| WO | WO 2010/142216 A1 | 12/2010 |
| WO | WO 2013/110433 A1 | 8/2013 |
| WO | WO 2013/151708 A1 | 10/2013 |
| WO | WO 2013/169631 A1 | 11/2013 |
| WO | WO 2015/094119 A1 | 6/2015 |

OTHER PUBLICATIONS

International Search Report and Written Opinion for PCT/SG2014/000602 dated Feb. 12, 2015.
International Preliminary Report on Patentability for PCT/SG2014/000602 dated Nov. 20, 2015.
Extended European Search Report for European Application No. 14870867.0 dated May 2, 2017.
Amit et al., Axin mediated CKI phosphorylation of beta-catenin at Ser 45: a molecular switch for the Wnt pathway. Genes Dev. 2002;16:1066-76.
Austin et al., A role for the Wnt gene family in hematopoiesis: expansion of multilineage progenitor cells. Blood. 1997;89:3624-35.
Barker et al., Mining the Wnt pathway for cancer therapeutics. Nat Rev Drug Discov. 2006;5:997-1014.
Bergmann et al., Inhibition of glycogen synthase kinase 3β induces dermal fibrosis by activation of the canonical Wnt pathway. Ann Rheum Dis. Dec. 2011;70(12):2191-8.
Cheng et al., Wnt antagonism inhibits hepatic stellate cell activation and liver fibrosis. Am J Physiol Gastrointest Liver Physiol. 2008;294:G39-G49.
Chilosi et al., Aberrant Wnt/beta-catenin pathway activation in idiopathic pulmonary fibrosis. Am J Pathol. 2003;162(5):1495-1502.
Clevers et al., Wnt/beta-catenin signaling in development and disease. Cell. 2006;127:469-80.
Cobas et al., Beta-catenin is dispensable for hematopoiesis and lymphopoiesis. J Exp Med. 2004;199:221-9.
Dahmen et al., Deletions of AXIN1, a Component of the WNT/wingless Pathway, in Sporadic Medullobastomas. Cancer Res. 2001;61:7039-43.
Dealmeida et al., The soluble wnt receptor Frizzled8CRD-hFc inhibits the growth of teratocarcinomas in vivo. Cancer Res. 2007;67(11):5371-9.
Fodde et al., Wnt/beta-catenin signaling in cancer stemness and malignant behavior. Curr Opin Cell Biol. Apr. 2007;19(2):150-8.
Gandhirajan et al., Wnt/β-catenin/LEF-1 signaling in chronic lymphocytic leukemia (CLL): a target for current and potential therapeutic options. Curr Cancer Drug Targets. Nov. 2010;10(7):716-27.

(Continued)

Primary Examiner — Susanna Moore
(74) Attorney, Agent, or Firm — Wolf, Greenfield & Sacks, P.C.

(57) ABSTRACT

The present invention relates to compounds of formula (I),

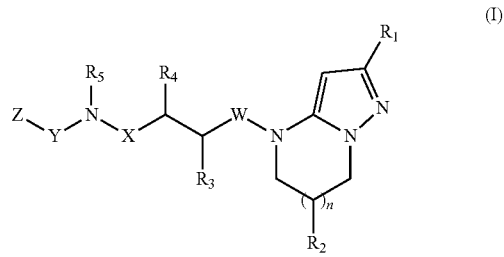

combinations and uses thereof for disease therapy, or a pharmaceutically acceptable salt, solvate or polymorph thereof, including all tautomers and stereoisomers thereof wherein each of $R_1$, $R_2$, $R_3$, $R_4$, $R_5$, W, X, Y, Z, and n is as defined herein.

19 Claims, 7 Drawing Sheets

(56) References Cited

OTHER PUBLICATIONS

Garcia-Rostan et al., Frequent mutation and nuclear localization of beta-catenin in anaplastic thyroid carcinoma. Cancer Res. Apr. 15, 1999;59(8):1811-5.
He et al., Wnt/beta-catenin signaling promotes renal interstitial fibrosis. J Am Soc Nephrol. Apr. 2009;20(4):765-76.
Henderson et al., Inhibition of Wnt/beta-catenin/CREB binding protein (CBP) signaling reverses pulmonary fibrosis. Proc Natl Acad Sci U S A. 2010;107(32):14309-14.
Herr et al., WNT secretion and signaling in human disease. Trends Mol Med. 2012;18(8):483-93.
Hoang et al., Expression of Ldl receptor-related protein 5 (Lrp5) as a novel marker for disease progression in high-grade osteosarcoma. Int J Cancer. 2004;109:106-11.
Holcombe et al., Expression of Wnt ligands and Frizzled receptors in colonic mucosa and in colon carcinoma. J Clin Pathol: Mol Pathol. 2002;55:220-6.
Jeannet et al., Long-term, multilineage hematopoiesis occurs in the combined absence of beta-catenin and gamma-catenin. Blood. 2008;111(1):142-9.
Kirikoshi et al., Up-regulation of Frizzled-7 (FZD7) in human gastric cancer. Int J Oncol 2001;19:111-15.
Klopocki et al., Loss of SFRP1 is associated with breast cancer progression and poor prognosis in early stage tumors. Int J Oncol. 2004;25:641-9.
Koesters et al., Nuclear accumulation of beta-catenin protein in Wilms' tumours. J Pathol. Jan. 2003;199(1):68-76.
Kuhnert et al., Essential requirement for Wnt signaling in proliferation of adult small intestine and colon revealed by adenoviral expression of Dickkopf-1. Proc Natl Acad Sci U S A. Jan. 6, 2004;101(1):266-71.
Lee et al., Expression of the secreted frizzled-related protein gene family is downregulated in human mesothelioma. Oncogene. 2004;23:6672-6.
Lee et al., Therapeutic potential of a monoclonal antibody blocking the wnt pathway in diabetic retinopathy. Diabetes. 2012;61:2948-57.
Lo Muzio et al., WNT-1 expression in basal cell carcinoma of head and neck. An immunohistochemical and confocal study with regard to the intracellular distribution of beta-catenin. Anticancer Res. 2002;22:565-76.
Logan et al., The Wnt signaling pathway in development and disease. Annu Rev Cell Dev Biol. 2004;20:781-810.
MacDonald et al., Wnt/beta-catenin signaling: Components, mechanisms, and diseases. Dev Cell. 2009;17(1):9-26.
Najdi et al., A uniform human Wnt expression library reveals a shared secretory pathway and unique signaling activities. Differentiation. 2012;84(2):203-13.
Noggle et al., A molecular basis for human embryonic stem cell pluripotency. Stem Cell Rev. 2005;1:111-18.
Ogaki et al., Wnt and Notch signals guide embryonic stem cell differentiation into the intestinal lineages. Stem Cells. Jun. 2013;31(6):1086-96. doi: 10.1002/stem.1344.
Pinto et al., Canonical Wnt signals are essential for homeostasis of the intestinal epithelium. Genes Dev. Jul. 15, 2003;17(14):1709-13.
Polakis et al., The many ways of Wnt in cancer. Curr Opin Genet Dev. 2007;17:45-51.
Ramachandran et al., Wnt inhibitory factor 1 induces apoptosis and inhibits cervical cancer growth, invasion and angiogenesis in vivo. Oncogene. 2012;31:2725-37.
Reifenberger et al., Molecular genetic analysis of malignant melanomas for aberrations of the WNT signaling pathway genes CTNNB1, APC, ICAT and BTRC. Int J Cancer. 2002;100:549-56.
Reya et al., A role for Wnt signaling in self-renewal of haematopoietic stem cells. Nature. 2003;423:409-14.
Reya et al., Wnt signaling in stem cells and cancer. Nature. 2005;434:843-50.
Rhee et al., Wnt and frizzled receptors as potential targets for immunotherapy in head and neck squamous cell carcinomas. Oncogene. 2002;21:6598-6605.
Ricken et al., Wnt Signalling in the Ovary: Identification and Compartmentalized Expression of wnt-2, wnt-2b, and Frizzled-4 mRNAs. Endocrinology. 2002;143:2741-9.
Robinson et al., Wnt signaling and prostate cancer. Curr Drug Targets. 2008;9:571-80.
Sato et al., Molecular signature of human embryonic stem cells and its comparison with the mouse. Dev. Biol. 2003;260:404-13.
Satoh et al., AXIN1 mutations in hepatocellular carcinomas, and growth suppression in cancer cells by virus-mediated transfer of AXIN. Nature Genet. 2000;24:245-50.
Schett et al., The role of Wnt proteins in arthritis. Nature clinical practice. Rheumatology. 2008;4:473-80.
STN-CAS database Registry No. 932344-85-9. Entered STN-CAS database on Apr. 25, 2007.
STN-CAS database Registry No. 932344-82-6. Entered STN-CAS database on Apr. 25, 2007.
STN-CAS database Registry No. 932481-41-9. Entered STN-CAS database on Apr. 25, 2007.
STN-CAS database Registry No. 950287-32-8. Entered STN-CAS database on Oct. 11, 2007.
STN-CAS database Registry No. 950287-37-3. Entered STN-CAS database on Oct. 11, 2007.
STN-CAS database Registry No. 1029768-94-2. Entered STN-CAS database on Jun. 22, 2008.
STN-CAS database Registry No. 1029768-58-8. Entered STN-CAS database on Jun. 22, 2008.
STN-CAS database Registry No. 1029768-60-2. Entered STN-CAS database on Jun. 22, 2008.
STN-CAS database Registry No. 1029768-41-9. Entered STN-CAS database on Jun. 22, 2008.
STN-CAS database Registry No. 1029768-50-0. Entered STN-CAS database on Jun. 22, 2008.
STN-CAS database Registry No. 1029783-45-6. Entered STN-CAS database on Jun. 22, 2008.
STN-CAS database Registry No. 1029783-29-6. Entered STN-CAS database on Jun. 22, 2008.
STN-CAS database Registry No. 1029783-11-6. Entered STN-CAS database on Jun. 22, 2008.
STN-CAS database Registry No. 1029783-05-8. Entered STN-CAS database on Jun. 22, 2008.
STN-CAS database Registry No. 1030101-56-4. Entered STN-CAS database on Jun. 24, 2008.
STN-CAS database Registry No. 1030101-44-0. Entered STN-CAS database on Jun. 24, 2008.
STN-CAS database Registry No. 1030101-27-9. Entered STN-CAS database on Jun. 24, 2008.
STN-CAS database Registry No. 1031965-97-5. Entered STN-CAS database on Jul. 1, 2008.
STN-CAS database Registry No. 1031966-21-8. Entered STN-CAS database on Jul. 1, 2008.
STN-CAS database Registry No. 1031966-13-8. Entered STN-CAS database on Jul. 1, 2008.
STN-CAS database Registry No. 1031966-17-2. Entered STN-CAS database on Jul. 1, 2008.
Stoehr et al., Deletions of chromosome 8p and loss of sFRP1 expression are progression markers of papillary bladder cancer. Lab Invest. 2004;84:465-78.
Suzuki et al., Epigenetic inactivation of SFRP genes allows constitutive WNT signalling in colorectal cancer. Nature genet. 2004;36(4):417-22.
Torres et al., Activities of the Wnt-1 class of secreted signaling factors are antagonized by the Wnt-5A class and by a dominant negative cadherin in early Xenopus development. J. Cell Bio. 1996;133:1123-37.
Ugolini et al., WNT pathway and mammary carcinogenesis: loss of expression of candidate tumor suppressor gene SFRP1 in most invasive carcinomas except of the medullary type, Oncogene 2001;20:5810-7.
Willert et al., Wnt proteins are lipid-modified and can act as stem cell growth factors. Nature. 2003;423:448-52.

(56) References Cited

OTHER PUBLICATIONS

Yap et al., Rapid and selective detection of fatty acylated proteins using omega-alkynyl-fatty acids and click chemistry. J Lipid Res. 2010;51(6):1566-80.

You et al., Inhibition of Wnt-2-mediated signaling induces programmed cell death in non-small-cell lung cancer cells. Oncogene. 2004;23:6170-4.

Zeng et al., Aberrant Wnt/B-Catenin Signaling in Pancreatic Adenocarcinoma. Neoplasia. 2006;8(4):279-89.

Bocchinfuso et al., A mouse mammary tumor virus-Wnt-1 transgene induces mammary gland hyperplasia and tumorigenesis in mice lacking estrogen receptor-alpha. Cancer Res. Apr. 15, 1999;59(8):1869-76.

Coombs et al., Modulation of Wnt/β-catenin signaling and proliferation by a ferrous iron chelator with therapeutic efficacy in genetically engineered mouse models of cancer. Oncogene. Jan. 12, 2012;31(2):213-25. doi: 10.1038/onc.2011.228. Epub Jun. 13, 2011.

Ettenberg et al., Inhibition of tumorigenesis driven by different Wnt proteins requires blockade of distinct ligand-binding regions by LRP6 antibodies. Proc Natl Acad Sci U S A. Aug. 31, 2010;107(35):15473-8. doi:10.1073/pnas.1007428107. Epub Aug. 16, 2010.

WNT PATHWAY MODULATORS

FIELD

The invention relates to WNT pathway modulators, processes for making them and methods for using them.

CROSS REFERENCE TO RELATED APPLICATIONS

This Application is a Division of and claims the benefit under 35 U.S.C. § 120 of U.S. application Ser. No. 15/105,224, filed Jun. 16, 2016, entitled "WNT PATHWAY MODULATORS", which is a national stage filing under 35 U.S.C. § 371 of international PCT application, PCT/SG2014/000602, filed Dec. 17, 2014, which claims priority to UK Patent Application No. 1322333.4, filed Dec. 17, 2013, each of which is incorporated herein by reference.

BACKGROUND

Wnt proteins are secreted glycoproteins acting as growth factors that regulate various cellular functions include proliferation, differentiation, death, migration, and polarity, by activating multiple intracellular signaling cascades, including the β-catenin-dependent and -independent pathways. There are 19 Wnt members have been found in humans and mice, and they exhibit unique expression patterns and distinct functions during development. In humans and mice, the 10 members of the Frizzled (Fz) family comprise a series of seven-pass transmembrane receptors that have been identified as Wnt receptors. In addition to Fz proteins, single-pass transmembrane proteins, such as low-density lipoprotein receptor-related protein 5 (LRP5), LRP6, receptor tyrosine kinase (RTK)-like orphan receptor 1 (Ror1), Ror2, and receptor-like tyrosine kinase (Ryk), have been shown to function as co-receptors for Wnt signaling. Therefore, it has been assumed traditionally that the binding of different Wnts to their specific receptors selectively triggers different outcomes via distinct intracellular pathways.

Diverse Wnts, Wnt receptors, and downstream pathway all contribute to the role of Wnt. These pathways all play a role in development, stem cell maintenance, cancer and metastasis.

In the absence of Wnt signaling, β-catenin is bound and phosphorylated by a "destruction complex" containing the adenomatous polyposis coli (APC) and Axin proteins, as well as glycogen synthase kinase 3 (GSK3) and casein kinase I (CKI). Phosphorylated β-catenin is bound by the F box protein Slimb/β-TrCP and polyubiquitinated, leading to proteosomal degradation. In addition, the complex acts to prevent nuclear localization of b-catenin. Upon Wnt binding to Frizzled (Fz) and low-density lipoprotein-related proteins 5 and 6 (LRP5/6), GSK3, Axin, and other destruction complex components are recruited to the receptor complex. The function of the destruction complex is inhibited, and unphosphorylated β-catenin accumulates in the cytoplasm and eventually translocates to the nucleus. There, it associates with TCF proteins, converting TCF from a repressor into an activator of Wnt-responsive gene transcription.

Wnt in Cancer & Stem Cell:

Deregulation of components of Wnt/β-catenin signaling is implied in a wide spectrum of diseases including degenerative diseases, metabolic diseases, and a number of cancers such as cervical, colon, breast, bladder, head and neck, gastric, lung, ovarian, prostate, thyroid, non-small-cell lung, as well as chronic lymphocytic leukemia, mesothelioma, melanoma, pancreatic adenocarcinoma, basal cell carcinoma, osteosarcoma, hepatocellular carcinoma, Wilm's tumor and medulloblastoma.

Wnt signaling plays a role both during development, and within stem cell niches in adults. This is best established in skin, hematopoietic stem cells, mammary gland and in intestinal proliferation. For example, high level expression of DKK1, an inhibitor of Wnt signaling, blocks normal stem cell proliferation in mouse intestine, suggesting there is an essential role for Wnt signaling in maintenance of stem cells in the digestive tract. Wnt roles in self renewal and expansion of stem cells have also been demonstrated for embryonic and neural stem cells, suggesting that Wnt signaling may be a general requirement of stem cell maintenance. Inhibition of Wnt signaling, e.g., by overexpression of axin or an extracellular Wnt-binding protein, sFRP, reduces hematopoietic stem cell (HSC) growth in vitro and the ability to reconstitute HSCs in vivo. Notably, while overexpression of activated β-catenin can expand HSC populations in culture for extended periods, two groups have reported that β-catenin is not required for HSC survival and serial transplantation, supporting the proposal that there is more to Wnt signaling than stabilization of β-catenin in stem cell survival. Diverse Wnts can regulate stem cell proliferation: Wnts 1, 5a, and 10b are able to stimulate expansion of HSC populations and Wnt5a acts synergistically with stem cell factor (SCF) to expand and promote self renewal of HSCs. The demonstration of a role for Wnt5a in HSC self renewal and its ability to synergize with stem cell factor is particularly interesting because Wnt5a often acts in a β-catenin independent manner. While Wnt signaling is critical for stem cell maintenance, it may therefore be via signaling pathways distinct from or in parallel to the β-catenin pathway.

Fibrosis:

Wnt/β-catenin signaling pathway is essential to embryonic development in general and organ morphogenesis, so it is not surprising that dysregulation of this pathway in adult has been linked to fibroblast biology and fibrosis. It has been demonstrated that Wnt/β-catenin signaling play a role in severe fibrotic diseases, such as pulmonary fibrosis, liver fibrosis, skin fibrosis and renal fibrosis.

Others:

Dysregulation of Wnt/β-catenin signaling contributes to the development of diabetic retinopathy by inducing retinal inflammation, vascular leakage, and neovascularization.

The binding of Wnt proteins to plasma membrane receptors on mesenchymal cells induces the differentiation of these cells into the osteoblast lineage and thereby supports bone formation. Wnts are also key signaling proteins in joint remodeling processes. Active Wnt signaling contributes to osteophyte formation and might have an essential role in the anabolic pattern of joint remodeling that is observed in ankylosing spondylitis and osteoarthritis. By contrast, blockade of Wnt signaling facilitates bone erosion and contributes to catabolic joint remodeling, a process that is observed in rheumatoid arthritis.

There is therefore a need for compounds that modulate and/or inhibit the WNT pathway so as to treat diseases associated with WNT activity.

Definitions

A measure of the binding of an inhibitor to and the subsequent release from an enzyme is the "$IC_{50}$" value, which reflects the inhibitor concentration, which at a given substrate concentration results in 50% enzyme activity.

The term "subject" as used herein, refers to an animal, preferably a mammal, most preferably a human, who has been the object of treatment, observation or experiment. In one embodiment the subject is not a human. The subject may for example be a non-human mammal.

The term "therapeutically effective amount" as used herein, means that amount of active compound or pharmaceutical agent that elicits the biological or medicinal response in a tissue system, animal or human being sought by a researcher, veterinarian, medical doctor or other clinician, which includes alleviation of the symptoms of the disease or disorder being treated.

As used herein, the term "pharmaceutically acceptable" embraces both human and veterinary use: For example the term "pharmaceutically acceptable" embraces a veterinarily acceptable compound or a compound acceptable in human medicine and health care. In one embodiment, human medicine and health care is excluded.

Throughout the description and the claims the expression "alkyl", unless specifically limited, denotes a $C_{1-12}$ alkyl group, suitably a $C_{1-6}$ alkyl group, e.g. $C_{1-4}$ alkyl group. Alkyl groups may be straight chain or branched. Suitable alkyl groups include, for example, methyl, ethyl, propyl (e.g. n-propyl and isopropyl), butyl (e.g n-butyl, iso-butyl, sec-butyl and tert-butyl), pentyl (e.g. n-pentyl), hexyl (e.g. n-hexyl), heptyl (e.g. n-heptyl) and octyl (e.g. n-octyl). The expression "alk", for example in the expressions "alkoxy", "haloalkyl" and "thioalkyl" should be interpreted in accordance with the definition of "alkyl". Exemplary alkoxy groups include methoxy, ethoxy, propoxy (e.g. n-propoxy), butoxy (e.g. n-butoxy), pentoxy (e.g. n-pentoxy), hexoxy (e.g. n-hexoxy), heptoxy (e.g. n-heptoxy) and octoxy (e.g. n-octoxy). Exemplary thioalkyl groups include methylthio-. Exemplary haloalkyl groups include fluoroalkyl e.g. $CF_3$.

The expression "alkenyl", unless specifically limited, denotes a $C_{2-12}$ alkenyl group, suitably a $C_{2-6}$ alkenyl group, e.g. a $C_{2-4}$ alkenyl group, which contains at least one double bond at any desired location and which does not contain any triple bonds. Alkenyl groups may be straight chain or branched. Exemplary alkenyl groups including one double bond include propenyl and butenyl. Exemplary alkenyl groups including two double bonds include pentadienyl, e.g. (1E, 3E)-pentadienyl.

The expression "alkynyl", unless specifically limited, denotes a $C_{2-12}$ alkynyl group, suitably a $C_{2-6}$ alkynyl group, e.g. a $C_{2-4}$ alkynyl group, which contains at least one triple bond at any desired location and may or may not also contain one or more double bonds. Alkynyl groups may be straight chain or branched. Exemplary alkynyl groups include propynyl and butynyl.

The expression "alkylene" denotes a chain of formula —$(CH_2)_n$— wherein n is an integer e.g. 1-12, 1-6, 2-6 or 2-5, unless specifically limited.

The expression "cycloalkyl", unless specifically limited, denotes a $C_{3-10}$ cycloalkyl group (i.e. 3 to 10 ring carbon atoms), more suitably a $C_{3-8}$ cycloalkyl group, e.g. a $C_{3-6}$ cycloalkyl group. Exemplary cycloalkyl groups include cyclopropyl, cyclobutyl, cyclopentyl, cyclohexyl, cycloheptyl and cyclooctyl. A most suitable number of ring carbon atoms is three to six.

The expression "cycloalkenyl", unless specifically limited, denotes a $C_{3-10}$ cycloalkenyl group (i.e. 3 to 10 ring carbon atoms), suitably a $C_{5-10}$ cycloalkenyl group (i.e. 5 to 10 ring carbon atoms), more suitably a $C_{5-8}$ cycloalkenyl group e.g. a $C_{5-6}$ cycloalkenyl group. Exemplary cycloalkenyl groups include cyclopropenyl, cyclohexenyl, cycloheptenyl and cyclooctenyl. A most suitable number of ring carbon atoms is five to six.

The expression "carbocyclyl", unless specifically limited, denotes any ring system in which all the ring atoms are carbon and which contains between three and twelve ring carbon atoms, suitably between three and ten carbon atoms and more suitably between three and eight carbon atoms. Carbocyclyl groups may be saturated or partially unsaturated, but do not include aromatic rings. Examples of carbocyclyl groups include monocyclic, bicyclic, and tricyclic ring systems, in particular monocyclic and bicyclic ring systems. Other carbocyclyl groups include bridged ring systems (e.g. bicyclo[2.2.1]heptenyl). A specific example of a carbocyclyl group is a cycloalkyl group. A further example of a carbocyclyl group is a cycloalkenyl group.

The expression "heterocyclyl", unless specifically limited, refers to a carbocyclyl group wherein one or more (e.g. 1, 2 or 3) ring atoms are replaced by heteroatoms. The heteroatom(s) are commonly selected from N, S and O. A specific example of a heterocyclyl group is a cycloalkyl group (e.g. cyclopentyl or more particularly cyclohexyl) wherein one or more (e.g. 1, 2 or 3, particularly 1 or 2, especially 1) ring atoms are replaced by heteroatoms selected from N, S or O. Exemplary heterocyclyl groups containing one hetero atom include pyrrolidine, tetrahydrofuran and piperidine, and exemplary heterocyclyl groups containing two hetero atoms include morpholine and piperazine. A further specific example of a heterocyclyl group is a cycloalkenyl group (e.g. a cyclohexenyl group) wherein one or more (e.g. 1, 2 or 3, particularly 1 or 2, especially 1) ring atoms are replaced by heteroatoms selected from N, S and O. An example of such a group is dihydropyranyl (e.g. 3,4-dihydro-2H-pyran-2-yl-). The heterocyclyl group may be linked to other part or parts of the molecule by a carbon ring atom or nitrogen ring atom.

The expression "aryl", unless specifically limited, denotes a $C_{6-12}$ aryl group, suitably a $C_{6-10}$ aryl group, more suitably a $C_{6-8}$ aryl group. Aryl groups will contain at least one aromatic ring (e.g. one, two or three rings). Aryl groups with multiple aromatic rings include fused aromatic rings and aromatic rings connected to each other by one single bond. An example of a typical aryl group with one aromatic ring is phenyl. An example of a typical aryl group with two fused aromatic rings is naphthyl. An example of an aromatic group with two directly connected aromatic rings is biphenyl.

The expression "heteroaryl", unless specifically limited, denotes an aryl residue, wherein one or more (e.g. 1, 2, 3, or 4, suitably 1, 2 or 3) ring atoms are replaced by heteroatoms, said heteroatoms commonly being selected from N, S and O, or else a 5-membered aromatic ring containing one or more (e.g. 1, 2, 3, or 4, suitably 1, 2 or 3) ring atoms, said heteroatoms commonly selected from N, S and O. In some embodiments a heteroaryl group will have no ring heteroatoms other than nitrogen. Exemplary monocyclic heteroaryl groups having one heteroatom include: five membered rings (e.g. pyrrole, furan, thiophene); and six membered rings (e.g. pyridine, such as pyridin-2-yl, pyridin-3-yl and pyridin-4-yl). Exemplary monocyclic heteroaryl groups having two heteroatoms include: five membered rings (e.g. pyrazole, oxazole, isoxazole, thiazole, isothiazole, imidazole, such as imidazol-1-yl, imidazol-2-yl imidazol-4-yl); and six membered rings (e.g. pyridazine, pyrimidine, pyrazine). Exemplary monocyclic heteroaryl groups having three heteroatoms include: 1,2,3-triazole, 1,2,4-triazole, 1,2,3-oxadiazole and 1,2,4-oxadiazole. Exemplary monocyclic heteroaryl groups having four heteroatoms include tetrazole. Exemplary bicyclic heteroaryl groups include: indole (e.g. indol-6-yl), benzofuran, benzthiophene, quinoline, isoquinoline, indazole, benzimidazole, benzthiazole, quinazoline and purine. The heteraryl group may be linked to other part or parts of the molecule by a carbon ring atom or nitrogen ring atom.

The aforementioned aryl and heteroaryl groups may, where appropriate, optionally be substituted by one or more (e.g. 1, 2 or 3, suitably 1 or 2) groups each independently selected from monovalent or multivalent (i.e. having valency greater than 1) functional groups. Suitable substituent groups include alkyl, alkenyl, alkynyl, haloalkyl, -alkoxy (e.g. OMe), cycloalkyl, alkenyloxy-, alkynyloxy-, alkoxyalkyl-, nitro, halogen (e.g. fluoro, chloro and bromo), cyano, hydroxyl, oxo, —C(O)-alkyl (e.g. COMe), C(O)OH, —C(O)Oalkyl (e.g. —C(O)OMe), —OC(O)alkyl (e.g. —OC(O)Me), —NH$_2$, —NHalkyl (e.g. —NHMe), —N(alkyl)$_2$ (e.g. dimethylamino-), —C(O)NH$_2$, —C(O)NH(alkyl) (e.g. —C(O)NHMe), —NHC(O)alkyl (e.g. —NHC(O)Me), —C(NH)NH$_2$, thioalkyl (e.g. -thiomethyl), —SO$_2$alkyl (e.g. SO$_2$Me), —SOalkyl (e.g. —SOMe), —SO$_2$cycloalkyl and —SOcycloalkyl. More typically, substituents will be selected from alkyl (e.g. Me), fluoroalkyl (e.g. CF$_3$ and CHF$_2$), alkoxy (e.g. OMe), halogen and hydroxyl.

The expression "-alkylaryl", unless specifically limited, denotes an aryl residue which is connected via an alkylene moiety e.g. a C$_{1-4}$alkylene moiety. An example of such a group is benzyl: PhCH$_2$—.

The term "halogen" or "halo" comprises fluorine (F), chlorine (Cl) and bromine (Br).

The term "amino" refers to the group —NH$_2$.

The term "oxo" refers to an oxygen atom which, together with the carbon atom which it substitutes, forms a carbonyl group C=O.

The term "-arylheterocyclyl" refers to a heterocyclyl residue which is connected via an aryl moiety.

Stereoisomers:

All possible stereoisomers of the claimed compounds are included in the present invention.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention.

Preparation and isolation of stereoisomers:

Where the processes for the preparation of the compounds according to the invention give rise to a mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their components enantiomers by standard techniques, such as the formation of diastereomeric pairs by salt formation with an optically active acid, such as (−)-di-p-toluoyl-d-tartaric acid and/or (+)-di-p-toluoyl-1-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

Pharmaceutically acceptable salts:

In view of the close relationship between the free compounds and the compounds in the form of their salts or solvates, whenever a compound is referred to in this context, a corresponding salt, solvate or polymorph is also intended, provided such is possible or appropriate under the circumstances.

Salts and solvates of the compounds of formula (I) and physiologically functional derivatives thereof which are suitable for use in medicine are those wherein the counter-ion or associated solvent is pharmaceutically acceptable. However, salts and solvates having non-pharmaceutically acceptable counter-ions or associated solvents are within the scope of the present invention, for example, for use as intermediates in the preparation of other compounds and their pharmaceutically acceptable salts and solvates.

Suitable salts according to the invention include those formed with both organic and inorganic acids or bases. Pharmaceutically acceptable acid addition salts include those formed from hydrochloric, hydrobromic, sulfuric, nitric, citric, tartaric, phosphoric, lactic, pyruvic, acetic, trifluoroacetic, triphenylacetic, sulfamic, sulfanilic, succinic, oxalic, fumaric, maleic, malic, mandelic, glutamic, aspartic, oxaloacetic, methanesulfonic, ethanesulfonic, arylsulfonic (for example p-toluenesulfonic, benzenesulfonic, naphthalenesulfonic or naphthalenedisulfonic), salicylic, glutaric, gluconic, tricarballylic, cinnamic, substituted cinnamic (for example, phenyl, methyl, methoxy or halo substituted cinnamic, including 4-methyl and 4-methoxycinnamic acid), ascorbic, oleic, naphthoic, hydroxynaphthoic (for example 1- or 3-hydroxy-2-naphthoic), naphthaleneacrylic (for example naphthalene-2-acrylic), benzoic, 4-methoxybenzoic, 2- or 4-hydroxybenzoic, 4-chlorobenzoic, 4-phenylbenzoic, benzeneacrylic (for example 1,4-benzenediacrylic), isethionic acids, perchloric, propionic, glycolic, hydroxyethanesulfonic, pamoic, cyclohexanesulfamic, salicylic, saccharinic and trifluoroacetic acid. Pharmaceutically acceptable base salts include ammonium salts, alkali metal salts such as those of sodium and potassium, alkaline earth metal salts such as those of calcium and magnesium and salts with organic bases such as dicyclohexylamine and N-methyl-D-glucamine.

All pharmaceutically acceptable acid addition salt forms of the compounds of the present invention are intended to be embraced by the scope of this invention.

Polymorph crystal forms:

Furthermore, some of the crystalline forms of the compounds may exist as polymorphs and as such are intended to be included in the present invention. In addition, some of the compounds may form solvates with water (i.e. hydrates) or common organic solvents, and such solvates are also intended to be encompassed within the scope of this invention. The compounds, including their salts, can also be obtained in the form of their hydrates, or include other solvents used for their crystallization.

Prodrugs:

The present invention further includes within its scope prodrugs of the compounds of this invention. In general, such prodrugs will be functional derivatives of the compounds which are readily convertible in vivo into the desired therapeutically active compound. Thus, in these cases, the methods of treatment of the present invention, the term "administering" shall encompass the treatment of the various disorders described with prodrug versions of one or more of the claimed compounds, but which converts to the above specified compound in vivo after administration to the subject. Conventional procedures for the selection and preparation of suitable prodrug derivatives are described, for example, in "Design of Prodrugs", ed. H. Bundgaard, Elsevier, 1985.

Protective Groups:

During any of the processes for preparation of the compounds of the present invention, it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991, fully incorporated herein by reference. The protecting groups may be removed at a convenient subsequent stage using methods known from the art.

As used herein, the term "composition" is intended to encompass a product comprising the claimed compounds in the therapeutically effective amounts, as well as any product which results, directly or indirectly, from combinations of the claimed compounds.

Carriers and Additives for galenic formulations:

Carriers, which can be added to the mixture, include necessary and inert pharmaceutical excipients, including, but not limited to, suitable binders, suspending agents, lubricants, flavorants, sweeteners, preservatives, coatings, disintegrating agents, dyes and coloring agents.

Thus, for liquid oral preparations, such as for example, suspensions, elixirs and solutions, suitable carriers and additives may advantageously include water, glycols, oils, alcohols, flavoring agents, preservatives, coloring agents and the like; for solid oral preparations such as, for example, powders, capsules, gelcaps and tablets, suitable carriers and additives include starches, sugars, diluents, granulating agents, lubricants, binders, disintegrating agents and the like.

Soluble polymers as targetable drug carriers can include polyvinylpyrrolidone, pyran copolymer, polyhydroxypropylmethacrylamidephenol, polyhydroxyethylaspartamide-phenol, or polyethyleneoxidepolyllysine substituted with palmitoyl residue. Furthermore, the compounds of the present invention may be coupled to a class of biodegradable polymers useful in achieving controlled release of a drug, for example, polyactic acid, polyepsilon caprolactone, polyhydroxy butyeric acid, polyorthoesters, polyacetals, polydihydropyrans, polycyanoacrylates and cross-linked or amphipathic block copolymers of hydrogels.

Suitable binders include, without limitation, starch, gelatin, natural sugars such as glucose or betalactose, corn sweeteners, natural and synthetic gums such as acacia, tragacanth or sodium oleate, sodium stearate, magnesium stearate, sodium benzoate, sodium acetate, sodium chloride and the like.

Disintegrators include, without limitation, starch, methyl cellulose, agar, bentonite, xanthan gum and the like.

SUMMARY OF INVENTION

According to the invention there is provided a compound of formula (I),

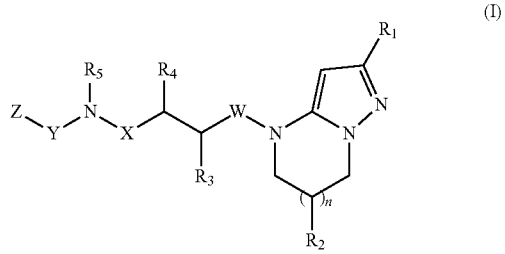

(I)

or a pharmaceutically acceptable salt, solvate or polymorph thereof, including all tautomers and stereoisomers thereof wherein:

$R_1$ represents H; optionally substituted alkyl (wherein optional substituents include one or more substituents each independently selected from $C_{1-6}$alkoxy, $NH_2$, —$NHC_{1-3}$alkyl and —$N(C_{1-3}$alkyl$)_2$); —C(O)Oalkyl; haloalkyl; haloalkoxy; or -alkylaryl;

each $R_2$ independently represents H; optionally substituted alkyl (wherein optional substituents include one or more substituents each independently selected from $C_{1-6}$alkoxy, $NH_2$, —$NHC_{1-3}$alkyl and —$N(C_{1-3}$alkyl$)_2$); -alkylaryl; optionally substituted carbocyclyl (wherein optional substituents include one or more substituents each independently selected from $C_{1-6}$alkyl, $C_{1-6}$alkoxy, $C_{1-6}$haloalkyl, $C_{1-6}$haloalkoxy and halo); optionally substituted heterocyclyl (wherein optional substituents include one or more substituents each independently selected from $C_{1-6}$alkyl, $C_{1-6}$alkoxy, —C(O)O$C_{1-6}$alkyl, —C(O)$C_{1-6}$alkyl and —C(O)NH$C_{1-6}$alkyl); —NHalkyl; —N(alkyl)$_2$; amino; hydroxyl; alkoxy or halo;

n represents 0, 1 or 2;

$R_3$ represents H or alkyl;

$R_4$ represents H or alkyl;

$R_5$ represents H or alkyl;

W and X each independently represent C=O; C=S; or $CH_2$;

Y represents aryl; heteroaryl; optionally substituted carbocyclyl (wherein optional substituents include one or more substituents each independently selected from $C_{1-6}$alkyl, $C_{1-6}$alkoxy, $C_{1-6}$haloalkyl, $C_{1-6}$haloalkoxy and halo); or optionally substituted heterocyclyl (wherein optional substituents include one or more substituents each independently selected from $C_{1-6}$alkyl, $C_{1-6}$alkoxy, —C(O)O$C_{1-6}$ alkyl, —C(O)$C_{1-6}$alkyl and —C(O)NH$C_{1-6}$alkyl); and Z represents optionally substituted alkyl (wherein optional substituents include one or more substituents each independently selected from $C_{1-6}$alkoxy, $NH_2$, —$NHC_{1-3}$alkyl and —$N(C_{1-3}$alkyl$)_2$); aryl; heteroaryl; -alkylaryl;-alkylheteroaryl; optionally substituted carbocyclyl (wherein optional substituents include one or more substituents each independently selected from $C_{1-6}$alkyl, $C_{1-6}$alkoxy, $C_{1-6}$haloalkyl, $C_{1-6}$haloalkoxy and halo); optionally substituted heterocyclyl (wherein optional substituents include one or more substituents each independently selected from $C_{1-6}$alkyl, $C_{1-6}$alkoxy, —C(O)O$C_{1-6}$alkyl, —C(O)$C_{1-6}$alkyl and —C(O)NH$C_{1-6}$alkyl); -alkylcarbocyclyl wherein carbocyclyl is optionally substituted (wherein optional substituents include one or more substituents each independently selected from $C_{1-6}$alkyl, $C_{1-6}$alkoxy, $C_{1-6}$haloalkoxy and halo); -alkylheterocyclyl wherein heterocyclyl is optionally substituted (wherein optional substituents include one or more substituents each independently selected from $C_{1-6}$alkyl, —C(O)O$C_{1-6}$alkyl, —C(O)$C_{1-6}$alkyl and —C(O)NH$C_{1-6}$alkyl); -arylcarbocyclyl wherein carbocyclyl is optionally substituted (wherein optional substituents include one or more substituents each independently selected from $C_{1-6}$alkyl, $C_{1-6}$alkoxy, $C_{1-6}$haloalkoxy and halo); or -arylheterocyclyl wherein heterocyclyl is optionally substituted (wherein optional substituents include one or more substituents each independently selected from $C_{1-6}$alkyl, —C(O)O$C_{1-6}$alkyl, —C(O)$C_{1-6}$alkyl and —C(O)NH$C_{1-6}$alkyl).

Further, according to the invention there is provided a compound of formula (I),

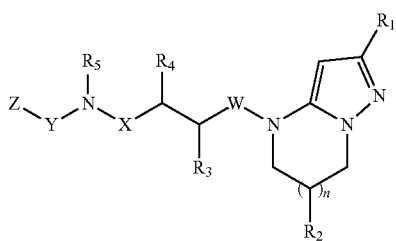

or a pharmaceutically acceptable salt, solvate or polymorph thereof, including all tautomers and stereoisomers thereof wherein:

$R_1$ represents H; alkyl which is optionally substituted by one or more substituents each independently selected from $C_{1-6}$alkoxy, $NH_2$, —$NHC_{1-3}$alkyl and —$N(C_{1-3}$alkyl$)_2$; —C(O)Oalkyl; haloalkyl; haloalkoxy; or -alkylaryl;

each $R_2$ independently represents H; alkyl which is optionally substituted by one or more substituents each independently selected from $C_{1-6}$alkoxy, $NH_2$, —$NHC_{1-3}$alkyl and —$N(C_{1-3}$alkyl$)_2$; -alkylaryl; carbocyclyl which is optionally substituted by one or more substituents each independently selected from $C_{1-6}$alkyl, $C_{1-6}$alkoxy, $C_{1-6}$haloalkyl, $C_{1-6}$haloalkoxy and halo; heterocyclyl which is optionally substituted by one or more substituents each independently selected from $C_{1-6}$alkyl, $C_{1-6}$alkoxy, —C(O)O$C_{1-6}$alkyl, —C(O)$C_{1-6}$alkyl and —C(O)NH$C_{1-6}$alkyl; —NHalkyl; —N(alkyl)$_2$; amino; hydroxyl; alkoxy or halo;

n represents 0, 1 or 2;

$R_3$ represents H or alkyl;

$R_4$ represents H or alkyl;

$R_5$ represents H or alkyl;

W and X each independently represent C=O; C=S; or $CH_2$;

Y represents aryl; heteroaryl; carbocyclyl which is optionally substituted by one or more substituents each independently selected from $C_{1-6}$alkyl, $C_{1-6}$alkoxy, $C_{1-6}$haloalkyl, $C_{1-6}$haloalkoxy and halo; or heterocyclyl which is optionally substituted by one or more substituents each independently selected from $C_{1-6}$alkyl, $C_{1-6}$alkoxy, —C(O)O$C_{1-6}$alkyl, —C(O)$C_{1-6}$alkyl and —C(O)NH$C_{1-6}$alkyl; and Z represents alkyl which is optionally substituted by one or more substituents each independently selected from $C_{1-6}$alkoxy, $NH_2$, —$NHC_{1-3}$alkyl and —$N(C_{1-3}$alkyl$)_2$; aryl; heteroaryl;-alkylaryl;-alkylheteroaryl; carbocyclyl which is optionally substituted by one or more substituents each independently selected from $C_{1-6}$alkyl, $C_{1-6}$alkoxy, $C_{1-6}$haloalkyl, $C_{1-6}$haloalkoxy and halo; heterocyclyl which is optionally substituted by one or more substituents each independently selected from $C_{1-6}$alkyl, $C_{1-6}$alkoxy, —C(O)O$C_{1-6}$alkyl, —C(O)$C_{1-6}$alkyl and —C(O)NH$C_{1-6}$alkyl; -alkylcarbocyclyl wherein carbocyclyl is optionally substituted by one or more substituents each independently selected from $C_{1-6}$alkyl, $C_{1-6}$alkoxy, $C_{1-6}$haloalkoxy and halo; -alkylheterocyclyl wherein heterocyclyl is optionally substituted by one or more substituents each independently selected from $C_{1-6}$alkyl, —C(O)O$C_{1-6}$alkyl, —C(O)$C_{1-6}$alkyl and —C(O)NH$C_{1-6}$alkyl; -arylcarbocyclyl wherein carbocyclyl is optionally substituted by one or more substituents each independently selected from $C_{1-6}$alkyl, $C_{1-6}$alkoxy, $C_{1-6}$haloalkoxy and halo; or -arylheterocyclyl wherein heterocyclyl is optionally substituted by one or more substituents each independently selected from $C_{1-6}$alkyl, —C(O)O$C_{1-6}$alkyl, —C(O)$C_{1-6}$alkyl and —C(O)NH$C_{1-6}$alkyl.

BRIEF DESCRIPTION OF DRAWINGS

FIG. 5 shows the results for Cell line AsPC-1 treated with Compound 51. FIG. 6 shows the results for Cell line HPAF-II treated with Compound 51. FIG. 7 shows the results for Cell line CFPAC-1 treated with Compound 51.

DETAILED DESCRIPTION

Figure 1:
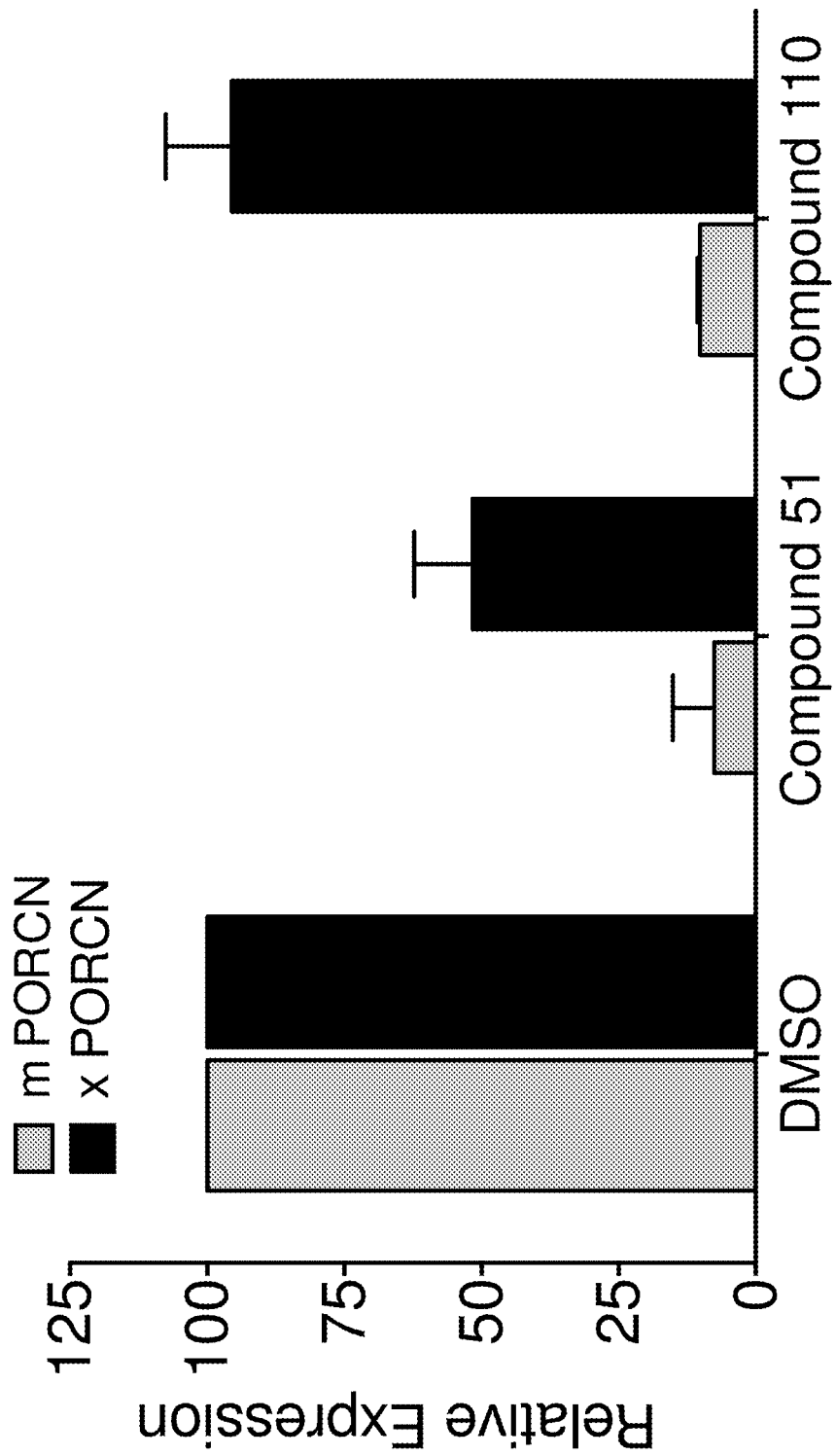
FIG. 1: A bar chart illustrating inhibition of the activity of mammalian porcupine by Compound 51 and Compound 110.

According to the invention there are provided compounds of formula (I),

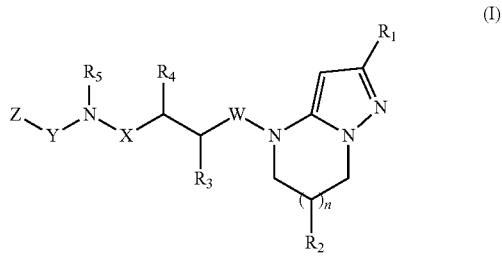

or a pharmaceutically acceptable salt, solvate or polymorph thereof, including all tautomers and stereoisomers thereof wherein:

$R_1$ represents H; alkyl which is optionally substituted by one or more substituents each independently selected from $C_{1-6}$alkoxy, $NH_2$, —$NHC_{1-3}$alkyl and —$N(C_{1-3}$alkyl$)_2$; —C(O)Oalkyl; haloalkyl; haloalkoxy; or -alkylaryl;

each $R_2$ independently represents H; alkyl which is optionally substituted by one or more substituents each independently selected from $C_{1-6}$alkoxy, $NH_2$, —$NHC_{1-3}$alkyl and —$N(C_{1-3}$alkyl$)_2$; -alkylaryl; carbocyclyl which is optionally substituted by one or more substituents each independently selected from $C_{1-6}$alkyl, $C_{1-6}$alkoxy, $C_{1-6}$haloalkyl, $C_{1-6}$haloalkoxy and halo; heterocyclyl which is optionally substituted by one or more substituents each independently selected from $C_{1-6}$alkyl, $C_{1-6}$alkoxy, —C(O)O$C_{1-6}$alkyl, —C(O)$C_{1-6}$alkyl and —C(O)NH$C_{1-6}$alkyl; —NHalkyl; —N(alkyl)$_2$; amino; hydroxyl; alkoxy or halo;

n represents 0, 1 or 2;

$R_3$ represents H or alkyl;

$R_4$ represents H or alkyl;

$R_5$ represents H or alkyl;

W and X each independently represent C=O; C=S; or $CH_2$;

Y represents aryl; heteroaryl; carbocyclyl which is optionally substituted by one or more substituents each independently selected from $C_{1-6}$alkyl, $C_{1-6}$alkoxy, $C_{1-6}$haloalkyl, $C_{1-6}$haloalkoxy and halo; or heterocyclyl which is optionally substituted by one or more substituents each independently selected from $C_{1-6}$alkyl, $C_{1-6}$alkoxy, —C(O)O$C_{1-6}$alkyl, —C(O)$C_{1-6}$alkyl and —C(O)NH$C_{1-6}$alkyl; and Z represents alkyl which is optionally substituted by one or more substituents each independently selected from $C_{1-6}$alkoxy, NH$_2$, —NH$C_{1-3}$alkyl and —N($C_{1-3}$alkyl)$_2$; aryl; heteroaryl;-alkylaryl; -alkylheteroaryl; carbocyclyl which is optionally substituted by one or more substituents each independently selected from $C_{1-6}$alkyl, $C_{1-6}$alkoxy, $C_{1-6}$haloalkyl, $C_{1-6}$haloalkoxy and halo; heterocyclyl which is optionally substituted by one or more substituents each independently selected from $C_{1-6}$alkyl, $C_{1-6}$alkoxy, —C(O)O$C_{1-6}$alkyl, —C(O)$C_{1-6}$alkyl and —C(O)NH$C_{1-6}$alkyl; -alkylcarbocyclyl wherein carbocyclyl is optionally substituted by one or more substituents each independently selected from $C_{1-6}$alkyl, $C_{1-6}$alkoxy, $C_{1-6}$haloalkyl, $C_{1-6}$haloalkoxy and halo; -alkylheterocyclyl wherein heterocyclyl is optionally substituted by one or more substituents each independently selected from $C_{1-6}$alkyl, —C(O)O$C_{1-6}$alkyl, —C(O)$C_{1-6}$alkyl and —C(O)NH$C_{1-6}$alkyl; -arylcarbocyclyl wherein carbocyclyl is optionally substituted by one or more substituents each independently selected from $C_{1-6}$alkyl, $C_{1-6}$alkoxy, $C_{1-6}$haloalkyl, $C_{1-6}$haloalkoxy and halo; or -arylheterocyclyl wherein heterocyclyl is optionally substituted by one or more substituents each independently selected from $C_{1-6}$alkyl, —C(O)O$C_{1-6}$alkyl, —C(O)$C_{1-6}$alkyl and —C(O)NH$C_{1-6}$alkyl.

In one embodiment, any one or more of, optionally all of, the following compounds are excluded from the scope of Formula (I):

(i)

(ii)

(iii)

(iv)

(v)
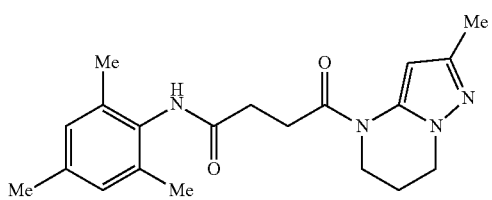

(vi)
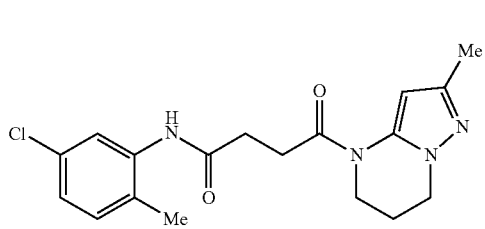

(vii)
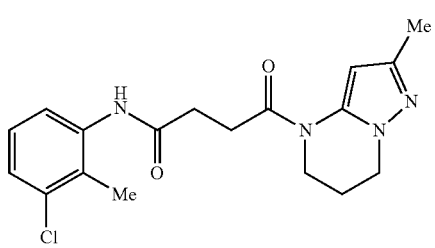

(viii)
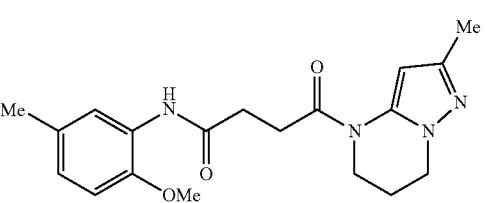

(ix)
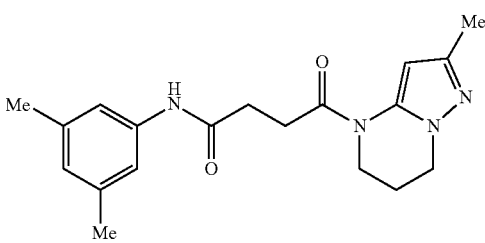

(x)
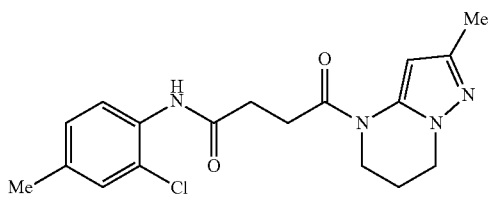

(xi)
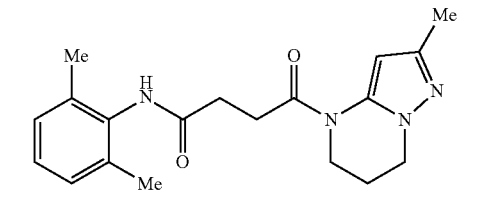

13

-continued

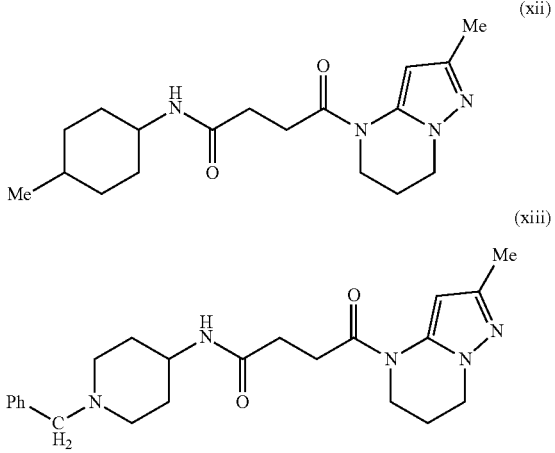

(xii)

(xiii)

In the context of variable Y, the term "aryl" is understood to mean "arylene" (e.g. "phenyl" is understood to mean "phenylene" (i.e. $C_6H_4$)) because Y is a linking group, not a terminal group. The terms for other Y rings (e.g. heteroaryl) are to be construed likewise. When Y is referred to as being unsubstituted, this is understood to mean no other substituents other than Z and $NR_5$. When Y is referred to as being monosubstitued, this is understood to mean one substituent other than Z and $NR_5$.

When $R_1$ represents alkyl which is optionally substituted by one or more substituents each independently selected from $C_{1-6}$alkoxy, $NH_2$, —$NHC_{1-3}$alkyl and —$N(C_{1-3}$alkyl$)_2$ exemplary substituents include methoxy, —$NH_2$, —NHmethyl and —NH(methyl)$_2$. Examples include $C_{1-6}$ alkyl (e.g. unsubstituted $C_{1-6}$alkyl), for example methyl, ethyl, propyl (e.g. n-propyl, isopropyl), butyl (e.g. n-butyl, iso-butyl, sec-butyl, tert-butyl), pentyl (e.g. n-pentyl) and hexyl (e.g. n-hexyl). Exemplary $C_{1-6}$ alkyl groups are methyl and ethyl, particularly methyl.

When $R_1$ represents —C(O)Oalkyl, examples include —C(O)OC$_{1-6}$alkyl such as —C(O)OMe, —C(O)OEt, —C(O)OPr and —C(O)OiPr. A specific example is —C(O)OMe.

When $R_1$ represents haloalkyl, examples include $C_{1-6}$haloalkyl such as $CH_2F$, $CHF_2$, $CF_3$, $CH_2CH_2F$, $CH_2CHF_2$, $CH_2CF_3$, $CHFCH_3$ and $CF_2CH_3$. A specific example is $CF_3$.

When $R_1$ represents haloalkoxy, examples include $C_{1-6}$haloalkoxy such as $OCF_3$.

When $R_2$ represents alkyl which is optionally substituted by one or more substituents each independently selected from $C_{1-6}$alkoxy, $NH_2$, —$NHC_{1-3}$alkyl and —$N(C_{1-3}$alkyl$)_2$, exemplary substituents include methoxy, —$NH_2$, —NHmethyl and —NH(methyl)$_2$. Examples include $C_{1-6}$ alkyl (e.g. unsubstituted $C_{1-6}$alkyl), for example methyl, ethyl, propyl (e.g. n-propyl, isopropyl), butyl (e.g. n-butyl, iso-butyl, sec-butyl, tert-butyl), pentyl (e.g. n-pentyl) and hexyl (e.g. n-hexyl). An exemplary $C_{1-6}$ alkyl group is methyl.

When $R_2$ represents -alkylaryl, examples include benzyl.

When $R_2$ represents carbocyclyl which is optionally substituted by one or more substituents each independently selected from $C_{1-6}$alkyl (e.g. methyl), $C_{1-6}$alkoxy (e.g. methoxy), $C_{1-6}$haloalkyl (e.g. fluoromethyl such as trifluoromethyl), $C_{1-6}$haloalkoxy (e.g. fluoromethoxy such as trifluoromethoxy) and halo (e.g. fluoro, e.g. chloro), examples include $C_3$-$C_6$ cycloalkyl such as cyclopropyl, cyclobutyl, cyclopentyl and cyclohexyl. Substituted examples include cyclohexyl substituted by methyl.

14

When $R_2$ represents heterocyclyl which is optionally substituted by one or more substituents each independently selected from $C_{1-6}$alkyl, $C_{1-6}$alkoxy, —C(O)OC$_{1-6}$alkyl, —C(O)C$_{1-6}$alkyl and —C(O)NHC$_{1-6}$alkyl, Y may represent heterocyclyl which is optionally substituted by $C_{1-6}$ alkyl (such as methyl). Examples include monocyclic heterocyclyl. The heterocyclyl group may be unsubstituted or may have for example one or two (e.g. one) substituent (e.g. one methyl group). Examples include piperidinyl, morpholinyl, pyrrolidinyl, 4,5-dihydropyrazolyl and 4,5-dihydroisoxazolyl. A specific example is pyrrolidinyl.

When $R_2$ represents —NHalkyl, examples include —NHMe, NHEt, NHPr and NHiPr, in particular NHMe.

When $R_2$ represents —N(alkyl)$_2$, examples include —N(Me)$_2$.

When $R_2$ represents alkoxy, examples include methoxy and ethoxy, especially methoxy.

When n represents 1, examples of —(CHR$_2$)$_n$— include —$CH_2$— and —CH(CH$_3$)—.

When n represents 2, examples of —(CHR$_2$)$_n$— include —$CH_2$—$CH_2$—, —$CH_2$CH(CH$_3$)—, —CH(CH$_3$)CH$_2$— and —CH(CH$_3$)—CH(CH$_3$)—. An example of a —(CHR$_2$)$_2$— group is —$CH_2$—$CH_2$—.

When $R_3$ represents alkyl, examples include $C_{1-6}$ alkyl such as methyl, ethyl, propyl (e.g. n-propyl, isopropyl), butyl (e.g. n-butyl, iso-butyl, sec-butyl, tert-butyl), pentyl (e.g. n-pentyl) and hexyl (e.g. n-hexyl). An exemplary $C_{1-6}$ alkyl group is methyl.

When $R_4$ represents alkyl, examples include $C_{1-6}$ alkyl, for example methyl, ethyl, propyl (e.g. n-propyl, isopropyl), butyl (e.g. n-butyl, iso-butyl, sec-butyl, tert-butyl), pentyl (e.g. n-pentyl) and hexyl (e.g. n-hexyl). An exemplary $C_{1-6}$ alkyl group is methyl.

When $R_5$ represents alkyl, examples include $C_{1-6}$ alkyl such as methyl, ethyl, propyl (e.g. n-propyl, isopropyl), butyl (e.g. n-butyl, iso-butyl, sec-butyl, tert-butyl), pentyl (e.g. n-pentyl) and hexyl (e.g. n-hexyl). An exemplary $C_{1-6}$ alkyl group is methyl.

When Y represents aryl, examples include optionally substituted phenyl. Exemplary substituents include one or more (e.g. one or two, especially one) substituents each independently selected from $C_{1-6}$ alkyl (such as methyl), $C_{1-6}$alkoxy (such as methoxy), halo and $C_{1-6}$haloalkyl (such as fluoroemethyl, e.g. trifluoromethyl). Examples include unsubstituted phenyl, methylphenyl, methoxyphenyl, fluorophenyl, chlorophenyl and trifluoromethylphenyl. Specific examples include unsubstituted phenyl. Specific examples also include methylphenyl, methoxyphenyl, fluorophenyl. Z and $NR_5$ may be positioned on the phenyl ring at the 1- and 4-positions relative to each other (i.e. Z and $NR_5$ have a para relationship).

When Y represents heteroaryl, examples include monocyclic (e.g. 5 and 6 membered) and bicyclic (e.g. 9 and 10 membered) heteroaryl rings, especially monocyclic heteroaryl rings, particularly 6-membered monocyclic heteroaryl rings. Examples of monocyclic heteroaryl may comprise one, two or three ring heteroatoms (e.g. one or two, e.g. one) including one or two nitrogen atoms (e.g. one or e.g. two) and optionally an oxygen or sulphur atom. Exemplary 5-membered monocyclic heteroaryl groups include pyrrolyl, pyrazolyl, imidazolyl, oxazolyl, isoxazolyl, thiazolyl, isothiazolyl, oxadiazolyl and thiadiazolyl. When Y is 5-membered monocyclic heteroaryl, Z and $NR_5$ may be positioned on the ring at non-adjacent ring atoms. Exemplary 6-membered monocyclic heteroaryl groups include pyridinyl. Exemplary 6-membered monocyclic heteroaryl groups also include pyridazinyl, pyrimidinyl and pyrazinyl. When Y is 6-membered monocyclic heteroaryl, Z and $NR_5$ may be positioned on the ring at 1- and 4-positions relative to each other (i.e. Z and $NR_5$ have a para relationship). The aforementioned heteroaryl group may either by unsubstituted or may be substituted by one or more (e.g. one or two, particularly one) substituents. Exemplary substituents are independently selected from $C_{1-6}$alkyl (such as methyl), $C_{1-6}$alkoxy (such as methoxy), halo (such as fluoro) and $C_{1-6}$haloalkyl (such as fluoromethyl, e.g. trifluoromethyl). When Y is unsubstituted heteroaryl, examples include isoxazolyl (e.g. isoxazolyl-5-yl (wherein $NR_5$ is at the 5-position and Z is at the 3-position) and isoxazolyl-3-yl (wherein $NR_5$ is at the 3-position and Z is at the 5-position), especially isoxazol-5-yl), oxadiazolyl, pyridinyl (e.g. pyridin-2-yl or pyridin-3-yl), pyridazinyl (e.g. pyridazin-3-yl), pyrimidinyl (e.g. pyrimidin-3-yl), pyrazinyl (e.g. pyrazin-2-yl). When Y is substituted heteroaryl, Y may for example be substituted by methyl or fluoro. When Y is substituted heteroaryl, examples include methylpyridinyl, fluoropyridinyl, methylpyridazinyl, methylpyrazinyl methylpyrimidinyl and 1-methylpyrazolyl.

When Y represents carbocyclyl which is optionally substituted by one or more substituents each independently selected from $C_{1-6}$alkyl (e.g. methyl), $C_{1-6}$alkoxy (e.g. methoxy), $C_{1-6}$haloalkyl (e.g. fluoromethyl such as trifluoromethyl), $C_{1-6}$haloalkoxy (e.g. fluoromethoxy) and halo (e.g. fluoro, e.g. chloro), Y may represent carbocyclyl which is optionally substituted by $C_{1-6}$alkyl. Examples include monocyclic carbocyclyl which is optionally substituted by $C_{1-6}$alkyl (such as methyl). Examples of carbocyclyl include $C_{3-8}$cycloalkyl (e.g. cyclohexyl) and $C_{5-8}$cycloalkenyl (e.g. cyclohexenyl). The carbocycyl ring is optionally substituted by one, two or three independently selected substituents (e.g. one or two, especially one, e.g. one methyl group). When Y represents carbocyclyl, Y may represent $C_{3-8}$cycloalkyl, such as $C_{5-6}$cycloalkyl. A specific example is cyclohexyl. When Y is 6-membered carbocyclyl, Z and $NR_5$ are may be positioned on the carbocyclyl ring at the 1- and 4-positions relative to each other.

When Y represents heterocyclyl which is optionally substituted by one or more substituents each independently selected from $C_{1-6}$alkyl, $C_{1-6}$alkoxy, —C(O)O$C_{1-6}$alkyl, —C(O)$C_{1-6}$alkyl and —C(O)NH$C_{1-6}$alkyl, Y may represent heterocyclyl which is optionally substituted by $C_{1-6}$ alkyl (such as methyl). Examples include monocyclic heterocyclyl. The heterocyclyl group may be unsubstituted or may have for example one or two (e.g. one) substituent (e.g. one methyl group). Examples include piperidinyl, morpholinyl, pyrrolidinyl, 4,5-dihydropyrazolyl and 4,5-dihydroisoxazolyl. Specific examples include 4,5-dihydroisoxazolyl (e.g. 4,5-dihydroisoxazol-5-yl) and piperidinyl (e.g. piperidin-4-yl). When Y is 6-membered heterocyclyl, Z and $NR_5$ may be positioned on the heterocyclyl ring at the 1- and 4-positions relative to each other. When Y represents heterocyclyl, in one embodiement Z does not represent -alkylaryl.

When Z represents alkyl which is optionally substituted by one or more substituents each independently selected from $C_{1-6}$alkoxy, $NH_2$, —NH$C_{1-3}$alkyl and —N($C_{1-3}$alkyl)$_2$, exemplary substituents include methoxy, —$NH_2$, —NHmethyl and —NH(methyl)$_2$. Examples include $C_{1-6}$alkyl (e.g. unsubstituted $C_{1-6}$alkyl), for example methyl, ethyl, propyl (e.g. n-propyl, isopropyl), butyl (e.g. n-butyl, iso-butyl, sec-butyl, tert-butyl), pentyl (e.g. n-pentyl) and hexyl (e.g. n-hexyl). Examples also include $C_{3-6}$alkyl (e.g. unsubstituted $C_{3-6}$alkyl), for example propyl (e.g. n-propyl, isopropyl), butyl (e.g. n-butyl, iso-butyl, sec-butyl, tert-butyl), pentyl (e.g. n-pentyl) and hexyl (e.g. n-hexyl). Exemplary $C_{1-6}$ alkyl groups are methyl and tert-butyl.

When Z represents aryl, examples include optionally substituted phenyl. Exemplary substituents include one or more (e.g. one or two, especially one) substituents each independently selected from fluoro, chloro, bromo, amino, methoxy, methyl, haloalkyl (e.g. fluoromethyl such as trifluoromethyl), —COOH, —C(O)NMe$_2$, dimethylamino and —NHC(O)Me. Examples include unsubstituted phenyl. Substituted examples include fluorophenyl (e.g. 2-fluorophenyl, 3-fluorophenyl and 4-fluorophenyl), chlorophenyl (e.g. 2-chlorophenyl, 3-chlorophenyl, 4-chlorophenyl and 3,4-dichlorophenyl), bromophenyl (e.g. 2-bromophenyl, 3-bromophenyl and 4-bromophenyl), aminophenyl (e.g. 2-aminophenyl, 3-aminophenyl, 4-aminophenyl), methoxyphenyl (e.g. 2-methoxyphenyl, 3-methoxyphenyl and 4-methoxyphenyl), methylphenyl (e.g. 2-methylphenyl, 3-methylphenyl and 4-methylphenyl), fluoromethylphenyl (e.g. 3-trifluoromethylphenyl and 4-trifluoromethylphenyl), carboxyphenyl (e.g. 3-(COOH)-phenyl), 3-(C(O)NMe$_2$)-phenyl), 3-dimethylaminophenyl and 3-(NHC(O)Me)-phenyl.

When Z represents heteroaryl, examples include monocyclic (e.g. 5 and 6 membered) and bicyclic (e.g. 9 and 10 membered) heteroaryl rings, especially monocyclic rings. Examples of monocyclic heteroaryl comprise one, two or three ring heteroatoms (e.g. one or two, e.g. one) including one or two nitrogen atoms (e.g. one or e.g. two) and optionally an oxygen or sulphur atom. Exemplary 5-membered monocyclic heteroaryl groups include pyrrolyl, pyrazolyl, imidazolyl, oxazolyl, isoxazolyl, thiazolyl, isothiazolyl, oxadiazolyl and thiadiazolyl. Exemplary 6-membered monocyclic heteroaryl groups include pyridinyl. Exemplary 6-membered monocyclic heteroaryl groups also include pyridazinyl, pyrimidinyl and pyrazinyl. The aforementioned heteroaryl group may either by unsubstituted or may be substituted by one or more (e.g. one or two, particularly one) substituents. Exemplary substituents are independently selected from methyl, fluoro, chloro, amino, halomethyl (e.g. fluoromethyl such as trifluoromethyl). Unsubstituted examples include pyridinyl (e.g. pyridin-2-yl, pyridin-3-yl and pyridin-4-yl), pyrazinyl (e.g. pyrazin-2-yl), pyridazinyl (e.g. pyridazin-3-yl), pyrimidinyl (e.g. pyrimidin-2-yl, pyrimidin-4-yl and pyrimidin-5-yl), oxazolyl (e.g. oxazol-2-yl and oxazol-5-yl), thiazolyl (e.g. thiazol-2-yl and thiazole-5-yl) and pyrazolyl (e.g. pyrazol-1-yl). Substituted examples include chloropyridinyl (e.g. 4-chloropyridin-2-yl, 5-chloropyridin-2-yl and 5-chloropyridin-3-yl), fluoropyridinyl (e.g. 4-fluoropyridin-2-yl, 5-fluoropyridin-2-yl and 5-fluoropyridin-3-yl), methylpyridinyl (e.g. 2-methylpyridin-5-yl, 6-methylpyridin-2-yl and 5-methylpyridin-3-yl), fluoromethylpyridinyl (e.g. 5-trifluoromethylpyridin-3-yl), aminopyridinyl (e.g. 5-aminopyridin-3-yl), methylpyrazinyl (e.g. 5-methylpyrazin-2-yl), methylthiazolyl (e.g. 2-methylthiazol-4-yl) and methylpyrazolyl (e.g. 1-methylpyrazol-5-yl).

When Z represents -alkylaryl, examples include benzyl.

When Z represents -alkylheteroaryl (e.g. —CH$_2$-heteroaryl), examples include -alkylpyrrolyl, -alkylpyrazolyl, -alkylimidazolyl, -alkyloxazolyl, -alkylisoxazolyl, -alkylthiazolyl, -alkylisothiazolyl, -alkyloxadiazolyl, -alkylthiadiazolyl, -alkylpyridinyl, -alkylpyridazinyl, -alkylpyrimidinyl and -alkylpyrazinyl.

When Z represents carbocyclyl which is optionally substituted by one or more substituents each independently selected from $C_{1-6}$alkyl (e.g. methyl), $C_{1-6}$alkoxy (e.g. methoxy), $C_{1-6}$haloalkyl (e.g. fluoromethyl), $C_{1-6}$haloalkoxy (e.g. fluoromethoxy) and halo (e.g. fluoro, e.g. chloro), Z may represent carbocyclyl which is optionally substituted by $C_{1-6}$ alkyl. Examples include monocyclic carbocyclyl which is optionally substituted by $C_{1-6}$ alkyl (such as methyl). Examples of carbocyclyl include $C_{3-8}$cycloalkyl (e.g. cyclohexyl) and $C_{5-8}$cycloalkenyl (e.g. cyclohexenyl). The carbocycyl ring is optionally substituted by one, two or three substituents (e.g. one or two, especially one, e.g. one methyl group). When Z represents carbocyclyl, Z may represent $C_{3-8}$cycloalkyl, such as $C_{5-6}$cycloalkyl. A specific example is cyclohexyl.

When Z represents heterocyclyl which is optionally substituted by one or more substituents each independently selected from $C_{1-6}$alkyl, $C_{1-6}$alkoxy, —C(O)OC$_{1-6}$alkyl, —C(O)C$_{1-6}$alkyl, —C(O)NHC$_{1-6}$alkyl $C_{1-6}$alkyl (e.g. methyl), —C(O)OC$_{1-6}$alkyl (e.g. —C(O)Omethyl), —C(O)C$_{1-6}$alkyl (e.g. —C(O)methyl), —C(O)NHC$_{1-6}$alkyl (e.g. —C(O)NHmethyl), examples include unsubstituted heterocyclyl and heterocyclyl with one or two (e.g. one) substituent. Examples include heterocyclyl groups containing one nitrogen atom (such as pyrrolidinyl and piperidinyl) or two nitrogen atoms (such as piperazinyl). Examples also include heterocyclyl groups containing one nitrogen atom and one oxygen atom (e.g. morpholinyl) or one sulfur atom (e.g. thiomorpholinyl). In one embodiment when Z is substituted, a ring nitrogen atom is substituted. Substituted examples include substituted piperazinyl, such as 4-substituted piperazinyl, e.g. 4-Boc-piperazinyl, 4-(C(O)Me)-piperazinyl, 4-(C(O)NHEt)piperazinyl and 4-methylpiperazinyl.

When Z represents -alkylcarbocyclyl (e.g. —CH$_2$-carbocyclyl) wherein carbocyclyl is optionally substituted by one or more substituents each independently selected from $C_{1-6}$alkyl (e.g. methyl), $C_{1-6}$haloalkyl (e.g. fluoromethyl such as trifluoromethyl), $C_{1-6}$alkoxy (e.g. methoxy), $C_{1-6}$haloalkoxy (e.g. fluoromethoxy) and halo (e.g. fluoro, e.g. chloro), examples include —CH$_2$-cyclopropyl and —CH$_2$-cyclobutyl.

When Z represents -alkylheterocyclyl wherein heterocyclyl is optionally substituted by one or more substituents each independently selected from $C_{1-6}$alkyl, —C(O)OC$_{1-6}$alkyl, —C(O)C$_{1-6}$alkyl, —C(O)NHC$_{1-6}$alkyl $C_{1-6}$alkyl (e.g. methyl), —C(O)OC$_{1-6}$alkyl (e.g. —C(O)Omethyl), —C(O)C$_{1-6}$alkyl (e.g. —C(O)methyl), —C(O)NHC$_{1-6}$alkyl (e.g. —C(O)NHmethyl), examples include —CH$_2$-heterocyclyl, such as —CH$_2$-morpholinyl, —CH$_2$-piperazinyl, —CH$_2$-piperidinyl and —CH$_2$-pyrrolidinyl.

When Z represents -arylcarbocyclyl wherein carbocyclyl is optionally substituted by one or more substituents each independently selected from $C_{1-6}$alkyl (e.g. methyl), $C_{1-6}$alkoxy (e.g. methoxy), $C_{1-6}$haloalkyl (e.g. fluoromethyl such as trifluoromethyl), $C_{1-6}$haloalkoxy (e.g. fluoromethoxy) and halo (e.g. fluoro, e.g. chloro), Z may be phenylcarbocyclyl. The carbocyclyl ring may be unsubstituted or may be substituted by one or more $C_{1-6}$alkyl groups. The carbocyclyl ring may be monocyclic. An exemplary carbocyclyl ring is cycloalkyl. Examples include cyclopropylphenyl- and cyclohexylphenyl-.

When Z represents -arylheterocyclyl wherein heterocyclyl is optionally substituted by one or more substituents each independently selected from $C_{1-6}$alkyl, $C_{1-6}$alkoxy, —C(O)OC$_{1-6}$alkyl, —C(O)C$_{1-6}$alkyl, —C(O)NHC$_{1-6}$alkyl $C_{1-6}$alkyl (e.g. methyl), —C(O)OC$_{1-6}$alkyl (e.g. —C(O)Omethyl), —C(O)C$_{1-6}$alkyl (e.g. —C(O)methyl), —C(O)NHC$_{1-6}$alkyl (e.g. —C(O)NHmethyl), Z may be -phenyl-heterocyclyl. The heterocyclyl ring may be monocyclic and may contain one or two (e.g. one) nitrogen atoms. Examples include morphinolylphenyl-, piperazinylphenyl-, piperidinylphenyl-, pyrrolidinylphenyl-. A specific example is 3-(morpholin-4-yl)phenyl-.

Suitably $R_1$ represents H, methyl, ethyl, —C(O)OMe, $CF_3$ or OMe. In one embodiment $R_1$ represents methyl.

Suitably each $R_2$ independently represents H or alkyl. More suitably $R_2$ represents H or methyl. In one embodiment, $R_2$ represents H. In one embodiment $R_2$ represents methyl.

Suitably n represents 0 or 1, for example n represents 1.

Suitably $R_3$ represents H or methyl, for example $R_3$ represents H.

Suitably $R_4$ represents H or methyl, for example $R_4$ represents H.

Suitably $R_5$ represents H or methyl, for example $R_5$ represents H.

Suitably W and X are the same as each other.

Suitably W and X each represent C=O.

Suitably Y represents aryl (e.g. phenyl) or heteroaryl (e.g. 5- or 6-membered monocyclic heteroaryl comprising one, two or three ring heteroatoms including one or two nitrogen atoms such as isoxazolyl, pyridinyl, pyridazinyl, pyrimidinyl or pyrazinyl). In one embodiment Y represents phenyl. In one embodiment Y represents monocyclic heteroaryl. In one embodiment Y is substituted by one or more substituents each independently selected from $C_{1-6}$ alkyl, $C_{1-6}$alkoxy, halo and $C_{1-6}$haloalkyl. In one embodiment Y is unsubstituted. In one embodiment Y is monosubstituted. When Y is 5-membered, suitably Z and NR$_5$ are positioned on the ring at non-adjacent ring atoms. When Y is 6-membered, suitably Z and NR$_5$ are positioned on the ring at 1- and 4-positions relative to each other (i.e. Z and NR$_5$ have a para relationship).

Suitably Z represents aryl (e.g. phenyl) or heteroaryl (for example 6-membered heteroaryl such as pyridinyl, pyridazinyl, pyrimidinyl or pyrazinyl especially pyridinyl; or 5-membered heteroaryl such as oxazolyl, thiazolyl, pyrazolyl). In one embodiment Z represents heteroaryl. In one embodiment Z represents aryl. In one embodiment, Z does not represent methyl or ethyl. In one embodiment Z does not represent unsubstituted alkyl.

In one embodiment there are provided compounds of formula (I) which are compounds of formula (IA)

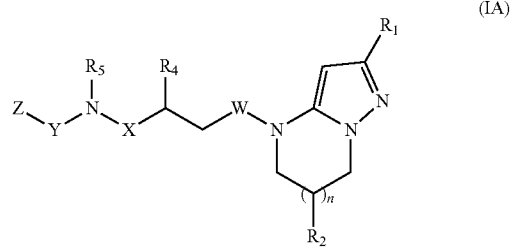

(IA)

or a pharmaceutically acceptable salt, solvate or polymorph thereof, including all tautomers and stereoisomers thereof wherein:

$R_1$ represents alkyl;

each $R_2$ independently represents H, alkyl, carbocyclyl which may be optionally substituted by one or more substituents each independently selected from $C_{1-6}$alkyl, $C_{1-6}$alkoxy, $C_{1-6}$haloalkoxy and halo, —NHalkyl, —N(alkyl)$_2$, amino, hydroxyl, alkoxy or halo;

n represents 0, 1 or 2;

R$_4$ represents H or alkyl;

R$_5$ represents H or alkyl;

W and X each independently represent C=O or C=S (in some embodiments, W and X are both C=O);

Y represents aryl; heteroaryl; carbocyclyl which is optionally substituted by one or more substituents each independently selected from C$_{1-6}$alkyl, C$_{1-6}$alkoxy, C$_{1-6}$haloalkyl, C$_{1-6}$haloalkoxy and halo; or heterocyclyl which is optionally substituted by one or more substituents each independently selected from C$_{1-6}$alkyl, —C(O)OC$_{1-6}$alkyl, —C(O)C$_{1-6}$alkyl and —C(O)NHC$_{1-6}$alkyl; and Z represents alkyl; aryl; heteroaryl; carbocyclyl which is optionally substituted by one or more substituents each independently selected from C$_{1-6}$alkyl, C$_{1-6}$alkoxy, C$_{1-6}$haloalkoxy (e.g. fluoromethoxy) C$_{1-6}$haloalkoxy and halo; heterocyclyl which is optionally substituted by one or more substituents each independently selected from C$_{1-6}$alkyl, —C(O)OC$_{1-6}$alkyl, —C(O)C$_{1-6}$alkyl and —C(O)NHC$_{1-6}$alkyl; -arylcarbocyclyl wherein carbocyclyl which is optionally substituted by one or more substituents each independently selected from C$_{1-6}$alkyl, C$_{1-6}$alkoxy, C$_{1-6}$haloalkoxy and halo; or -arylheterocyclyl wherein heterocyclyl which is optionally substituted by one or more substituents each independently selected from C$_{1-6}$alkyl, —C(O)OC$_{1-6}$alkyl, —C(O)C$_{1-6}$alkyl and —C(O)NHC$_{1-6}$alkyl.

In one embodiment, compounds of formula (I) are provided in which R$_1$ represents methyl; R$_2$ represents H; n represents 1; W and X each represent C=O; R$_3$ represents H; R$_4$ represents H; Y represents isoxazolyl; and Z represents phenyl which is optionally substituted by chloro, fluoro, bromo, methyl or methoxy.

In one embodiment, compounds of formula (I) are provided in which R$_1$ represents methyl; R$_2$ represents H; n represents 1; W and X each represent C=O; R$_3$ represents H; R$_4$ represents H; Y represents phenyl; and Z represents phenyl which is optionally substituted by fluoro, chloro, amino, methyl or methoxy.

In one embodiment, compounds of formula (I) are provided in which R$_1$ represents methyl; R$_2$ represents H; n represents 1; W and X each represent C=O; R$_3$ represents H; R$_4$ represents H; Y represents pyridinyl; and Z represents pyridinyl which is optionally substituted by fluoro, chloro, methyl, amino or trifluoromethyl.

In one embodiment, compounds of formula (I) are provided in which R$_1$ represents methyl; R$_2$ represents H; n represents 1; W and X each represent C=O; R$_3$ represents H; R$_4$ represents H; Y represents pyridazinyl, pyrimidinyl or pyrazinyl; and Z represents pyridinyl which is optionally substituted by fluoro, chloro, methyl, amino or trifluoromethyl.

In one embodiment, R$_2$, R$_4$ and R$_5$ are all H, n=1 and W and X are both C=O.

In one embodiment the following compounds of formula (I) are excluded:

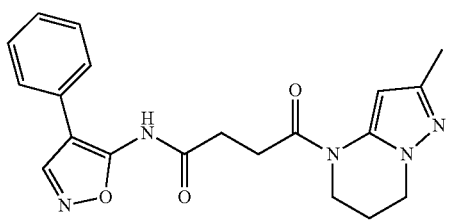

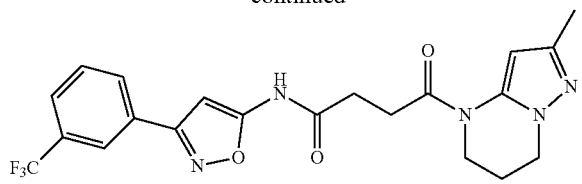

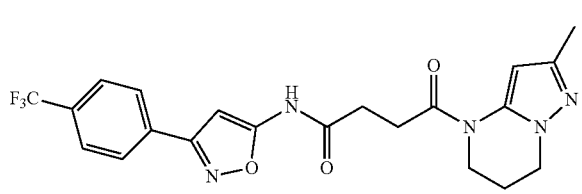

In one embodiment, Z is not phenyl substituted by trifluoroalkyl.

In one embodiment, when Y is isoxazolyl, Z is not positioned at the 4-position of the isoxazolyl ring.

In one embodiment, the compounds of formula (I) have an IC$_{50}$ against HEK293-STF3A cells of less than about 10 micromolar.

Processes

The present invention further provides a process for preparation of compounds of formula (I), wherein W and X each represent C=O, which comprises an amide coupling reaction of a compound of formula (II):

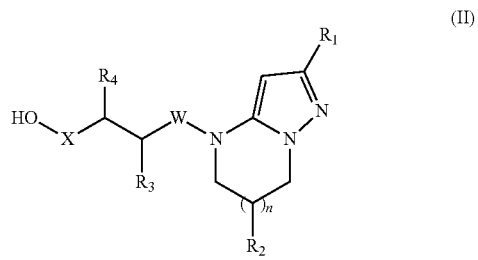

or a protected derivative thereof, wherein R$_1$, R$_2$, n, R$_3$, R$_4$, W and X are as defined above, with a compound of formula (III)

or a protected derivative thereof, wherein R$_5$, Y and Z are as defined above.

Compounds of formula (II) may be prepared by reaction of compounds of formula (IV)

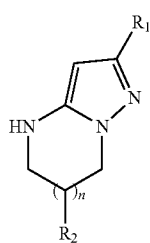

(IV)

wherein $R_1$, $R_2$ and n are as defined above, with a compound of formula (V)

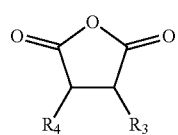

(V)

wherein $R_3$ and $R_4$ are as defined above. An exemplary solvent for this reaction is chloroform.

Compounds of formula (IV) can be prepared by reaction of compounds of formula (VI)

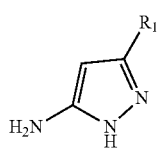

(VI)

wherein $R_1$ is defined as above; with a compound of formula (VII)

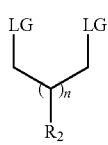

(VII)

wherein $R_2$ and n are as defined above and wherein LG represents a leaving group such as Br, I, tosylate etc. The reaction may take place in the presence of triethylamine or other amine base (DBU, DBN etc.) and a solvent such as 1,4-dioxane or other dipolar aprotic solvent.

Compounds of formula (III) may be synthesized by a coupling reaction, such as a Suzuki coupling reaction. When Y is isoxazole, compounds of formula (III) may alternatively be synthesized from the corresponding oxopropanenitrile by reaction with hydroxylamine hydrochloride in the presence of sodium hydroxide. The oxopropanenitrile can be obtained from the corresponding ester.

The present invention further provides a process for preparation of compounds of formula (I), wherein W and X each represent $CH_2$ or a protected derivative thereof, which comprises conversion of the W and X groups of compounds of formula (I) from C=O groups into $CH_2$ groups. This conversion can be carried out, for example, by reduction using borane dimethylsulfide.

The present invention further provides a process for preparation of compounds of formula (I), wherein W and X each represent C=S, or a protected derivative thereof, which comprises conversion of the W and X groups of compounds of formula (I) from C=O groups into C=S groups. This conversion can be carried out, for example, by using Lawesson's reagent.

Therapeutic Uses

The present invention provides a compound of formula (I) for use as a medicament.

The compounds of the present invention may have an $IC_{50}$ against STF3A of less than 20 micromolar, e.g. less than 10 micromolar. The $IC_{50}$ may be less than 5, 2, 1, 0.5, 0.2 or 0.1 micromolar. It may be between about 0.01 and about 10 micromolar, or between about 0.01 and 5, 0.01 and 1, 0.01 and 0.5, 0.01 and 0.1, 0.01 and 0.05, 0.1 and 5, 0.1 and 1, 0.1 and 0.5, 0.1 and 10, 0.5 and 10, 1 and 10, 5 and 10, 1 and 5 or 0.1 and 0.5, e.g. about 0.01, 0.02, 0.03, 0.04, 0.05, 0.1, 0.2, 0.3, 0.4, 0.5, 0.6, 0.7, 0.8, 0.9, 1, 2, 3, 4, 5, 6, 7, 8, 9 or 10 micromolar.

The present invention provides compounds of formula (I) for use in modulation of the WNT pathway.

The present invention also provides a method of modulating WNT activity comprising exposing a WNT protein or a WNT receptor to a compound of formula (I).

In addition, the present invention provides use of a compound of formula (I) for modulating WNT activity.

The present invention additionally provides compounds of formula (I) for use in the treatment of a disease or condition associated with WNT pathway activity.

A method of treating a disease or condition associated with WNT pathway activity comprising administering to a subject in need thereof a therapeutically effective amount of a compound of formula (I) is also provided by the present invention.

The present invention further provides use of a compound of formula (I) for treatment of a disease or condition associated with WNT pathway activity.

Also provided by the present invention is use of a compound of formula (I) in the manufacture of a medicament for the treatment of a disease or condition associated with WNT pathway activity.

The aforementioned disease or condition is suitably selected from the group consisting of cancer, fibrosis, stem cell and diabetic retinopathy, rheumatoid arthritis, psoriasis and myocardial infarction.

The cancer may be a cancer characterized by high WNT activity.

The disease or condition may be a cancer, such as cervical, colon, breast, bladder, head and neck, gastric, lung, ovarian, prostate, thyroid, non-small-cell lung, as well as chronic lymphocytic leukemia, mesothelioma, melanoma, pancreatic adenocarcinoma, basal cell carcinoma, osteosarcoma, hepatocellular carcinoma, Wilm's tumor or medulloblastoma, or a fibrotic disease, such as pulmonary fibrosis, liver fibrosis, skin fibrosis or renal fibrosis, or a degenerative disease, or a metabolic disease such as diabetic retinopathy.

The present invention also provides use of a compound of formula (I) in diagnosis.

Pharmaceutical Compositions

To prepare the pharmaceutical compositions of this invention, at least one compound of formula (I) optionally in combination with at least one of the other aforementioned agents can be used as the active ingredient(s). The active ingredient(s) is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, though other ingredients, for example, for purposes such as aiding solubility or for preservation, may be included.

Injectable suspensions may also prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient(s) necessary to deliver an effective dose as described above. The pharmaceutical compositions herein will contain, per dosage unit, e.g., tablet, capsule, powder, injection, suppository, teaspoonful and the like, from about 0.03 mg to 100 mg/kg (preferred 0.1-30 mg/kg) and may be given at a dosage of from about 0.1-300 mg/kg per day (preferred 1-50 mg/kg per day) of each active ingredient or combination thereof. The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.1 to about 500 mg of each active ingredient or combinations thereof of the present invention.

The tablets or pills of the compositions of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

This liquid forms in which the compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinylpyrrolidone or gelatin.

The pharmaceutical composition may contain between about 0.01 mg and 100 mg, preferably about 5 to 50 mg, of each compound, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixirs, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or betalactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitable flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

The compounds or combinations of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine or phosphatidylcholines.

Compounds or combinations of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polyhydroxyethylaspartamid-ephenol, or polyethyl eneoxidepolyllysine substituted with palmitoyl residue. Furthermore, the compounds of the present invention may be coupled to a class of biodegradable polymers useful in achieving controlled release of a drug, for example, polyactic acid, polyepsilon caprolactone, polyhydroxy butyeric acid, polyorthoesters, polyacetals, polydihydropyrans, polycyanoacrylates and cross-linked or amphipathic block copolymers of hydrogels.

Compounds or combinations of this invention may be administered in any of the foregoing compositions and according to dosage regimens established in the art whenever treatment of the addressed disorders is required.

The daily dosage of the products may be varied over a wide range from 0.01 to 1.000 mg per mammal per day. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of each active ingredient or combinations thereof for the symptomatic adjustment of the dosage to the patient to be treated. An effective amount of the drug is ordinarily supplied at a dosage level of from about 0.1 mg/kg to about 300 mg/kg of body weight per day. Preferably, the range is from about 1 to about 50 mg/kg of body weight per day. The compounds or combinations may be administered on a regimen of 1 to 4 times per day.

Optimal dosages to be administered may be readily determined by those skilled in the art, and will vary with the particular compound used, the mode of administration, the strength of the preparation, the mode of administration, and the advancement of disease condition. In addition, factors associated with the particular patient being treated, including patient age, weight, diet and time of administration, will result in the need to adjust dosages.

In a further aspect, the invention also provides a process for preparing a pharmaceutical composition comprising at least one compound of formula (I), optionally in combination with at least one of the other aforementioned agents and a pharmaceutically acceptable carrier.

The compositions are preferably in a unit dosage form in an amount appropriate for the relevant daily dosage.

Suitable dosages, including especially unit dosages, of the compounds of the present invention include the known dosages including unit doses for these compounds as described or referred to in reference text such as the British and US Pharmacopoeias, Remington's Pharmaceutical Sciences (Mack Publishing Co.), Martindale The Extra Pharmacopoeia (London, The Pharmaceutical Press) (for example see the 31st Edition page 341 and pages cited therein) or the above mentioned publications.

EXAMPLES

| Cpd ID | Structure | IUPAC Name | STF3A IC50 µM |
|---|---|---|---|
| 1 | 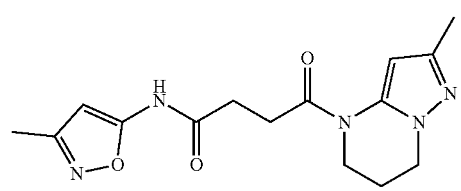 | 4-(2-methyl-6,7-dihydropyrazolo[1,5-a]pyrimidin-4(5H)-yl)-N-(3-methylisoxazol-5-yl)-4-oxobutanamide | >10 |
| 2 | 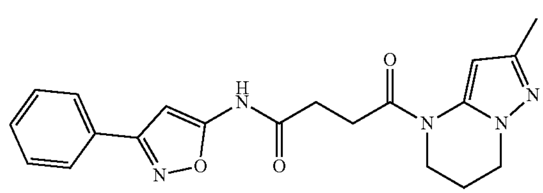 | 4-(2-methyl-6,7-dihydropyrazolo[1,5-a]pyrimidin-4(5H)-yl)-4-oxo-N-(3-phenylisoxazol-5-yl)butanamide | <1 |
| 3 | 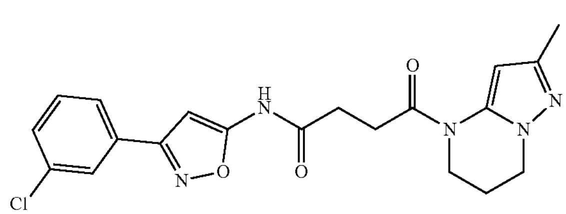 [SMILES: Cc1cc2n(n1)CCCN2C(=O)CCC(=O)Nc1cc(-c2cccc(Cl)c2)no1] | N-(3-(3-chlorophenyl)isoxazol-5-yl)-4-(2-methyl-6,7-dihydropyrazolo[1,5-a]pyrimidin-4(5H)-yl)-4-oxobutanamide | <0.1 |

-continued

| Cpd ID | Structure | IUPAC Name | STF3A IC50 μM |
|---|---|---|---|
| 4 | 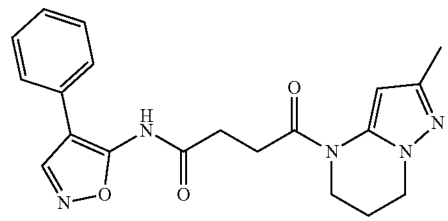 [SMILES: Cc1cc2n(n1)CCCN2C(=O)CCC(=O)Nc1oncc1-c1ccccc1] | 4-(2-methyl-6,7-dihydropyrazolo[1,5-a]pyrimidin-4(5H)-yl)-4-oxo-N-(4-phenylisoxazol-5-yl)butanamide | >10 |
| 5 | 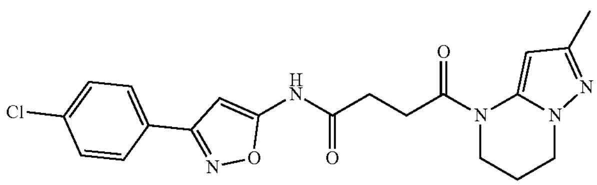 [SMILES: Cc1cc2n(n1)CCCN2C(=O)CCC(=O)Nc1cc(-c2ccc(Cl)cc2)no1] | N-(3-(4-chlorophenyl)isoxazol-5-yl)-4-(2-methyl-6,7-dihydropyrazolo[1,5-a]pyrimidin-4(5H)-yl)-4-oxobutanamide | <0.1 |
| 6 | 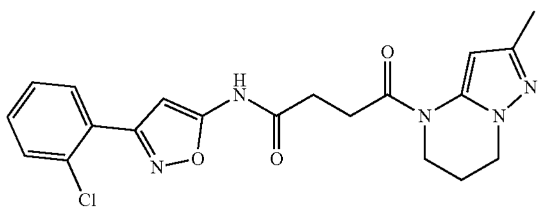 [SMILES: Cc1cc2n(n1)CCCN2C(=O)CCC(=O)Nc1cc(-c2ccccc2Cl)no1] | N-(3-(2-chlorophenyl)isoxazol-5-yl)-4-(2-methyl-6,7-dihydropyrazolo[1,5-a]pyrimidin-4(5H)-yl)-4-oxobutanamide | >10 |
| 7 | 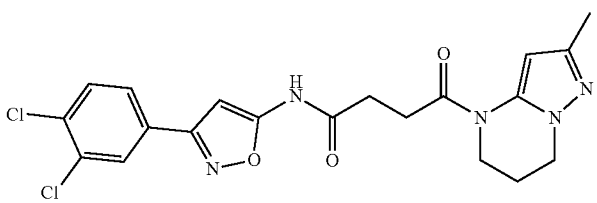 [SMILES: Cc1cc2n(n1)CCCN2C(=O)CCC(=O)Nc1cc(-c2ccc(Cl)c(Cl)c2)no1] | N-(3-(3,4-dichlorophneyl)isoxazol-5-yl)-4-(2-methyl-6,7-dihydropyrazolo[1,5-a]pyrimidin-4(5H)-yl)-4-oxobutanamide | >10 |
| 8 | 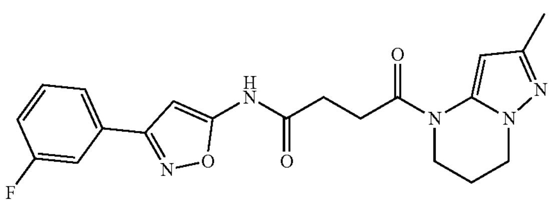 [SMILES: Cc1cc2n(n1)CCCN2C(=O)CCC(=O)Nc1cc(-c2cccc(F)c2)no1] | N-(3-(3-fluorophenyl)isoxazol-5-yl)-4-(2-methyl-6,7-dihydropyrazolo[1,5-a]pyrimidin-4(5H)-yl)-4-oxobutanamide | <0.1 |
| 9 | 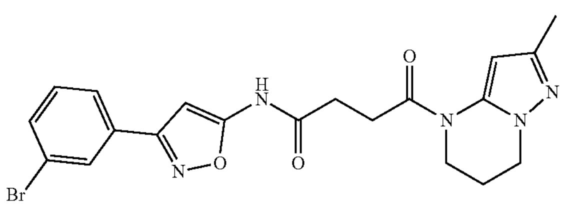 [SMILES: Cc1cc2n(n1)CCCN2C(=O)CCC(=O)Nc1cc(-c2cccc(Br)c2)no1] | N-[3-(3-bromophenyl)-1,2-oxazol-5-yl]-4-{2-methyl-5H,6H,7H-pyrazolo[1,5-a]pyrimidin-4-yl}-4-oxobutanamide | <1 |
| 10 | 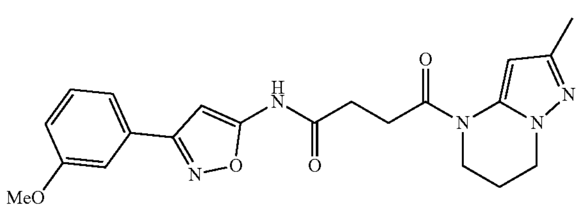 [SMILES: COc1cccc(-c2cc(NC(=O)CCC(=O)N3CCCn4nc(C)cc43)on2)c1] | N-[3-(3-methoxyphenyl)-1,2-oxazol-5-yl]-4-{2-methyl-5H,6H,7H-pyrazolo[1,5-a]pyrimidin-4-yl}-4-oxobutanamide | <5 |

-continued

| Cpd ID | Structure | IUPAC Name | STF3A IC50 μM |
|---|---|---|---|
| 11 | 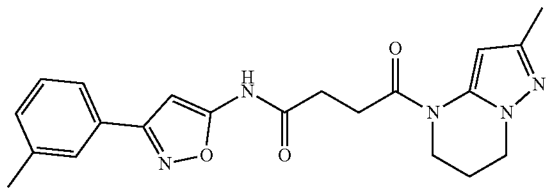 | 4-{2-methyl-5H,6H,7H-pyrazolo[1,5-a]pyrimidin-4-yl}-N-[3-(3-methylphenyl)-1,2-oxazol-5-yl]-4-oxabutanamide | >10 |
| 12 | 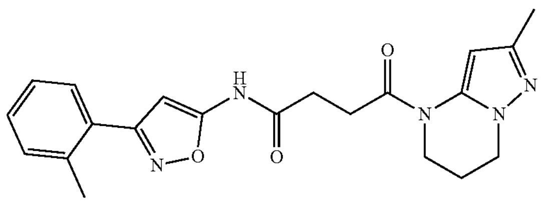 [SMILES: Cc1cc2n(n1)CCCN2C(=O)CCC(=O)Nc1cc(-c2ccccc2C)no1] | 4-(2-methyl-6,7-dihydropyrazolo[1,5-a]pyrimidin-4(5H)-yl)-4-oxo-N-(3-(o-tolyl)isoxazol-5-yl)butanamide | <0.1 |
| 13 | 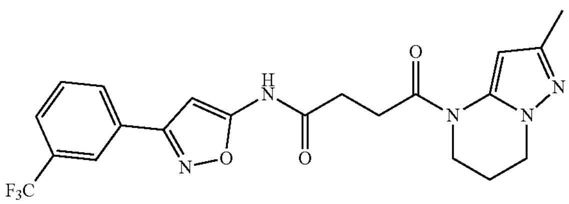 [SMILES: Cc1cc2n(n1)CCCN2C(=O)CCC(=O)Nc1cc(-c2cccc(C(F)(F)F)c2)no1] | 4-{2-methyl-5H,6H,7H-pyrazolo[1,5-a]pyrimidin-4-yl}-4-oxo-N-{3-[3-(trifluoromethyl)phenyl]-1,2-oxazol-5-yl}butanamide | >10 |
| 14 | 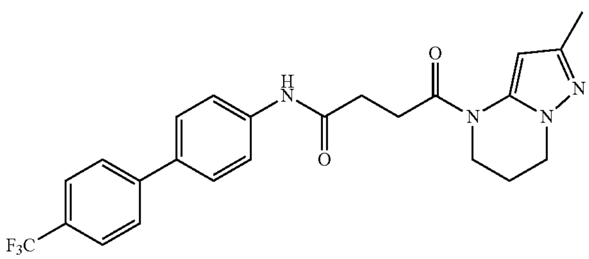 [SMILES: Cc1cc2n(n1)CCCN2C(=O)CCC(=O)Nc1ccc(-c2ccc(C(F)(F)F)cc2)cc1] | 4-(2-methyl-6,7-dihydropyrazolo[1,5-a]pyrimidin-4(5H)-yl)-4-oxo-N-(4'-(trifluoromethyl)-[1,1'-biphenyl]-4-yl)butanamide | >10 |
| 15 | 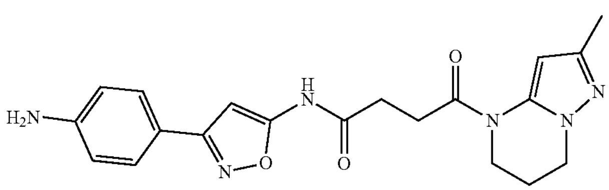 [SMILES: Cc1cc2n(n1)CCCN2C(=O)CCC(=O)Nc1cc(-c2ccc(N)cc2)no1] | N-[3-(4-aminophenyl)-1,2-oxazol-5-yl]-4-{2-methyl-5H,6H,7H-pyrazolo[1,5-a]pyrimidin-4-yl}-4-oxobutanamide | >10 |
| 16 | 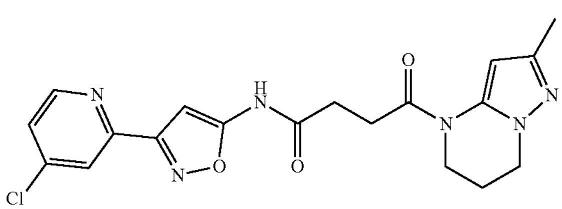 [SMILES: Cc1cc2n(n1)CCCN2C(=O)CCC(=O)Nc1cc(-c2cc(Cl)ccn2)no1] | N-(3-(4-chloropyridin-2-yl)isoxazol-5-yl)-4-(2-methyl-6,7-dihydropyrazolo[1,5-a]pyrimidin-4(5H)-yl)-4-oxobutanamide | >10 |
| 17 | 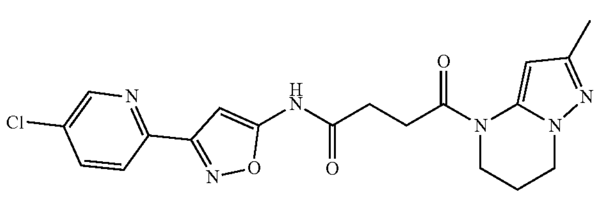 [SMILES: Cc1cc2n(n1)CCCN2C(=O)CCC(=O)Nc1cc(-c2ccc(Cl)cn2)no1] | N-(3-(5-chloropyridin-2-yl)isoxazol-5-yl)-4-(2-methyl-6,7-dihydropyrazolo[1,5-a]pyrimidin-4(5H)-yl)-4-oxobutanamide | >10 |

-continued

| Cpd ID | Structure | IUPAC Name | STF3A IC50 μM |
|---|---|---|---|
| 18 | 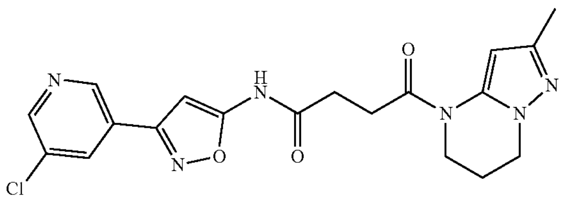 [SMILES: Cc1cc2n(n1)CCCN2C(=O)CCC(=O)Nc1cc(-c2cncc(Cl)c2)no1] | N-[3-(5-chloropyridin-3-yl)-1,2-oxazol-5-yl]-4-{2-methyl-5H,6H,7H-pyrazolo[1,5-a]pyrimidin-4-yl}-4-oxobutanamide | <5 |
| 19 | 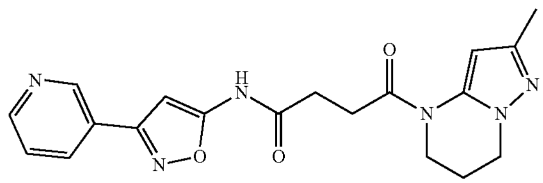 [SMILES: Cc1cc2n(n1)CCCN2C(=O)CCC(=O)Nc1cc(-c2cccnc2)no1] | 4-(2-methyl-6,7-dihydropyrazolo[1,5-a]pyrimidin-4(5H)-yl)-4-oxo-N-(3-(pyridin-3-yl)isoxazol-5-yl)butanamide | >10 |
| 20 | 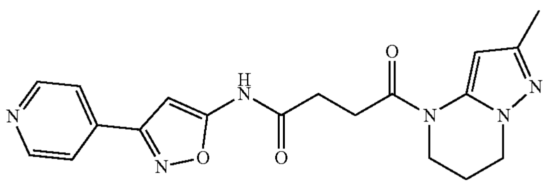 [SMILES: Cc1cc2n(n1)CCCN2C(=O)CCC(=O)Nc1cc(-c2ccncc2)no1] | 4-{2-methyl-5H,6H,7H-pyrazolo[1,5-a]pyrimidin-4-yl}-4-oxo-N-[3-(pyridin-4-yl)-1,2-oxazol-5-yl]butanamide | >10 |
| 21 | 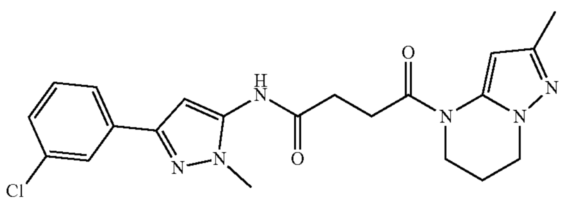 [SMILES: Cc1cc2n(n1)CCCN2C(=O)CCC(=O)Nc1cc(-c2cccc(Cl)c2)nn1C] | N-(3-(3-chlorophenyl)-1-methyl-1H-pyrazol-5-yl)-4-(2-methyl-6,7-dihydropyrazolo[1,5-a]pyrimidin-4(5H)-yl)-4-oxobutanamide | >10 |
| 22 | 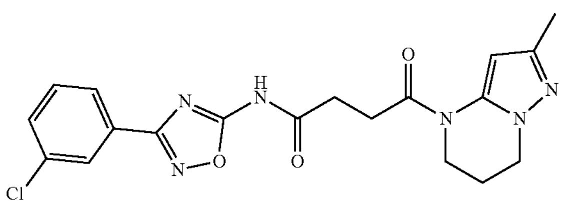 [SMILES: Cc1cc2n(n1)CCCN2C(=O)CCC(=O)Nc1nc(-c2cccc(Cl)c2)no1] | N-(3-(3-chlorophenyl)-1,2,4-oxadiazol-5-yl)-4-(2-methyl-6,7-dihydropyrazolo[1,5-a]pyrimidin-4(5H)-yl)-4-oxobutanamide | >10 |
| 23 | 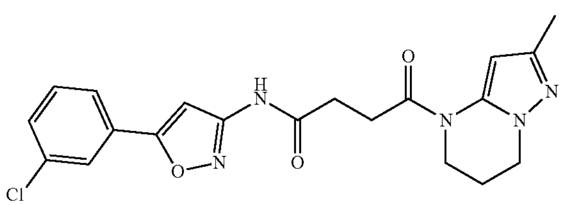 [SMILES: Cc1cc2n(n1)CCCN2C(=O)CCC(=O)Nc1cc(-c2cccc(Cl)c2)on1] | N-[5-(3-chlorophenyl)-1,2-oxazol-3-yl]-4-{2-methyl-5H,6H,7H-pyrazolo[1,5-a]pyrimidin-4-yl}-4-oxobutanamide | <1 |
| 24 | 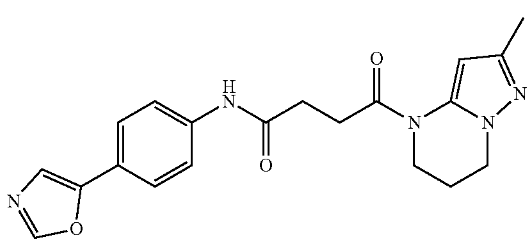 [SMILES: Cc1cc2n(n1)CCCN2C(=O)CCC(=O)Nc1ccc(-c2cnco2)cc1] | 4-(2-methyl-6,7-dihydropyrazolo[1,5-a]pyrimidin-4(5H)-yl)-N-(4-(oxazol-5-yl)phenyl)-4-oxobutanamide | <5 |

-continued

| Cpd ID | Structure | IUPAC Name | STF3A IC50 μM |
|---|---|---|---|
| 25 | 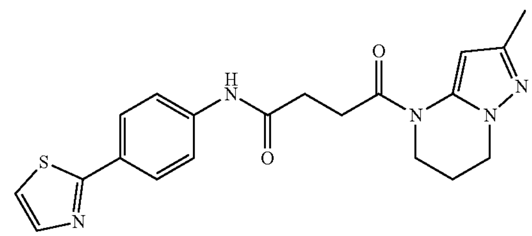 [SMILES: Cc1cc2n(n1)CCCN2C(=O)CCC(=O)Nc1ccc(-c2nccs2)cc1] | 4-(2-methyl-6,7-dihydropyrazolo[1,5-a]pyrimidin-4(5H)-yl)-N-(4-(oxazol-5-yl)phenyl)-4-oxobutanamide | <0.1 |
| 26 | 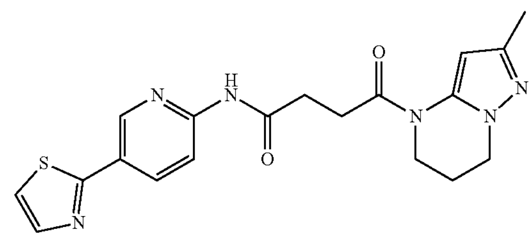 [SMILES: Cc1cc2n(n1)CCCN2C(=O)CCC(=O)Nc1ccc(-c2nccs2)cn1] | 4-(2-methyl-6,7-dihydropyrazolo[1,5-a]pyrimidin-4(5H)-yl)-4-oxo-N-(5-(thiazol-2-yl)pyridin-2-yl)butanamide | <0.1 |
| 27 | 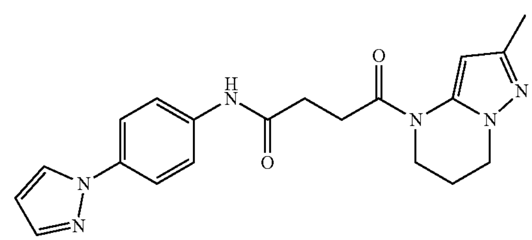 [SMILES: Cc1cc2n(n1)CCCN2C(=O)CCC(=O)Nc1ccc(-n2cccn2)cc1] | N-(4-(1H-imidazol-1-yl)phenyl)-4-(2-methyl-6,7-dihydropyrazolo[1,5-a]pyrimidin-4(5H)-yl)-4-oxobutanamide | <1 |
| 28 | 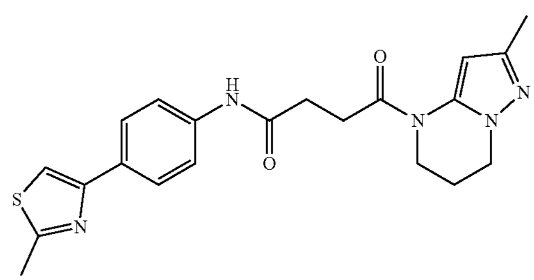 [SMILES: Cc1cc2n(n1)CCCN2C(=O)CCC(=O)Nc1ccc(-c2csc(C)n2)cc1] | 4-(2-methyl-6,7-dihydropyrazolo[1,5-a]pyrimidin-4(5H)-yl)-N-(4-(2-methylthiazol-4-yl)phenyl)-4-oxobutanamide | <0.1 |
| 29 | 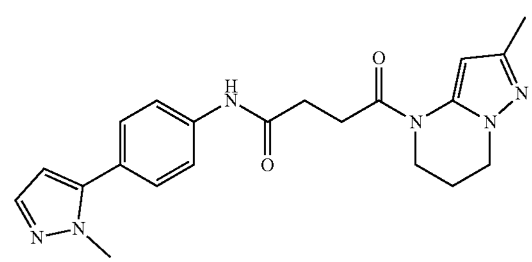 [SMILES: Cc1cc2n(n1)CCCN2C(=O)CCC(=O)Nc1ccc(-c2ccnn2C)cc1] | N-(4-(1-methyl-1H-pyrazol-5-yl)phenyl)-4-(2-methyl-6,7-dihydropyrazolo[1,5-a]pyrimidin-4(5H)-yl)-4-oxobutanamide | <1 |
| 30 | 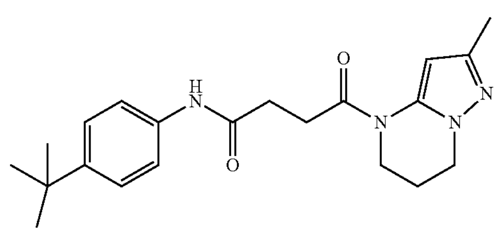 [SMILES: Cc1cc2n(n1)CCCN2C(=O)CCC(=O)Nc1ccc(C(C)(C)C)cc1] | N-(4-(tert-butyl)phenyl)-4-(2-methyl-6,7-dihydropyrazolo[1,5-a]pyrimidin-4(5H)-yl)-4-oxobutanamide | >10 |

-continued

| Cpd ID | Structure | IUPAC Name | STF3A IC50 μM |
|---|---|---|---|
| 31 | 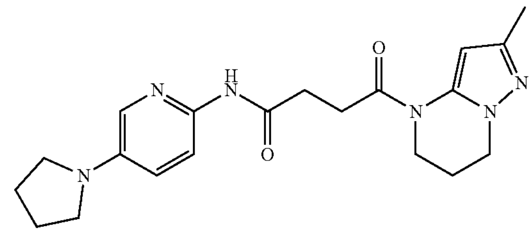 [SMILES: Cc1cc2n(n1)CCCN2C(=O)CCC(=O)Nc1ccc(N2CCCC2)cn1] | 4-(2-methyl-6,7-dihydropyrazolo[1,5-a]pyrimidin-4(5H)-yl)-4-oxo-N-(4-(pyrrolidin-1-yl)phenyl)butanamide | <5 |
| 32 | 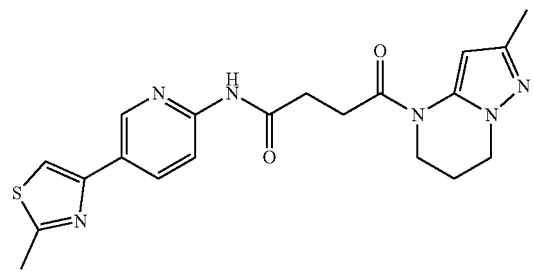 | 4-(2-methyl-6,7-dihydropyrazolo[1,5-a]pyrimidin-4(5H)-yl)-N-(4-(2-methylthiazol-4-yl)phenyl)-4-oxobutanamide | <0.1 |
| 33 | 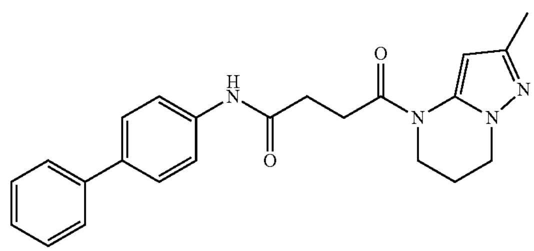 | N-([1,1'-biphenyl]-4-yl)-4-(2-methyl-6,7-dihydropyrazolo[1,5-a]pyrimidin-4(5H)-yl)-4-oxobutanamide | <0.1 |
| 34 | 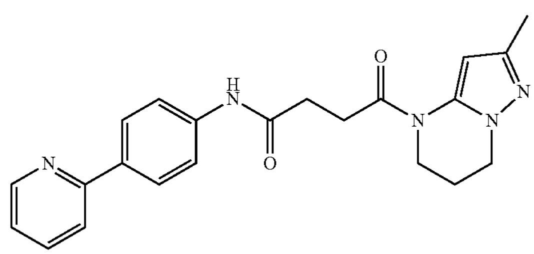 | 4-(2-methyl-6,7-dihydropyrazolo[1,5-a]pyrimidin-4(5H)-yl)-4-oxo-N-(4-(pyridin-2-yl)phenyl)butanamide | <0.1 |
| 35 | 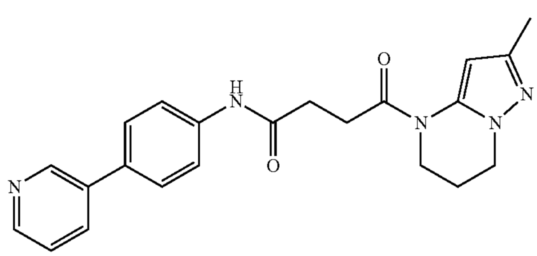 | 4-(2-methyl-6,7-dihydropyrazolo[1,5-a]pyrimidin-4(5H)-yl)-4-oxo-N-(4-(pyridin-3-yl)phenyl)butanamide | <0.1 |
| 36 | 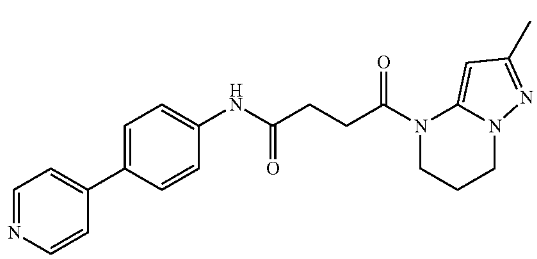 [SMILES: Cc1cc2n(n1)CCCN2C(=O)CCC(=O)Nc1ccc(-c2ccncc2)cc1] | 4-(2-methyl-6,7-dihydropyrazolo[1,5-a]pyrimidin-4(5H)-yl)-4-oxo-N-(4-(pyridin-4-yl)phenyl)butanamide | <1 |

-continued

| Cpd ID | Structure | IUPAC Name | STF3A IC50 μM |
|---|---|---|---|
| 37 | 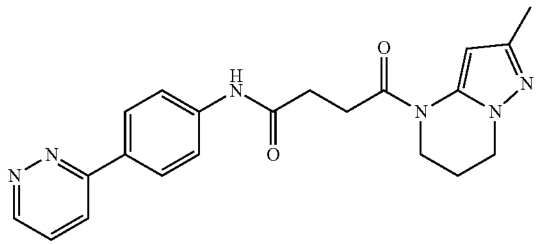 [SMILES: Cc1cc2n(n1)CCCN2C(=O)CCC(=O)Nc1ccc(-c2cccnn2)cc1] | 4-{2-methyl-5H,6H,7H-pyrazolo[1,5-a]pyrimidin-4-yl}-4-oxo-N-[4-(pyridazin-3-yl)phenyl]butanamide | <1 |
| 38 | 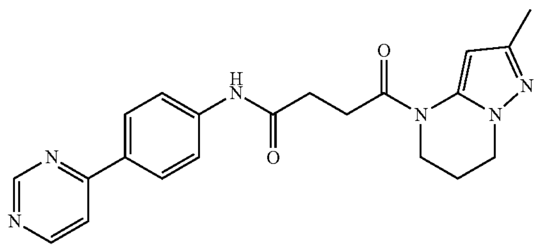 [SMILES: Cc1cc2n(n1)CCCN2C(=O)CCC(=O)Nc1ccc(-c2ccncn2)cc1] | 4-(2-methyl-6,7-dihydropyrazolo[1,5-a]pyrimidin-4(5H)-yl)-4-oxo-N-(4-(pyrimidin-4-yl)phenyl)butanamide | >10 |
| 39 | 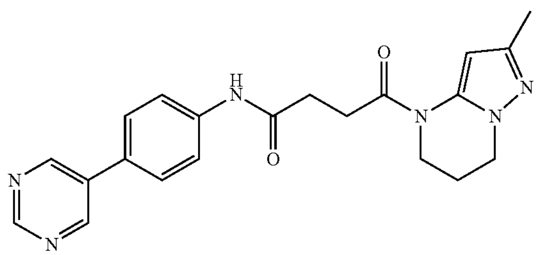 [SMILES: Cc1cc2n(n1)CCCN2C(=O)CCC(=O)Nc1ccc(-c2cncnc2)cc1] | 4-{2-methyl-5H,6H,7H-pyrazolo[1,5-a]pyrimidin-4-yl}-4-oxo-N-[4-(pyrimidin-5-yl)phenyl]butanamide | <0.1 |
| 40 | 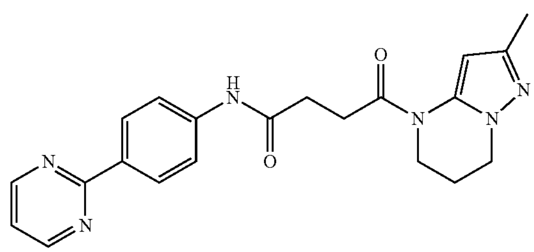 | 4-{2-methyl-5H,6H,7H-pyrazolo[1,5-a]pyrimidin-4-yl}-4-oxo-N-[4-(pyrimidin-2-yl)phenyl]butanamide | <1 |
| 41 | 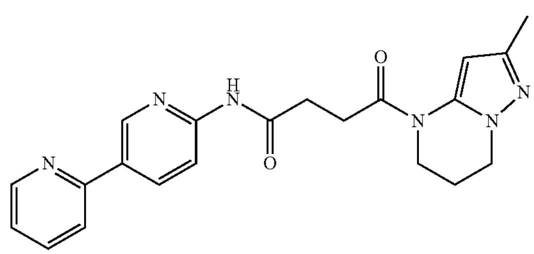 | N-([2,3'-bipyridin]-6'-yl)-4-(2-methyl-6,7-dihydropyrazolo[1,5-a]pyrimidin-4(5H)-yl)-4-oxobutanamide | <0.1 |
| 42 | 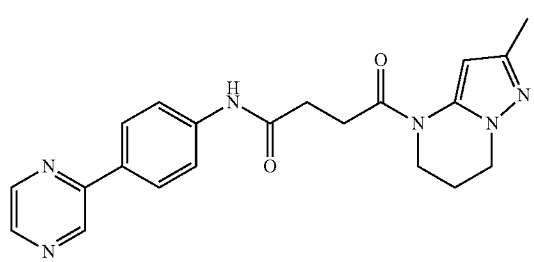 [SMILES: Cc1cc2n(n1)CCCN2C(=O)CCC(=O)Nc1ccc(-c2cnccn2)cc1] | 4-(2-methyl-6,7-dihydropyrazolo[1,5-a]pyrimidin-4(5H)-yl)-4-oxo-N-(4-(pyrazin-2-yl)phenyl)butanamide | <0.1 |

-continued

| Cpd ID | Structure | IUPAC Name | STF3A IC50 μM |
|---|---|---|---|
| 43 | 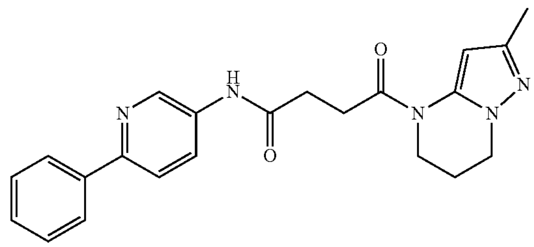 | 4-(2-methyl-6,7-dihydropyrazolo[1,5-a]pyrimidin-4(5H)-yl)-4-oxo-N-(6-phenylpyridin-3-yl)butanamide | <0.1 |
| 44 | 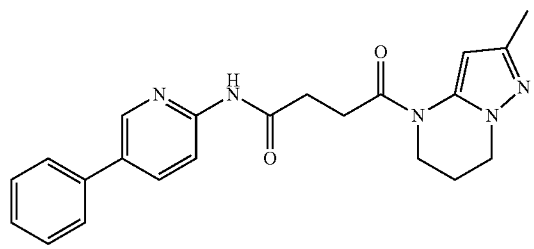 | 44Synthesis of 4-(2-methyl-6,7-dihydropyrazolo[1,5-a]pyrimidin-4(5H)-yl)-4-oxo-N-(5-phenylpyridin-2-yl)butanamide | <0.1 |
| 45 | 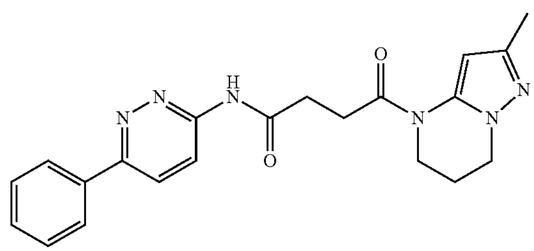 | 4-(2-methyl-6,7-dihydropyrazolo[1,5-a]pyrimidin-4(5H)-yl)-4-oxo-N-(6-phenylpyridazin-3-yl)butanamide | <0.1 |
| 46 | 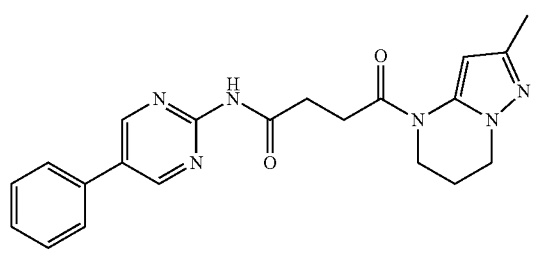 | 4-{2-methyl-5H,6H,7H-pyrazolo[1,5-a]pyrimidin-4-yl}-4-oxo-N-(5-phenylpyrimidin-2-yl)butanamide | <1 |
| 47 | 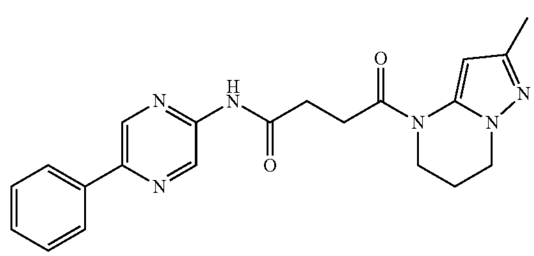 | 4-(2-methyl-6,7-dihydropyrazolo[1,5-a]pyrimidin-4(5H)-yl)-4-oxo-N-(5-phenylpyrazin-2-yl)butanamide | <0.1 |
| 48 | 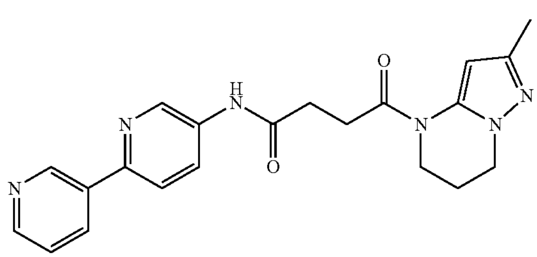 [SMILES: Cc1cc2n(n1)CCCN2C(=O)CCC(=O)Nc1ccc(-c2cccnc2)nc1] | N-([2,3'-bipyridin]-5-yl)-4-(2-methyl-6,7-dihydropyrazolo[1,5-a]pyrimidin-4(5H)-yl)-4-oxobutanamide | <0.1 |

| Cpd ID | Structure | IUPAC Name | STF3A IC50 μM |
|---|---|---|---|
| 49 | 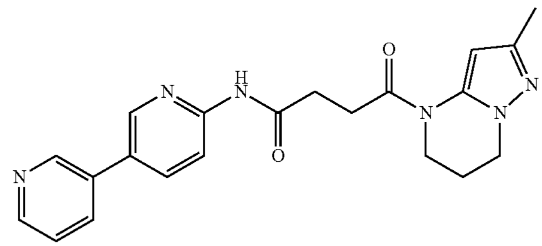 [SMILES: Cc1cc2n(n1)CCCN2C(=O)CCC(=O)Nc1ccc(-c2cccnc2)cn1] | 4-{2-methyl-5H,6H,7H-pyrazolo[1,5-a]pyrimidin-4-yl}-4-oxo-N-[5-(pyridin-3-yl)pyridin-2-yl]butanamide | <0.1 |
| 50 | 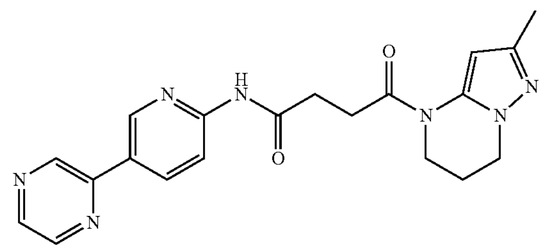 [SMILES: Cc1cc2n(n1)CCCN2C(=O)CCC(=O)Nc1ccc(-c2cnccn2)cn1] | 4-(2-methyl-6,7-dihydropyrazolo[1,5-a]pyrimidin-4(5H)-yl)-4-oxo-N-(5-(pyrazin-2-yl)pyridin-2-yl)butanamide | <0.1 |
| 51 | 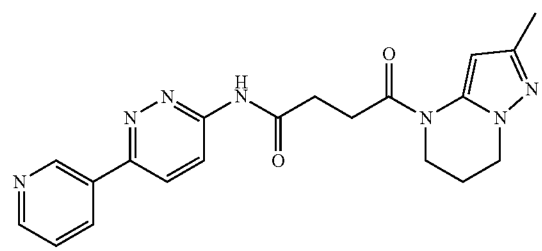 [SMILES: Cc1cc2n(n1)CCCN2C(=O)CCC(=O)Nc1ccc(-c2cccnc2)nn1] | 4-(2-methyl-6,7-dihydropyrazolo[1,5-a]pyrimidin-4(5H)-yl)-4-oxo-N-(6-(pyridin-3-yl)pyridazin-3-yl)butanamide | <0.1 |
| 52 | 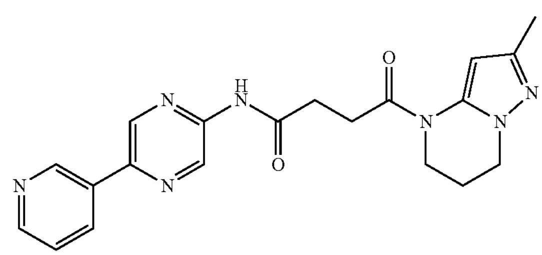 [SMILES: Cc1cc2n(n1)CCCN2C(=O)CCC(=O)Nc1cnc(-c2cccnc2)cn1] | 4-(2-methyl-6,7-dihydropyrazolo[1,5-a]pyrimidin-4(5H)-yl)-4-oxo-N-(5-(pyridin-3-yl)pyrazin-2-yl)butanamide | <0.1 |
| 53 | 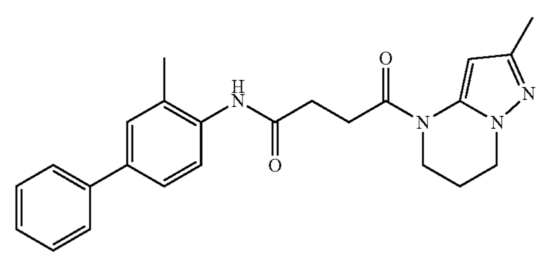 | 4-(2-methyl-6,7-dihydropyrazolo[1,5-a]pyrimidin-4(5H)-yl)-N-(3-methyl-[1,1'-biphenyl]-4-yl)-4-oxobutanamide | >10 |
| 54 | 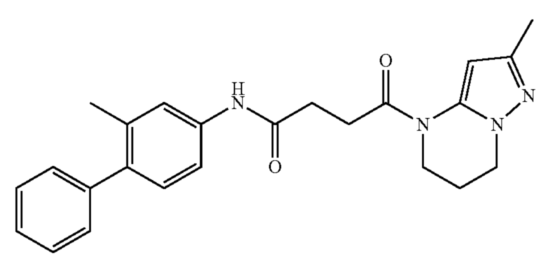 | 4-(2-methyl-6,7-dihydropyrazolo[1,5-a]pyrimidin-4(5H)-yl)-N-(2-methyl-[1,1'-biphenyl]-4-yl)-4-oxobutanamide | <0.1 |

-continued

| Cpd ID | Structure | IUPAC Name | STF3A IC50 μM |
|---|---|---|---|
| 55 | 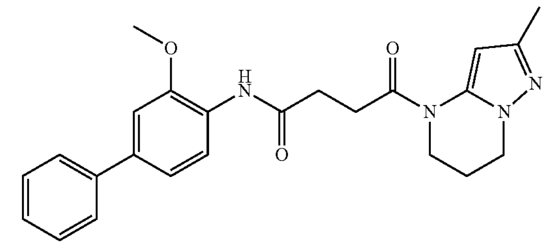 [SMILES: COc1cc(-c2ccccc2)ccc1NC(=O)CCC(=O)N1CCCn2nc(C)cc21] | N-(3-methoxy-[1,1'-biphenyl]-4-yl)-4-(2-methyl-6,7-dihydropyrazolo[1,5-a]pyrimidin-4(5H)-yl)-4-oxobutanamide | >10 |
| 56 | 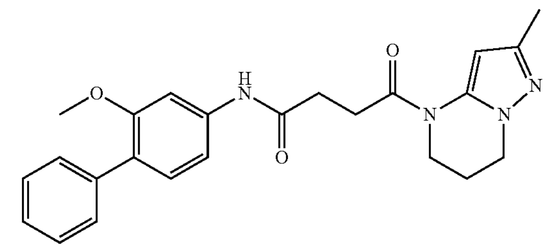 [SMILES: COc1cc(NC(=O)CCC(=O)N2CCCn3nc(C)cc32)ccc1-c1ccccc1] | N-(2-methoxy-[1,1'-biphenyl]-4-yl)-4-(2-methyl-6,7-dihydropyrazolo[1,5-a]pyrimidin-4(5H)-yl)-4-oxobutanamide | <5 |
| 57 | 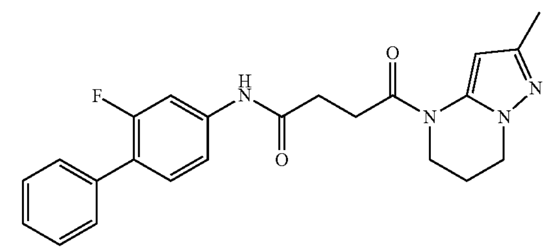 | N-(2-fluorobiphenyl-4-yl)-4-(2-methyl-6,7-dihydropyrazolo[1,5-a]pyrimidin-4(5H)-yl)-4-oxobutanamide | <0.1 |
| 58 | 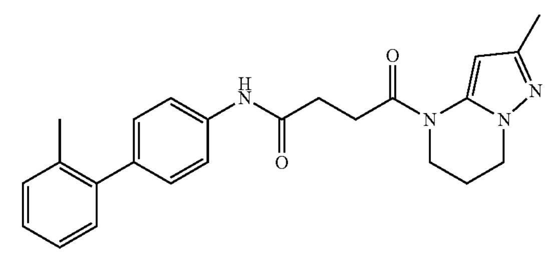 | 4-(2-methyl-6,7-dihydropyrazolo[1,5-a]pyrimidin-4(5H)-yl)-N-(2'-methyl-[1,1'-biphenyl]-4-yl)-4-oxobutanamide | <0.1 |
| 59 | 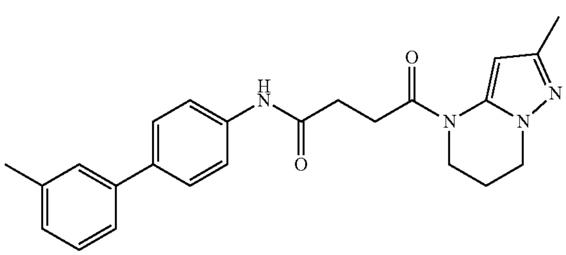 | 4-(2-methyl-6,7-dihydropyrazolo[1,5-a]pyrimidin-4(5H)-yl)-N-(3'-methyl-[1,1'-biphenyl]-4-yl)-4-oxobutanamide | <0.1 |
| 60 | 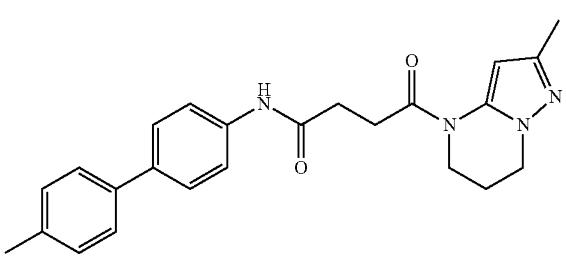 | 4-(2-methyl-6,7-dihydropyrazolo[1,5-a]pyrimidin-4(5H)-yl)-N-(4'-methyl-[1,1'-biphenyl]-4-yl)-4-oxobutanamide | <0.1 |

-continued

| Cpd ID | Structure | IUPAC Name | STF3A IC50 µM |
|---|---|---|---|
| 61 | 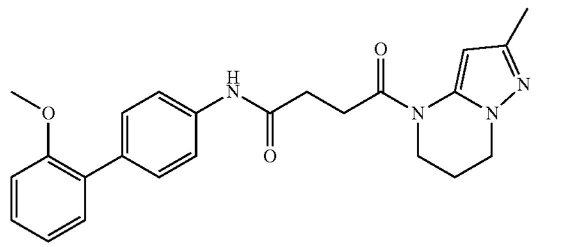 [SMILES: COc1ccccc1-c1ccc(NC(=O)CCC(=O)N2CCCn3nc(C)cc32)cc1] | N-(2'-methoxy-[1,1'-biphenyl]-4-yl)-4-(2-methyl-6,7-dihydropyrazolo[1,5-a]pyrimidin-4(5H)-yl)-4-oxobutanamide | >10 |
| 62 | 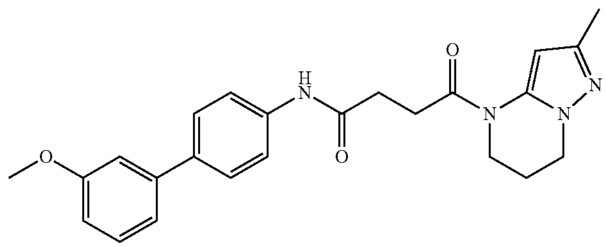 | N-(3'-methoxy-[1,1'-biphenyl]-4-yl)-4-(2-methyl-6,7-dihydropyrazolo[1,5-a]pyrimidin-4(5H)-yl)-4-oxobutanamide | <0.1 |
| 63 | 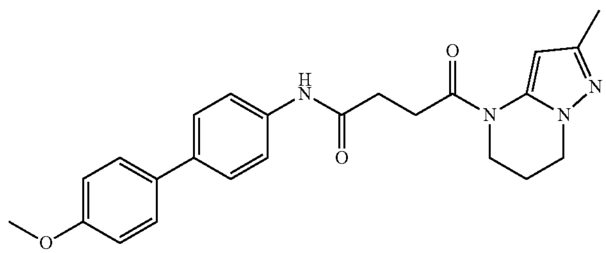 | N-(4'-methoxy-[1,1'-biphenyl]-4-yl)-4-(2-methyl-6,7-dihydropyrazolo[1,5-a]pyrimidin-4(5H)-yl)-4-oxobutanamide | <0.1 |
| 64 | 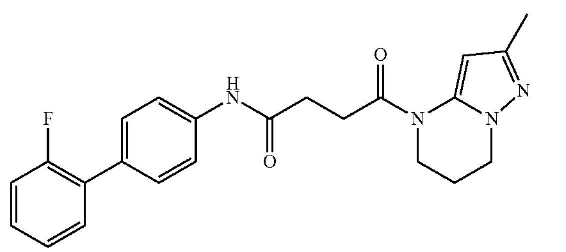 [SMILES: Cc1cc2n(n1)CCCN2C(=O)CCC(=O)Nc1ccc(-c2ccccc2F)cc1] | N-(2'-fluoro-[1,1'-biphenyl]-4-yl)-4-(2-methyl-6,7-dihydropyrazolo[1,5-a]pyrimidin-4(5H)-yl)-4-oxobutanamide | <0.1 |
| 65 | 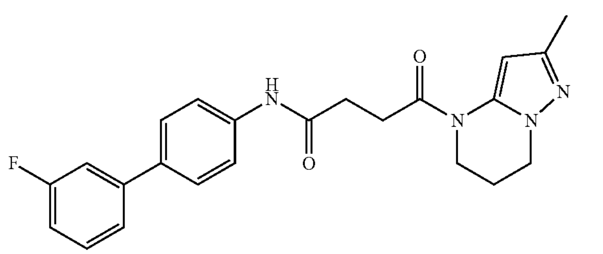 | N-(3'-fluoro-[1,1'-biphenyl]-4-yl)-4-(2-methyl-6,7-dihydropyrazolo[1,5-a]pyrimidin-4(5H)-yl)-4-oxobutanamide | <0.1 |
| 66 | 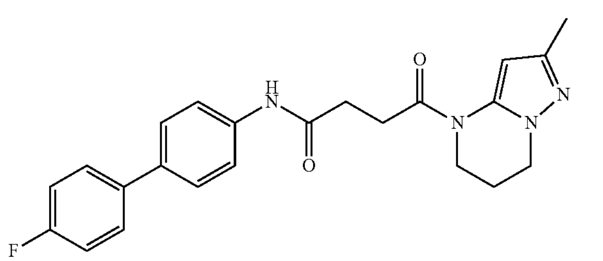 [SMILES: Cc1cc2n(n1)CCCN2C(=O)CCC(=O)Nc1ccc(-c2ccc(F)cc2)cc1] | N-(4'-fluorobiphenyl-4-yl)-4-(2-methyl-6,7-dihydropyrazolo[1,5-a]]pyrimidin-4(5H)-yl)-4-oxobutanamide | <1 |

-continued

| Cpd ID | Structure | IUPAC Name | STF3A IC50 μM |
|---|---|---|---|
| 67 | 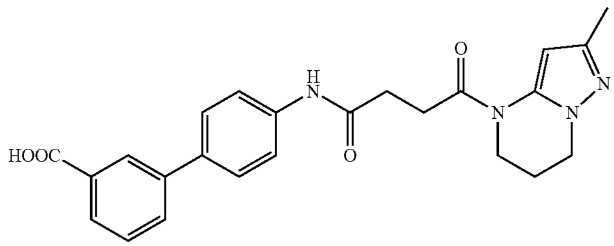 [SMILES: Cc1cc2n(n1)CCCN2C(=O)CCC(=O)Nc1ccc(-c2cccc(C(=O)O)c2)cc1] | 4'-(4-(2-methyl-6,7-dihydropyrazolo[1,5-a]pyrimidin-4(5H)-yl)-4-oxobutanamido)-[1,1'-biphenyl]-3-carboxylic acid | >10 |
| 68 | 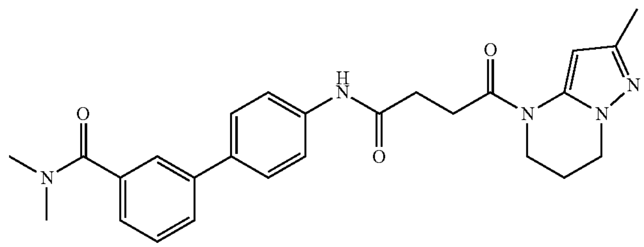 | N,N-dimethyl-4'-(4-(2-methyl-6,7-dihydropyrazolo[1,5-a]pyrimidin-4(5H)-yl)-4-oxobutanamido)-[1,1'-biphenyl]-3-carboxamide | >10 |
| 69 | 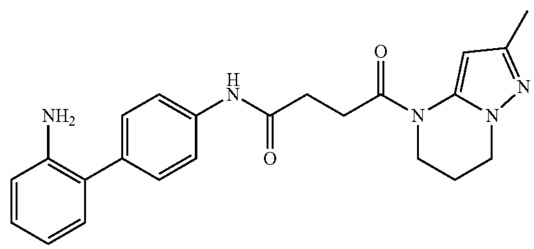 [SMILES: Cc1cc2n(n1)CCCN2C(=O)CCC(=O)Nc1ccc(-c2ccccc2N)cc1] | N-(2'-amino-[1,1'-biphenyl]-4-yl)-4-(2-methyl-6,7-dihydropyrazolo[1,5-a]pyrimidin-4(5H)-yl)-4-oxobutanamide | <1 |
| 70 | 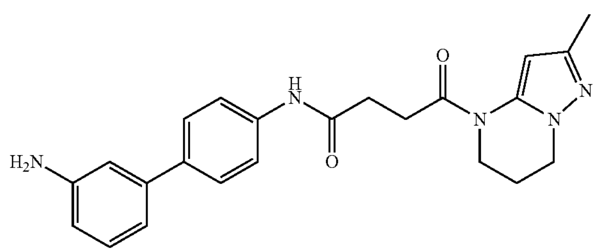 [SMILES: Cc1cc2n(n1)CCCN2C(=O)CCC(=O)Nc1ccc(-c2cccc(N)c2)cc1] | N-(3'-amino-[1,1'-biphenyl]-4-yl)-4-(2-methyl-6,7-dihydropyrazolo[1,5-a]pyrimidin-4(5H)-yl)-4-oxobutanamide | <0.1 |
| 71 | 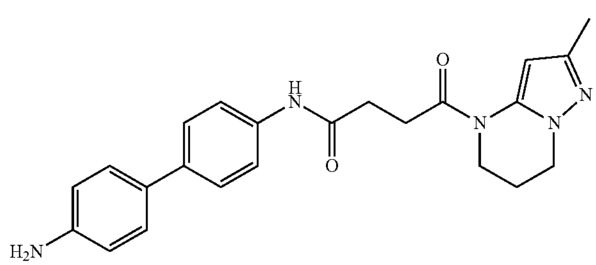 [SMILES: Cc1cc2n(n1)CCCN2C(=O)CCC(=O)Nc1ccc(-c2ccc(N)cc2)cc1] | N-(4'-amino-[1,1'-biphenyl]-4-yl)-4-(2-methyl-6,7-dihydropyrazolo[1,5-a]pyrimidin-4(5H)-yl)-4-oxobutanamide | <0.1 |
| 72 | 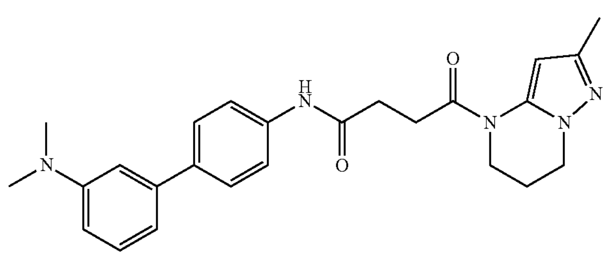 | N-(3'-(dimethylamino)-[1,1'-biphenyl]-4-yl)-4-(2-methyl-6,7-dihydropyrazolo[1,5-a]pyrimidin-4(5H)-yl)-4-oxobutanamide | >10 |

| Cpd ID | Structure | IUPAC Name | STF3A IC50 μM |
|---|---|---|---|
| 73 | 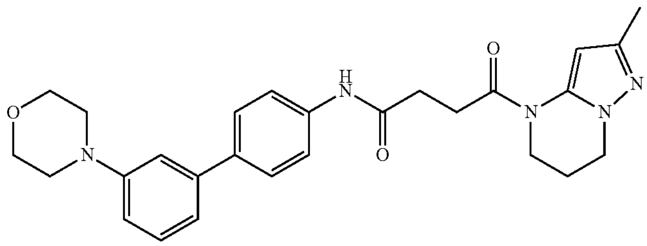 [SMILES: Cc1cc2n(n1)CCCN2C(=O)CCC(=O)Nc1ccc(-c2cccc(N3CCOCC3)c2)cc1] | 4-(2-methyl-6,7-dihydropyrazolo[1,5-a]pyrimidin-4(5H)-yl)-N-(3'-morpholinobiphenyl-4-yl)-4-oxobutanamide | <5 |
| 74 | 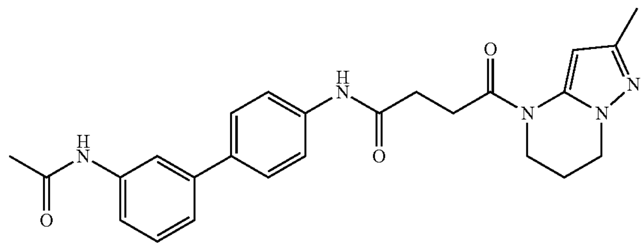 [SMILES: CC(=O)Nc1cccc(-c2ccc(NC(=O)CCC(=O)N3CCCn4nc(C)cc43)cc2)c1] | N-(3'-acetamido-[1,1'-biphenyl]-4-yl)-4-(2-methyl-6,7-dihydropyrazolo[1,5-a]pyrimidin-4(5H)-yl)-4-oxobutanamide | <5 |
| 75 | 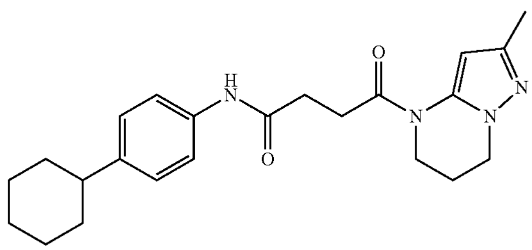 [SMILES: Cc1cc2n(n1)CCCN2C(=O)CCC(=O)Nc1ccc(C2CCCCC2)cc1] | N-(4-cyclohexylphenyl)-4-(2-methyl-6,7-dihydropyrazolo[1,5-a]pyrimidin-4(5H)-yl)-4-oxobutanamide | >10 |
| 76 | 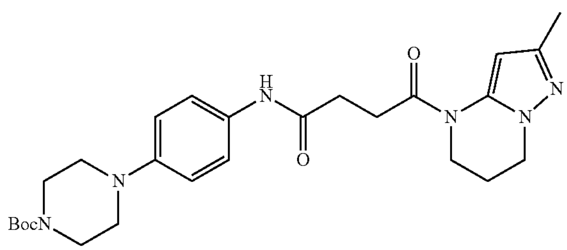 [SMILES: Cc1cc2n(n1)CCCN2C(=O)CCC(=O)Nc1ccc(N2CCN(C(=O)OC(C)(C)C)CC2)cc1] | tert-butyl 4-(4-(4-(2-methyl-6,7-dihydropyrazolo[1,5-a]pyrimidin-4(5H)-yl)-4-oxobutanamido)phenyl)piperazine-1-carboxylate | <0.1 |
| 77 | 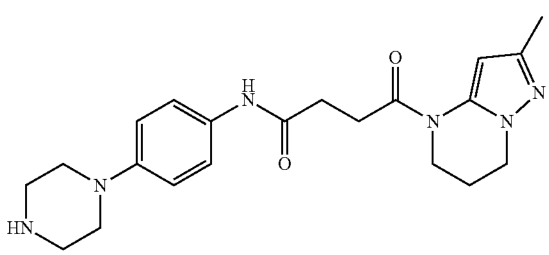 [SMILES: Cc1cc2n(n1)CCCN2C(=O)CCC(=O)Nc1ccc(N2CCNCC2)cc1] | 4-(2-methyl-6,7-dihydropyrazolo[1,5-a]pyrimidin-4(5H)-yl)-4-oxo-N-(4-(piperazin-1-yl)phenyl)butanamide | >10 |
| 78 | 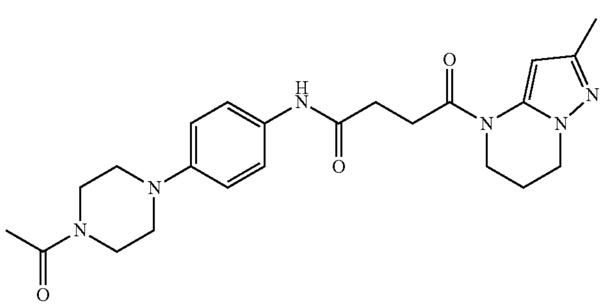 [SMILES: CC(=O)N1CCN(c2ccc(NC(=O)CCC(=O)N3CCCn4nc(C)cc43)cc2)CC1] | N-(4-(4-acetylpiperazin-1-yl)phenyl)-4-(2-methyl-6,7-dihydropyrazolo[1,5-a]pyrimidin-4(5H)-yl)-4-oxobutanamide | >10 |

-continued

| Cpd ID | Structure | IUPAC Name | STF3A IC50 μM |
|---|---|---|---|
| 79 | 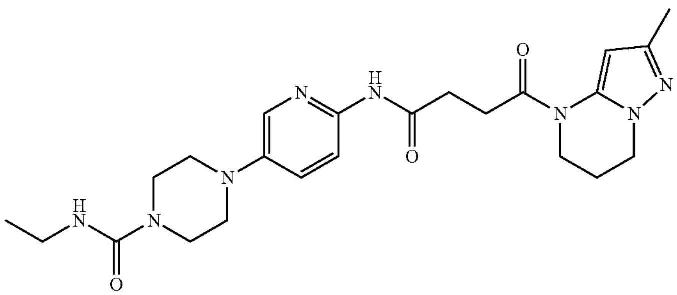 [SMILES: CCNC(=O)N1CCN(c2ccc(NC(=O)CCC(=O)N3CCCn4nc(C)cc43)nc2)CC1] | Synthesis of N-ethyl-4-(6-(4-(2-methyl-6,7-dihydropyrazolo[1,5-a]pyrimidin-4(5H)-yl)-4-oxobutanamido)pyridin-3-yl)piperazine-1-carboxamide | <5 |
| 80 | 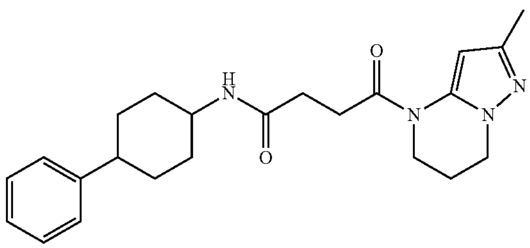 [SMILES: Cc1cc2n(n1)CCCN2C(=O)CCC(=O)NC1CCC(c2ccccc2)CC1] | 4-(2-methyl-6,7-dihydropyrazolo[1,5-a]pyrimidin-4(5H)-yl)-4-oxo-N-(4-phenylcyclohexyl)butanamide | >10 |
| 81 | 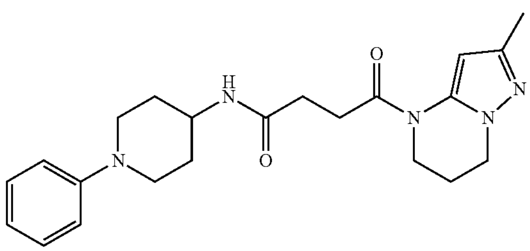 [SMILES: Cc1cc2n(n1)CCCN2C(=O)CCC(=O)NC1CCN(c2ccccc2)CC1] | 4-(2-methyl-6,7-dihydropyrazolo[1,5-a]pyrimidin-4(5H)-yl)-4-oxo-N-(1-phenylpiperidin-4-yl)butanamide | >10 |
| 82 | 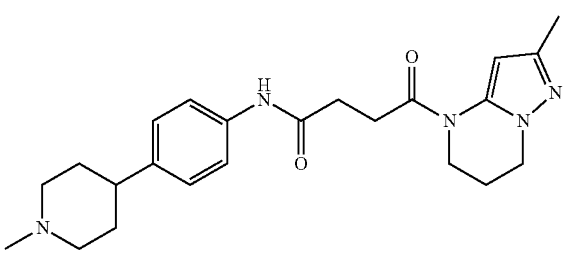 | 4-(2-methyl-6,7-dihydropyrazolo[1,5-a]pyrimidin-4(5H)-yl)-N-(4-(1-methylpiperidin-4-yl)phenyl)-4-oxobutanamide | >10 |
| 83 | 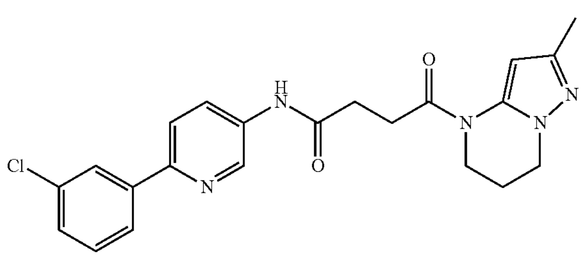 [SMILES: Cc1cc2n(n1)CCCN2C(=O)CCC(=O)Nc1ccc(-c2cccc(Cl)c2)nc1] | N-(6-(3-chlorophenyl)pyridin-3-yl)-4-(2-methyl-6,7-dihydropyrazolo[1,5-a]pyrimidin-4(5H)-yl)-4-oxobutanamide | <0.1 |

-continued

| Cpd ID | Structure | IUPAC Name | STF3A IC50 μM |
|---|---|---|---|
| 84 | 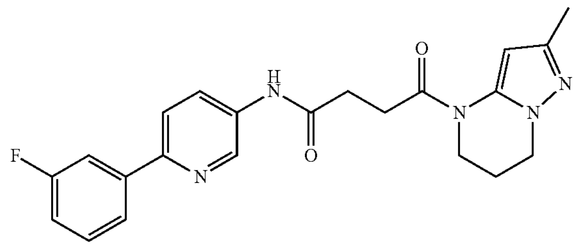 [SMILES: Cc1cc2n(n1)CCCN2C(=O)CCC(=O)Nc1ccc(-c2cccc(F)c2)nc1] | N-(6-(3-fluorophenyl)pyridin-3-yl)-4-(2-methyl-6,7-dihydropyrazolo[1,5-a]pyrimidin-4(5H)-yl)-4-oxobutanamide | <0.1 |
| 85 | 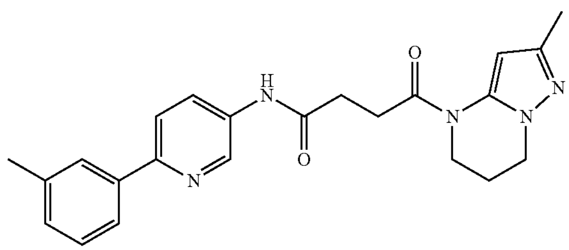 | 4-(2-methyl-6,7-dihydropyrazolo[1,5-a]pyrimidin-4(5H)-yl)-4-oxo-N-(6-m-tolyl)pyridin-3-yl)butanamide | <0.1 |
| 86 | 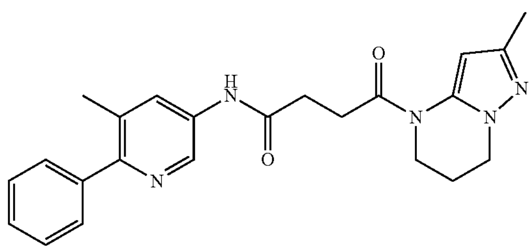 [SMILES: Cc1cc2n(n1)CCCN2C(=O)CCC(=O)Nc1cnc(-c2ccccc2)c(C)c1] | 4-(2-methyl-6,7-dihydropyrazolo[1,5-a]pyrimidin-4(5H)-yl)-N-(5-methyl-6-phenylpyridin-3-yl)-4-oxobutanamide | <5 |
| 87 | 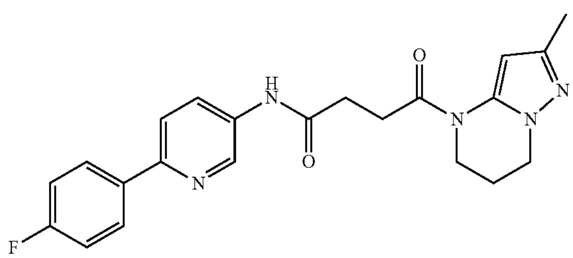 | N-(6-(4-fluorophenyl)pyridin-3-yl)-4-(2-methyl-6,7-dihydropyrazolo[1,5-a]pyrimidin-4(5H)-yl)-4-oxobutanamide | <1 |
| 88 | 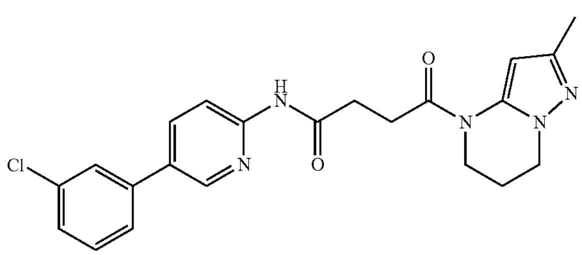 [SMILES: Cc1cc2n(n1)CCCN2C(=O)CCC(=O)Nc1ccc(-c2cccc(Cl)c2)cn1] | N-(6-(3-fluorophenyl)pyridazin-3-yl)-4-(2-methyl-6,7-dihydropyrazolo[1,5-a]pyrimidin-4(5H)-yl)-4-oxobutanamide | <0.1 |
| 89 | 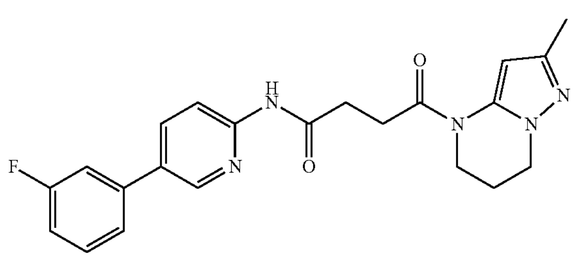 | N-(5-(3-fluorophenyl)pyridin-2-yl)-4-(2-methyl-6,7-dihydropyrazolo[1,5-a]pyrimidin-4(5H)-yl)-4-oxobutanamide | <0.1 |

| Cpd ID | Structure | IUPAC Name | STF3A IC50 µM |
|---|---|---|---|
| 90 | 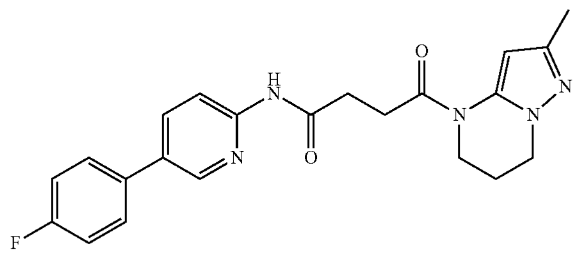 [SMILES: Cc1cc2n(n1)CCCN2C(=O)CCC(=O)Nc1ccc(-c2ccc(F)cc2)cn1] | N-(5-(4-fluorophenyl)pyridin-2-yl)-4-(2-methyl-6,7-dihydropyrazolo[1,5-a]pyrimidin-4(5H)-yl)-4-oxobutanamide | <0.1 |
| 91 | 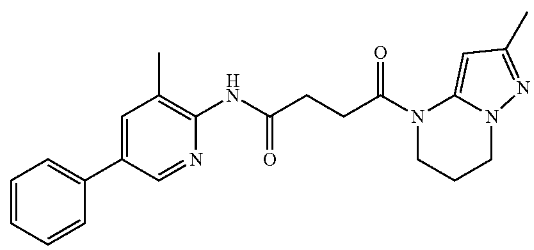 [SMILES: Cc1cc2n(n1)CCCN2C(=O)CCC(=O)Nc1ncc(-c2ccccc2)cc1C] | N-(3-methyl-5-phenylpyridin-2-yl)-4-(2-methyl-6,7-dihydropyrazolo[1,5-a]pyrimidin-4(5H)-yl)-4-oxobutana | <5 |
| 92 | 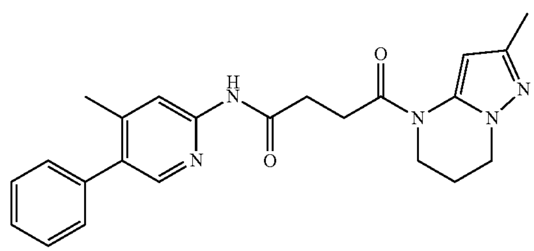 | N-(4-methyl-5-phenylpyridin-2-yl)-4-(2-methyl-6,7-dihydropyrazolo[1,5-a]pyrimidin-4(5H)-yl)-4-oxobutanamide | <1 |
| 93 | 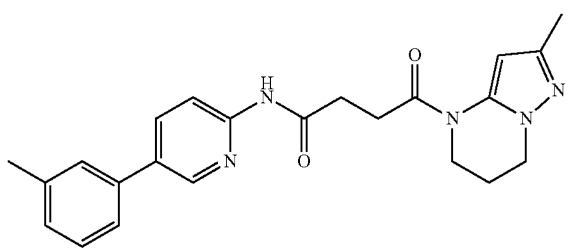 | 4-(2-methyl-6,7-dihydropyrazolo[1,5-a]pyrimidin-4(5H)-yl)-4-oxo-N-(5-(m-tolyl)pyridin-2-yl)butanamide | <0.1 |
| 94 | 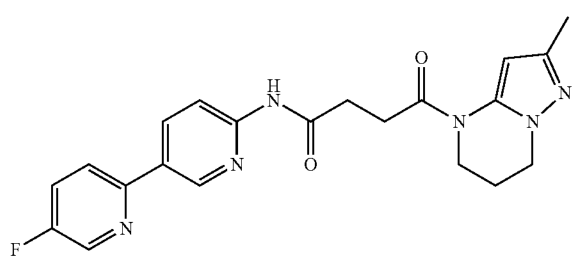 | N-(5-fluoro-2,3'-bipyridin-6'-yl)-4-(2-methyl-6,7-dihydropyrazolo[1,5-a]pyrimidin-4(5H)-yl)-4-oxobutanamide | <0.1 |
| 95 | 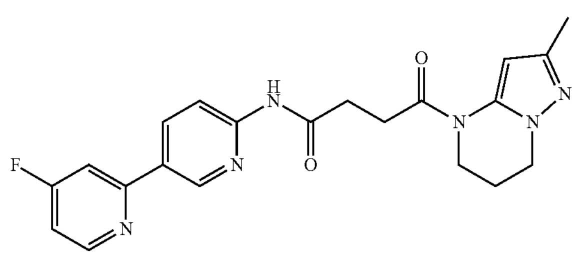 [SMILES: Cc1cc2n(n1)CCCN2C(=O)CCC(=O)Nc1ccc(-c2cc(F)ccn2)cn1] | N-(4-fluoro-2,3'-bipyridin-6'-yl)-4-(2-methyl-6,7-dihydropyrazolo[1,5-a]pyrimidin-4(5H)-yl)-4-oxobutanamide | <0.1 |

-continued

| Cpd ID | Structure | IUPAC Name | STF3A IC50 μM |
|---|---|---|---|
| 96 | 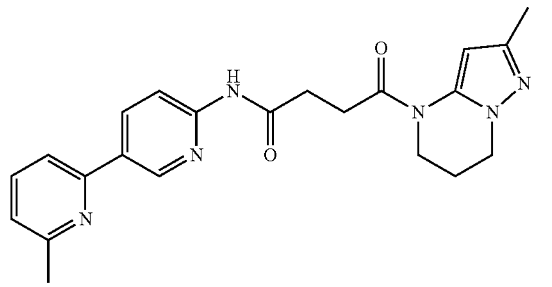 [SMILES: Cc1cccc(-c2ccc(NC(=O)CCC(=O)N3CCCn4nc(C)cc43)nc2)n1] | 4-(2-methyl-6,7-dihydropyrazolo[1,5-a]pyrimidin-4(5H)-yl)-N-(6-methyl-[2,3'-bipyridin]-6'-yl)-4-oxobutanamide | <0.1 |
| 97 | 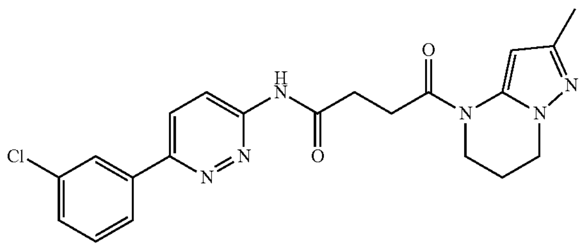 | N-(6-(3-chlorophenyl)pyridazin-3-yl)-4-(2-methyl-6,7-dihydropyrazolo[1,5-a]pyrimidin-4(5H)-yl)-4-oxobutanamide | <0.1 |
| 98 | 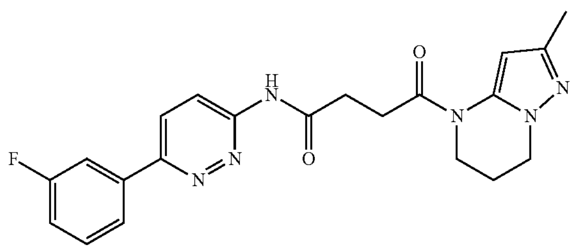 | N-(6-(3-fluorophenyl)pyridazin-3-yl)-4-(2-methyl-6,7-dihydropyrazolo[1,5-a]pyrimidin-4(5H)-yl)-4-oxobutanamide | <0.1 |
| 99 | 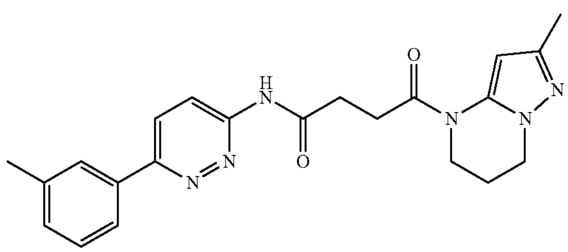 | 4-(2-methyl-6,7-dihydropyrazolo[1,5-a]pyrimidin-4(5H)-4-oxo-N-(6-(m-tolyl)pyridazin-3-yl)butanamide | <0.1 |
| 100 | 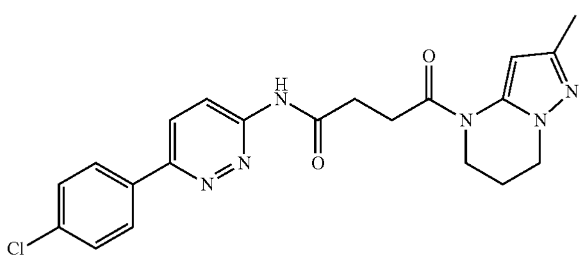 [SMILES: Cc1cc2n(n1)CCCN2C(=O)CCC(=O)Nc1ccc(-c2ccc(Cl)cc2)nn1] | N-[6-(4-chlorophenyl)pyridazin-3-yl]-4-{2-methyl-5H,6H,7H-pyrazolo[1,5-a]pyrimidin-4-yl}-4-oxobutanamide | <0.1 |
| 101 | 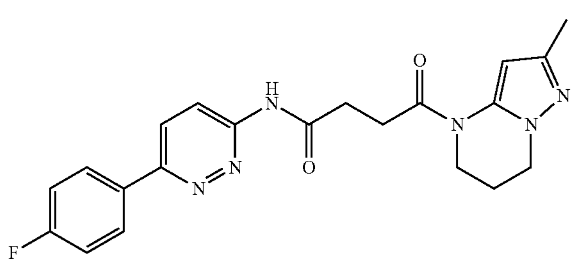 [SMILES: Cc1cc2n(n1)CCCN2C(=O)CCC(=O)Nc1ccc(-c2ccc(F)cc2)nn1] | N-(6-(4-fluorophenyl)pyridazin-3-yl)-4-(2-methyl-6,7-dihydropyrazolo[1,5-a]pyrimidin-4(5H)-yl)-4-oxobutanamide | <0.1 |

-continued

| Cpd ID | Structure | IUPAC Name | STF3A IC50 μM |
|---|---|---|---|
| 102 | 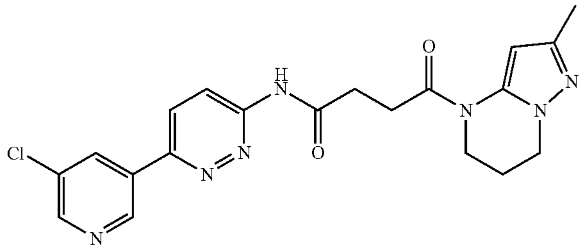 | N-(6-(5-chloropyridin-3-yl)pyridazin-3-yl)-4-(2-methyl-6,7-dihydropyrazolo[1,5-a]pyrimidin-4(5H)-yl)-4-oxobutanamide | <0.1 |
| 103 | 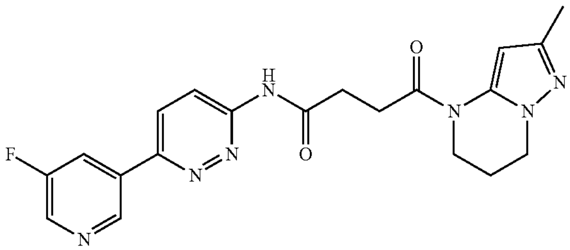 | N-(6-(5-fluoropyridin-3-yl)pyridazin-3-yl)-4-(2-methyl-6,7-dihydropyrazolo[1,5-a]pyrimidin-4(5H)-yl)-4-oxobutanamide | <0.1 |
| 104 | 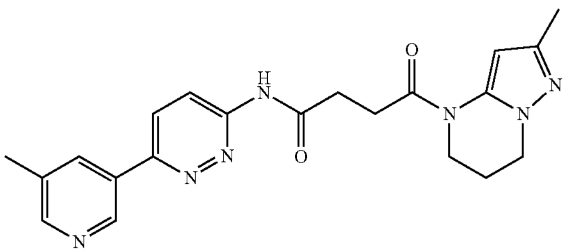 | 4-(2-methyl-6,7-dihydropyrazolo[1,5-a]pyrimidin-4(5H)-yl)-N-(6-(5-methylpyridin-3-yl)pyridazin-3-yl)-4-oxobutanamide | <0.1 |
| 105 | 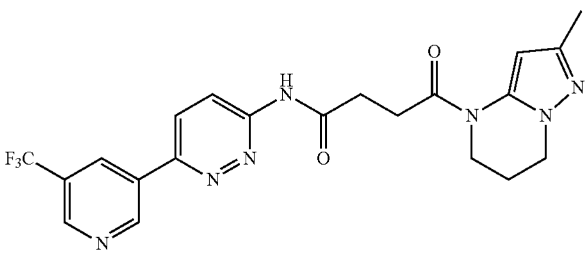 [SMILES: Cc1cc2n(n1)CCCN2C(=O)CCC(=O)Nc1ccc(-c2cncc(C(F)(F)F)c2)nn1] | 4-(2-methyl-6,7-dihydropyrazolo[1,5-a]pyrimidin-4(5H)-yl)-4-oxo-N-(6-(5-(trifluoromethyl)pyridin-3-yl)pyridazin-3-yl)butanamide | <0.1 |
| 106 | 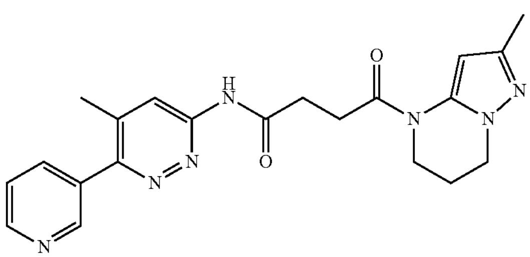 [SMILES: Cc1cc2n(n1)CCCN2C(=O)CCC(=O)Nc1cc(C)c(-c2cccnc2)nn1] | 4-(2-methyl-6,7-dihydropyrazolo[1,5-a]pyrimidin-4(5H)-yl)-N-(5-methyl-6-(pyridin-3-yl)pyridazin-3-yl)-4-oxobutanamide | <5 |
| 107 | 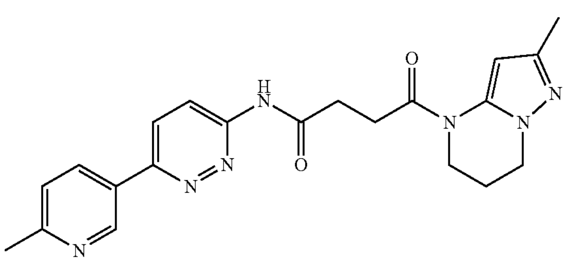 | 4-(2-methyl-6,7-dihydropyrazolo[1,5-a]pyrimidin-4(5H)-yl)-N-(6-(6-methylpyridin-3-yl)pyridazin-3-yl)-4-oxobutanamide | <0.1 |

| Cpd ID | Structure | IUPAC Name | STF3A IC50 μM |
|---|---|---|---|
| 108 | 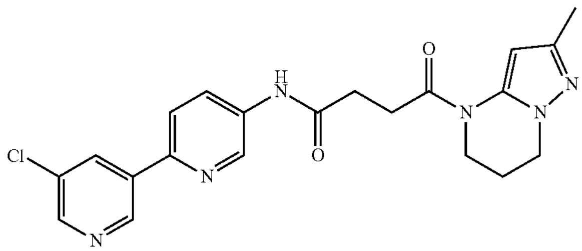 [SMILES: Cc1cc2n(n1)CCCN2C(=O)CCC(=O)Nc1ccc(-c2cncc(Cl)c2)nc1] | N-(5'-chloro-[2,3'-bipyridin]-5-yl)-4-(2-methyl-6,7-dihydropyrazolo[1,5-a]pyrimidin-4(5H)-yl)-4-oxobutanamide | <0.1 |
| 109 | 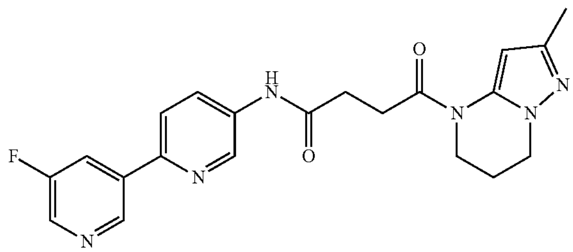 [SMILES: Cc1cc2n(n1)CCCN2C(=O)CCC(=O)Nc1ccc(-c2cncc(F)c2)nc1] | N-(5'-fluoro-[2,3'-bipyridin]-5-yl)-4-(2-methyl-6,7-dihydropyrazolo[1,5-a]pyrimidin-4(5H)-yl)-4-oxobutanamide | <0.1 |
| 110 | 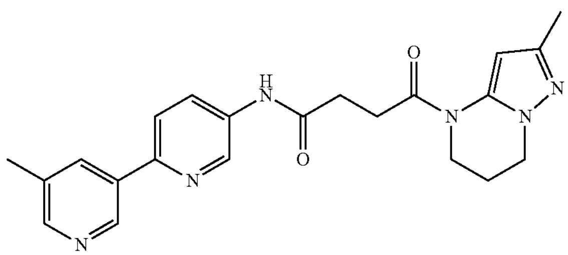 | N-(5'-methyl-2,3'-bipyridin-5-yl)-4-(2-methyl-6,7-dihydropyrazolo[1,5-a]pyrimidin-4(5H)-yl)-4-oxobutanamide | <0.1 |
| 111 | 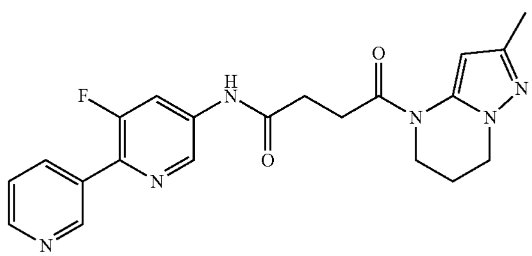 [SMILES: Cc1cc2n(n1)CCCN2C(=O)CCC(=O)Nc1cnc(-c2cccnc2)c(F)c1] | N-(3-fluoro-2,3'-bipyridin-5-yl)-4-(2-methyl-6,7-dihydropyrazolo[1,5-a]pyrimidin-4(5H)-yl)-4-oxobutanamide | <0.1 |
| 112 | 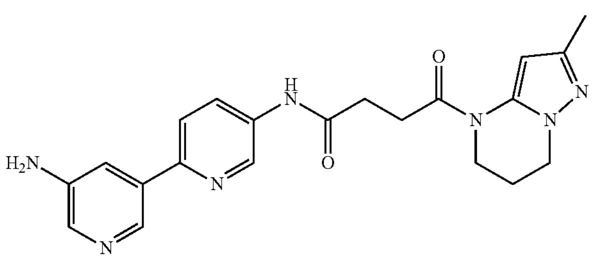 [SMILES: Cc1cc2n(n1)CCCN2C(=O)CCC(=O)Nc1ccc(-c2cncc(N)c2)nc1] | N-(5'-amino-2,3'-bipyridin-5-yl)-4-(2-methyl-6,7-dihydropyrazolo[1,5-a]pyrimidin-4(5H)-yl)-4-oxobutanamide | <1 |
| 113 | 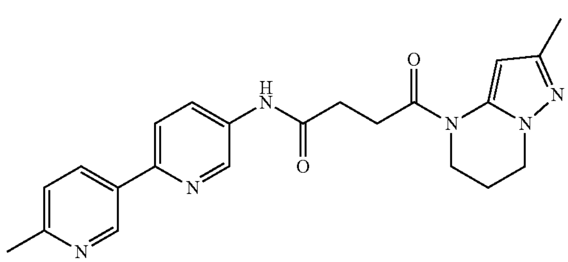 | 4-(2-methyl-6,7-dihydropyrazolo[1,5-a]pyrimidin-4(5H)-yl)-N-(6'-methyl-[2,3'-bipyridin]-5-yl)-4-oxobutanamide | <0.1 |

-continued

| Cpd ID | Structure | IUPAC Name | STF3A IC50 μM |
|---|---|---|---|
| 114 | 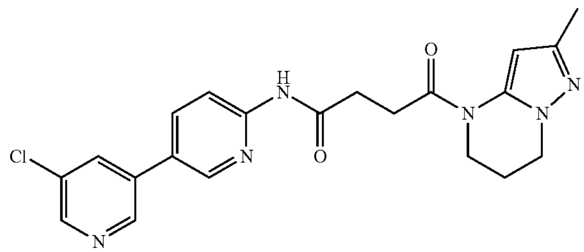 [SMILES: Cc1cc2n(n1)CCCN2C(=O)CCC(=O)Nc1ccc(-c2cncc(Cl)c2)cn1] | N-(5'-chloro-[3,3'-bipyridin]-6-yl)-4-(2-methyl-6,7-dihydropyrazolo[1,5-a]pyrimidin-4(5H)-yl)-4-oxobutanamide | <0.1 |
| 115 | 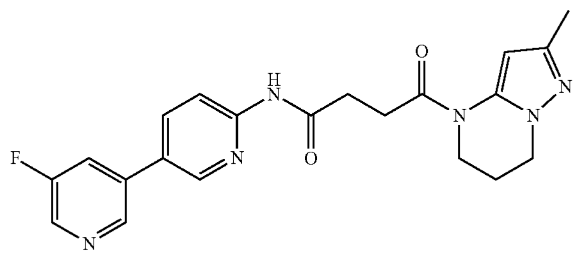 [SMILES: Cc1cc2n(n1)CCCN2C(=O)CCC(=O)Nc1ccc(-c2cncc(F)c2)cn1] | N-(5'-fluoro-[3,3'-bipyridin]-6-yl)-4-(2-methyl-6,7-dihydropyrazolo[1,5-a]pyrimidin-4(5H)-yl)-4-oxobutanamide | <0.1 |
| 116 | 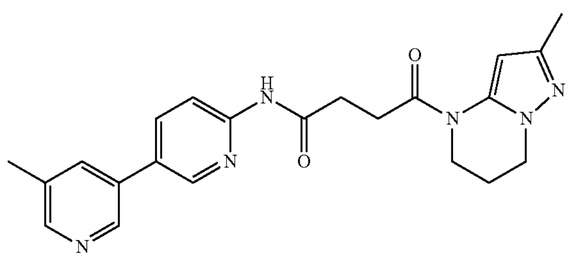 | 4-(2-methyl-6,7-dihydropyrazolo[1,5-a]pyrimidin-4(5H)-yl)-N-(5'-methyl-[3,3'-bipyridin]-6-yl)-4-oxobutanamide | <0.1 |
| 117 | 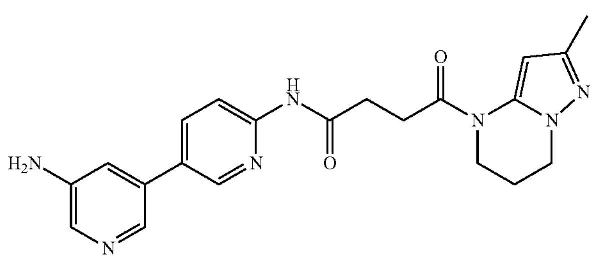 | 4-(2-methyl-6,7-dihydropyrazolo[1,5-a]pyrimidin-4(5H)-yl)-4-oxo-N-(4-(piperazin-1-yl)phenyl)butanamide | <0.1 |
| 118 | 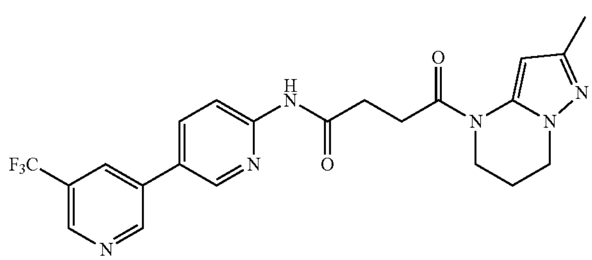 [SMILES: Cc1cc2n(n1)CCCN2C(=O)CCC(=O)Nc1ccc(-c2cncc(C(F)(F)F)c2)cn1] | 4-(2-methyl-6,7-dihydropyrazolo[1,5-a]pyrimidin-4(5H)-yl)-4-oxo-N-(5'-(trifluoromethyl)-[3,3'-bipyridin]-6-yl)butanamide | <0.1 |
| 119 | 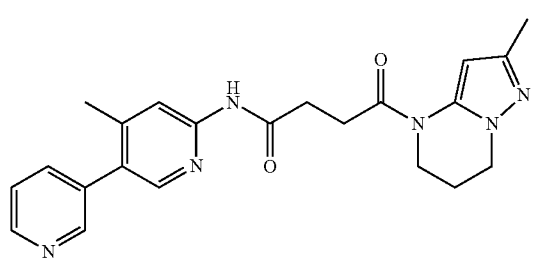 [SMILES: Cc1cc2n(n1)CCCN2C(=O)CCC(=O)Nc1cc(C)c(-c2cccnc2)cn1] | N-(4-methyl-3,3'-bipyridin-6-yl)-4-(2-methyl-6,7-dihydropyrazolo[1,5-a]pyrimidin-4(5H)-yl)-4-oxobutanamide | <5 |

-continued

| Cpd ID | Structure | IUPAC Name | STF3A IC50 μM |
|---|---|---|---|
| 120 | 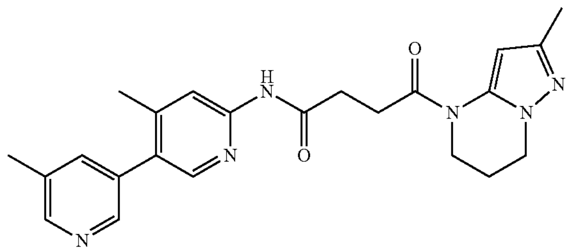 | N-(4,5'-dimethyl-3,3'-bipyridin-6-yl)-4-(2-methyl-6,7-dihydropyrazolo[1,5-a]pyrimidin-4(5H)-yl)-4-oxobutanamide | <5 |
| 121 | 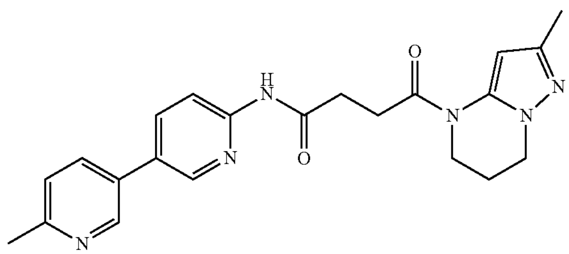 | N-(6'-methyl-3,3'-bipyridin-6-yl)-4-(2-methyl-6,7-dihydropyrazolo[1,5-a]pyrimidin-4(5H)-yl)-4-oxobutanamide | <0.1 |
| 122 | 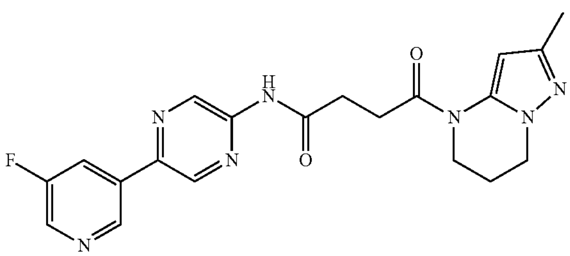 [SMILES: Cc1cc2n(n1)CCCN2C(=O)CCC(=O)Nc1cnc(-c2cncc(F)c2)cn1] | N-(5-(5-fluoropyridin-3-yl)pyrazin-2-yl)-4-(2-methyl-6,7-dihydropyrazolo[1,5-a]pyrimidin-4(5H)-yl)-4-oxobutanamide | <0.1 |
| 123 | 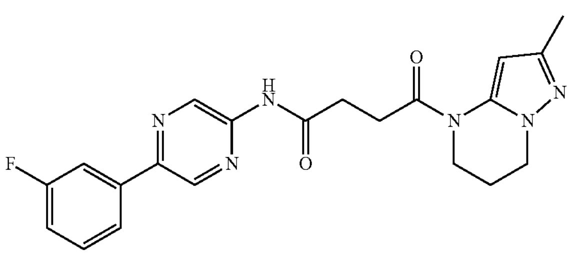 [SMILES: Cc1cc2n(n1)CCCN2C(=O)CCC(=O)Nc1cnc(-c2cccc(F)c2)cn1] | N-(5-(3-fluorophenyl)pyrazin-2-yl)-4-(2-methyl-6,7-dihydropyrazolo[1,5-a]pyrimidin-4(5H)-yl)-4-oxobutanamide | <0.1 |
| 124 | 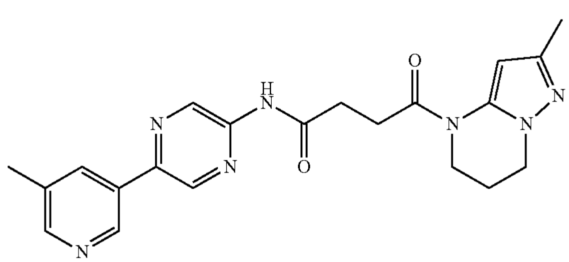 | 4-(2-methyl-6,7-dihydropyrazolo[1,5-a]pyrimidin-4(5H)-yl)-N-(5-(5-methylpyridin-3-yl)pyrazin-2-yl)-4-oxobutanamide | <0.1 |
| 125 | 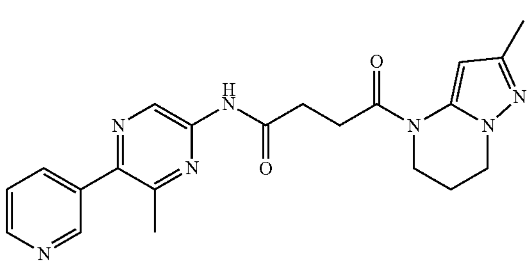 [SMILES: Cc1cc2n(n1)CCCN2C(=O)CCC(=O)Nc1cnc(-c2cccnc2)c(C)n1] | N-(6-methyl-5-(pyridin-3-yl)pyrazin-2-yl)-4-(2-methyl-6,7-dihydropyrazolo[1,5-a]pyrimidin-4(5H)-yl)-4-oxobutanamide | >10 |

-continued

| Cpd ID | Structure | IUPAC Name | STF3A IC50 μM |
|---|---|---|---|
| 126 | 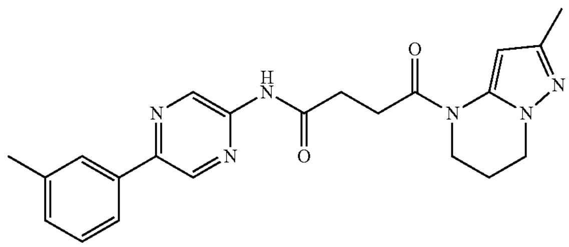 | 4-(2-methyl-6,7-dihydropyrazolo[1,5-a]pyrimidin-4(5H)-yl)-4-oxo-N-(5-(m-tolyl)pyrazin-2-yl)butanamide | <0.1 |
| 127 | 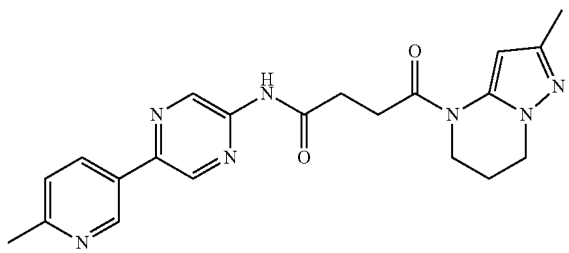 | 4-(2-methyl-6,7-dihydropyrazolo[1,5-a]pyrimidin-4(5H)-yl)-N-(5-(6-methylpyridin-3-yl)pyrazin-2-yl)-4-oxobutanamide | <1 |
| 128 | 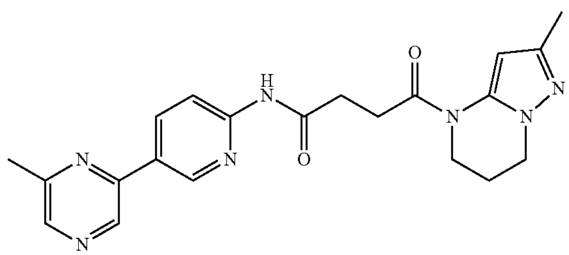 | 4-(2-methyl-6,7-dihydropyrazolo[1,5-a]pyrimidin-4(5H)-yl)-N-(5-(6-methylpyrazin-2-yl)pyridin-2-yl)-4-oxobutanamide | <0.1 |
| 129 | 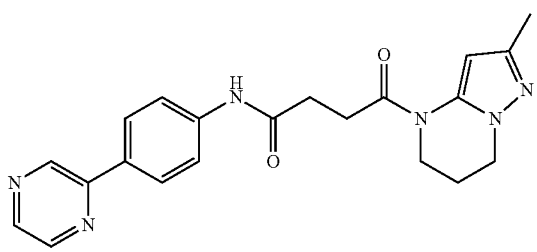 | 4-(2-methyl-6,7-dihydropyrazolo[1,5-a]pyrimidin-4(5H)-yl)-4-oxo-N-(4-(pyrazin-2-yl)phenyl)butanamide | <0.1 |
| 130 | 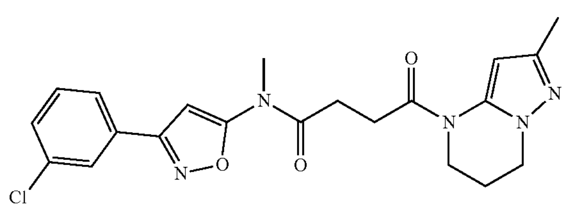 [SMILES: Cc1cc2n(n1)CCCN2C(=O)CCC(=O)N(C)c1cc(-c2cccc(Cl)c2)no1] | N-(3-(3-chlorophenyl)isoxazol-5-yl)-N-methyl-4-(2-methyl-6,7-dihydropyrazolo[1,5-a]pyrimidin-4(5H)-yl)-4-oxobutanamide | >10 |
| 131 | 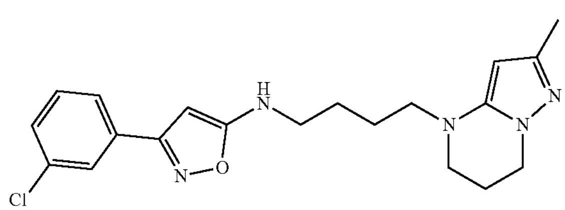 [SMILES: Cc1cc2n(n1)CCCN2CCCCNc1cc(-c2cccc(Cl)c2)no1] | 3-(3-chlorophenyl)-N-(4-(2-methyl-6,7-dihydropyrazolo[1,5-a]pyrimidin-4(5H)-yl)butyl)isoxazol-5-amine | >10 |

| Cpd ID | Structure | IUPAC Name | STF3A IC50 μM |
|---|---|---|---|
| 132 | 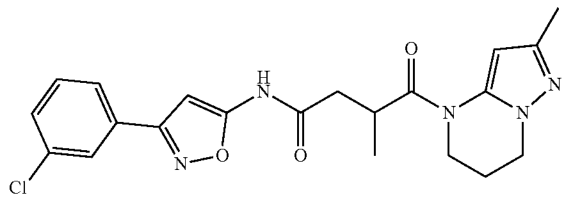 [SMILES: Cc1cc2n(n1)CCCN2C(=O)C(C)CC(=O)Nc1cc(-c2cccc(Cl)c2)no1] | N-(3-(3-chlorophenyl)isoxazol-5-yl)-3-methyl-4-(2-methyl-6,7-dihydropyrazolo[1,5-a]pyrimidin-4(5H)-yl)-4-oxobutanamide | >10 |
| 133 | 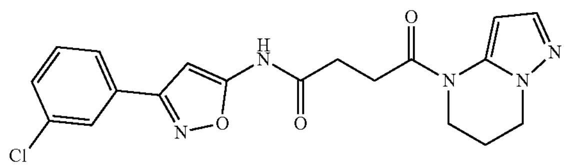 [SMILES: O=C(CCC(=O)N1CCCn2nccc21)Nc1cc(-c2cccc(Cl)c2)no1] | N-(3-(3-chlorophneyl)isoxazol-5-yl)-4-(6,7-dihydropyrazolo[1,5-a]pyrimidin-4(5H)-yl)-4-oxobutanamide | >10 |
| 134 | 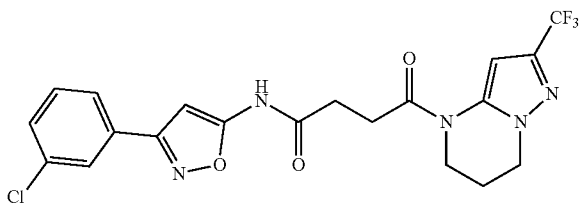 [SMILES: O=C(CCC(=O)N1CCCn2nc(C(F)(F)F)cc21)Nc1cc(-c2cccc(Cl)c2)no1] | N-(3-(3-chlorophenyl)isoxazol-5-yl)-4-oxo-4-(2-(trifluoromethyl)-6,7-dihydropyrazolo[1,5-a]pyrimidin-4(5H)-yl)butanamide | <0.1 |
| 135 | 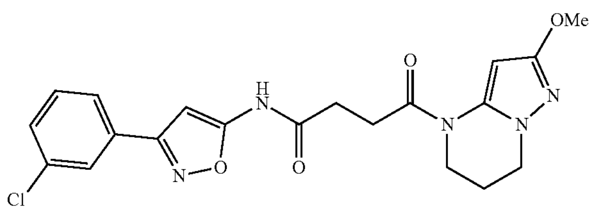 [SMILES: COc1cc2n(n1)CCCN2C(=O)CCC(=O)Nc1cc(-c2cccc(Cl)c2)no1] | N-(3-(3-chlorophenyl)isoxazol-5-yl)-4-(2-methoxy-6,7-dihydropyrazolo[1,5-a]pyrimidin-4(5H)-yl)-4-oxobutanamide | >10 |
| 136 | 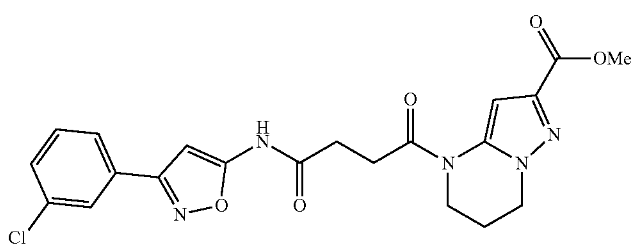 [SMILES: COC(=O)c1cc2n(n1)CCCN2C(=O)CCC(=O)Nc1cc(-c2cccc(Cl)c2)no1] | methyl 4-(4-(3-(3-chlorophenyl)isoxazol-5-ylamino)-4-oxobutanoyl)-4,5,6,7-tetrahydropyrazolo[1,5-a]pyrimidine-2-carboxylate | >10 |
| 137 | 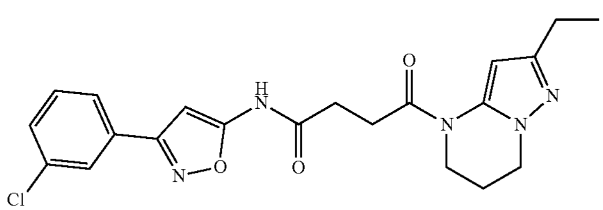 [SMILES: CCc1cc2n(n1)CCCN2C(=O)CCC(=O)Nc1cc(-c2cccc(Cl)c2)no1] | N-(3-(3-chlorophenyl)isoxazol-5-yl)-4-(2-ethyl-6,7-dihydropyrazolo[1,5-a]pyrimidin-4(5H)-yl)-4-oxobutanamide | <0.1 |
| 138 | 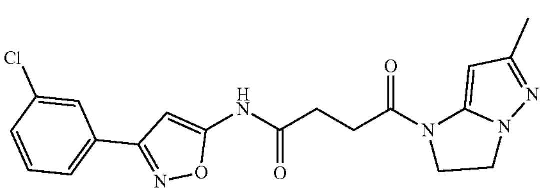 [SMILES: Cc1cc2n(n1)CCN2C(=O)CCC(=O)Nc1cc(-c2cccc(Cl)c2)no1] | N-(3-(3-chlorophenyl)isoxazol-5-yl)-4-(6-methyl-2,3-dihydro-1H-imidazo[1,2-b]pyrazol-1-yl)-4-oxobutanamide | >10 |

| Cpd ID | Structure | IUPAC Name | STF3A IC50 μM |
|---|---|---|---|
| 139 | 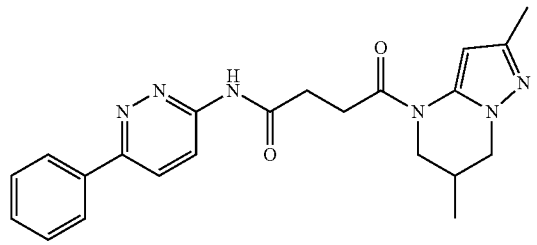 | 4-(2,6-dimethyl-6,7-dihydropyrazolo[1,5-a]pyrimidin-4(5H)-yl)-4-oxo-N-(6-phenylpyridazin-3-yl)butanamide | <0.1 |
| 140 | 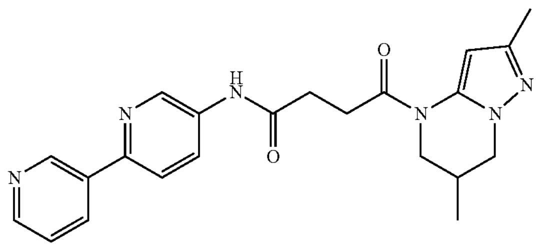 [SMILES: Cc1cc2n(n1)CC(C)CN2C(=O)CCC(=O)Nc1ccc(-c2cccnc2)nc1] | N-(2,3'-pyridin-5-yl)-4-(2,6-dimethyl-6,7-dihydropyrazolo[1,5-a]pyrimidin-4(5H)-yl)-4-oxobutanamide | <0.1 |
| 141 | 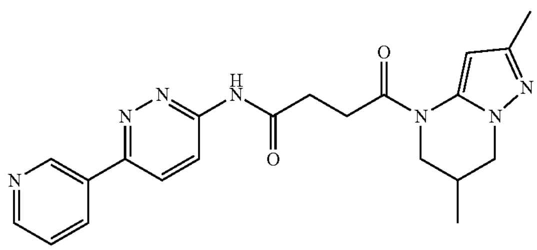 [SMILES: Cc1cc2n(n1)CC(C)CN2C(=O)CCC(=O)Nc1ccc(-c2cccnc2)nn1] | 4-(2,6-dimethyl-6,7-dihydropyrazolo[1,5-a]pyrimidin-4(5H)-yl)-4-oxo-N-(6-(pyridin-3-yl)pyridazin-3-yl)butanamide | <0.1 |
| 142 | 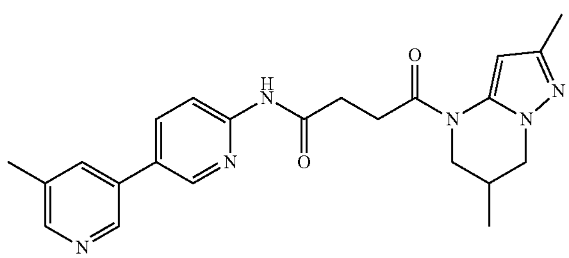 | 4-(2,6-dimethyl-6,7-dihydropyrazolo[1,5-a]pyrimidin-4(5H)-yl)-N-(5'-methyl-[3,3'-bipyridin]-6-yl)-4-oxobutanamide | <0.1 |
| 143 | 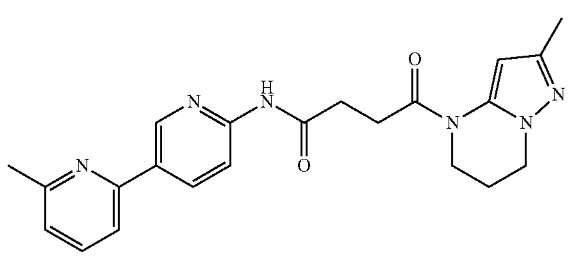 | 4-(2-methyl-6,7-dihydropyrazolo[1,5-a]pyrimidin-4(5H)-yl)-N-(6-methyl-[2,3'-bipyridin]-6'-yl)-4-oxobutanamide | <0.1 |
| 144 | 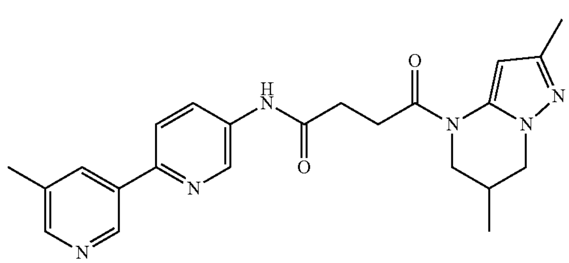 | 4-(2,6-dimethyl-6,7-dihydropyrazolo[1,5-a]pyrimidin-4(5H)-yl)-N-(5'-methyl-[2,3'-bipyridin]-5-yl)-4-oxobutanamide | <0.1 |

| Cpd ID | Structure | IUPAC Name | STF3A IC50 μM |
|---|---|---|---|
| 145 | 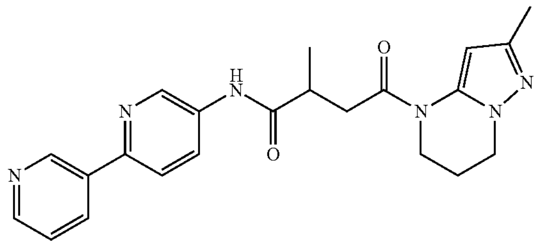 | N-([2,3'-bipyridin]-5-yl)-2-methyl-4-(2-methyl-6,7-dihydropyrazolo[1,5-a]pyrimidin-4(5H)-yl)-4-oxobutanamide | <0.1 |
| 146 | 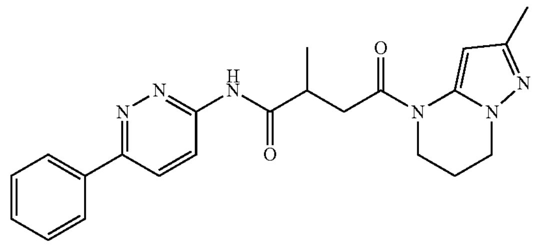 [SMILES: Cc1cc2n(n1)CCCN2C(=O)CC(C)C(=O)Nc1ccc(-c2ccccc2)nn1] | 2-methyl-4-(2-methyl-6,7-dihydropyrazolo[1,5-a]pyrimidin-4(5H)-yl)-4-oxo-N-(6-phenylpyridazin-3-yl)butanamide | <0.1 |
| 147 | 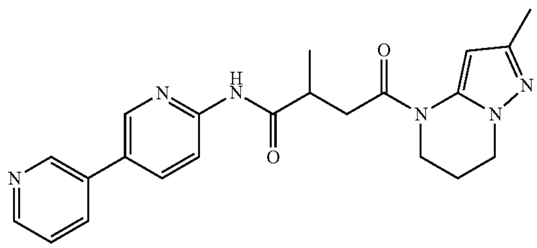 | N-([3,3'-bipyridin]-6-yl)-2-methyl-4-(2-methyl-6,7-dihydropyrazolo[1,5-a]pyrimidin-4(5H)-yl)-4-oxobutanamide | <0.1 |
| 148 | 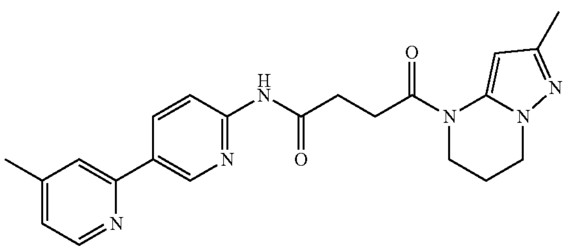 | N-(4-methyl-2,3'-bipyridin-6'-yl)-4-(2-methyl-6,7-dihydropyrazolo[1,5-a]pyrimidin-4(5H)-yl)-4-oxobutanamide | <0.1 |
| 149 | 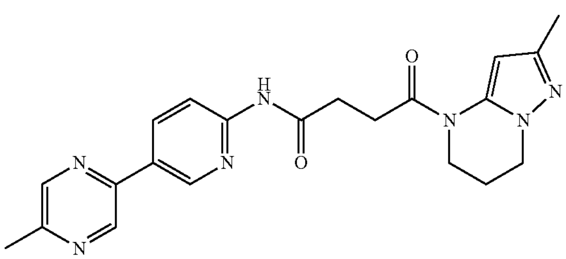 | 4-(2-methyl-6,7-dihydropyrazolo[1,5-a]pyrimidin-4(5H)-yl)-N-(5-(5-methylpyrazin-2-yl)pyridin-2-yl)-4-oxobutanamide | <0.1 |
| 150 | 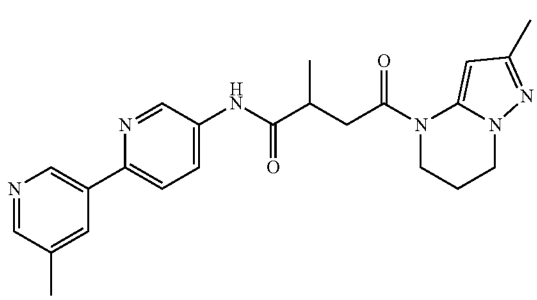 [SMILES: Cc1cncc(-c2ccc(NC(=O)C(C)CC(=O)N3CCCn4nc(C)cc43)cn2)c1] | 2-methyl-4-(2-methyl-6,7-dihydropyrazolo[1,5-a]pyrimidin-4(5H)-yl)-N-(5'-methyl-[2,3'-bipyridin]-5-yl)-4-oxobutanamide | <0.1 |

-continued

| Cpd ID | Structure | IUPAC Name | STF3A IC50 μM |
|---|---|---|---|
| 151 | 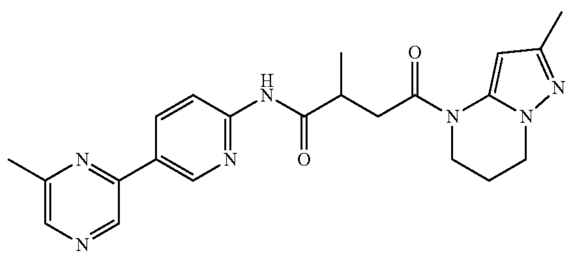 | 2-methyl-4-(2-methyl-6,7-dihydropyrazolo[1,5-a]pyrimidin-4(5H)-yl)-N-(5-(6-methylpyrazin-2-yl)pyridin-2-yl)-4-oxobutanamide | <0.1 |
| 152 | 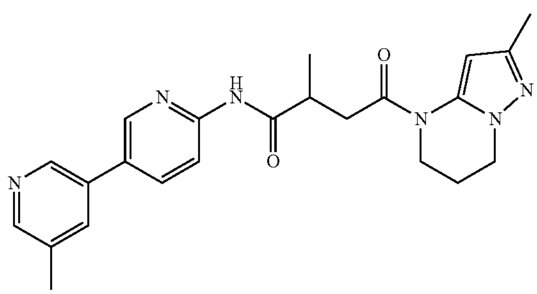 [SMILES: Cc1cncc(-c2ccc(NC(=O)C(C)CC(=O)N3CCCn4nc(C)cc43)nc2)c1] | 2-methyl-4-(2-methyl-6,7-dihydropyrazolo[1,5-a]pyrimidin-4(5H)-yl)-N-(5'-methyl-[3,3'-bipyridin]-6-yl)-4-oxobutanamide | <0.1 |
| 153 | 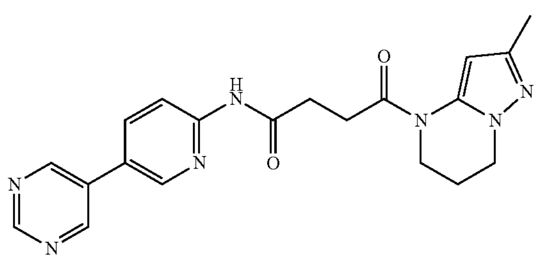 [SMILES: Cc1cc2n(n1)CCCN2C(=O)CCC(=O)Nc1ccc(-c2cncnc2)cn1] | 4-(2-methyl-6,7-dihydropyrazolo[1,5-a]pyrimidin-4(5H)-yl)-4-oxo-N-(5-(pyrimidin-5-yl)pyridin-2-yl)butanamide | <0.1 |
| 154 | 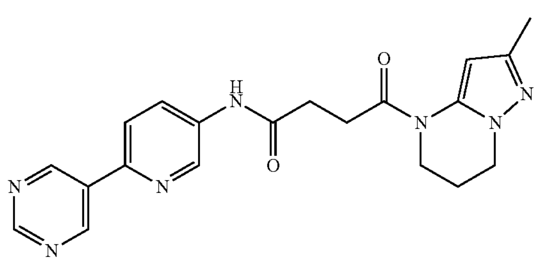 [SMILES: Cc1cc2n(n1)CCCN2C(=O)CCC(=O)Nc1ccc(-c2cncnc2)nc1] | 4-(2-methyl-6,7-dihydropyrazolo[1,5-a]pyrimidin-4(5H)-yl)-4-oxo-N-(6-(pyrimidin-5-yl)pyridin-3-yl)butanamide | <1 |
| 155 | 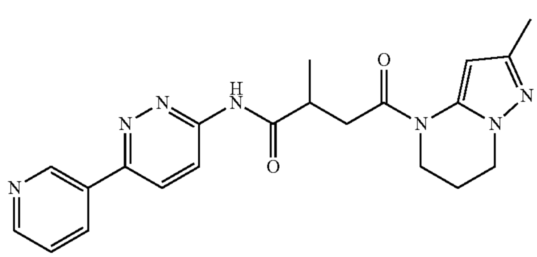 [SMILES: Cc1cc2n(n1)CCCN2C(=O)CC(C)C(=O)Nc1ccc(-c2cccnc2)nn1] | N-(2-fluorobiphenyl-4-yl)-4-(2-methyl-6,7-dihydropyrazolo[1,5-a]pyrimidin-4(5H)-yl)-4-oxobutanamide | <0.1 |

-continued

| Cpd ID | Structure | IUPAC Name | STF3A IC50 μM |
|---|---|---|---|
| 156 | 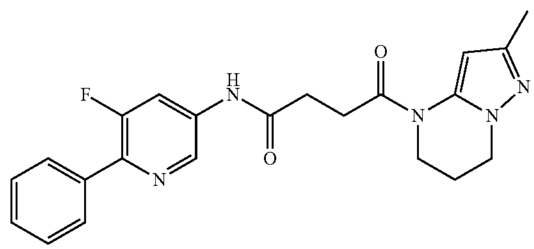 | N-(5-fluoro-6-phenylpyridin-3-yl)-4-(2-methyl-6,7-dihydropyrazolo[1,5-a]pyrimidin-4(5H)-yl)-4-oxobutanamide | <0.1 |
| 157 | 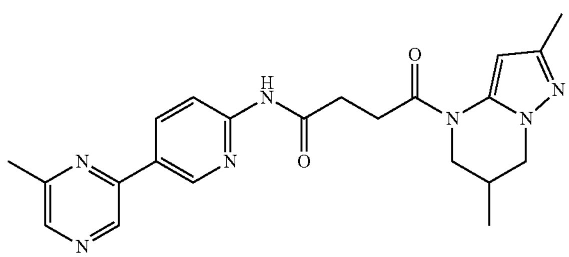 | 4-(2,6-dimethyl-6,7-dihydropyrazolo[1,5-a]pyrimidin-4(5H)-yl)-N-(5-(6-methylpyrazin-2-yl)pyridin-2-yl)-4-oxobutanamide | <0.1 |
| 158 | 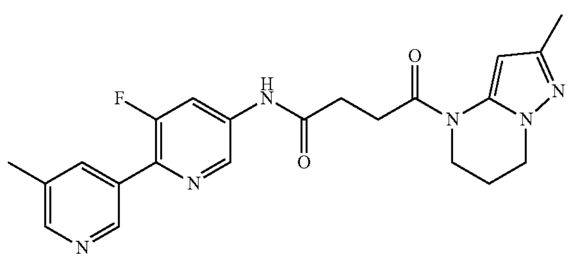 | N-(3-fluoro-5'-methyl-[2,3'-bipyridin]-4-yl)-4-(2-methyl-6,7-dihydropyrazolo[1,5-a]pyrimidin-4(5H)-yl)-4-oxobutanamide | <0.1 |
| 159 | 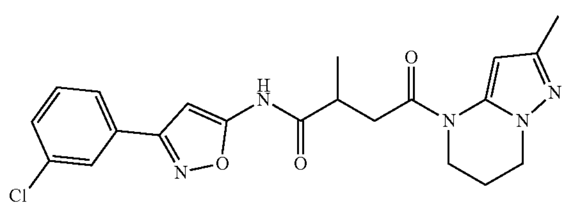 [SMILES: Cc1cc2n(n1)CCCN2C(=O)CC(C)C(=O)Nc1cc(-c2cccc(Cl)c2)no1] | N-(3-(3-chlorophenyl)isoxazol-5-yl)-2-methyl-4-(2-methyl-6,7-dihydropyrazolo[1,5-a]pyrimidin-4(5H)-yl)-4-oxobutanamide | <5 |
| 160 | 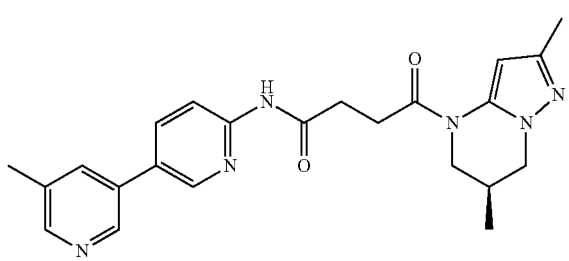 | (S)-4-(2,6-dimethyl-6,7-dihydropyrazolo[1,5-a]pyrimidin-4(5H)-yl)-N-(5'-methyl-[3,3'-bipyridin]-6-yl)-4-oxobutanamide | <0.1 |
| 161 | 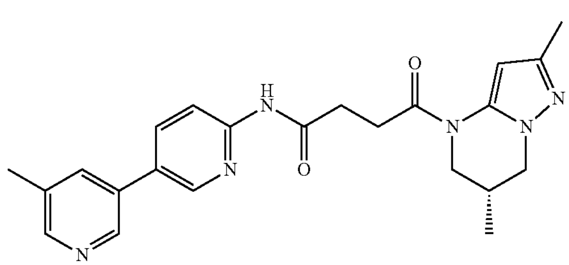 | (R)-4-(2,6-dimethyl-6,7-dihydropyrazolo[1,5-a]pyrimidin-4(5H)-yl)-N-(5'-methyl-[3,3'-bipyridin]-6-yl)-4-oxobutanamide | <0.1 |

-continued

| Cpd ID | Structure | IUPAC Name | STF3A IC50 μM |
|---|---|---|---|
| 162 | 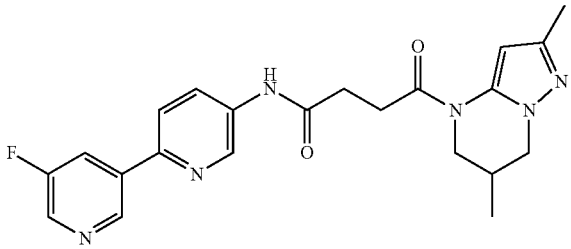 [SMILES: Cc1cc2n(n1)CC(C)CN2C(=O)CCC(=O)Nc1ccc(-c2cncc(F)c2)nc1] | 4-(2,6-dimethyl-6,7-dihydropyrazolo[1,5-a]pyrimidin-4(5H)-yl)-N-(5'-fluoro-[2,3'-bipyridin]-5-yl)-4-oxobutanamide | <0.1 |
| 163 | 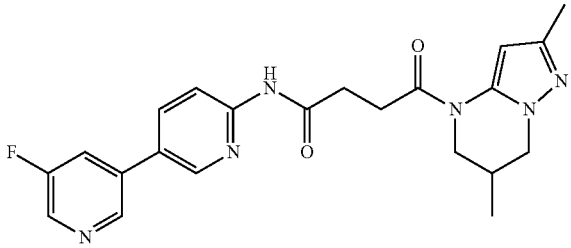 [SMILES: Cc1cc2n(n1)CC(C)CN2C(=O)CCC(=O)Nc1ccc(-c2cncc(F)c2)cn1] | 4-(2,6-dimethyl-6,7-dihydropyrazolo[1,5-a]pyrimidin-4(5H)-yl)-N-(5'-fluoro-[3,3'-bipyridin]-6-yl)-4-oxobutanamide | <0.1 |
| 164 | 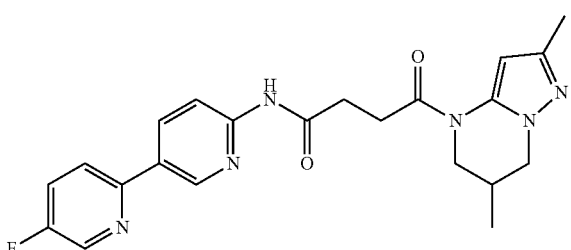 | 4-(2,6-dimethyl-6,7-dihydropyrazolo[1,5-a]pyrimidin-4(5H)-yl)-N-(5-fluoro-[2,3'-bipyridin]-6'-yl)-4-oxobutanamide | <1 |
| 165 | 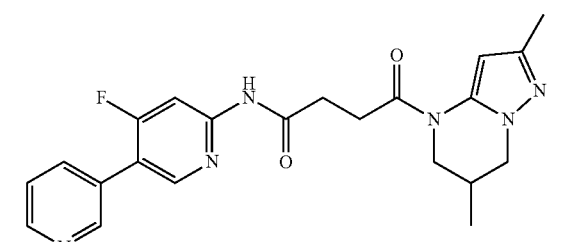 | 4-(2,6-dimethyl-6,7-dihydropyrazolo[1,5-a]pyrimidin-4(5H)-yl)-N-(4-fluoro-[3,3'-bipyridin]-6-yl)-4-oxobutanamide | <0.1 |
| 166 | 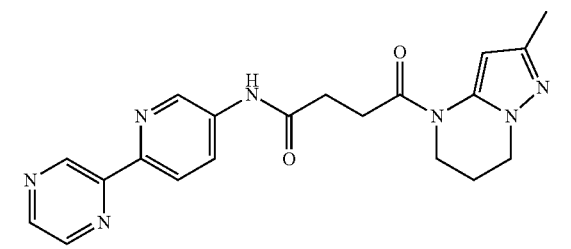 [SMILES: Cc1cc2n(n1)CCCN2C(=O)CCC(=O)Nc1ccc(-c2cnccn2)nc1] | 4-(2-methyl-6,7-dihydropyrazolo[1,5-a]pyrimidin-4(5H)-yl)-4-oxo-N-(6-(pyrazin-2-yl)pyridin-3-yl)butanamide | <1 |
| 167 | 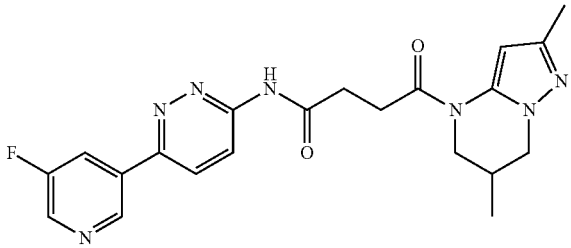 [SMILES: Cc1cc2n(n1)CC(C)CN2C(=O)CCC(=O)Nc1ccc(-c2cncc(F)c2)nn1] | 4-(2,6-dimethyl-6,7-dihydropyrazolo[1,5-a]pyrimidin-4(5H)-yl)-N-(6-(5-fluoropyridin-3-yl)pyridazin-3-yl)-4-oxobutanamide | <0.1 |

-continued

| Cpd ID | Structure | IUPAC Name | STF3A IC50 μM |
|---|---|---|---|
| 168 | 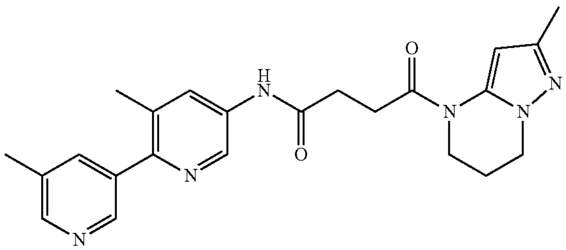 | N-(3,5'-dimethyl-[2,3'-bipyridin]-5-yl)-4-(2-methyl-6,7-dihydropyrazolo[1,5-a]pyrimidin-4(5H)-yl)-4-oxobutanamide | <1 |
| 169 | 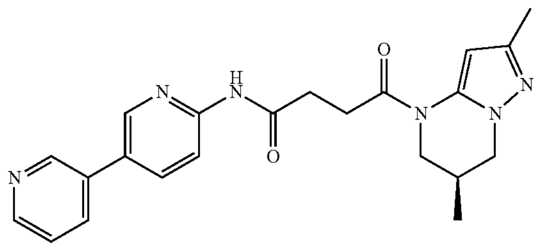 [SMILES: Cc1cc2n(n1)C[C@@H](C)CN2C(=O)CCC(=O)Nc1ccc(-c2cccnc2)cn1] | (S)-N-([3,3'-bipyridin]-6-yl)-4-(2,6-dimethyl-6,7-dihydropyrazolo[1,5-a]pyrimidin-4(5H)-yl)-4-oxobutanamide | <0.1 |
| 170 | 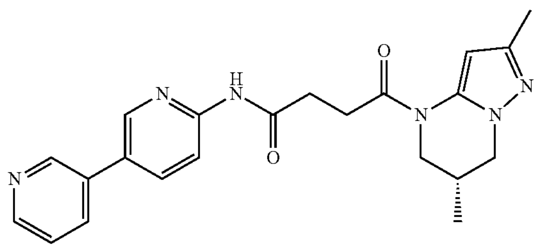 [SMILES: Cc1cc2n(n1)C[C@H](C)CN2C(=O)CCC(=O)Nc1ccc(-c2cccnc2)cn1] | (R)-N-([3,3'-bipyridin]-6-yl)-4-(2,6-dimethyl-6,7-dihydropyrazolo[1,5-a]pyrimidin-4(5H)-yl)-4-oxobutanamide | <0.1 |
| 171 | 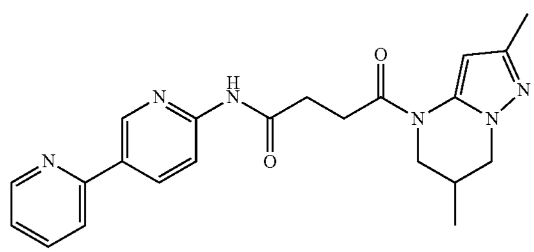 [SMILES: Cc1cc2n(n1)CC(C)CN2C(=O)CCC(=O)Nc1ccc(-c2ccccn2)cn1] | N-([2,3'-bipyridin]-6'-yl)-4-(2,6-dimethyl-6,7-dihydropyrazolo[1,5-a]pyrimidin-4(5H)-yl)-4-oxobutanamide | <0.1 |

In one embodiment, compounds selected from Examples 1 to 171 having an IC$_{50}$ against STF3A cells of 10 micromolar or more are excluded.

Synthesis of the Examples

The compounds were synthesized according to the following general synthesis schemes:

Compounds of formula (I) in which W and X each represent C=O, and can be synthesised according to the following scheme:

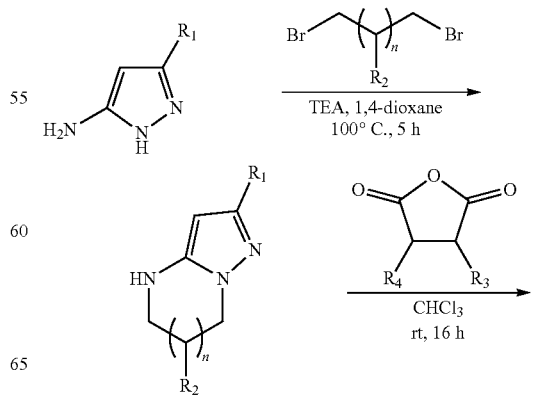

Compounds of formula (I) in which W and X each represent $CH_2$, and can be synthesised according to the following scheme:

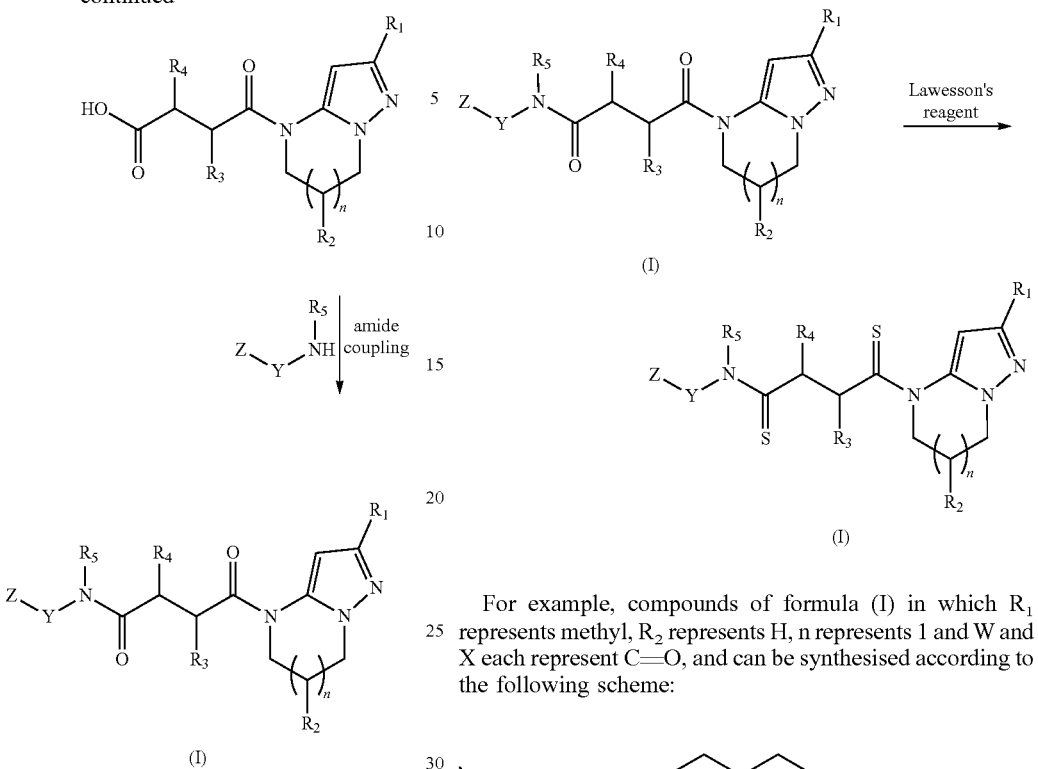

Compounds of formula (I) in which W and X each represent C=S, and can be synthesised according to the following scheme:

For example, compounds of formula (I) in which $R_1$ represents methyl, $R_2$ represents H, n represents 1 and W and X each represent C=O, and can be synthesised according to the following scheme:

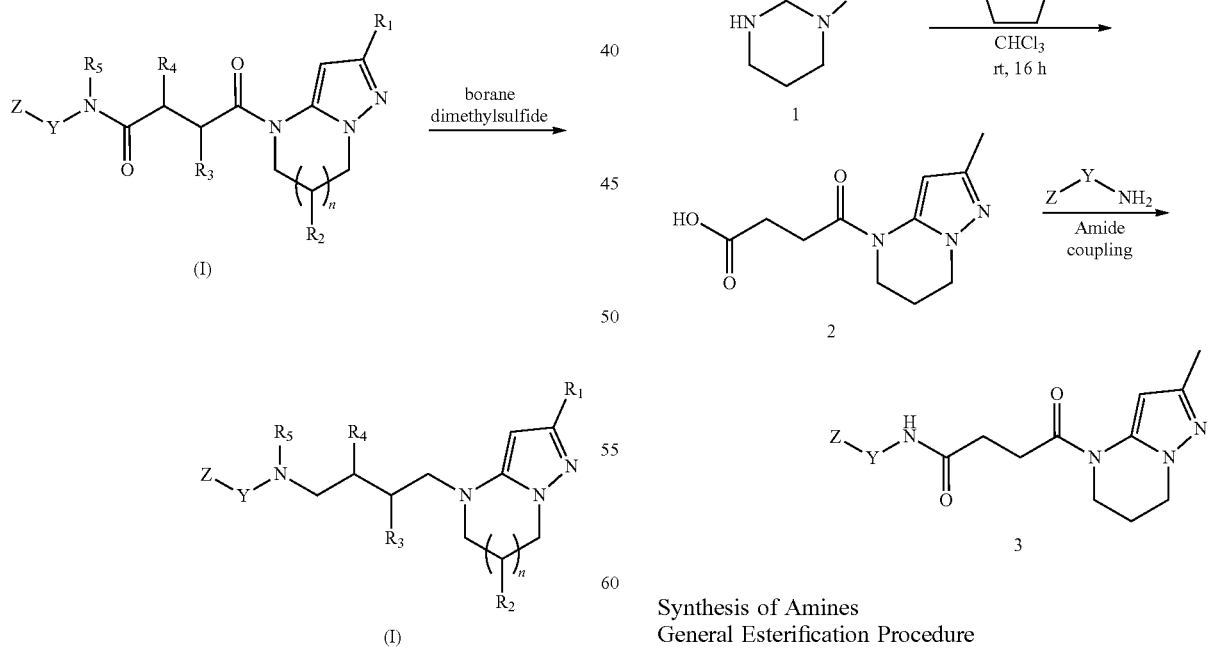

Synthesis of Amines
General Esterification Procedure

To a solution of the corresponding benzoic acid (1 equiv.) in methanol (0.65 M) was added concentrated sulphuric (32 M), and the resulting reaction mixture was heated at 70° C. for 10 h. After completion, the reaction mixture concentrated, water was added and extracted with ethyl acetate. The combined organic layers were washed with aqueous sodium bicarbonate solution and brine, dried over sodium sulphate and concentrated under vacuum to give the desired ester.

General Formation of 3-phenyl-3-oxopropanenitrile Procedure

The corresponding ester prepared above (1 equiv.) in tetrahydrofuran (0.9 M) and acetonitrile (1 equiv.) was added dropwise to a stirred solution of sodium hydride (1.5 equiv.) in tetrahydrofuran (0.65M). The resulting reaction mixture was stirred at 70° C. for 16 h. After completion of starting material, the reaction mixture was quenched with ice cold water and acidified to pH 5 with concentrated hydrochloric acid and extracted with ethyl acetate. The combined organic layers were washed brine, dried over sodium sulphate and concentrated under vacuum to give the desired product.

General Formation of Amines

To a stirred solution of the corresponding 3-phenyl-3-oxopropanenitrile (1 equiv.) in water (0.7M) was added aqueous sodium hydroxide (2 equiv.) solution and hydroxylamine hydrochloride (1.1 equiv.) at room temperature. The resulting reaction mixture was stirred at 100° C. for 5 h. After completion of starting material, the reaction mixture was cooled to room temperature and precipitated solid was collected by filtration and dried to give the desired product.

Synthesis of 3-(2-chlorophenyl)isoxazol-5-amine

Step 1: Preparation of methyl 2-chlorobenzoate

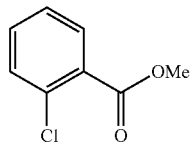 [SMILES: COC(=O)c1ccccc1Cl]

$^1$H NMR (400 MHz, DMSO-d$_6$): 7.84-7.82 (dd, J$_1$=7.6 Hz, J$_2$=1.2 Hz, 1H), 7.47-7.40 (m, 2H), 7.34-7.26 (m, 1H), 3.94 (s, 3H). LC-MS: m/z 170.9 [M+H]$^+$.

Step 2: Preparation of 3-(2-chlorophenyl)-3-oxopropanenitrile

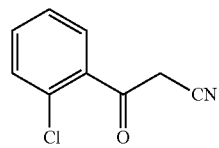 [SMILES: N#CCC(=O)c1ccccc1Cl]

LC-MS: 178.0 [M+H]$^+$.

Step 3: Preparation of 3-(2-chlorophenyl)isoxazol-5-amine

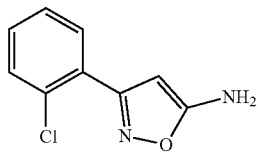 [SMILES: Nc1cc(-c2ccccc2Cl)no1]

$^1$H NMR (400 MHz, DMSO-d$_6$): 7.70-7.67 (m, 1H), 7.49-7.42 (m, 1H), 7.39-7.32 (m, 2H), 5.60 (s, 1H), 4.52 (brs, 2H). LC-MS: 194.9 [M+H]$^+$.

Synthesis of 3-phenylisoxazol-5-amine

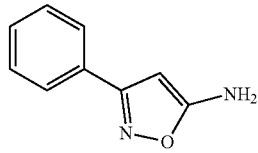 [SMILES: Nc1cc(-c2ccccc2)no1]

$^1$H NMR (400 MHz, DMSO-d$_6$): 7.73-7.74 (d, J=8.4 Hz, 2H), 7.45-7.43 (m, 3H), 6.78 (brs, 2H), 5.40 (s, 1H). LC-MS: m/z 161.0 [M+H]$^+$.

Synthesis of 3-(3-chlorophenyl)isoxazol-5-amine

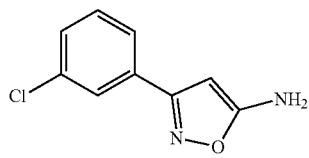 [SMILES: Nc1cc(-c2cccc(Cl)c2)no1]

LC-MS: m/z 195 [M+H]$^+$.

Synthesis of 3-(4-chlorophenyl)isoxazol-5-amine

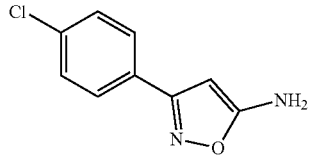 [SMILES: Nc1cc(-c2ccc(Cl)cc2)no1]

$^1$H NMR (400 MHz, DMSO-d$_6$): 7.76-7.74 (d, J=8.4 Hz, 2H), 7.52-7.50 (d, J=8.4 Hz, 2H), 6.85 (brs, 2H), 5.42 (s, 1H). LC-MS: m/z 194.9 [M+H]$^+$.

Synthesis of 3-(3,4-dichlorophenyl)isoxazol-5-amine (VCW-WNT-168B)

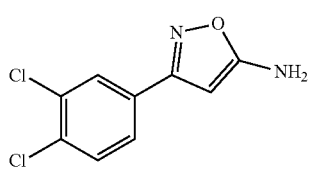 [SMILES: Nc1cc(-c2ccc(Cl)c(Cl)c2)no1]

$^1$H NMR (400 MHz, DMSO-d$_6$): 7.97-7.96 (m, 1H), 7.73-7.72 (m, 2H), 6.88 (s, 2H), 5.51 (s, 1H). LC-MS: m/z 230 [M+H]$^+$.

Synthesis of 3-(3-fluorophenyl)isoxazol-5-amine

Step 1: Preparation of 3-(3-fluorophenyl)-3-oxopropanenitrile

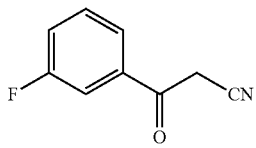 [SMILES: N#CCC(=O)c1cccc(F)c1]

LC-MS: m/z 162.0 [M+H]+.

Step 2: Preparation of 3-(3-fluorophenyl)isoxazol-5-amine

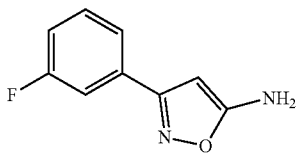 [SMILES: Nc1cc(-c2cccc(F)c2)no1]

$^1$H NMR (400 MHz, DMSO-d$_6$): 7.60-7.47 (m, 3H), 7.30-7.26 (t, J=8.4 Hz, 1H), 6.88 (brs, 2H), 5.42 (s, 1H). LC-MS: m/z 177.0 [M+H]+.

Synthesis of 3-(o-tolyl)isoxazol-5-amine

Step 1: Preparation of 3-oxo-3-(o-tolyl)propanenitrile

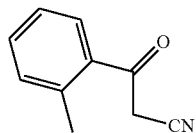

$^1$H NMR (400 MHz, DMSO-d$_6$): 7.63-7.61 (m, 1H), 7.50-7.46 (m, 1H), 7.34-7.31 (m, 2H), 4.03 (s, 2H), 2.57 (s, 3H).

Step 2: Preparation 3-(o-tolyl)isoxazol-5-amine

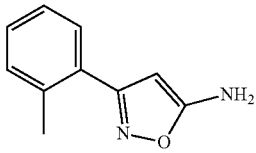

$^1$H NMR (400 MHz, DMSO-d$_6$): 7.44-7.42 (m, 1H), 7.35-7.23 (m, 3H), 6.70 (s, 2H), 5.18 (s, 1H), 2.39 (s, 3H). LC-MS: m/z 175 [M+H]+.

Synthesis of 3-(4-chloropyridin-2-yl)isoxazol-5-amine

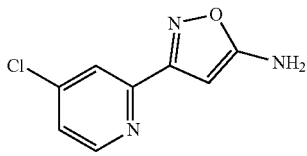 [SMILES: Nc1cc(-c2cc(Cl)ccn2)no1]

$^1$H NMR (400 MHz, Methanol-d$_4$): 8.55 (d, J=4.8 Hz, 1H), 7.92 (m, 1H), 7.50 (dd, J=4 Hz, 2 Hz, 1H), 5.61 (s, 1H). LC-MS: m/z 196 [M+H]+.

Synthesis of 3-(5-chloropyridin-2-yl)isoxazol-5-amine

Step 1: Preparation of 3-(5-chloropyridin-2-yl)-3-oxopropanenitrile

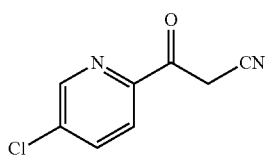 [SMILES: N#CCC(=O)c1ccc(Cl)cn1]

$^1$H NMR (400 MHz, DMSO-d$_6$): 8.81 (br s, 1H), 8.17 (br s, 1H), 8.04-8.02 (m, 1H), 4.70 (br s, 2H). LC-MS: m/z 182 [M+H]+.

Step 2: Preparation of 3-(5-chloropyridin-2-yl)isoxazol-5-amine

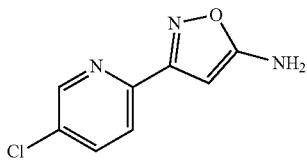 [SMILES: Nc1cc(-c2ccc(Cl)cn2)no1]

$^1$H NMR (400 MHz, DMSO-d$_6$): 8.70 (m, 1H), 8.03-8.00 (m, 1H), 7.89-7.87 (m, 1H), 6.88 (s, 2H), 5.44 (s, 1H). LC-MS: m/z 196 [M+H]+.

Synthesis of 3-(5-chloropyridin-3-yl)isoxazol-5-amine

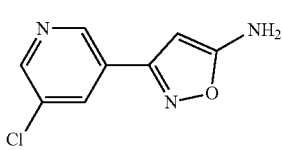 [SMILES: Nc1cc(-c2cncc(Cl)c2)no1]

$^1$H NMR (400 MHz, DMSO-d$_6$): 8.90 (s, 1H), 8.69 (s, 1H), 8.24 (s, 1H), 6.96 (s, 2H), 5.59 (s, 1H). LC-MS: m/z 196 [M+H]+.

Synthesis of 3-(3-chlorophenyl)-1-methyl-1H-pyrazol-5-amine

Step 1: Preparation of 3-(3-chlorophenyl)-3-oxopropanenitrile

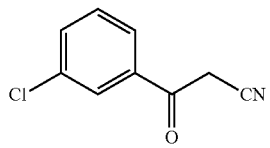 [SMILES: N#CCC(=O)c1cccc(Cl)c1]

LC-MS: m/z 178.0 [M+H]$^+$.

Step 2: Preparation of 3-(3-chlorophenyl)-1-methyl-1H-pyrazol-5-amine

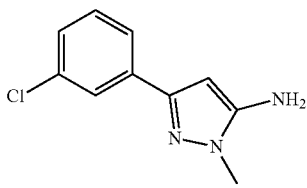

$^1$H NMR (400 MHz, DMSO-d$_6$): 7.81-7.77 (m, 1H), 7.72-7.70 (m, 1H), 7.46-7.42 (m, 3H), 5.99 (s, 2H), 3.68 (s, 3H). LC-MS: 208 [M+H]$^+$.

Synthesis of 5-(3-chlorophenyl)isoxazol-3-amine

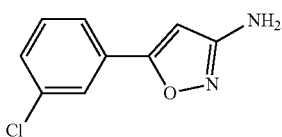 [SMILES: Nc1cc(-c2cccc(Cl)c2)on1]

A stirred solution of 3-(3-chlorophenyl)-3-oxopropanenitrile (1 equiv.) and hydroxylamine hydrochloride (1.2 equiv.) in a mixture of ethanol (0.02 M) and water (0.02 M) was adjusted to pH 8 using sodium hydroxide solution and heated at 60° C. for 18 h. The reaction mixture was then acidified to pH 2 using hydrochloride solution and further heated at 80° C. for 1 h. It was then allowed to cool to room temperature, basified to pH 10, diluted with water and extracted with ethyl acetate. The combined organic layers were dried over magnesium sulphate and concentrated under vacuum. The crude residue was purified by column chromatography to afford the purified product.

$^1$H NMR (400 MHz, DMSO-d$_6$): 7.83 (s, 1H), 7.74-7.71 (m, 1H), 7.52-7.51 (m, 2H), 6.44 (s, 1H), 5.71 (s, 2H). LC-MS: m/z 195 [M+H]$^+$.

Synthesis of 4-(pyrrolidin-1-yl)aniline

Step 1: Preparation of 1-(4-nitrophenyl)pyrrolidine

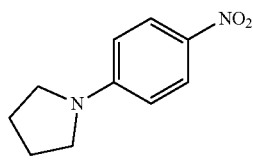 [SMILES: O=[N+]([O-])c1ccc(N2CCCC2)cc1]

Triethylamine was added to a stirred solution of 1-fluoro-4-nitrobenzene (1.0 equiv.) and pyrrolidine (1.3 equiv.) in 2-propanol (0.1 M). The reaction was allowed to stir at reflux for 6 h. Upon consumption of starting material, solvent was evaporated to dryness; the crude diluted with water; extracted with dichloromethane; organic layers combined; washed with brine; dried over magnesium sulphate and concentrated in vacuo. The crude was dissolved in isopropanol and filtered to afford the pure product as a bright yellow solid.

1H NMR (400 MHz, DMSO-d$_6$): 8.05 (d, J=9.2 Hz, 2H), 6.61 (d, J=9.2 Hz, 2H), 3.39 (m, 4H), 2.00-1.97 (m, 4H). LC-MS: m/z 193 [M+H]$^+$.

Step 2: Preparation of 4-(pyrrolidin-1-yl)aniline

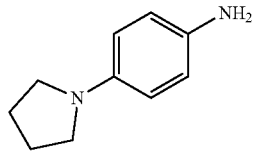

$^1$H NMR (400 MHz, DMSO-d$_6$): 6.49 (d, J=8.4 Hz, 2H), 6.35 (d, J=8.4 Hz, 2H), 4.24 (br s, 2H), 3.07 (br s, 4H), 1.90-1.87 (m, 4H). LC-MS: m/z 163 [M+H]$^+$.

Synthesis of 1-phenylpiperidin-4-amine

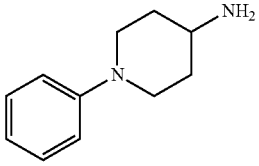 [SMILES: NC1CCN(c2ccccc2)CC1]

To a stirred solution of chlorobenzene (1.0 g, 8.92 mmol) in xylene (20 mL) were added 4-amino piperidine (0.93 mL, 8.92 mmol), KO$^t$Bu (2.0 g, 17.84 mmol), X-Phos (636 mg, 1.33 mmol) and Pd$_2$(dba)$_3$ (816 mg, 0.89 mmol), degassed with argon for 10 min. The reaction mixture was heated at 130° C. for 16 h. TLC indicated some starting material and formation of a new spot. The reaction mixture was filtered and concentrated under reduced pressure, poured into ice-cold water and extracted with EtOAc. The combined organic layer was washed with water and brine solution, dried over anhydrous sodium sulphate, filtered, concentrated under reduced pressure and purified by column chromatography to afford the desired product.

LC-MS: m/z 175 [M+H]$^+$.

Suzuki Coupling

General Suzuki Procedure A

Degassed solution of bromoaniline derivative (1.0 equiv.) in 1,4-dioxane (4 mL). Add potassium carbonate (3.0 equiv.) in water (1 mL) and boronic acid/pinacol ester to solution. Degassed for 10 minutes before adding tetrakistriphenylphosphine palladium catalyst (0.1 eq). Degas for another 10 minutes and heat at reflux for 18 h. Solution is filtered through Celite® and extracted with water and dichloromethane. The organic phase combined, dried over sodium sulphate, filtered and evaporated to dryness in vacuo. Crude was dissolved in dimethylformamide, acetonitrile and water and purified with preparative HPLC or by flash column chromatography to yield the desired product.

Synthesis of 4-(1-methyl-1H-pyrazol-5-yl)aniline

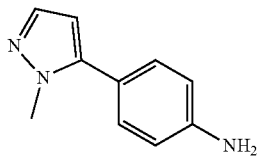

$^1$H NMR (400 MHz, DMSO-d$_6$): 7.36 (s, 1H), 7.14 (d, J=8.4 Hz, 2H), 6.64 (d, J=8.4 Hz, 2H), 6.18 (s, 1H), 5.33 (s, 2H), 3.77 (s, 3H). LC-MS: m/z 174 [M+H]$^+$.

Synthesis of 5-phenylpyrazin-2-amine

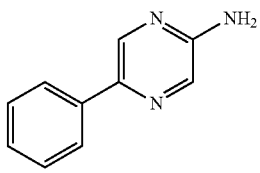 [SMILES: Nc1cnc(-c2ccccc2)cn1]

$^1$H NMR (400 MHz, DMSO-d$_6$): 8.49 (m, 1H), 7.96 (m, 1H), 7.92-7.90 (m, 2H), 7.43-7.40 (m, 2H), 7.33-7.29 (m, 1H), 6.53 (s, 2H). LC-MS: m/z 172 [M+H]$^+$.

Synthesis of 3-methoxy-[1,1'-biphenyl]-4-amine

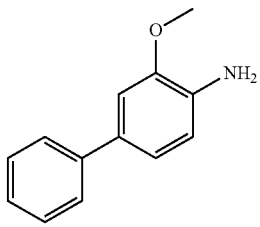

LC-MS: m/z 200 [M+H]$^+$.

Synthesis of 4'-nitro-[1,1'-biphenyl]-4-amine

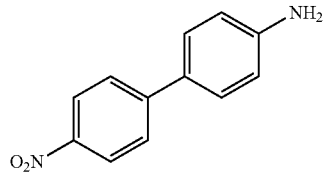 [SMILES: Nc1ccc(-c2ccc([N+](=O)[O-])cc2)cc1]

$^1$H NMR (400 MHz, Chloroform-d): 8.24 (d, J=9.2 Hz, 2H), 7.66 (d, J=9.2 Hz, 2H), 7.47 (d, J=8.4 Hz, 2H), 6.77 (d, J=8.4 Hz, 2H), 3.87 (s, 2H). LC-MS: m/z 215 [M+H]$^+$.

Synthesis of 6-(3-chlorophenyl)pyridin-3-amine

Step 1: Preparation of 2-(3-chlorophenyl)-5-nitropyridine

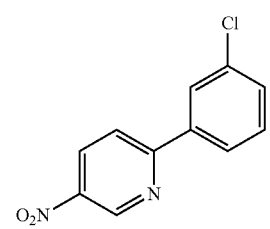 [SMILES: O=[N+]([O-])c1ccc(-c2cccc(Cl)c2)nc1]

$^1$H NMR (400 MHz, Chloroform-d): 9.49-9.50 (m, 1H), 8.54-8.56 (m, 1H), 8.11 (s, 1H), 7.95-7.97 (m, 1H), 7.89-7.91 (m, 1H), 7.48-7.51 (m, 2H). LC-MS: m/z 235 [M+H]$^+$.

Step 2: Preparation of 6-(3-chlorophenyl)pyridin-3-amine

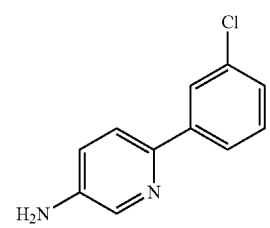

A solution of 2-(3-chlorophenyl)-5-nitropyridine in 2:1 ethanol and water (0.1M) was added iron powder (5 equiv.) and acetic acid (5 equiv.). The reaction was stirred vigorously at room temperature under ambient atmosphere for 30 min. After completion of starting material, the reaction mixture was basify with 1N NaOH (pH 8-10) and extracted with ethyl acetate. The combined organic layers were washed with brine, dried with sodium sulphate and concentrated under vacuum to afford product.

$^1$H NMR (400 MHz, Chloroform-d): 8.17-8.18 (m, 1H), 7.89-7.90 (m, 1H), 7.74-7.77 (m, 1H), 7.50-7.52 (m, 1H), 7.32-7.36 (m, 1H), 7.27-7.30 (m, 1H), 7.03-7.06 (m, 1H). LC-MS: m/z 205 [M+H]$^+$.

Synthesis of 6-(3-fluorophenyl)pyridin-3-amine

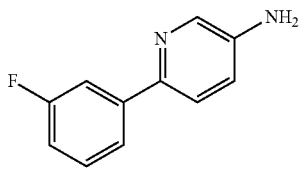 [SMILES: Nc1ccc(-c2cccc(F)c2)nc1]

$^1$H NMR (400 MHz, DMSO-$d_6$): 8.14 (s, 1H), 8.02 (s, 1H), 7.76-7.74 (m, 1H), 7.68-7.66 (m, 1H), 7.44-7.38 (m, 2H), 7.10-7.07 (m, 1H), 7.05-6.97 (m, 1H), 5.55 (s, 2H). LC-MS: m/z 189 [M+H]$^+$.

Synthesis of 6-(m-tolyl)pyridin-3-amine

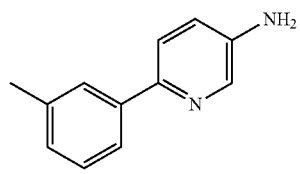

$^1$H NMR (400 MHz, DMSO-$d_6$): 8.01-8.00 (m, 1H), 7.74 (bs, 1H), 7.69-7.67 (m, 1H), 7.60 (d, J=8.4 Hz, 1H), 7.26 (t, J=7.6 Hz, 1H), 7.09-7.07 (m, 1H), 6.99-6.97 (m, 1H), 5.42 (s, 2H), 2.35 (s, 3H). LC-MS: m/z 185 [M+H]$^+$.

Synthesis of 5-(3-chlorophenyl)pyridin-2-amine

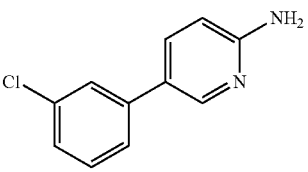 [SMILES: Nc1ccc(-c2cccc(Cl)c2)cn1]

LC-MS: m/z 205 [M+H]$^+$.

Synthesis of 5-(3-fluorophenyl)pyridin-2-amine

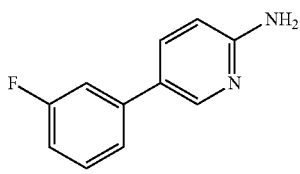 [SMILES: Nc1ccc(-c2cccc(F)c2)cn1]

$^1$H NMR (400 MHz, DMSO-$d_6$): 8.29 (s, 1H), 7.73 (dd, J=8.6 Hz, J=2.6 Hz, 1H), 7.43-7.39 (m, 3H), 7.09-7.05 (m, 1H), 6.52 (d, J=8.8 Hz, 1H), 6.12 (s, 2H). LC-MS: m/z 189 [M+H]$^+$.

Synthesis of 5-(4-fluorophenyl)pyridin-2-amine

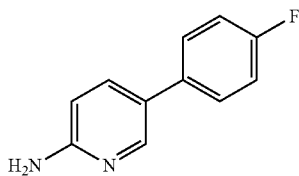 [SMILES: Nc1ccc(-c2ccc(F)cc2)cn1]

$^1$H NMR (400 MHz, Methanol-$d_4$): 8.20 (s, 1H), 8.09-8.10 (m, 1H), 7.87-7.90 (m, 1H), 7.54-7.57 (m, 2H), 7.14-7.18 (m, 2H), 6.80-6.82 (m, 1H).

Synthesis of 3-methyl-5-phenylpyridin-2-amine

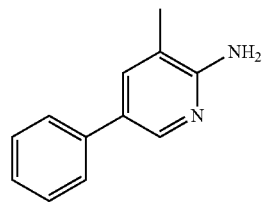

$^1$H NMR (400 MHz, DMSO-$d_6$): 8.11 (s, 1H), 7.56-7.54 (m, 3H), 7.39 (t, J=7.2 Hz, 2H), 7.25 (t, J=7.6 Hz, 1H), 5.80 (s, 2H), 2.11 (s, 3H). LC-MS: m/z 185 [M+H]$^+$.

Synthesis of 5-(m-tolyl)pyridin-2-amine

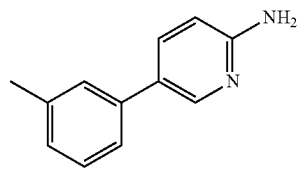

$^1$H NMR (400 MHz, DMSO-$d_6$): 8.22-8.21 (m, 1H), 7.68-7.66 (m, 1H), 7.37-7.32 (m, 2H), 7.27 (m, 1H), 7.08-7.06 (m, 1H), 6.51 (d, J=8.8 Hz, 1H), 6.01 (s, 2H), 2.34 (s, 3H). LC-MS: m/z 185 [M+H]$^+$.

Synthesis of 6-(3-chlorophenyl)pyridazin-3-amine

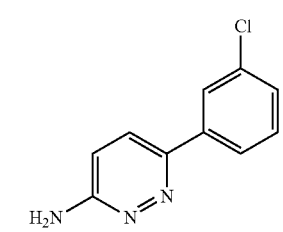 [SMILES: Nc1ccc(-c2cccc(Cl)c2)nn1]

$^1$H NMR (400 MHz, Methanol-$d_4$): 7.96 (s, 1H), 7.81-7.88 (m, 2H), 7.41-7.48 (m, 2H). LC-MS: m/z 206 [M+H]$^+$.

Synthesis of 6-(3-fluorophenyl)pyridazin-3-amine

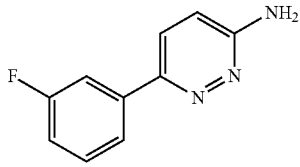 [SMILES: Nc1ccc(-c2cccc(F)c2)nn1]

¹H NMR (400 MHz, DMSO-d₆): 7.86-7.76 (m, 3H), 7.53-7.47 (m, 1H), 7.23-7.18 (m, 1H), 6.85 (d, J=9.6 Hz, 1H), 6.55 (s, 2H). LC-MS: m/z 190 [M+H]⁺.

Synthesis of 6-(m-tolyl)pyridazin-3-amine

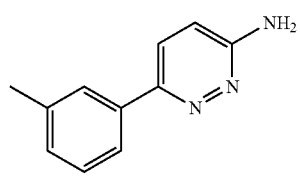

¹H NMR (400 MHz, DMSO-d₆): 7.79-7.77 (m, 2H), 7.74-7.72 (m, 1H), 7.34 (t, J=7.6 Hz, 1H), 7.21-7.19 (m, 1H), 6.84 (d, J=9.6 Hz, 1H), 6.44 (s, 2H), 2.38 (s, 3H). LC-MS: m/z 186 [M+H]⁺.

Synthesis of 6-(5-methylpyridin-3-yl)pyridazin-3-amine

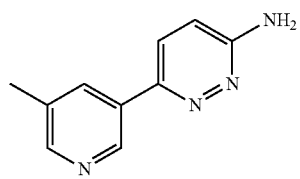

¹H NMR (400 MHz, DMSO-d₆): 8.92 (d, J=2.0 Hz, 1H), 8.42 (d, J=1.6 Hz, 1H), 8.15 (s, 1H), 7.86 (d, J=9.2 Hz, 1H), 6.87 (d, J=9.2 Hz, 1H), 6.56 (s, 2H), 2.37 (s, 3H). LC-MS: m/z 187 [M+H]⁺.

Synthesis of 6-(6-methylpyridin-3-yl)pyridazin-3-amine

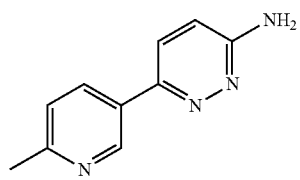

LC-MS: m/z 187 [M+H]⁺.

Synthesis of 5'-fluoro-[2,3'-bipyridin]-5-amine

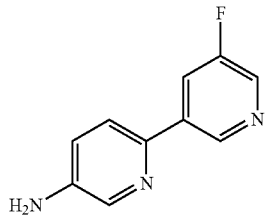 [SMILES: Nc1ccc(-c2cncc(F)c2)nc1]

LC-MS: m/z 190 [M+H]⁺.

Synthesis of 6'-methyl-[2,3'-bipyridin]-5-amine

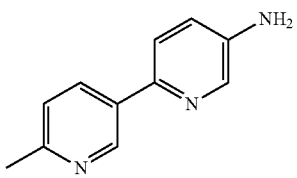

LC-MS: m/z 186 [M+H]⁺.

Synthesis of 5'-chloro-[3,3'-bipyridin]-6-amine

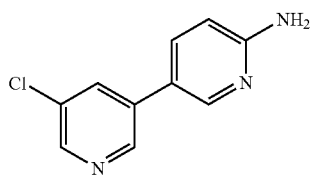 [SMILES: Nc1ccc(-c2cncc(Cl)c2)cn1]

LC-MS: m/z 206 [M+H]⁺.

Synthesis of 5'-fluoro-[3,3'-bipyridin]-6-amine

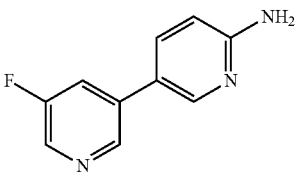 [SMILES: Nc1ccc(-c2cncc(F)c2)cn1]

LC-MS: m/z 190 [M+H]⁺.

Synthesis of 5-(m-tolyl)pyrazin-2-amine

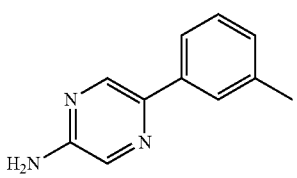

$^1$H NMR (400 MHz, DMSO-d$_6$): 8.47 (d, J=1.6 Hz, 1H), 7.94 (d, J=1.6 Hz, 1H), 7.73 (s, 1H), 7.68 (d, J=8.0 Hz, 1H), 7.29 (t, J=7.6 Hz, 1H), 7.12 (d, J=7.2 Hz, 1H), 6.50 (s, 2H), 2.35 (s, 3H). LC-MS: m/z 186 [M+H]$^+$.

General Suzuki Procedure B

To a stirred solution of the arylhalide (1 equiv.), boronic acid (1.1 equiv.) and sodium carbonate (2 equiv.) in dioxane (0.02 M) and water (0.05 M) was degassed for 10 min with nitrogen. Bis(cyclopentyldiphenylphosphane) dichloromethane palladium chloride iron (0.1 equiv.) was added to the reaction mixture and it was heated to reflux for 16 h. The reaction mixture was allowed to cool and filtered over Celite®. It was diluted with water and extracted with ethyl acetate. The combined organic layers were dried with magnesium sulphate and concentrated under vacuum. The crude compound was purified by column chromatography to afford the desired product.

Synthesis of 4-(pyridazin-3-yl)aniline

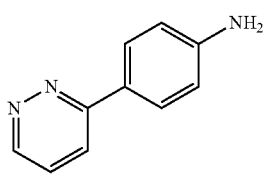 [SMILES: Nc1ccc(-c2cccnn2)cc1]

$^1$H NMR (400 MHz, DMSO-d$_6$): 9.01-9.00 (m, 1H), 7.99 (d, J=7.2 Hz, 1H), 7.87 (d, J=8.8 Hz, 2H), 7.62-7.59 (m, 1H), 6.68 (d, J=8.4 Hz, 2H), 5.58 (s, 2H). LC-MS: m/z 172 [M+H]$^+$.

Synthesis of 4-(pyrimidin-2-yl)aniline

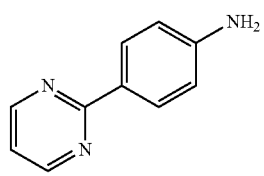 [SMILES: Nc1ccc(-c2ncccn2)cc1]

$^1$H NMR (400 MHz, DMSO-d$_6$): 8.72 (d, J=4.8 Hz, 2H), 8.08 (d, J=8.8 Hz, 2H), 7.19 (t, J=4.8 Hz, 1H), 6.62 (d, J=8.4 Hz, 2H), 5.64 (s, 2H). LC-MS: m/z 172 [M+H]$^+$.

Synthesis of 4-(pyrimidin-5-yl)aniline

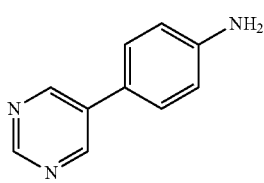 [SMILES: Nc1ccc(-c2cncnc2)cc1]

$^1$H NMR (400 MHz, DMSO-d$_6$): 9.00 (m, 3H), 7.49 (d, J=8.8 Hz, 2H), 6.68 (d, J=8.4 Hz, 2H), 5.45 (s, 2H). LC-MS: m/z 172 [M+H]$^+$.

Synthesis of 5-phenylpyrimidin-2-amine

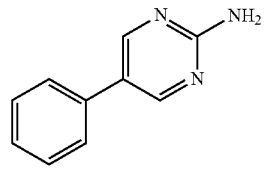 [SMILES: Nc1ncc(-c2ccccc2)cn1]

$^1$H NMR (400 MHz, DMSO-d$_6$): 8.56 (s, 2H), 7.61 (d, J=7.2 Hz, 2H), 7.43 (t, J=7.6 Hz, 2H), 7.31 (t, J=7.2 Hz, 1H), 6.75 (s, 2H). LC-MS: m/z 172 [M+H]$^+$.

Synthesis of [3,3'-bipyridin]-6-amine

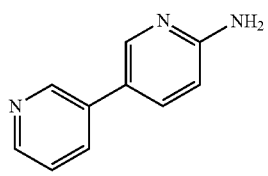 [SMILES: Nc1ccc(-c2cccnc2)cn1]

$^1$H NMR (400 MHz, DMSO-d$_6$): 8.79 (d, J=1.6 Hz, 1H), 8.47-8.45 (m, 1H), 8.29 (d, J=2.0 Hz, 1H), 7.97-7.94 (m, 1H), 7.77-7.74 (m, 1H), 7.42-7.38 (m, 1H), 6.55-6.53 (m, 1H), 6.15 (s, 2H). LC-MS: m/z 172 [M+H]$^+$.

Synthesis of 6-(pyridin-3-yl)pyridazin-3-amine

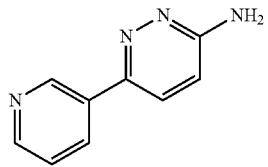 [SMILES: Nc1ccc(-c2cccnc2)nn1]

$^1$H NMR (400 MHz, DMSO-d$_6$): 9.14-9.13 (m, 1H), 8.60-8.59 (m, 1H), 8.34-8.31 (m, 1H), 8.13 (s, 1H), 7.92 (d, J=9.6 Hz, 1H), 7.51-7.48 (m, 1H), 6.92 (d, J=9.2 Hz, 1H), 6.71 (bs, 1H). LC-MS: m/z 173 [M+H]$^+$.

Synthesis of 2-methyl-[1,1'-biphenyl]-4-amine

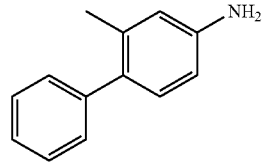

LC-MS: m/z 184 [M+H]$^+$.

Synthesis of 3-methyl-[1,1'-biphenyl]-4-amine

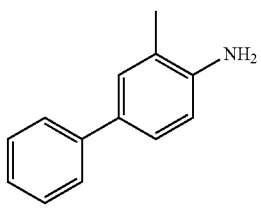

LC-MS: m/z 184 [M+H]$^+$.

Synthesis of 2'-fluoro-[1,1'-biphenyl]-4-amine

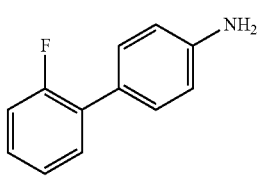 [SMILES: Nc1ccc(-c2ccccc2F)cc1]

LC-MS: m/z 188 [M+H]$^+$.

Synthesis of 3'-fluoro-[1,1'-biphenyl]-4-amine

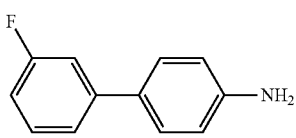 [SMILES: Nc1ccc(-c2cccc(F)c2)cc1]

1H NMR (400 MHz, DMSO-d$_6$): 7.41-7.32 (m, 5H), 7.02-6.99 (m, 1H), 6.63 (d, J=8.4 Hz, 2H), 5.29 (s, 2H). LC-MS: m/z 188 [M+H]$^+$.

Synthesis of 3'-nitro-[1,1'-biphenyl]-4-amine

$^1$H NMR (400 MHz, DMSO-d$_6$): 8.29 (t, J=2.0 Hz, 1H), 8.05-8.00 (m, 2H), 7.64 (t, J=8.0 Hz, 1H), 7.48 (d, J=8.8 Hz, 2H), 6.67 (d, J=8.4 Hz, 2H), 5.41 (s, 2H).

Synthesis of 4-(pyrazin-2-yl)aniline

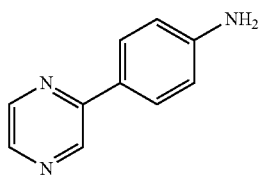 [SMILES: Nc1ccc(-c2cnccn2)cc1]

MS (ESI) m/z 172 [M+H]$^+$.

Synthesis of 2-fluorobiphenyl-4-amine

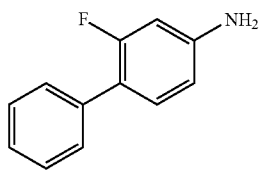 [SMILES: Nc1ccc(-c2ccccc2)c(F)c1]

MS (ESI) m/z 188 [M+H]$^+$.

Synthesis of 4'-fluorobiphenyl-4-amine

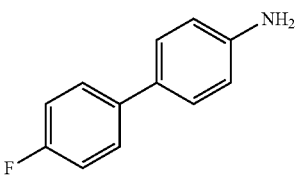 [SMILES: Nc1ccc(-c2ccc(F)cc2)cc1]

MS (ESI) m/z 188 [M+H]$^+$.

Synthesis of 5-methyl-6-phenylpyridin-3-amine

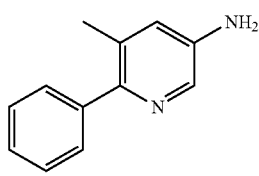

MS (ESI) m/z 185 [M+H]$^+$.

Synthesis of 4-methyl-5-phenylpyridin-2-amine

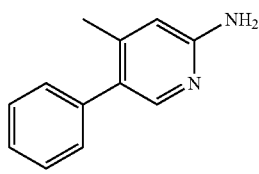

MS (ESI) m/z 186 [M+H]$^+$.

Synthesis of 5-fluoro-2,3'-bipyridin-6'-amine

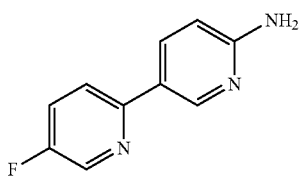 [SMILES: Nc1ccc(-c2ccc(F)cn2)cn1]

MS (ESI) m/z 190 [M+H]$^+$.

Synthesis of 6-(4-chlorophenyl)pyridazin-3-amine

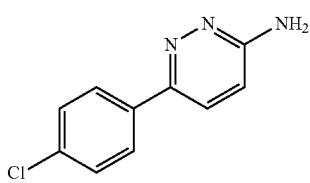 [SMILES: Nc1ccc(-c2ccc(Cl)cc2)nn1]

LC-MS: m/z 206 [M+H]$^+$.

Synthesis of 6-(5-chloropyridin-3-yl)pyridazin-3-amine

Step-1: Preparation of 3-chloro-5-(4,4,5,5-tetramethyl-1,3,2-dioxaborolan-2-yl)pyridine

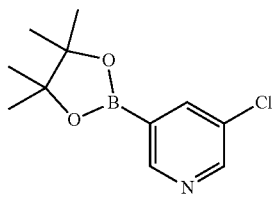 [SMILES: CC1(C)OB(c2cncc(Cl)c2)OC1(C)C]

A stirred solution of 3-bromo-5-chloropyridine (1 equiv.), bis(pinacaloto) diborane (1.2 equiv.), potassium acetate (3 equiv.) in 1,4-dioxane (0.2 M) was degassed with argon for 20 min. To the reaction mixture was added Pd(dppf)Cl$_2$.DCM (0.05 equiv.) under argon atmosphere. The reaction mixture was heated at 100° C. for 16 h. The worked-up material was used in the next step without purification.

Step-2: Preparation of 6-(5-chloropyridin-3-yl)pyridazin-3-amine

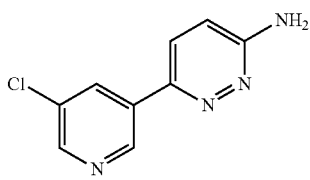 [SMILES: Nc1ccc(-c2cncc(Cl)c2)nn1]

LC-MS: m/z 207 [M+H]$^+$.

Synthesis of 5-methyl-6-(pyridin-3-yl)pyridazin-3-amine

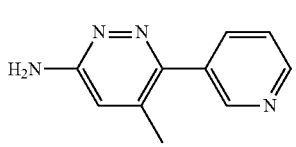

$^1$H NMR (400 MHz, DMSO-d$_6$): 8.71 (s, 1H), 8.60-8.59 (d, J=4.8 Hz, 1H), 7.94-7.92 (d, J=7.6 Hz, 1H), 7.49-7.46 (m, 1H), 6.68 (s, 1H), 6.36 (brs, 2H), 2.18 (s, 3H). LC-MS: 187.0 [M+H]$^+$

Synthesis of 5'-methyl-2,3'-bipyridin-5-amine

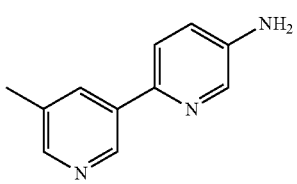

LC-MS: m/z 186 [M+H]$^+$.

Synthesis of 5'-methyl-[3,3'-bipyridin]-6-amine

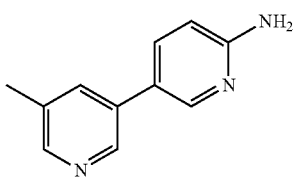

$^1$H NMR (400 MHz, DMSO-d$_6$): 8.58 (s, 1H), 8.30-8.29 (m, 1H), 8.27-8.26 (m, 1H), 7.78 (bs, 1H), 7.74 (dd, J=9.2 Hz, J=2.6 Hz, 1H), 6.54 (d, J=8.4 Hz, 1H), 6.12 (s, 2H), 2.33 (s, 3H). LC-MS: m/z 186 [M+H]$^+$.

Synthesis of 4-methyl-3,3'-bipyridin-6-amine

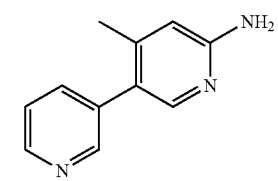

LC-MS: m/z 186 [M+H]$^+$.

Synthesis of 6'-methyl-3,3'-bipyridin-6-amine

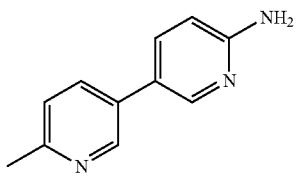

MS (ESI) m/z 186 [M+H]⁺.

Synthesis of 5-(6-methylpyridin-3-yl)pyrazin-2-amine

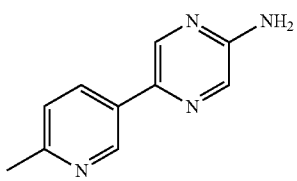

MS (ESI) m/z 187 [M+H]⁺.

Synthesis of 4-(pyrazin-2-yl)aniline

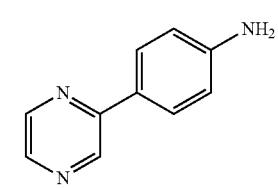 [SMILES: Nc1ccc(-c2cnccn2)cc1]

MS (ESI) m/z 172 [M+H]⁺.

Synthesis of Di tert-butyl (6'-amino-[3,3'-bipyridin]-5-yl)carbamate

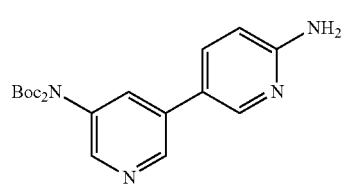

$^1$H NMR (400 MHz, DMSO-d$_6$): 8.75 (s, 1H), 8.31 (d, J=8.0 Hz, 2H), 7.94 (s, 1H), 7.78 (d, J=6.8 Hz, 1H), 6.54 (d, J=8.8 Hz, 1H), 6.19 (bs, 2H), 1.39 (s, 18H); MS (ESI) m/z 387.30 [M+H]⁺.

Synthesis of 5-(pyridin-3-yl)pyrazin-2-amine

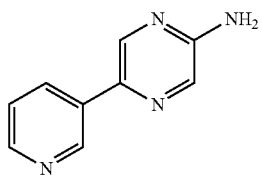 [SMILES: Nc1cnc(-c2cccnc2)cn1]

$^1$H NMR (400 MHz, DMSO-d$_6$): 9.11 (s, 1H), 8.58 (s, 1H), 8.51 (d, J=4.0 Hz, 1H), 8.25 (d, J=11.6 Hz, 1H), 7.99 (s, 1H), 7.46-7.40 (m, 1H), 6.67 (bs, 2H); MS (ESI) m/z 173.0 [M+H]⁺.

Synthesis of 4,5'-dimethyl-3,3'-bipyridin-6-amine

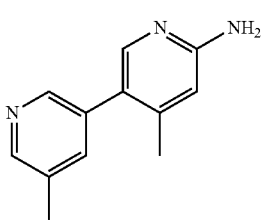

$^1$H NMR (400 MHz, DMSO-d$_6$): 8.35 (s, 1H), 8.31 (s, 1H), 7.73 (s, 1H), 7.55 (s, 1H), 6.37 (s, 1H), 5.93 (bs, 2H), 8.31 (s, 1H), 2.33 (s, 1H), 2.11 (s, 1H); MS (ESI) m/z 200.0 [M+H]⁺.

Synthesis of 5-(5-fluoropyridin-3-yl)pyrazin-2-amine

Step 1: Preparation of 3-fluoro-5-(4,4,5,5-tetramethyl-1,3,2-dioxaborolan-2-yl)pyridine

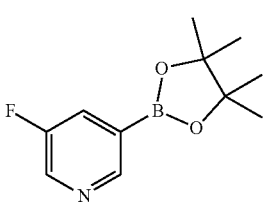 [SMILES: CC1(C)OB(c2cncc(F)c2)OC1(C)C]

A stirred solution of 3-bromo-5-fluoropyridine (1 equiv.), Bis(pinacolato) diborane (1.1 equiv.), KOAc (2 equiv.) in 1,4-dioxane (0.4 M) was degassed with argon for 20 min. To the reaction mixture, Pd(dppf)Cl$_2$.DCM (0.1 equiv.) was added under argon atmosphere. The reaction mixture was heated at 110° C. for 4 h. The worked-up material was used in the next step without further purification.

MS (ESI) m/z 224 [M+H]⁺.

Step 2: Preparation of 5-(5-fluoropyridin-3-yl)pyrazin-2-amine

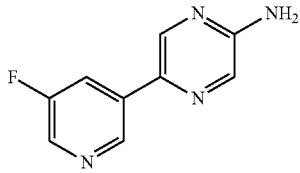 [SMILES: Nc1cnc(-c2cncc(F)c2)cn1]

¹H NMR (400 MHz, DMSO-d₆): 9.01 (t, J=1.7 Hz, 1H), 8.65 (d, J=1.3 Hz, 1H), 8.49 (d, J=3.0 Hz, 1H), 8.16-8.12 (m, 1H), 7.99 (d, J=1.3 Hz, 1H), 6.79 (s, 2H); MS (ESI) m/z 191.17 [M+H]⁺.

Procedure for Acid-Intermediate:

Synthesis of 4-(2-methyl-6,7-dihydropyrazolo[1,5-a]pyrimidin-4(5H)-yl)-4-oxobutanoic acid

Step 1: Preparation of 2-methyl-4,5,6,7-tetrahydropyrazolo[1,5-a]pyrimidine

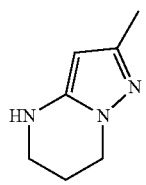

A stirred solution of 3-methyl-1H-pyrazol-5-amine (1 equiv.) in 1,4-dioxane (0.5 M) was added TEA (5 equiv.) at 0° C. After 15 minutes 1,3-dibromopropane (1.2 equiv.) was added to the reaction mixture at 0° C. The reaction mixture was stirred at 100° C. for 5 h. After completion of the reaction, the reaction mixture was filtered and washed with ethyl acetate. The filtrate was concentrated under reduced pressure to afford the intermediate.

Step 2: Preparation of 4-(2-methyl-6,7-dihydropyrazolo[1,5-a]pyrimidin-4(5H)-yl)-4-oxobutanoic acid

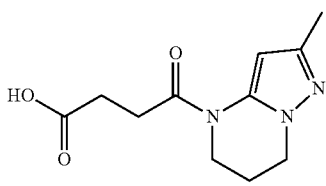 [SMILES: Cc1cc2n(n1)CCCN2C(=O)CCC(=O)O]

To a stirred solution of 2-methyl-4,5,6,7-tetrahydropyrazolo[1,5-a]pyrimidine (1 equiv.) in chloroform (0.5 M) was added succinic anhydride (1.3 equiv.). The reaction mixture was stirred at room temperature for 16 h. After completion, the solid which was precipitated was filtered and washed with n-pentane and dried to afford the product.

¹H NMR (400 MHz, DMSO-d₆): 12.11 (s, 1H), 6.34 (bs, 1H), 4.02-3.99 (t, J=5.2 Hz, 2H), 3.82 (m, 2H), 2.77-2.75 (m, 2H), 2.41 (m, 2H), 2.08 (bs, 5H). MS (ESI) m/z 238 [M+H]⁺.

Synthesis of 4-(6,7-dihydropyrazolo[1,5-a]pyrimidin-4(5H)-yl)-4-oxobutanoic acid

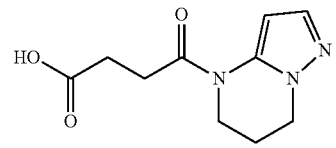 [SMILES: O=C(O)CCC(=O)N1CCCn2nccc21]

To a solution of 4,5,6,7-tetrahydropyrazolo[1,5-a]pyrimidine (1 equiv.) in chloroform (0.4 M) was added succinic anhydride (1.3 equiv.) at room temperature. The reaction mixture was stirred at room temperature for 16 h. After completion, the reaction mixture was filtered and solid was washed with chloroform and dried to afford the product.

¹H NMR (400 MHz, DMSO-d₆): 12.14 (s, 1H), 7.30 (s, 1H), 6.55 (s, 1H), 4.12-4.09 (t, J=5.6 Hz, 2H), 3.88-3.86 (m, 2H), 2.80-2.77 (t, J=6.4 Hz, 2H), 2.52-2.50 (m, 2H), 2.10-2.08 (m, 2H). LC-MS (ESI): MS m/z 224.0 [M+H]⁺.

Synthesis of 4-oxo-4-(2-(trifluoromethyl)-6,7-dihydropyrazolo[1,5-a]pyrimidin-4(5H)-yl)butanoic acid

Step 1: Preparation of 2-(trifluoromethyl)-4,5,6,7-tetrahydropyrazolo[1,5-a]pyrimidine

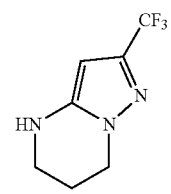 [SMILES: FC(F)(F)c1cc2n(n1)CCCN2]

A solution of 3-(trifluoromethyl)-1H-pyrazol-5-amine (1 equiv.) in 1,4-dioxane (0.2 M) was treated with 1,3-dibromopropane (1.2 equiv.) and triethylamine (5 equiv.) at 0° C. and the reaction mixture was heated to 100° C. for 12 h. After completion, reaction mixture was cooled to room temperature, filtered under reduced pressure and concentrated to afford crude product. The crude product was purified by flash chromatography to afford the product.

¹H-NMR (400 MHz; DMSO-d₆): 12.25 (brs, 1H), 6.40 (s, 1H), 5.52 (s, 1H), 4.03-4.00 (t, 2H), 3.58 (s, 1H), 3.18-3.15 (m, 2H), 2.05-1.97 (m, 2H). LC-MS: MS m/z 192 [M+H]⁺.

Step 2: Preparation of 4-oxo-4-(2-(trifluoromethyl)-6,7-dihydropyrazolo[1,5-a]pyrimidin-4(5H)-yl)butanoic acid

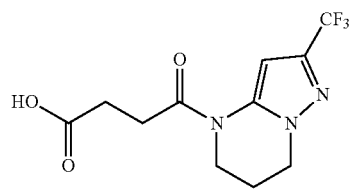 [SMILES: O=C(O)CCC(=O)N1CCCn2nc(C(F)(F)F)cc21]

To a solution of compound 2-(trifluoromethyl)-4,5,6,7-tetrahydropyrazolo[1,5-a]pyrimidine (1 equiv.) in CHCl$_3$ (0.15 M) was added succinic anhydride (2 equiv.) at room temperature. The resulted reaction mixture was stirred at room temperature for 60 h. After completion, the reaction mixture was concentrated to afford crude product. The crude product was purified by column chromatography to afford the product.

$^1$H NMR (400 MHz, DMSO-d$_6$): 12.20 (s, 2H), 6.88 (s, 1H), 4.20 (t, J=6 Hz, 2H), 3.92 (t, J=5.2 Hz, 2H), 2.82 (t, J=6 Hz, 2H), 2.53-2.49 (m, 3H), 2.41 (s, 3H), 2.17 (brs, 2H). LC-MS: MS m/z 290 [M+H]$^+$.

Synthesis of 4-(2,6-dimethyl-6,7-dihydropyrazolo[1,5-a]pyrimidin-4(5H)-yl)-4-oxobutanoic acid

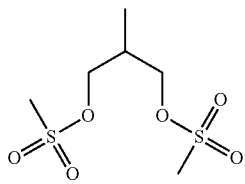

Step 1: Preparation of 2-methylpropane-1,3-diyl dimethanesulfonate

To a stirred solution of 2-methylpropane-1,3-diol (1 equiv.) in dichloromethane (0.45 M) was added methane sulfonyl chloride (2.8 equiv.), using triethylamine (2.8 equiv.) at 0° C. to room temperature for 16 h. Upon completion of reaction, the reaction mixture was washed with water and brine solution, dried over anhydrous sodium sulphate, filtered and concentrated under reduced pressure to afford the crude intermediate.

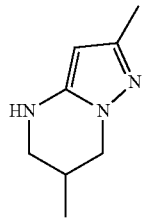

Step 2: Preparation of 2,6-dimethyl-4,5,6,7-tetrahydropyrazolo[1,5-a]pyrimidine

To a stirred solution of 2-methylpropane-1,3-diyl dimethanesulfonate (1.2 equiv.) in 1,4-dioxane (0.5 M) were added 3-methyl-1H-pyrazol-5-amine (1 equiv.) and triethylamine (5 equiv.). The reaction mixture was heated at 100° C. for 48 h. Upon completion, the reaction mixture was filtered and concentrated under reduced pressure, purified by column chromatography to afford the intermediate.

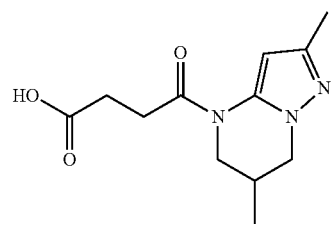 [SMILES: Cc1cc2n(n1)CC(C)CN2C(=O)CCC(=O)O]

Step 3: Preparation of 4-(2,6-dimethyl-6,7-dihydropyrazolo[1,5-a]pyrimidin-4(5H)-yl)-4-oxobutanoic acid To a stirred solution of 2,6-dimethyl-4,5,6,7-tetrahydropyrazolo[1,5-a]pyrimidine (1 equiv.) in chloroform (0.15 M) was added succinic anhydride (1 equiv.) and the reaction mixture was stirred at room temperature for 16 h. The reaction mixture was concentrated under reduced pressure to afford the product.

$^1$H NMR (400 MHz, DMSO-d$_6$): 12.08 (s, 1H), 6.35 (brs, 1H), 4.12-4.08 (m, 1H), 3.99 (brs, 1H), 3.64-3.58 (m, 1H), 3.35 (brs, 1H), 2.85-2.79 (m, 1H), 2.74-2.70 (brs, 1H), 2.49-2.48 (m, 2H), 2.25 (brs, 1H), 2.08 (brs, 3H), 1.04-1.02 (d, J=6.1 Hz, 3H). MS (ESI) m/z 252.07 [M+H]$^+$.

Synthesis of ethyl 2-methyl-4-(2-methyl-6,7-dihydropyrazolo[1,5-a]pyrimidin-4(5H)-yl)-4-oxobutanoate

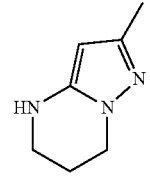

Step 1: Preparation of 2-methyl-4,5,6,7-tetrahydropyrazolo[1,5-a]pyrimidine

To a stirred solution of 3-methyl-1H-pyrazol-5-amine (1 equiv.) in 1,4-dioxane (0.1 M) was added triethylamine (5 equiv.) at 0° C. After 15 minutes, 1,3-dibromopropane (1.2 equiv.) was added to the reaction mixture at 0° C. The reaction mixture was stirred at 100° C. for 5 h. The reaction mixture was filtered and washed with ethyl acetate. The filtrate was concentrated under reduced pressure to afford the intermediate.

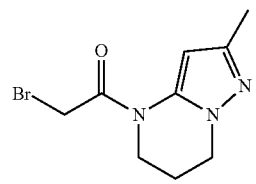

Step 2: Preparation of 2-bromo-1-(2-methyl-6,7-dihydropyrazolo[1,5-a]pyrimidin-4(5H)-yl)ethanone To a stirred solution of 2-methyl-4,5,6,7-tetrahydropyrazolo[1,5-a]pyrimidine (1 equiv.) in dichloromethane (0.6 M) was added 2-bromoacetyl bromide (2 equiv.) drop wise at 0° C. The reaction mixture was stirred at room temperature for 12 h. The solid thus formed was filtered and washed with n-pentane then dried to afford the intermediate.

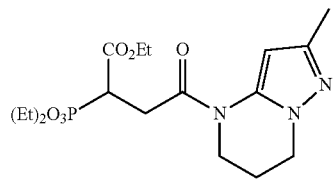

Step 3: Preparation of ethyl 2-(diethoxyphosphoryl)-4-(2-methyl-6,7-dihydropyrazolo[1,5-a]pyrimidin-4(5H)-yl)-4-oxobutanoate To a stirred solution of NaH (60% suspension in mineral oil) (1.2 equiv.) in DMSO (0.5 M) was added ethyl 2-(diethoxyphosphoryl)acetate (1.1 equiv.) at room temperature. After 30 min, to the reaction mixture was added 2-bromo-1-(2-methyl-6,7-dihydropyrazolo[1,5-a]pyrimidin-4(5H)-yl)ethanone (1 equiv.) portion-wise at room temperature. The reaction mixture was stirred at 70° C. for 4 h. The reaction mixture was quenched with ice-cold water and extracted with ethyl acetate. The organic layer was dried over anhydrous sodium sulphate and concentrated under reduced pressure to obtain the crude product. The crude product was purified by column chromatography to afford the intermediate. LC-MS: m/z 402 [M+H]$^+$.

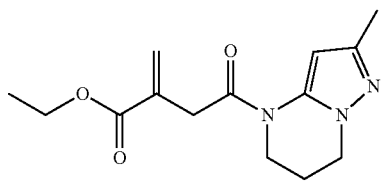 [SMILES: C=C(CC(=O)N1CCCn2nc(C)cc21)C(=O)OCC]

Step 4: Preparation of ethyl 4-(2-methyl-6,7-dihydropyrazolo[1,5-a]pyrimidin-4(5H)-yl)-2-methylene-4-oxobutanoate To a stirred solution of ethyl 2-(diethoxyphosphoryl)-4-(2-methyl-6,7-dihydropyrazolo[1,5-a]pyrimidin-4(5H)-yl)-4-oxobutanoate (1 equiv.) in THF (0.4 M) was added aqueous $K_2CO_3$ (1.5 equiv., 2 M) followed by aq. HCHO (20 equiv.) at room temperature. The reaction mixture was stirred at 80° C. for 45 min. The reaction mixture was diluted with water and extracted with ethyl acetate. The organic layer was dried over anhydrous sodium sulphate and concentrated under reduced pressure to obtain the crude product. The crude product was purified by column chromatography to afford the product. LC-MS: m/z 278 [M+H]$^+$.

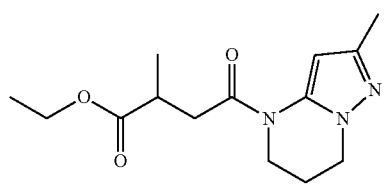 [SMILES: CCOC(=O)C(C)CC(=O)N1CCCn2nc(C)cc21]

Step 5: Preparation of ethyl 2-methyl-4-(2-methyl-6,7-dihydropyrazolo[1,5-a]pyrimidin-4(5H)-yl)-4-oxobutanoate To a solution of ethyl 4-(2-methyl-6,7-dihydropyrazolo[1,5-a]pyrimidin-4(5H)-yl)-2-methylene-4-oxobutanoate (1 equiv.) in ethanol (0.1 M) was added a slurry of 10% Pd/C (10% w/w) in methanol under nitrogen and the reaction mixture was hydrogenated under $H_2$ (50 psi) at room temperature for 8 h. The reaction mixture was filtered through celite bed and washed with methanol. The filtrate was concentrated under reduced pressure to give crude product. The crude product was purified by column chromatography to afford the product. $^1$H NMR (400 MHz, DMSO-$d_6$): 6.33 (brs, 1H), 4.08-4.03 (m, 4H), 3.99-3.81 (m, 2H), 2.93-2.79 (m, 2H), 2.72-2.67 (m, 1H), 2.08 (brs, 5H), 1.19-1.13 (m, 6H). MS (ESI) m/z 280 [M+H]$^+$.

General Procedure for Amide Coupling Reactions:

Amide Coupling Method A:

A solution of the respective amine (1 equiv.) and acid-intermediate (1.1 equiv.) in pyridine (0.1 M) was cooled to 0° C. under nitrogen atmosphere and treated with $POCl_3$ (3 equiv.). The reaction mixture stirred for 45 min. After consumption of starting material, the reaction mixture was quenched with saturated sodium bicarbonate and extracted with DCM. The combined organic layers were washed with brine, dried over $Na_2SO_4$ and concentrated under vacuum. The crude compound was purified by reversed phase chromatography to afford desired product.

Synthesis of 4-(2-methyl-6,7-dihydropyrazolo[1,5-a]pyrimidin-4(5H)-yl)-N-(3-methylisoxazol-5-yl)-4-oxobutanamide, Compound 1

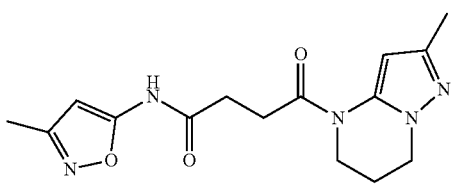

$^1$H NMR (400 MHz, Methanol-$d_4$): 6.15 (s, 1H), 4.55 (s, 1H), 4.10 (t, J=6.0 Hz, 2H), 3.91-3.94 (m, 2H), 2.96-2.98 (m, 2H), 2.78 (t, J=6.0 Hz, 2H), 2.22 (bs, 2H), 2.17 (s, 3H). LC-MS: m/z 318 [M+H]$^+$.

Synthesis of 4-(2-methyl-6,7-dihydropyrazolo[1,5-a]
pyrimidin-4(5H)-yl)-4-oxo-N-(3-phenylisoxazol-5-
yl)butanamide, Compound 2

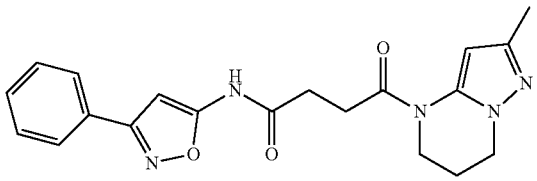

¹H NMR (400 MHz, DMSO-d₆): 11.80 (s, 1H), 7.84-7.83 (d, J=2.8 Hz, 2H), 7.50-7.48 (m, 3H), 6.68 (s, 1H), 6.34 (s, 1H), 4.07 (m, 2H), 3.86 (m, 2H), 2.92-2.90 (m, 2H), 2.73-2.71 (t, J=5.2 Hz, 2H), 2.07-2.05 (m, 5H). LC-MS: 380.2 [M+H]⁺.

Synthesis of N-(3-(3-chlorophenyl)isoxazol-5-yl)-4-
(2-methyl-6,7-dihydropyrazolo[1,5-a]pyrimidin-4
(5H)-yl)-4-oxobutanamide, Compound 3

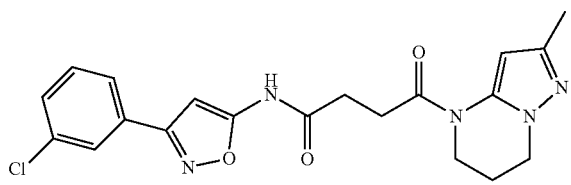 [SMILES: Cc1cc2n(n1)CCCN2C(=O)CCC(=O)Nc1cc(-c2cccc(Cl)c2)no1]

¹H NMR (400 MHz, Methanol-d₄): 7.66 (s, 1H), 7.60-7.58 (m, 1H), 7.33-7.29 (m, 2H), 6.53 (s, 1H), 6.13 (brs, 1H), 3.81 (brs, 2H), 3.64 (s, 1H), 2.70 (brs, 2H), 2.52-2.51 (m, 2H), 2.29 (s, 2H), 1.86 (brs, 5H). LC-MS: MS m/z 414 [M+H]⁺.

Synthesis of 4-(2-methyl-6,7-dihydropyrazolo[1,5-a]
pyrimidin-4(5H)-yl)-4-oxo-N-(4-phenylisoxazol-5-
yl)butanamide, Compound 4

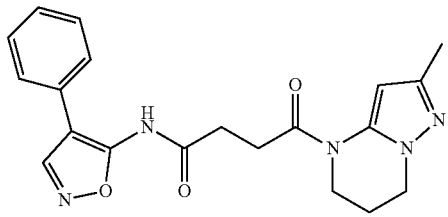 [SMILES: Cc1cc2n(n1)CCCN2C(=O)CCC(=O)Nc1oncc1-c1ccccc1]

¹H NMR (400 MHz, DMSO-d₆): 8.99 (s, 1H), 7.58-7.57 (d, J=7.2 Hz, 1H), 7.38-7.34 (t, J=7.2 Hz, 2H), 7.29-7.25 (t, J=7.2 Hz, 1H), 6.68 (brs, 1H), 6.35 (brs, 1H), 4.00-3.97 (t, J=6.0 Hz, 2H), 3.83-3.80 (t, J=6.0 Hz, 2H), 2.67-2.64 (m, 2H), 2.07 (brs, 5H). LC-MS: MS m/z 380 [M+H]⁺.

Synthesis of N-(3-(4-chlorophenyl)isoxazol-5-yl)-4-
(2-methyl-6,7-dihydropyrazolo[1,5-a]pyrimidin-4
(5H)-yl)-4-oxobutanamide, Compound 5

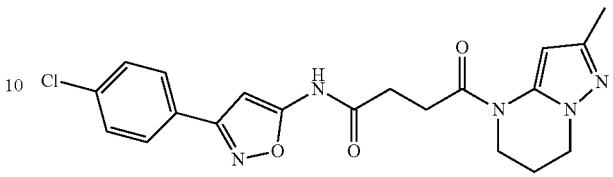

¹H NMR (400 MHz, DMSO-d₆): 11.83 (s, 1H), 7.88-7.86 (d, J=8 Hz, 2H), 7.57-7.55 (d, J=8.8 Hz, 2H), 6.71 (s, 1H), 6.33 (s, 1H), 4.02-4.01 (t, J=5.2 Hz, 2H), 3.87-3.85 (m, 2H), 2.92-2.89 (m, 2H), 2.73-2.70 (t, J=6.4 Hz, 2H), 2.05-2.03 (m, 5H). LC-MS: 414.2 [M+H]⁺

Synthesis of N-(3-(2-chlorophenyl)isoxazol-5-yl)-4-
(2-methyl-6,7-dihydropyrazolo[1,5-a]pyrimidin-4
(5H)-yl)-4-oxobutanamide, Compound 6

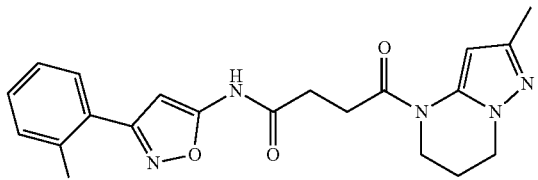

¹H NMR (400 MHz, DMSO-d₆): 11.89 (s, 1H), 7.69-7.67 (d, J=7.2 Hz, 1H), 7.64-7.62 (d, J=8.4 Hz, 1H), 7.55-7.53 (t, J=7.6 Hz, 1H), 7.49-7.45 (t, J=7.2 Hz, 1H), 6.57 (s, 1H), 6.34 (s, 1H), 4.03-3.99 (m, 2H), 3.86-3.83 (m, 2H), 2.93-2.90 (m, 2H), 2.72-2.70 (t, J=6 Hz, 2H), 2.08-2.05 (m, 5H). LC-MS: 414.15 [M+H]⁺.

Synthesis of N-(3-(3,4-dichlorophenyl)isoxazol-5-
yl)-4-(2-methyl-6,7-dihydropyrazolo[1,5-a]pyrimi-
din-4(5H)-yl)-4-oxobutanamide, Compound 7

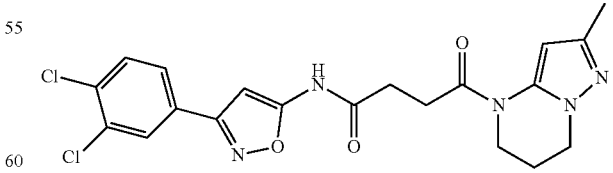

¹H NMR (400 MHz, DMSO-d₆): 11.84 (br s, 1H), 8.10 (d, J=2 Hz, 1H), 7.86-7.83 (m, 1H), 7.76 (d, J=8.4 Hz, 1H), 6.78 (s, 1H), 4.02 (t, J=6.0 Hz, 2H), 3.86 (br s, 2H), 2.91-2.89 (m, 2H), 2.71-2.67 (m, 2H), 2.08 (br s, 5H). LC-MS: m/z 449 [M+H]⁺.

113

Synthesis of N-(3-(3-fluorophenyl)isoxazol-5-yl)-4-(2-methyl-6,7-dihydropyrazolo[1,5-a]pyrimidin-4(5H)-yl)-4-oxobutanamide, Compound 8

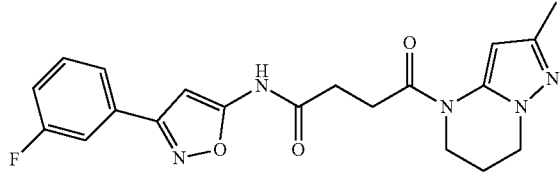 [SMILES: Cc1cc2n(n1)CCCN2C(=O)CCC(=O)Nc1cc(-c2cccc(F)c2)no1]

$^1$H NMR (400 MHz, DMSO-$d_6$): 11.84 (s, 1H), 7.71-7.67 (t, J=7.2 Hz, 2H), 7.57-7.52 (q, J=8.4 Hz 1H), 7.37-7.32 (m, 1H), 6.76 (s, 1H), 6.34 (s, 1H), 4.03-4.01 (m, 2H), 3.88-2.85 (m, 2H), 2.92-2.90 (m, 2H), 2.73-2.70 (t, J=5.6 Hz, 2H), 2.09-2.05 (m, 5H). LC-MS: 398.2 [M+H]$^+$.

Synthesis of N-[3-(3-bromophenyl)-1,2-oxazol-5-yl]-4-{2-methyl-5H,6H,7H-pyrazolo[1,5-a]pyrimidin-4-yl}-4-oxobutanamide, Compound 9

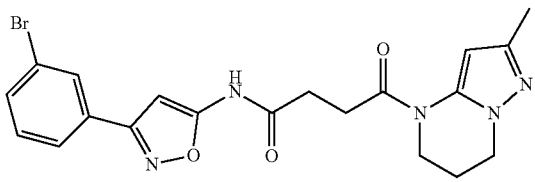

$^1$H NMR (400 MHz, Methanol-$d_4$) 7.97 (s, 1H), 7.77 (d, J=7.6 Hz, 1H), 7.62 (d, J=8.0 Hz, 1H), 7.40 (t, J=8.0 Hz, 1H), 6.68 (s, 1H), 6.44 (br s, 1H), 4.10 (t, J=6.0 Hz, 2H), 3.94 (br s, 2H), 3.00 (br s, 2H), 2.82 (t, J=6.8 Hz, 2H), 2.22-2.17 (m, 5H). LC-MS: m/z 459 [M+H]$^+$.

Synthesis of N-[3-(3-methoxyphenyl)-1,2-oxazol-5-yl]-4-{2-methyl-5H,6H,7H-pyrazolo[1,5-a]pyrimidin-4-yl}-4-oxobutanamide, Compound 10

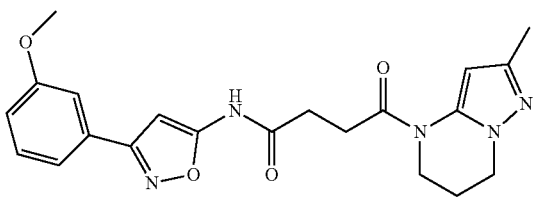 [SMILES: COc1cccc(-c2cc(NC(=O)CCC(=O)N3CCCn4nc(C)cc43)on2)c1]

$^1$H NMR (400 MHz, Methanol-$d_4$) 7.40-7.33 (m, 3H), 7.04-7.01 (m, 1H), 6.65 (s, 1H), 6.45 (br s, 1H), 4.10 (t, J=6.0 Hz, 2H), 3.95 (t, J=5.6 Hz, 2H), 3.84 (s, 3H), 3.00 (br s, 2H), 2.82 (t, J=6.8 Hz, 2H), 2.22-2.17 (m, 5H). LC-MS: m/z 410 [M+H]$^+$.

114

Synthesis of 4-{2-methyl-5H,6H,7H-pyrazolo[1,5-a]pyrimidin-4-yl}-N-[3-(3-methylphenyl)-1,2-oxazol-5-yl]-4-oxobutanamide, Compound 11

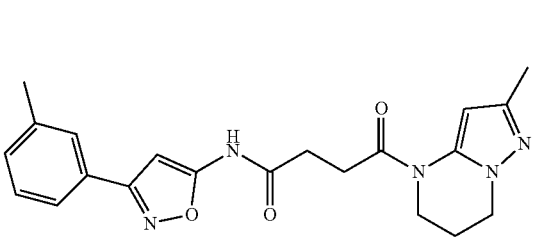 [SMILES: Cc1cccc(-c2cc(NC(=O)CCC(=O)N3CCCn4nc(C)cc43)on2)c1]

$^1$H NMR (400 MHz, Methanol-$d_4$) 7.61-7.56 (m, 2H), 7.36-7.27 (m, 2H), 6.64 (s, 1H), 6.46 (br s, 1H), 4.10 (t, J=Hz, 2H), 3.95-3.93 (m, 2H), 3.00 (s, 2H), 2.82 (t, J=6.4 Hz, 2H), 2.39 (s, 3H), 2.22-2.17 (m, 5H). LC-MS: m/z 394 [M+H]$^+$.

Synthesis of 4-(2-methyl-6,7-dihydropyrazolo[1,5-a]pyrimidin-4(5H)-yl)-4-oxo-N-(3-(o-tolyl)isoxazol-5-yl)butanamide, Compound 12

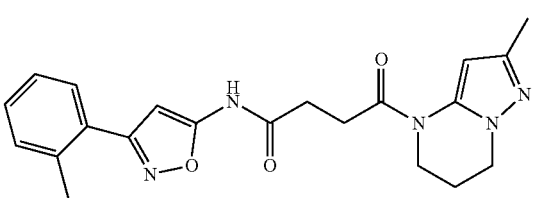 [SMILES: Cc1cc2n(n1)CCCN2C(=O)CCC(=O)Nc1cc(-c2ccccc2C)no1]

$^1$H NMR (400 MHz, DMSO-$d_6$) 11.79 (br s, 1H), 7.50-7.49 (m, 1H), 7.40-7.28 (m, 3H), 6.45 (s, 1H), 6.33 (br s, 1H), 4.02 (t, J=6.0 Hz, 2H), 3.85 (s, 2H), 2.91-2.90 (m, 2H), 2.73-2.70 (m, 2H), 2.41 (s, 3H), 2.08 (s, 5H). LC-MS: m/z 394 [M+H]$^+$.

Synthesis of 4-{2-methyl-5H,6H,7H-pyrazolo[1,5-a]pyrimidin-4-yl}-4-oxo-N-{3-[3-(trifluoromethyl)phenyl]-1,2-oxazol-5-yl}butanamide, Compound 13

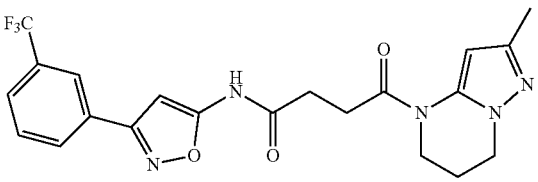

$^1$H NMR (400 MHz, Chloroform-d) 9.34-9.25 (m, 1H), 8.05 (s, 1H), 7.97 (d, J=7.6 Hz, 1H), 7.68 (d, J=7.6 Hz, 1H)), 7.56 (t, J=8.0 Hz, 1H), 6.71 (s, 1H), 4.17 (t, J=6.4 Hz, 2H), 3.99-3.88 (m, 2H), 3.09-2.98 (m, 2H), 2.88-2.86 (m, 2H), 2.24-2.19 (m, 5H). LC-MS: m/z 448 [M+H]$^+$.

Synthesis of 4-(2-methyl-6,7-dihydropyrazolo[1,5-a]pyrimidin-4(5H)-yl)-4-oxo-N-(4'-(trifluoromethyl)-[1,1'-biphenyl]-4-yl)butanamide, Compound 14

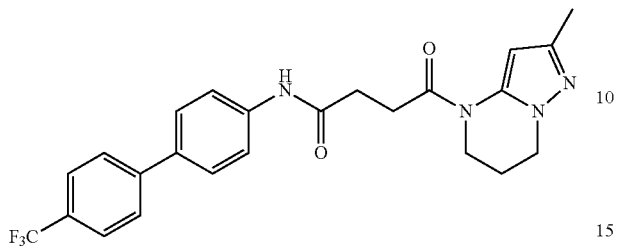

$^1$H NMR (400 MHz, Methanol-d$_4$) 7.78-7.80 (m, 2H), 7.68-7.72 (m, 4H), 7.63-7.65 (m, 2H), 4.55 (s, 1H), 4.10 (t, J=6.0 Hz, 2H), 3.94-3.96 (m, 2H), 2.98-3.00 (m, 2H), 2.79 (t, J=6.0 Hz, 2H), 2.22 (bs, 2H), 2.18 (s, 3H). LC-MS: m/z 457 [M+H]$^+$.

Synthesis of N-[3-(4-aminophenyl)-1,2-oxazol-5-yl]-4-{2-methyl-5H,6H,7H-pyrazolo[1,5-a]pyrimidin-4-yl}-4-oxobutanamide, Compound 15

Step 1: Preparation of 4-(2-methyl-6,7-dihydropyrazolo[1,5-a]pyrimidin-4(5H)-yl)-N-(5-(4-nitrophenyl)isoxazol-3-yl)-4-oxobutanamide

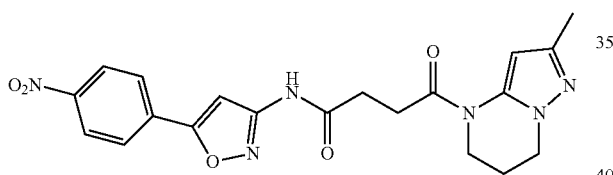

$^1$H NMR (400 MHz, DMSO-d$_6$) 11.90 (s, 1H), 8.33 (d, J=8.8 Hz, 2H), 8.14 (d, J=8.8 Hz, 2H), 6.85 (s, 1H), 6.34 (br s, 1H), 4.02 (t, J=5.6 Hz, 2H), 3.86 (s, 2H), 2.92 (s, 2H), 2.73 (t, J=6.4 Hz, 2H), 2.08 (s, 5H). LC-MS: m/z 425 [M+H]$^+$.

Step 2: Preparation of N-[3-(4-aminophenyl)-1,2-oxazol-5-yl]-4-{2-methyl-5H,6H,7H-pyrazolo[1,5-a]pyrimidin-4-yl}-4-oxobutanamide

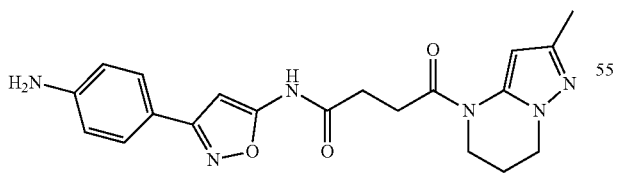

4-{2-methyl-5H,6H,7H-pyrazolo[1,5-a]pyrimidin-4-yl}-N-[3-(4-nitrophenyl)-1,2-oxazol-5-yl]-4-oxobutanamide (1 equiv.), ammonium chloride (4 equiv.), and iron (2 equiv.) were added to a solution of ethanol (0.02 M) and water (0.08 M), and heated at 40° C. for 3 h. The reaction mixture was then filtered, diluted with water and extracted with ethyl acetate. The combined organic layers were dried over MgSO$_4$ and concentrated under vacuum. The crude product was purified by reversed phase preparative HPLC to afford the purified product.

$^1$H NMR (400 MHz, DMSO-d$_6$) 11.61 (br s, 1H), 7.46 (d, J=8.8 Hz, 2H), 6.61 (d, J=8.8 Hz, 2H), 6.46 (s, 1H), 6.34 (br s, 1H), 5.50 (s, 2H), 4.02 (t, J=5.6 Hz, 2H), 3.85 (s, 2H), 2.90 (s, 2H), 2.69 (t, J=6.4 Hz, 2H), 2.08 (s, 5H). LC-MS: m/z 395 [M+H]$^+$.

Synthesis of N-(3-(4-chloropyridin-2-yl)isoxazol-5-yl)-4-(2-methyl-6,7-dihydropyrazolo[1,5-a]pyrimidin-4(5H)-yl)-4-oxobutanamide, Compound 16

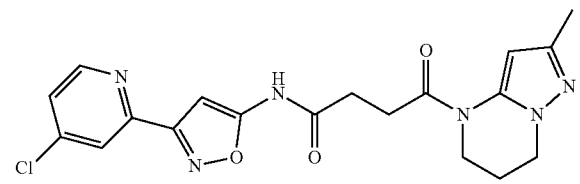 [SMILES: Cc1cc2n(n1)CCCN2C(=O)CCC(=O)Nc1cc(-c2cc(Cl)ccn2)no1]

$^1$H NMR (400 MHz, DMSO-d$_6$): 11.90 (br s, 1H), 8.69 (d, J=5.6 Hz, 1H), 8.03 (d, J=1.6 Hz, 1H), 7.67 (dd, J=4.0 Hz, 2 Hz, 1H), 6.71 (s, 1H), 6.33 (br s, 1H), 4.02 (t, J=6.0 Hz, 2H), 3.86 (br s, 2H), 2.93-2.89 (m, 2H), 2.72-2.70 (m, 2H), 2.08 (br s, 5H). LC-MS: m/z 415 [M+H]$^+$.

Synthesis of N-(3-(5-chloropyridin-2-yl)isoxazol-5-yl)-4-(2-methyl-6,7-dihydropyrazolo[1,5-a]pyrimidin-4(5H)-yl)-4-oxobutanamide, Compound 17

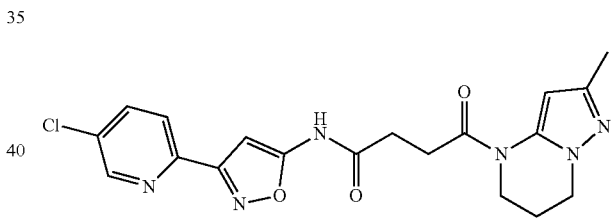

$^1$H NMR (400 MHz, DMSO-d$_6$): 11.88 (br s, 1H), 8.76 (d, J=2 Hz, 1H), 8.09-8.07 (m, 1H), 8.01-7.99 (m, 1H), 6.68 (s, 1H), 6.33 (br s, 1H), 4.02 (t, J=5.8 Hz, 2H), 3.86 (br s, 2H), 2.91 (t, J=6 Hz, 2H), 2.70 (t, J=6.2 Hz, 2H), 2.08 (br s, 5H). LC-MS: m/z 415 [M+H]$^+$.

Synthesis of N-[3-(5-chloropyridin-3-yl)-1,2-oxazol-5-yl]-4-{2-methyl-5H,6H,7H-pyrazolo[1,5-a]pyrimidin-4-yl}-4-oxobutanamide, Compound 18

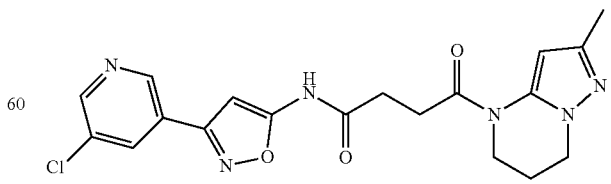

$^1$H NMR (400 MHz, DMSO-d$_6$) 11.83 (br s, 1H), 9.01 (d, J=1.6 Hz, 1H), 8.75 (d, J=2.4 Hz, 1H), 4.05 (t, J=2.0 Hz, 1H), 6.90 (s, 1H), 6.33 (br s, 1H), 4.03 (t, J=6.0 Hz, 2H), 3.86 (s, 2H), 2.92-2.91 (m, 2H), 2.74-2.71 (m, 2H), 2.08 (s, 5H). LC-MS: m/z 415 [M+H]⁺.

Synthesis of 4-(2-methyl-6,7-dihydropyrazolo[1,5-a]pyrimidin-4(5H)-yl)-4-oxo-N-(3-(pyridin-3-yl)isoxazol-5-yl)butanamide, Compound 19

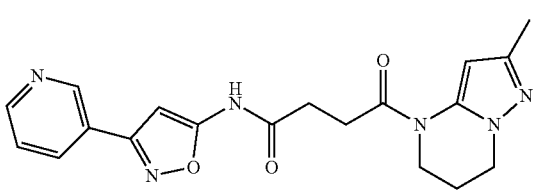 [SMILES: Cc1cc2n(n1)CCCN2C(=O)CCC(=O)Nc1cc(-c2cccnc2)no1]

¹H NMR (400 MHz, DMSO-d₆): 11.85 (br s, 1H), 9.03 (s, 1H), 8.69-8.67 (m, 1H), 8.23 (d, J=8.0 Hz, 1H), 7.55-7.51 (m, 1H), 6.78 (s, 1H), 6.33 (br s, 1H), 4.02 (t, J=5.8 Hz, 2H), 3.86 (br s, 2H), 2.91-2.90 (m, 2H), 2.71 (t, J=6.0 Hz, 2H), 2.08 (br s, 5H). LC-MS: m/z 381 [M+H]⁺.

Synthesis of 4-{2-methyl-5H,6H,7H-pyrazolo[1,5-a]pyrimidin-4-yl}-4-oxo-N-[3-(pyridin-4-yl)-1,2-oxazol-5-yl]butanamide, Compound 20

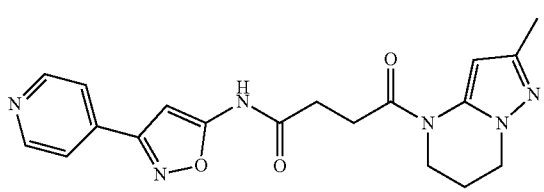 [SMILES: Cc1cc2n(n1)CCCN2C(=O)CCC(=O)Nc1cc(-c2ccncc2)no1]

¹H NMR (400 MHz, Methanol-d₄): 8.66 (d, J=6.4 Hz, 2H), 8.09 (s, 1H), 7.84 (d, J=6.4 Hz, 2H), 6.79 (s, 1H), 6.44 (br s, 1H), 4.10 (t, J=7.6 Hz, 2H), 3.95-3.93 (m, 2H), 3.01 (s, 2H), 2.84-2.81 (m, 2H), 2.21-2.17 (m, 5H). LC-MS: m/z 381 [M+H]⁺.

Synthesis of N-(3-(3-chlorophenyl)-1-methyl-1H-pyrazol-5-yl)-4-(2-methyl-6,7-dihydropyrazolo[1,5-a]pyrimidin-4(5H)-yl)-4-oxobutanamide, Compound 21

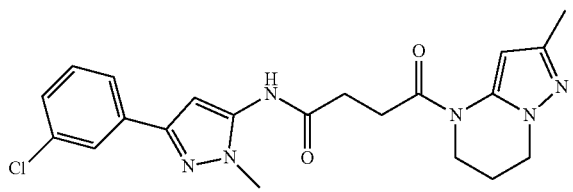 [SMILES: Cc1cc2n(n1)CCCN2C(=O)CCC(=O)Nc1cc(-c2cccc(Cl)c2)nn1C]

¹H NMR (400 MHz, DMSO-d₆): 10.13 (s, 1H), 7.79 (s, 1H), 7.72-7.70 (d, J=8 Hz, 1H), 7.43-7.39 (t, J=8 Hz, 1H), 7.34-7.32 (d, J=8.8 Hz, 1H), 6.70 (s, 1H), 6.36 (s, 1H), 4.02-4.00 (t, J=5.6 Hz, 2H), 3.88-3.85 (m, 2H), 3.72 (s, 3H), 2.92-288 (m, 2H), 2.70-2.67 (t, J=6.4 Hz, 2H), 2.09-2.07 (m, 5H). LC-MS: 427.1 [M+H]⁺.

Synthesis of N-(3-(3-chlorophenyl)-1,2,4-oxadiazol-5-yl)-4-(2-methyl-6,7-dihydropyrazolo[1,5-a]pyrimidin-4(5H)-yl)-4-oxobutanamide, Compound 22

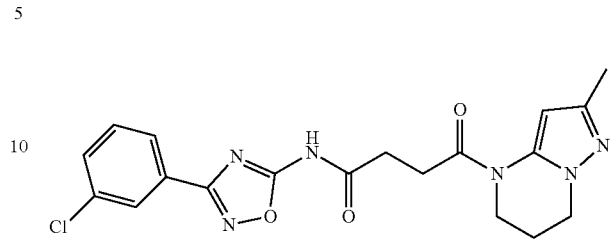

¹H NMR (400 MHz, Chloroform-d): 8.05 (1H, t), 7.93-7.95 (1H, m), 7.46-7.52 (1H, m), 7.40 (1H, t), 4.17 (2H, t), 3.66 (2H, bs), 3.07 (4H, m), 2.18 (5H, m). LC-MS: m/z 415.1 [M+H]⁺.

Synthesis of N-[5-(3-chlorophenyl)-1,2-oxazol-3-yl]-4-{2-methyl-5H,6H,7H-pyrazolo[1,5-a]pyrimidin-4-yl}-4-oxobutanamide, Compound 23

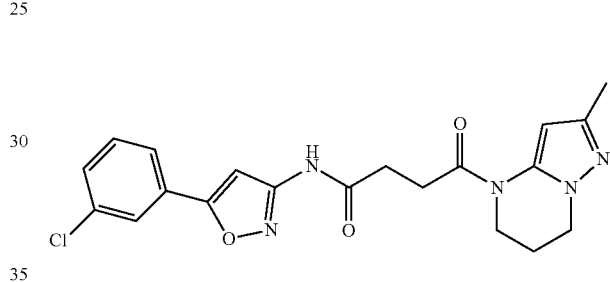

¹H NMR (400 MHz, DMSO-d₆): 11.14 (s, 1H), 7.97 (s, 1H), 7.86-7.84 (m, 1H), 7.57-7.56 (m, 2H), 7.45 (s, 1H), 6.33 (br s, 1H), 4.03 (t, J=6.0 Hz, 2H), 3.86 (s, 2H), 2.91-2.88 (m, 2H), 2.72-2.69 (m, 2H), 2.09 (s, 5H). LC-MS: m/z 414 [M+H]⁺.

Synthesis of 4-(2-methyl-6,7-dihydropyrazolo[1,5-a]pyrimidin-4(5H)-yl)-N-(4-(oxazol-5-yl)phenyl)-4-oxobutanamide, Compound 24

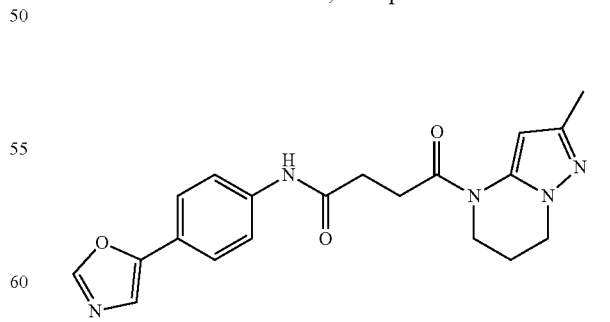

¹H NMR (400 MHz, DMSO-d₆): 10.18 (s, 1H), 8.38 (s, 1H), 7.71-7.64 (m, 5H), 7.56 (s, 1H), 6.34 (bs, 1H), 4.04-4.01 (t, J=6 Hz, 2H), 3.86 (bs, 2H), 2.88-2.87 (m, 2H), 2.67-2.64 (m, 2H), 2.08 (bs, 5H). LC-MS: m/z 380 [M+H]⁺.

119

Synthesis of 4-(2-methyl-6,7-dihydropyrazolo[1,5-a]pyrimidin-4(5H)-yl)-N-(4-(oxazol-5-yl)phenyl)-4-oxobutanamide, Compound 25

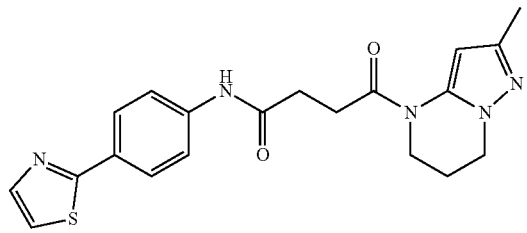 [SMILES: Cc1cc2n(n1)CCCN2C(=O)CCC(=O)Nc1ccc(-c2nccs2)cc1]

¹H NMR (400 MHz, DMSO-d$_6$): 10.25 (s, 1H), 7.90-7.86 (m, 3H), 7.73-7.70 (m, 3H), 4.04-4.01 (m, 2H), 3.86 (br s, 2H), 2.90-2.87 (m, 2H), 2.69-2.66 (m, 2H), 2.08 (br s, 5H). LC-MS: m/z 396 [M+H]$^+$.

Synthesis of 4-(2-methyl-6,7-dihydropyrazolo[1,5-a]pyrimidin-4(5H)-yl)-4-oxo-N-(5-(thiazol-2-yl)pyridin-2-yl)butanamide, Compound 26

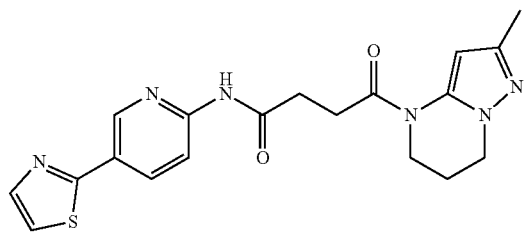 [SMILES: Cc1cc2n(n1)CCCN2C(=O)CCC(=O)Nc1ccc(-c2nccs2)cn1]

¹H NMR (400 MHz, DMSO-d$_6$): 8.87 (s, 1H), 8.49 (br s, 1H), 8.28-8.21 (m, 2H), 7.88 (d, J=3.2 Hz, 1H), 7.34 (d, J=3.2 Hz, 1H), 6.55 (br s, 0.5H), 5.81 (br s, 0.5H), 4.16 (t, J=6.2 Hz, 2H), 3.93 (br s, 2H), 3.05-2.96 (m, 2H), 2.86-2.84 (m, 2H), 2.23-2.18 (m, 5H). LC-MS: m/z 397 [M+H]$^+$.

Synthesis of N-(4-(1H-imidazol-1-yl)phenyl)-4-(2-methyl-6,7-dihydropyrazolo[1,5-a]pyrimidin-4(5H)-yl)-4-oxobutanamide, Compound 27

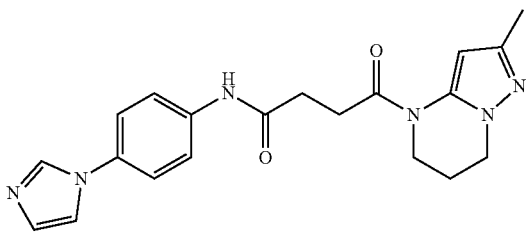 [SMILES: Cc1cc2n(n1)CCCN2C(=O)CCC(=O)Nc1ccc(-n2ccnc2)cc1]

¹H NMR (400 MHz, DMSO-d$_6$): 10.17 (s, 1H), 8.17 (br s, 1H), 7.72-7.68 (m, 3H), 7.57-7.55 (m, 2H), 7.09 (br s, 1H), 6.34 (br s, 1H), 4.02 (t, J=6.0 Hz, 2H), 3.86 (br s, 2H), 2.88 (t, J=6.4 Hz, 2H), 2.65 (t, J=6.4 Hz, 2H), 2.08 (br s, 5H). LC-MS: m/z 379 [M+H]$^+$.

120

Synthesis of 4-(2-methyl-6,7-dihydropyrazolo[1,5-a]pyrimidin-4(5H)-yl)-N-(4-(2-methylthiazol-4-yl)phenyl)-4-oxobutanamide, Compound 28

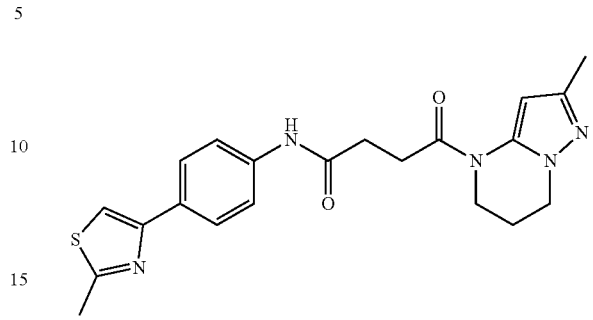

¹H NMR (400 MHz, DMSO-d$_6$): 10.08 (s, 1H), 7.85 (d, J=8.4 Hz, 2H), 7.78)s, 1H), 7.64 (d, J=8.8 Hz, 2H), 6.31 (bs, 1H), 4.02 (t, J=6.0 Hz, 2H), 3.86 (bs, 2H), 2.88 (t, J=6.2 Hz, 2H), 2.70 (s, 3H), 2.67-2.64 (m, 2H), 2.08 (bs, 5H). LC-MS: m/z 410 [M+H]$^+$.

Synthesis of N-(4-(1-methyl-1H-pyrazol-5-yl)phenyl)-4-(2-methyl-6,7-dihydropyrazolo[1,5-a]pyrimidin-4(5H)-yl)-4-oxobutanamide, Compound 29

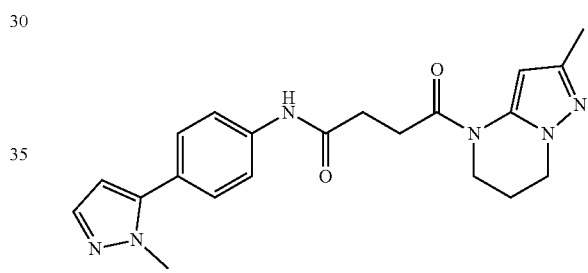

¹H NMR (400 MHz, DMSO-d$_6$): 10.17 (s, 1H), 7.71 (d, J=8.4 Hz, 2H), 7.46-7.43 (m, 3H), 6.34 (d, J=2 Hz, 2H), 4.02 (t, J=6 Hz, 2H), 3.87 (br s, 2H), 3.83 (s, 3H), 2.89 (t, J=6.2 Hz, 2H), 2.67 (t, J=6.4 Hz, 2H), 2.08 (br s, 5H). LC-MS: m/z 393 [M+H]$^+$.

Synthesis of N-(4-(tert-butyl)phenyl)-4-(2-methyl-6,7-dihydropyrazolo[1,5-a]pyrimidin-4(5H)-yl)-4-oxobutanamide, Compound 30

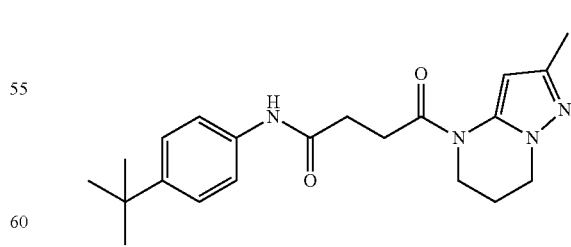

¹H NMR (400 MHz, DMSO-d$_6$): 9.90 (s, 1H), 7.48 (d, J=8.4 Hz, 2H), 7.29 (d, J=8.8 Hz, 2H), 6.34 (br s, 1H), 4.01 (t, J=6.0 Hz, 2H), 3.85 (br s, 2H), 2.87-2.84 (m, 2H), 2.61 (t, J=6.4 Hz, 2H), 2.07 (br s, 5H), 1.25 (s, 9H). LC-MS: m/z 369 [M+H]$^+$.

121

Synthesis of 4-(2-methyl-6,7-dihydropyrazolo[1,5-a]pyrimidin-4(5H)-yl)-4-oxo-N-(4-(pyrrolidin-1-yl)phenyl)butanamide, Compound 31

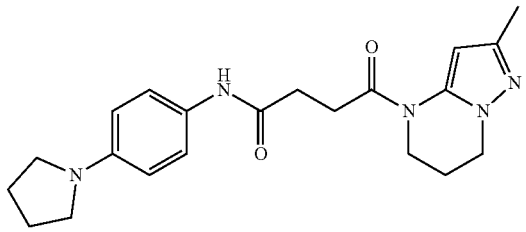 [SMILES: Cc1cc2n(n1)CCCN2C(=O)CCC(=O)Nc1ccc(N2CCCC2)cc1]

$^1$H NMR (400 MHz, Methanol-d$_4$): 7.30 (d, J=8.8 Hz, 2H), 6.53 (d, J=8.8 Hz, 2H), 4.10 (t, J=6.2 Hz, 2H), 3.93 (t, J=5.6 Hz, 2H), 3.26-3.23 (m, 4H), 2.95 (bs, 2H), 2.72 (t, J=6.6 Hz, 2H), 2.33-2.18 (m, 6H), 2.02-2.00 (m, 4H). LC-MS: m/z 382 [M+H]$^+$.

Synthesis of 4-(2-methyl-6,7-dihydropyrazolo[1,5-a]pyrimidin-4(5H)-yl)-N-(4-(2-methylthiazol-4-yl)phenyl)-4-oxobutanamide, Compound 32

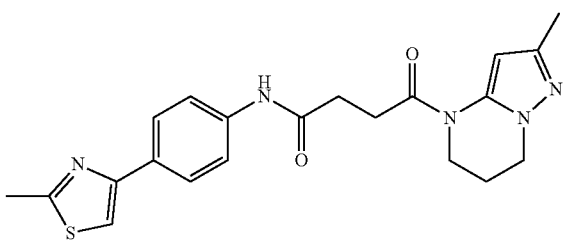

$^1$H NMR (400 MHz, DMSO-d$_6$) 10.65 (s, 1H), 8.87 (s, 1H), 8.26-8.24 (m, 1H), 8.12-8.10 (m, 1H), 7.96 (s, 1H), 6.33 (br s, 1H), 4.02 (t, J=6.0 Hz, 2H), 3.85 (s, 2H), 2.89-2.86 (m, 2H), 2.74-2.72 (m, 5H), 2.07 (s, 5H). LC-MS: m/z 411 [M+H]$^+$.

Synthesis of N-([1,1'-biphenyl]-4-yl)-4-(2-methyl-6,7-dihydropyrazolo[1,5-a]pyrimidin-4(5H)-yl)-4-oxobutanamide, Compound 33

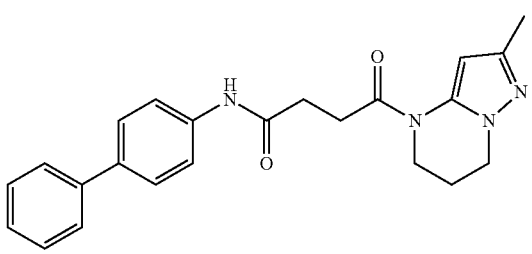

$^1$H NMR (400 MHz, DMSO-d$_6$): 10.09 (s, 1H), 7.70-7.68 (m, 2H), 7.64-7.60 (m, 4H), 7.43 (m, 2H), 7.33-7.31 (m, 1H), 6.35 (bs, 1H), 4.02 (t, J=6 Hz, 2H), 3.87 (bs, 2H), 2.89 (t, J=6.4 Hz, 2H), 2.68-2.65 (m, 2H), 2.08 (bs, 5H). LC-MS: m/z 389 [M+H]$^+$.

122

Synthesis of 4-(2-methyl-6,7-dihydropyrazolo[1,5-a]pyrimidin-4(5H)-yl)-4-oxo-N-(4-(pyridin-2-yl)phenyl)butanamide, Compound 34

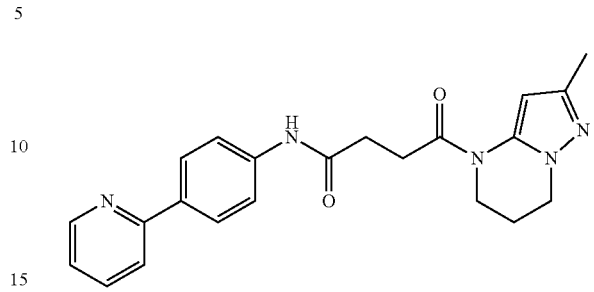

$^1$H NMR (400 MHz, DMSO-d$_6$): 10.15 (s, 1H), 8.62 (d, J=4.4 Hz, 1H), 8.04 (d, J=8.4 Hz, 2H), 7.91-7.89 (m, 1H), 7.86-7.82 (m, 1H), 7.71 (d, J=8.4 Hz, 2H), 7.31-7.27 (m, 1H), 6.34 (br s, 1H), 4.03 (t, J=5.8 Hz, 2H), 3.87 (br s, 2H), 2.91-2.88 (m, 2H), 2.69-2.66 (m, 2H), 2.08 (br s, 5H). LC-MS: m/z 390 [M+H]$^+$.

Synthesis of 4-(2-methyl-6,7-dihydropyrazolo[1,5-a]pyrimidin-4(5H)-yl)-4-oxo-N-(4-(pyridin-3-yl)phenyl)butanamide, Compound 35

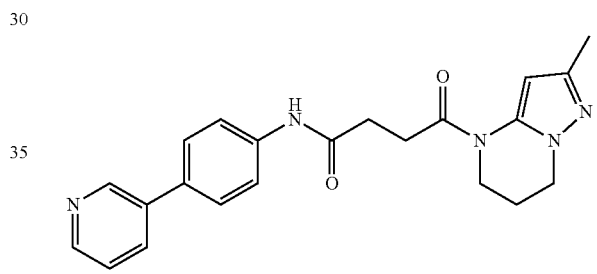

$^1$H NMR (400 MHz, DMSO-d$_6$): 10.14 (s, 1H), 8.87 (s, 1H), 8.52 (s, 1H), 8.04 (d, J=8.0 Hz, 1H), 7.70 (q, J=9.2 Hz, 4H) 7.47-7.44 (m, 1H), 6.35 (br s, 1H), 4.03 (t, J=6.0 Hz, 2H), 3.87 (br s, 2H), 2.89 (t, J=6.2 Hz, 2H), 2.67 (t, J=6.2 Hz, 2H), 2.08 (br s, 5H). LC-MS: m/z 390 [M+H]$^+$.

Synthesis of 4-(2-methyl-6,7-dihydropyrazolo[1,5-a]pyrimidin-4(5H)-yl)-4-oxo-N-(4-(pyridin-4-yl)phenyl)butanamide, Compound 36

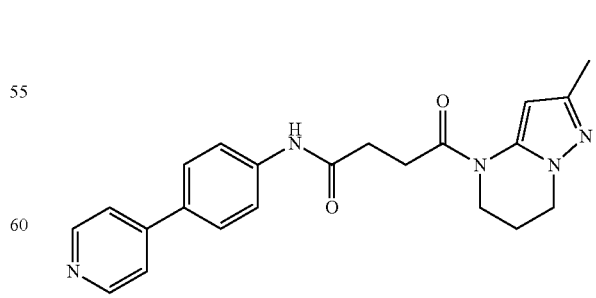

$^1$H NMR (400 MHz, DMSO-d$_6$): 10.20 (s, 1H), 8.59 (d, J=5.4 Hz, 2H), 7.76 (q, J=8.8 Hz, 4H), 7.68 (d, J=6 Hz, 2H), 6.34 (br s, 1H), 4.10-4.01 (t, J=6.0 Hz, 2H), 3.86 (br s, 2H), 2.91-2.88 (t, J=6.2 Hz, 2H), 2.67 (t, J=6.2 Hz, 2H), 2.08 (br s, 5H). LC-MS: m/z 390 [M+H]⁺.

Synthesis of 4-{2-methyl-5H,6H,7H-pyrazolo[1,5-a]pyrimidin-4-yl}-4-oxo-N-[4-(pyridazin-3-yl)phenyl]butanamide, Compound 37

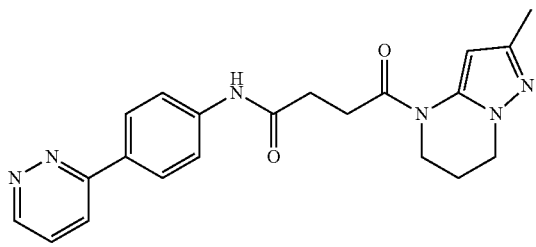 [SMILES: Cc1cc2n(n1)CCCN2C(=O)CCC(=O)Nc1ccc(-c2cccnn2)cc1]

¹H NMR (400 MHz, DMSO-d₆): 10.24 (s, 1H), 8.18-8.11 (m, 3H), 7.79-7.73 (m, 3H), 6.35 (br s, 1H), 4.02 (t, J=6.0 Hz, 2H), 3.87 (s, 2H), 2.90-2.88 (m, 2H), 2.69 (t, J=6.4 Hz, 2H), 2.08 (s, 5H). LC-MS: m/z 391 [M+H]⁺.

Synthesis of 4-(2-methyl-6,7-dihydropyrazolo[1,5-a]pyrimidin-4(5H)-yl)-4-oxo-N-(4-(pyrimidin-4-yl)phenyl)butanamide, Compound 38

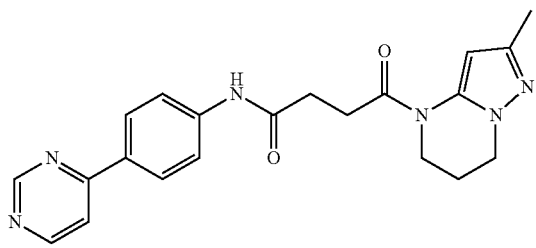 [SMILES: Cc1cc2n(n1)CCCN2C(=O)CCC(=O)Nc1ccc(-c2ccncn2)cc1]

¹H NMR (400 MHz, DMSO-d₆): 10.29 (s, 1H), 9.17 (d, J=1.2 Hz, 1H), 8.79 (d, J=5.2 Hz, 1H), 8.19-8.17 (m, 2H), 8.03-8.01 (m, 1H), 7.78-7.76 (m, 2H), 6.33 (br s, 1H), 4.02 (t, J=5.6 Hz, 2H), 3.86 (s, 2H), 2.91-2.88 (m, 2H), 2.70-2.67 (m, 2H), 2.39 (s, 3H), 2.08 (s, 5H). LC-MS: m/z 391 [M+H]⁺.

Synthesis of 4-{2-methyl-5H,6H,7H-pyrazolo[1,5-a]pyrimidin-4-yl}-4-oxo-N-[4-(pyrimidin-5-yl)phenyl]butanamide, Compound 39

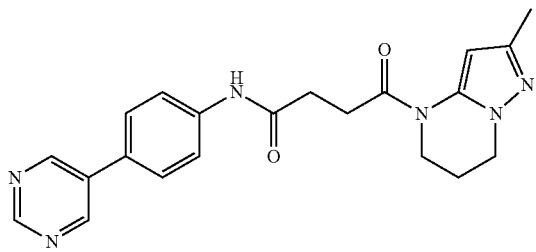

¹H NMR (400 MHz, DMSO-d₆): 10.20 (s, 1H), 9.13-9.11 (m, 3H), 7.79-7.74 (m, 4H), 6.34 (br s, 1H), 4.04-4.01 (m, 2H), 3.86 (s, 2H), 2.89 (t, J=6.4 Hz, 2H), 2.67 (t, J=6.8 Hz, 2H), 2.08 (br s, 5H). LC-MS: m/z 391 [M+H]⁺.

Synthesis of 4-{2-methyl-5H,6H,7H-pyrazolo[1,5-a]pyrimidin-4-yl}-4-oxo-N-[4-(pyrimidin-2-yl)phenyl]butanamide, Compound 40

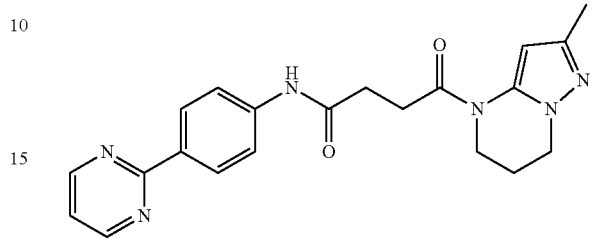

¹H NMR (400 MHz, Methanol-d₄): 8.82 (d, J=4.8 Hz, 2H), 8.36 (d, J=8.8 Hz, 2H), 7.73 (d, J=8.8 Hz, 2H), 7.32 (t, J=4.8 Hz, 1H), 4.12 (t, J=6.0 Hz, 2H), 3.98-3.96 (m, 2H), 3.01 (br s, 2H), 2.82 (t, J=6.8 Hz, 2H), 2.24-2.20 (m, 5H). LC-MS: m/z 391 [M+H]⁺.

Synthesis of N-([2,3'-bipyridin]-6'-yl)-4-(2-methyl-6,7-dihydropyrazolo[1,5-a]pyrimidin-4(5H)-yl)-4-oxobutanamide, Compound 41

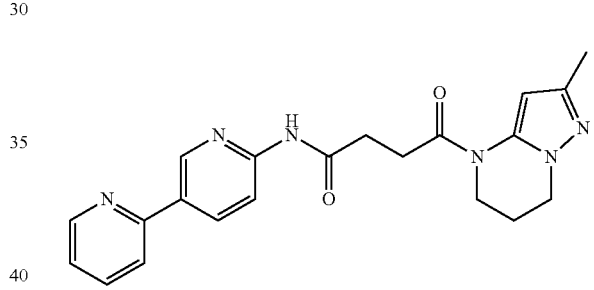

¹H NMR (400 MHz, Chloroform-d): 10.72 (1H, s), 9.02 (1H, d, J=2.0 Hz), 8.66 (1H, d, J=4.4 Hz), 8.43 (1H, dd, J=8.4, 2.4 Hz), 8.17 (1H, d, J=8.8 Hz), 8.00 (1H, d, J=8.0 Hz), 7.86-7.91 (1H, m), 7.35-7.38 (1H, m), 6.34 (1H, bs), 4.02 (2H, t), 3.86 (2H, bs), 2.89 (2H, t), 2.74 (2H, t), 2.08 (5H, m). LC-MS: m/z 391.1 [M+H]⁺.

Synthesis of 4-(2-methyl-6,7-dihydropyrazolo[1,5-a]pyrimidin-4(5H)-yl)-4-oxo-N-(4-(pyrazin-2-yl)phenyl)butanamide, Compound 42

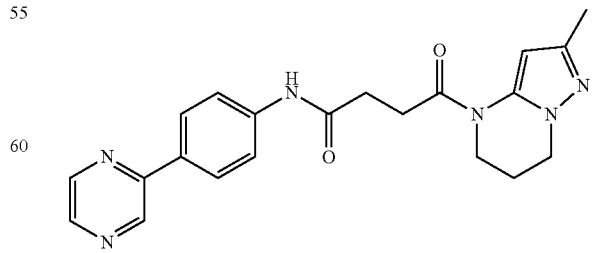

¹H NMR (400 MHz, DMSO-d₆): 10.24 (s, 1H), 9.21 (d, J=1.6 Hz, 1H), 8.68-8.65 (m, 1H), 8.55 (d, J=2.4 Hz, 1H), 8.12-8.08 (m, 2H), 7.80-7.72 (m, 2H), 6.35 (bs, 1H), 4.03 (t, J=6.0 Hz, 2H), 3.87 (bs, 2H), 2.95-2.85 (m, 2H), 2.72-2.65 (m, 2H), 2.08 (bs, 5H). MS (ESI) m/z 391 [M+H]+.

Synthesis of 4-(2-methyl-6,7-dihydropyrazolo[1,5-a]pyrimidin-4(5H)-yl)-4-oxo-N-(6-phenylpyridin-3-yl)butanamide, Compound 43

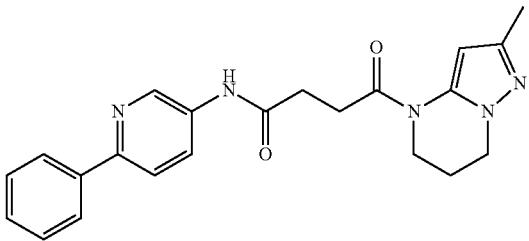

¹H NMR (400 MHz, Chloroform-d): 8.66 (1H, s), 8.52 (1H, bs), 8.23 (1H, bs), 8.10 (1H, s), 7.89 (2H, d, J=7.6 Hz), 7.65 (1H, d, J=8.8 Hz), 7.37-7.47 (3H, m), 4.17 (2H, t), 3.90 (2H, bs), 2.98 (2H, m), 2.82 (2H, t), 2.23 (5H, m). LC-MS: m/z 390.1 [M+H]+.

Synthesis of 4-(2-methyl-6,7-dihydropyrazolo[1,5-a]pyrimidin-4(5H)-yl)-4-oxo-N-(5-phenylpyridin-2-yl)butanamide, Compound 44

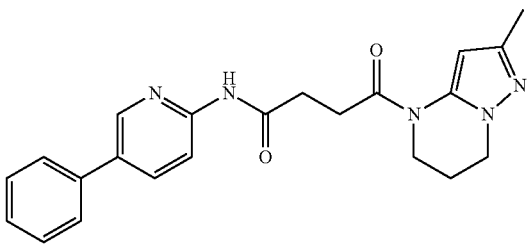 [SMILES: Cc1cc2n(n1)CCCN2C(=O)CCC(=O)Nc1ccc(-c2ccccc2)cn1]

¹H NMR (400 MHz, Chloroform-d): 8.66 (1H, s), 8.52 (1H, bs), 8.23 (1H, bs), 8.10 (1H, s), 7.89 (2H, d, J=7.6 Hz), 7.65 (1H, d, J=8.8 Hz), 7.37-7.47 (3H, m), 4.17 (2H, t), 3.90 (2H, bs), 2.98 (2H, m), 2.82 (2H, t), 2.23 (5H, m). LC-MS: m/z 390.1 [M+H]+.

Synthesis of 4-(2-methyl-6,7-dihydropyrazolo[1,5-a]pyrimidin-4(5H)-yl)-4-oxo-N-(6-phenylpyridazin-3-yl)butanamide, Compound 45

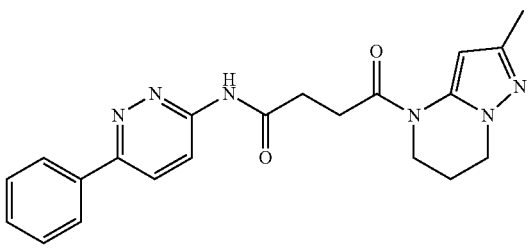

¹H NMR (400 MHz, DMSO-d₆): 11.25 (1H, s), 8.36 (1H, d, J=9.6 Hz), 8.21 (1H, d, J=9.6 Hz), 8.09 (2H, d, J=7.2 Hz), 7.49-7.56 (3H, m), 6.33 (1H, bs), 4.02 (2H, t), 3.86 (2H, bs), 2.91 (2H, t), 2.80 (2H, t), 2.08 (5H, m). LC-MS: m/z 391.1 [M+H]+.

Synthesis of 4-{2-methyl-5H,6H,7H-pyrazolo[1,5-a]pyrimidin-4-yl}-4-oxo-N-(5-phenylpyrimidin-2-yl)butanamide, Compound 46

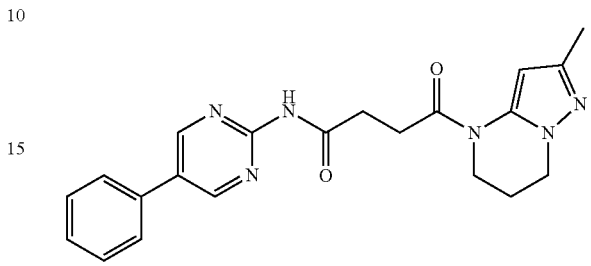

¹H NMR (400 MHz, DMSO-d₆): 10.71 (s, 1H), 8.98 (s, 2H), 7.77 (d, J=7.2 Hz, 2H), 7.51 (t, J=7.2 Hz, 2H), 7.43 (t, J=7.2 Hz, 1H), 6.34 (br s, 1H), 4.02 (t, J=6.0 Hz, 2H), 3.86 (s, 2H), 2.90-2.87 (s, 4H), 2.08 (s, 5H). LC-MS: m/z 391 [M+H]+.

Synthesis of 4-(2-methyl-6,7-dihydropyrazolo[1,5-a]pyrimidin-4(5H)-yl)-4-oxo-N-(5-phenylpyrazin-2-yl)butanamide, Compound 47

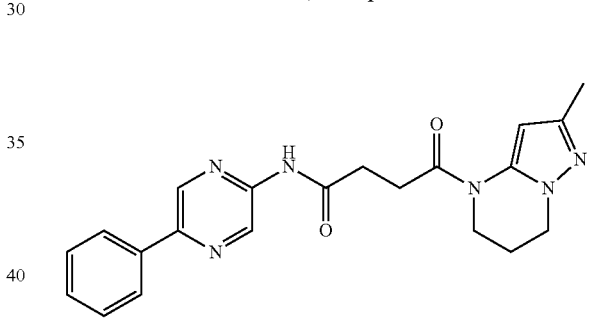

¹H NMR (400 MHz, DMSO-d₆): 10.93 (s, 1H), 9.37 (s, 1H), 9.00 (s, 1H), 8.10-8.08 (m, 2H), 7.53-7.45 (m, 3H), 6.34 (bs, 1H), 4.03 (t, J=6.0 Hz, 2H), 3.87 (bs, 2H), 2.93-2.90 (m, 2H), 2.79-2.76 (m, 2H), 2.08 (bs, 5H). LC-MS: m/z 391 [M+H]+.

Synthesis of N-([2,3'-bipyridin]-5-yl)-4-(2-methyl-6,7-dihydropyrazolo[1,5-a]pyrimidin-4(5H)-yl)-4-oxobutanamide, Compound 48

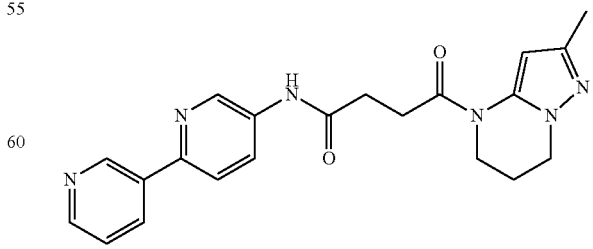

¹H NMR (400 MHz, DMSO-d₆): 10.50 (s, 1H), 9.21 (s, 1H), 8.89 (d, J=2.0 Hz, 1H), 8.58 (dd, J=4 Hz, 1.2 Hz, 1H), 8.39-8.36 (m, 1H), 8.20-8.17 (m, 1H), 8.01 (d, J=8.8 Hz, 1H), 7.50-7.47 (m, 1H), 6.35 (bs, 1H), 4.02 (t, J=5.8 Hz, 2H), 2.67 (bs, 2H), 2.93-2.89 (m, 2H), 2.73-2.69 (m, 2H), 2.08 (bs, 5H). LC-MS: m/z 391 [M+H]⁺.

Synthesis of 4-{2-methyl-5H,6H,7H-pyrazolo[1,5-a]pyrimidin-4-yl}-4-oxo-N-[5-(pyridin-3-yl)pyridin-2-yl]butanamide, Compound 49

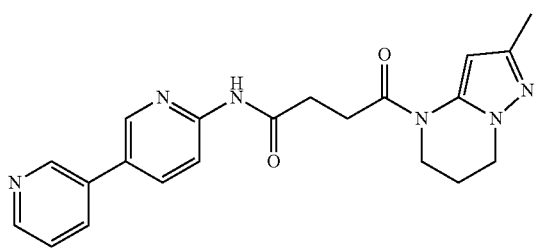 [SMILES: Cc1cc2n(n1)CCCN2C(=O)CCC(=O)Nc1ccc(-c2cccnc2)cn1]

¹H NMR (400 MHz, DMSO-d₆) 10.68 (s, 1H), 8.94 (d, J=2.0 Hz, 1H), 8.71 (s, 1H), 8.58-8.57 (m, 1H), 8.16-8.12 (m, 3H), 7.51-7.47 (m, 1H), 6.34 (br s, 1H), 4.02 (t, J=5.6 Hz, 2H), 3.86 (s, 2H), 2.90-2.87 (m, 2H), 2.76-2.73 (m, 2H), 2.08 (s, 5H). LC-MS: m/z 391 [M+H]⁺.

Synthesis of 4-(2-methyl-6,7-dihydropyrazolo[1,5-a]pyrimidin-4(5H)-yl)-4-oxo-N-(5-(pyrazin-2-yl)pyridin-2-yl)butanamide, Compound 50

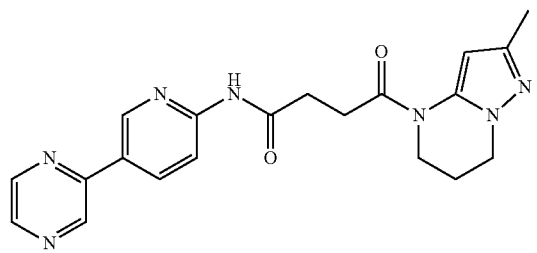 [SMILES: Cc1cc2n(n1)CCCN2C(=O)CCC(=O)Nc1ccc(-c2cnccn2)cn1]

¹H NMR (400 MHz, Chloroform-d): 9.01 (1H, d, J=1.2 Hz), 8.94 (1H, s), 8.63 (1H, t), 8.53 (1H, d, J=2.4 Hz), 8.45 (1H, s), 8.33 (2H, m), 4.16 (2H, t), 3.94 (2H, bs), 2.97 (2H, m), 2.87 (2H, t), 2.23 (4H, m), 1.25 (3H, s). LC-MS: m/z 392.1 [M+H]⁺.

Synthesis of 4-(2-methyl-6,7-dihydropyrazolo[1,5-a]pyrimidin-4(5H)-yl)-4-oxo-N-(5-(pyridin-3-yl)pyrazin-2-yl)butanamide, Compound 52

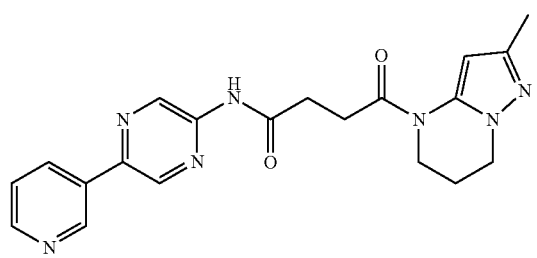

¹H NMR (400 MHz, DMSO-d₆): 11.00 (s, 1H), 9.40 (s, 1H), 9.27 (m, 1H), 9.08 (m, 1H), 8.65-8.64 (m, 1H), 8.45-8.43 (m, 1H), 7.55-7.52 (m, 1H), 6.34 (bs, 1H), 4.03 (t, J=5.8 Hz, 2H), 3.87 (bs, 2H), 2.93-2.90 (m, 2H), 2.80-2.77 (m, 2H), 2.08 (bs, 5H). LC-MS: m/z 392 [M+H]⁺.

Synthesis of 4-(2-methyl-6,7-dihydropyrazolo[1,5-a]pyrimidin-4(5H)-yl)-N-(3-methyl-[1,1'-biphenyl]-4-yl)-4-oxobutanamide, Compound 53

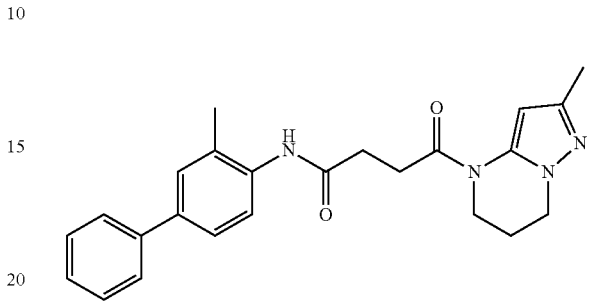

¹H NMR (400 MHz, DMSO-d₆): 9.38 (s, 1H), 7.65-7.63 (m, 2H), 7.52-7.42 (m, 5H), 7.35-7.31 (m, 1H), 6.36 (br s, 1H), 4.02 (t, J=6.0 Hz, 2H), 3.86 (s, 2H), 2.89-2.88 (m, 2H), 2.71-2.68 (m, 2H), 2.28 (s, 3H), 2.09 (s, 5H). LC-MS: m/z 403 [M+H]⁺.

Synthesis of 4-(2-methyl-6,7-dihydropyrazolo[1,5-a]pyrimidin-4(5H)-yl)-N-(2-methyl-[1,1'-biphenyl]-4-yl)-4-oxobutanamide, Compound 54

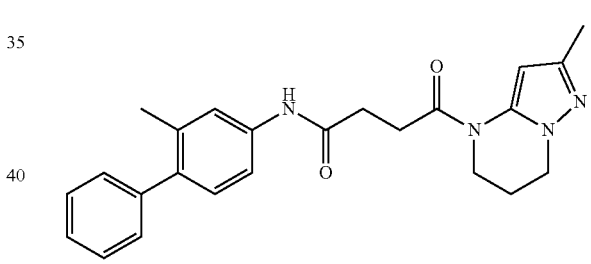

¹H NMR (400 MHz, DMSO-d₆): 9.99 (s, 1H), 7.52-7.40 (m, 4H), 7.35-7.29 (m, 3H), 7.12-7.10 (m, 1H), 6.35 (br s, 1H), 4.02 (t, J=6.0 Hz, 2H), 3.86 (s, 2H), 2.89-2.86 (m, 2H), 2.66-2.63 (m, 2H), 2.20 (s, 3H), 2.08 (s, 5H). LC-MS: m/z 403 [M+H]⁺.

Synthesis of N-(3-methoxy-[1,1'-biphenyl]-4-yl)-4-(2-methyl-6,7-dihydropyrazolo[1,5-a]pyrimidin-4(5H)-yl)-4-oxobutanamide, Compound 55

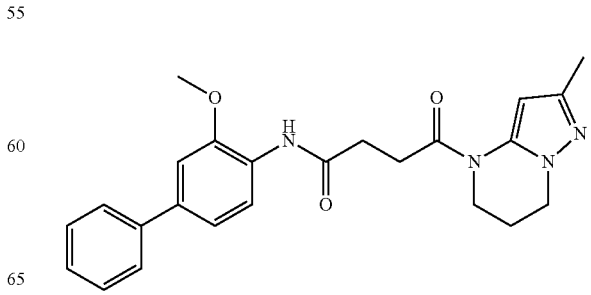

¹H NMR (400 MHz, DMSO-d₆): 9.22 (s, 1H), 8.07 (d, J=8.0 Hz, 1H), 7.68 (d, J=7.2 Hz, 2H), 7.44 (t, J=7.2 Hz, 2H), 7.35-7.33 (m, 1H), 7.28 (s, 1H), 7.21-7.18 (m, 1H), 6.35 (br s, 1H), 4.02 (t, J=6.0 Hz, 2H), 3.94 (s, 3H), 3.86 (s, 2H), 2.88-2.85 (m, 2H), 2.75-2.72 (m, 2H), 2.08 (s, 5H). LC-MS: m/z 419 [M+H]⁺.

Synthesis of N-(2-methoxy-[1,1'-biphenyl]-4-yl)-4-(2-methyl-6,7-dihydropyrazolo[1,5-a]pyrimidin-4(5H)-yl)-4-oxobutanamide, Compound 56

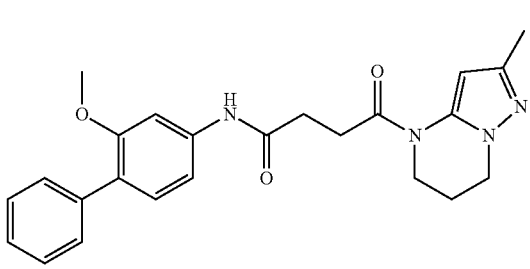

¹H NMR (400 MHz, DMSO-d₆): 10.10 (s, 1H), 7.51 (bs, 1H), 7.46-7.44 (m, 2H), 7.37 (t, J=7.6 Hz, 2H), 7.29-7.26 (m, 1H), 7.21 (s, 2H), 6.35 (bs, 1H), 4.03 (t, J=5.8 Hz, 2H), 3.87 (bs, 2H), 2.90-2.87 (m, 2H), 2.68-2.64 (m, 2H), 2.08 (bs, 5H). LC-MS: m/z 419 [M+H]⁺.

Synthesis of N-(2-fluorobiphenyl-4-yl)-4-(2-methyl-6,7-dihydropyrazolo[1,5-a]pyrimidin-4(5H)-yl)-4-oxobutanamide, Compound 57

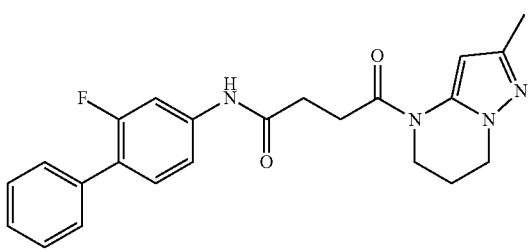

¹H NMR (400 MHz, DMSO-d₆): 10.31 (s, 1H), 7.73-7.67 (m, 1H), 7.54-7.42 (m, 5H), 7.41-7.34 (m, 2H), 6.35 (bs, 1H), 4.03 (t, J=6.4 Hz, 2H), 3.87 (bs, 2H), 2.92-2.83 (m, 2H), 2.70-2.63 (m, 2H), 2.08 (bs, 5H). MS (ESI) m/z 407 [M+H]⁺.

Synthesis of 4-(2-methyl-6,7-dihydropyrazolo[1,5-a]pyrimidin-4(5H)-yl)-N-(2'-methyl-[1,1'-biphenyl]-4-yl)-4-oxobutanamide, Compound 58

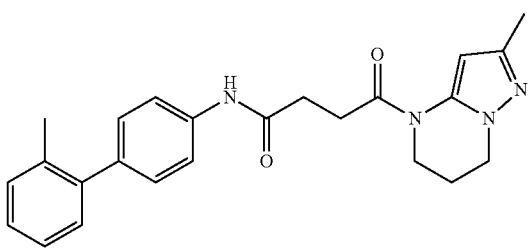

¹H NMR (400 MHz, DMSO-d₆): 10.08 (s, 1H), 7.66-7.64 (m, 2H), 7.29-7.16 (m, 6H), 6.35 (br s, 1H), 4.03 (t, J=6.0 Hz, 2H), 3.87 (s, 2H), 2.91-2.88 (m, 2H), 2.68-2.65 (m, 2H), 2.23 (s, 3H), 2.09 (s, 5H). LC-MS: m/z 403 [M+H]⁺.

Synthesis of 4-(2-methyl-6,7-dihydropyrazolo[1,5-a]pyrimidin-4(5H)-yl)-N-(3'-methyl-[1,1'-biphenyl]-4-yl)-4-oxobutanamide, Compound 59

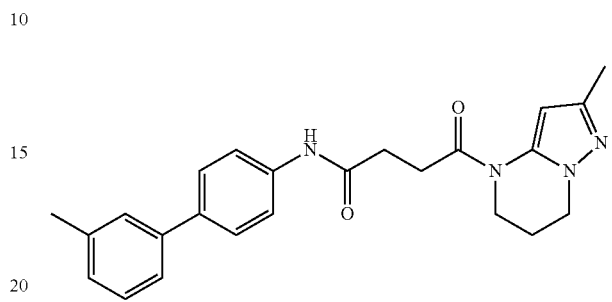

¹H NMR (400 MHz, DMSO-d₆): 10.09 (s, 1H), 7.69-7.66 (m, 2H), 7.60-7.58 (m, 2H), 7.45-7.41 (m, 2H), 7.34-7.30 (m, 1H), 7.14-7.12 (m, 1H), 6.34 (br s, 1H), 4.03 (t, J=6.0 Hz, 2H), 3.87 (s, 2H), 2.91-2.87 (m, 2H), 2.68-2.65 (m, 2H), 2.36 (s, 3H), 2.08 (s, 5H). LC-MS: m/z 403 [M+H]⁺.

Synthesis of 4-(2-methyl-6,7-dihydropyrazolo[1,5-a]pyrimidin-4(5H)-yl)-N-(4'-methyl-[1,1'-biphenyl]-4-yl)-4-oxobutanamide, Compound 60

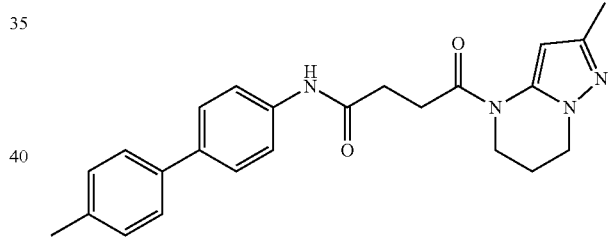

¹H NMR (400 MHz, DMSO-d₆): 10.07 (s, 1H), 7.67-7.65 (m, 2H), 7.58-7.51 (m, 4H), 7.24 (d, J=8.0 Hz, 2H), 6.34 (bs, 1H), 4.02 (t, J=6.0 Hz, 2H), 3.86 (bs, 2H), 2.88 (t, J=6.4 Hz, 2H), 2.67-2.64 (m, 2H), 2.32 (s, 3H), 2.08 (bs, 5H). LC-MS: m/z 403 [M+H]⁺.

Synthesis of N-(2'-methoxy-[1,1'-biphenyl]-4-yl)-4-(2-methyl-6,7-dihydropyrazolo[1,5-a]pyrimidin-4(5H)-yl)-4-oxobutanamide, Compound 61

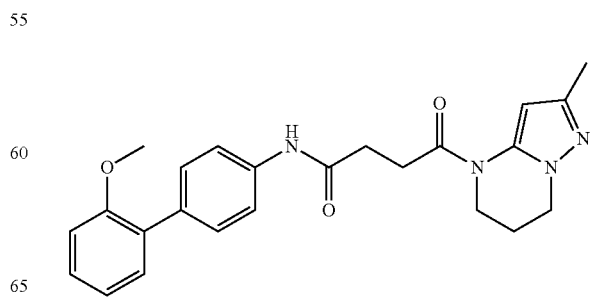

¹H NMR (400 MHz, DMSO-d₆): 10.05 (s, 1H), 7.61 (d, J=8.4 Hz, 2H), 7.39 (d, J=8.8 Hz, 2H), 7.33-7.25 (m, 2H), 7.08 (d, J=7.6 Hz, 1H), 7.00 (t, J=4.2 Hz, 1H), 6.30 (bs, 1H), 4.02 (t, J=6.0 Hz, 2H), 3.86 (bs, 2H), 3.75 (s, 3H), 2.88 (t, J=6.4 Hz, 2H), 2.67-2.64 (m, 2H), 2.08 (bs, 5H). LC-MS: m/z 419 [M+H]⁺.

Synthesis of N-(3'-methoxy-[1,1'-biphenyl]-4-yl)-4-(2-methyl-6,7-dihydropyrazolo[1,5-a]pyrimidin-4(5H)-yl)-4-oxobutanamide, Compound 62

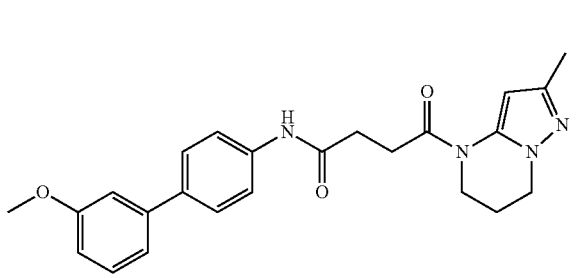

¹H NMR (400 MHz, DMSO-d₆): 10.10 (s, 1H), 7.69-7.67 (m, 2H), 7.63-7.60 (m, 6H), 7.37-7.33 (m, 1H), 7.21-7.16 (m, 2H), 6.91-6.88 (m, 1H), 6.35 (br s, 1H), 4.03 (t, J=5.6 Hz, 2H), 3.87-3.82 (m, 5H), 2.91-2.87 (m, 2H), 2.68-2.65 (m, 2H), 2.08 (s, 5H). LC-MS: m/z 419 [M+H]⁺.

Synthesis of N-(4'-methoxy-[1,1'-biphenyl]-4-yl)-4-(2-methyl-6,7-dihydropyrazolo[1,5-a]pyrimidin-4(5H)-yl)-4-oxobutanamide, Compound 63

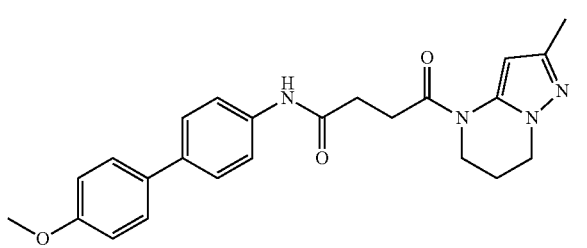

¹H NMR (400 MHz, DMSO-d₆): 10.05 (s, 1H), 7.65-7.63 (m, 2H), 7.58-7.53 (m, 4H), 6.99 (d, J=8.8 Hz, 2H), 6.30 (bs, 1H), 4.02 (t, J=6 Hz, 2H), 3.87 (bs, 2H), 3.78 (s, 3H), 2.90-2.86 (m, 2H), 2.65 (t, J=6.2 Hz, 2H), 2.08 (bs, 5H). LC-MS: m/z 419 [M+H]⁺.

Synthesis of N-(3'-fluoro-[1,1'-biphenyl]-4-yl)-4-(2-methyl-6,7-dihydropyrazolo[1,5-a]pyrimidin-4(5H)-yl)-4-oxobutanamide, Compound 65

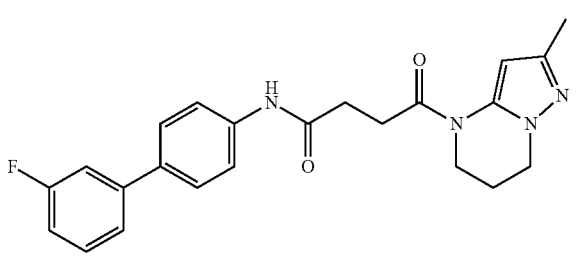 [SMILES: Cc1cc2n(n1)CCCN2C(=O)CCC(=O)Nc1ccc(-c2cccc(F)c2)cc1]

¹H NMR (400 MHz, DMSO-d₆): 10.13 (s, 1H), 7.71-7.65 (m, 4H), 7.51-7.46 (m, 3H), 7.16-7.12 (m, 1H), 6.35 (br, 1H), 4.03 (t, J=5.8 Hz, 2H), 3.87 (br, 2H), 2.91-2.88 (m, 2H), 2.68-2.65 (m, 2H), 2.08 (br, 5H). LC-MS: m/z 407 [M+H]⁺.

Synthesis of N-(4'-fluorobiphenyl-4-yl)-4-(2-methyl-6,7-dihydropyrazolo[1,5-a]pyrimidin-4(5H)-yl)-4-oxobutanamide, Compound 66

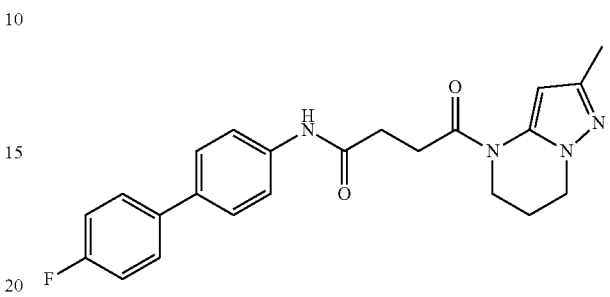

¹H NMR (400 MHz, DMSO-d₆): 10.10 (s, 1H), 7.70-7.62 (m, 4H), 7.61-7.57 (m, 2H), 7.30-7.20 (m, 2H), 6.35 (bs, 1H), 4.02 (t, J=6.4 Hz, 2H), 3.87 (bs, 2H), 2.92-2.85 (m, 2H), 2.70-2.63 (m, 2H), 2.08 (bs, 5H); MS (ESI) m/z 407 [M+H]⁺.

Synthesis of 4'-(4-(2-methyl-6,7-dihydropyrazolo[1,5-a]pyrimidin-4(5H)-yl)-4-oxobutanamido)-[1,1'-biphenyl]-3-carboxylic acid, Compound 67

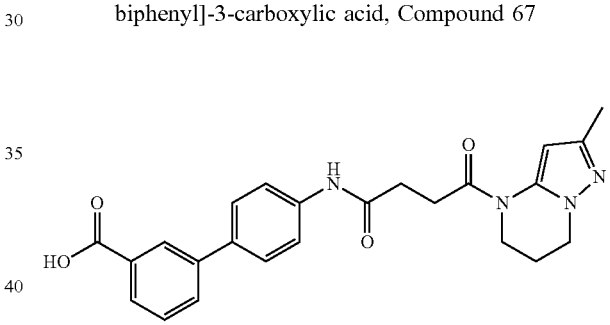

¹H NMR (400 MHz, DMSO-d₆): 10.12 (s, 1H), 8.15 (s, 1H), 7.98-7.94 (m, 1H), 7.90-7.87 (m, 2H), 7.73-7.64 (m, 4H), 7.56 (t, J=7.6 Hz, 1H), 6.35 (bs, 1H), 4.03 (t, J=5.8 Hz, 2H), 3.87 (bs, 2H), 2.91-2.88 (m, 2H), 2.67 (t, J=6.6 Hz, 2H), 2.08 (s, 5H). LC-MS: m/z 433 [M+H]⁺.

Synthesis of N-(2'-amino-[1,1'-biphenyl]-4-yl)-4-(2-methyl-6,7-dihydropyrazolo[1,5-a]pyrimidin-4(5H)-yl)-4-oxobutanamide, Compound 69

Step 1: Preparation of N-(4-bromophenyl)-4-(2-methyl-6,7-dihydropyrazolo[1,5-a]pyrimidin-4(5H)-yl)-4-oxobutanamide

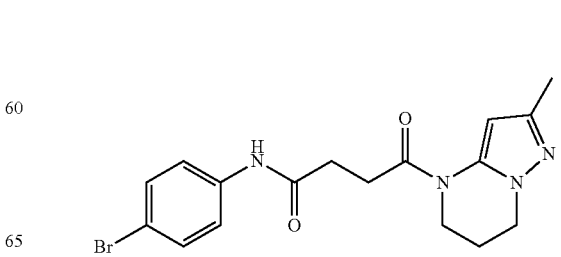

¹H NMR (400 MHz, DMSO-d₆): 10.13 (s, 1H), 7.57-7.55 (m, 2H), 7.47-7.45 (m, 2H), 6.33 (br s, 1H), 4.01 (t, J=6.0 Hz, 2H), 3.85 (s, 2H), 2.88-2.85 (m, 2H), 2.65-2.61 (m, 2H), 2.08 (s, 5H). LC-MS: m/z 392 [M+H]⁺.

Step 2: Preparation of N-(2'-amino-[1,1'-biphenyl]-4-yl)-4-(2-methyl-6,7-dihydropyrazolo[1,5-a]pyrimidin-4(5H)-yl)-4-oxobutanamide

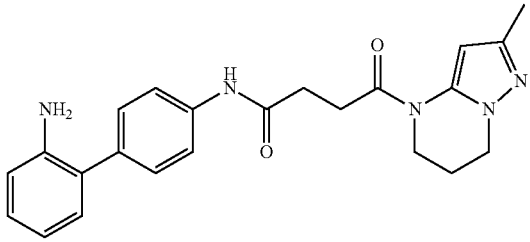

The desired product was obtained using general Suzuki procedure A.

¹H NMR (400 MHz, DMSO-d₆): 10.06 (s, 1H), 7.66-7.64 (m, 2H), 7.33-7.31 (m, 2H), 7.03-6.94 (m, 2H), 6.74-6.72 (m, 1H), 6.61 (t, J=7.2 Hz, 1H) 6.35 (br s, 1H), 4.70 (s, 2H), 4.02 (t, J=6.0 Hz, 2H), 3.86 (s, 2H), 2.90-2.87 (m, 2H), 2.67-2.64 (m, 2H), 2.08 (s, 5H). LC-MS: m/z 404 [M+H]⁺.

Synthesis of N-(3'-amino-[1,1'-biphenyl]-4-yl)-4-(2-methyl-6,7-dihydropyrazolo[1,5-a]pyrimidin-4(5H)-yl)-4-oxobutanamide, Compound 70

Step 1: Preparation of 4-(2-methyl-6,7-dihydropyrazolo[1,5-a]pyrimidin-4(5H)-yl)-N-(2-methyl-[1,1'-biphenyl]-4-yl)-4-oxobutanamide

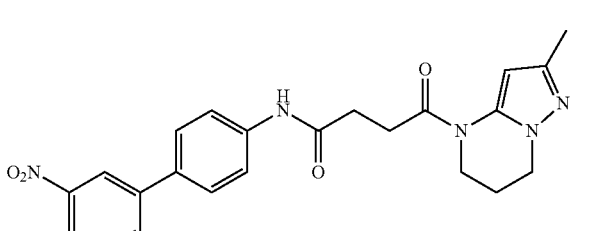

¹H NMR (400 MHz, DMSO-d₆): 10.17 (s, 1H), 8.41 (s, 1H), 8.18-8.12 (m, 2H), 7.75-7.71 (m, 5H), 6.35 (br s, 1H), 4.02 (t, J=6.0 Hz, 2H), 3.87 (s, 2H), 2.91-2.88 (m, 2H), 2.69-2.66 (m, 2H), 2.08 (s, 5H). LC-MS: m/z 434 [M+H]⁺.

Step 2: Preparation of N-(3'-amino-[1,1'-biphenyl]-4-yl)-4-(2-methyl-6,7-dihydropyrazolo[1,5-a]pyrimidin-4(5H)-yl)-4-oxobutanamide

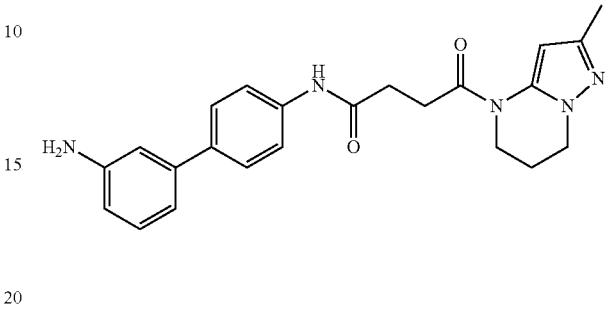

4-{2-methyl-5H,6H,7H-pyrazolo[1,5-a]pyrimidin-4-yl}-N-[4-(3-nitrophenyl)phenyl]-4-oxobutanamide (1 equiv.), ammonium chloride (4 equiv.), and iron (2 equiv.) were added to a solution of ethanol (0.02 M) and water (0.08 M), and heated at 40° C. for 4 h. The reaction mixture was then filtered, diluted with water and extracted with ethyl acetate. The combined organic layers were dried over magnesium sulphate and concentrated under vacuum. The crude product was purified by reversed phase preparative HPLC to afford the purified product.

¹H NMR (400 MHz, DMSO-d₆): 10.05 (s, 1H), 7.65-7.63 (m, 2H), 7.49-7.47 (m, 2H), 7.06 (t, J=7.6 Hz, 1H), 6.80 (s, 1H), 6.75-6.73 (m, 1H), 6.52-6.50 (m, 1H), 6.34 (br s, 1H), 5.09 (s, 2H), 4.02 (t, J=6.0 Hz, 2H), 3.86 (s, 2H), 2.89-2.86 (m, 2H), 2.67-2.63 (m, 2H), 2.08 (s, 5H). LC-MS: m/z 404 [M+H]⁺.

Synthesis of N-(4'-amino-[1,1'-biphenyl]-4-yl)-4-(2-methyl-6,7-dihydropyrazolo[1,5-a]pyrimidin-4(5H)-yl)-4-oxobutanamide, Compound 71

Step 1: Preparation of 4-(2-methyl-6,7-dihydropyrazolo[1,5-a]pyrimidin-4(5H)-yl)-N-(4'-nitro-[1,1'-biphenyl]-4-yl)-4-oxobutanamide

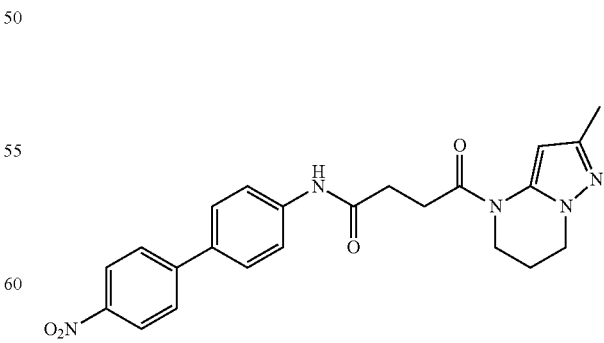

MS: m/z 434 [M+H]⁺.

Step 2: Preparation of N-(4'-amino-[1,1'-biphenyl]-4-yl)-4-(2-methyl-6,7-dihydropyrazolo[1,5-a]pyrimidin-4(5H)-yl)-4-oxobutanamide

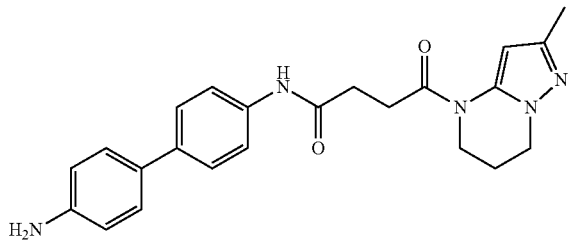 [SMILES: Cc1cc2n(n1)CCCN2C(=O)CCC(=O)Nc1ccc(-c2ccc([N+](=O)[O-])cc2)cc1]

The desired product was obtained in a similar fashion as compound 70.

¹H NMR (400 MHz, DMSO-d₆): 9.97 (s, 1H), 7.60-7.58 (m, 2H), 7.47-7.45 (m, 2H), 7.36-7.34 (m, 2H), 6.67 (d, J=8.0 Hz, 2H), 6.34 (br s, 1H), 5.70-5.60 (br s, 2H), 4.02 (t, J=5.6 Hz, 2H), 3.86 (s, 2H), 2.89-2.86 (m, 2H), 2.65-2.62 (m, 2H), 2.08 (s, 5H). LC-MS: m/z 404 [M+H]⁺.

Synthesis of N-(3'-(dimethylamino)-[1,1'-biphenyl]-4-yl)-4-(2-methyl-6,7-dihydropyrazolo[1,5-a]pyrimidin-4(5H)-yl)-4-oxobutanamide, Compound 72

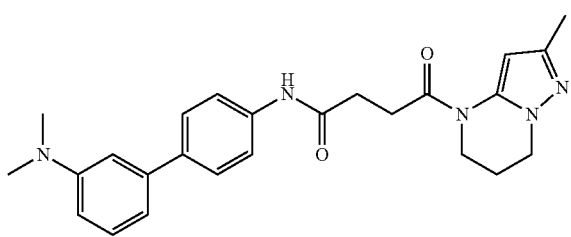

¹H NMR (400 MHz, DMSO-d₆): 10.03 (s, 1H), 7.63 (d, J=8.4 Hz, 2H), 7.45 (d, J=8.4 Hz, 2H), 7.25-7.21 (m, 1H), 7.14-7.12 (m, 1H), 7.04-6.96 (m, 2H), 6.34 (bs, 1H), 4.02 (t, J=6.0 Hz, 2H), 3.87 (bs, 2H), 2.90-2.87 (m, 2H), 2.67-2.64 (m, 2H), 2.47 (s, 6H), 2.08 (bs, 5H). LC-MS: m/z 432 [M+H]⁺.

Synthesis of N-(3'-acetamido-[1,1'-biphenyl]-4-yl)-4-(2-methyl-6,7-dihydropyrazolo[1,5-a]pyrimidin-4(5H)-yl)-4-oxobutanamide, Compound 74

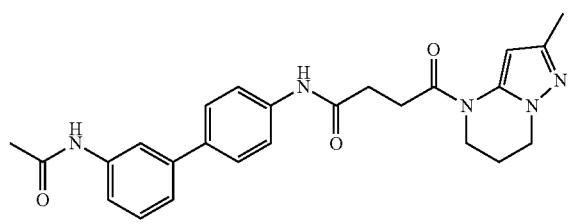 [SMILES: CC(=O)Nc1cccc(-c2ccc(NC(=O)CCC(=O)N3CCCn4nc(C)cc43)cc2)c1]

N-[4-(3-aminophenyl)phenyl]-4-{2-methyl-5H,6H,7H-pyrazolo[1,5-a]pyrimidin-4-yl}-4-oxobutanamide (1 equiv.) was dissolved in dichloromethane (0.02 M) at 0° C. Triethylamine (1 equiv.), followed by acetyl chloride (1.05 equiv.), was added to the solution, and the reaction mixture allowed to stir for 30 min. It was then diluted with water and extracted with dichloromethane. The combined organic layers were dried over magnesium sulphate and concentrated under vacuum. The crude product was purified by reversed phase preparative HPLC to afford the purified product.

¹H NMR (400 MHz, DMSO-d₆) 10.09 (s, 1H), 9.98 (s, 1H), 7.83 (s, 1H), 7.69-7.67 (m, 2H), 7.54-7.52 (m, 3H), 7.36-7.27 (m, 2H), 6.34 (br s, 1H), 4.03 (t, J=6.0 Hz, 2H), 3.86 (s, 2H), 2.90-2.87 (m, 2H), 2.67-2.64 (m, 2H), 2.08-2.05 (m, 8H). LC-MS: m/z 446 [M+H]⁺.

Synthesis of N-(4-cyclohexylphenyl)-4-(2-methyl-6,7-dihydropyrazolo[1,5-a]pyrimidin-4(5H)-yl)-4-oxobutanamide, Compound 75

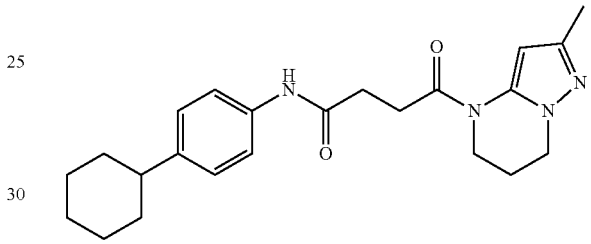

¹H NMR (400 MHz, DMSO-d₆): 9.88 (s, 1H), 7.47 (d, J=8.4 Hz, 2H), 7.11 (d, J=8.4 Hz, 2H), 6.34 (bs, 1H), 4.02 (t, J=5.6 Hz, 2H), 3.85 (bs, 2H), 2.87-2.84 (m, 2H), 2.61 (t, J=6.4 Hz, 2H), 2.42 (m, 1H), 2.08 (bs, 5H), 1.76-1.67 (m, 5H), 1.41-1.19 (m, 5H). LC-MS: m/z 395 [M+H]⁺.

Synthesis of tert-butyl 4-(4-(4-(2-methyl-6,7-dihydropyrazolo[1,5-a]pyrimidin-4(5H)-yl)-4-oxobutanamido)phenyl)piperazine-1-carboxylate, Compound 76

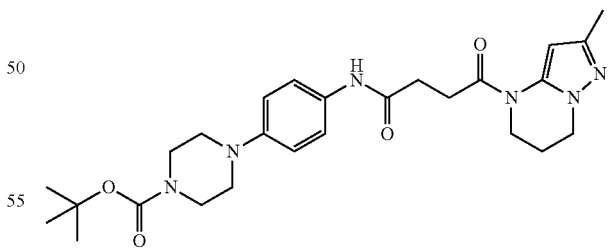

¹H NMR (400 MHz, DMSO-d₆): 9.77 (s, 1H), 7.44 (d, J=8.8 Hz, 2H), 6.88 (d, J=9.2 Hz, 2H), 6.30 (bs, 1H), 4.02 (t, J=6.0 Hz, 2H), 3.85 (bs, 2H), 3.45-3.43 (m, 4H), 3.02-2.99 (m, 4H), 2.87-2.83 (m, 2H), 2.60-2.57 (m, 2H), 2.08 (bs, 5H), 1.42 (s, 9H). LC-MS: m/z 497 [M+H]⁺.

Synthesis of 4-(2-methyl-6,7-dihydropyrazolo[1,5-a]pyrimidin-4(5H)-yl)-4-oxo-N-(4-(piperazin-1-yl)phenyl)butanamide, Compound 77

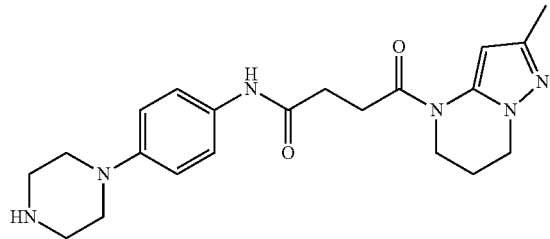

4M HCl in dioxane (15 equiv.) was added to the boc-protected amine (1 equiv.) and stirred at room temperature for 16 h. Upon completion, reaction was extracted with saturated sodium bicarbonate, organic layers combined, dried over magnesium sulphate, filtered and concentrated to dryness in vacuo. Crude was purified by recrystallisation with dichloromethane/hexane and lyophilized to afford pure product as an off white solid.

$^1$H NMR (400 MHz, DMSO-$d_6$): 9.73 (s, 1H), 7.42 (d, J=8.8 Hz, 2H), 6.84 (d, J=8.8 Hz, 2H), 6.34 (bs, 1H), 4.02 (t, J=6.0 Hz, 2H), 3.85 (bs, 2H), 2.98-2.95 (m, 4H), 2.84-2.81 (m, 6H), 2.58 (t, J=6.6 Hz, 2H), 2.08 (bs, 5H). LC-MS: m/z 397 [M+H]$^+$.

Synthesis of N-(4-(4-acetylpiperazin-1-yl)phenyl)-4-(2-methyl-6,7-dihydropyrazolo[1,5-a]pyrimidin-4(5H)-yl)-4-oxobutanamide, Compound 78

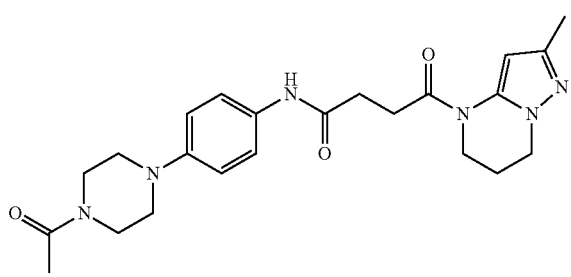 [SMILES: CC(=O)N1CCN(c2ccc(NC(=O)CCC(=O)N3CCCn4nc(C)cc43)cc2)CC1]

A solution of compound 77 (1.0 equiv.) in dry tetrahydrofuran was added to a stirred mixture of acid chloride (1.0 equiv.) and triethylamine (1.2 equiv.) in tetrahydrofuran at 0° C. The reaction mixture was allowed to warm to room temperature with continued stirring for 3 h. Upon completion of reaction, solvent was evaporated to dryness in vacuo and crude extracted with ethyl acetate and dried over magnesium sulphate. Crude was purified by crashing out solids with DCM/methanol/hexane to afford a white solid.

$^1$H NMR (400 MHz, DMSO-$d_6$): 9.77 (s, 1H), 7.45 (d, J=9.2 Hz, 2H), 6.89 (d, J=9.2 Hz, 2H), 6.30 (bs, 1H), 4.02 (t, J=6.0 Hz, 2H), 3.85 (bs, 2H), 3.57-3.54 (m, 4H), 3.08-3.06 (m, 2H), 3.01-2.99 (m, 2H), 2.87-2.84 (m, 2H), 2.59 (t, J=6.6 Hz, 2H), 2.08 (bs, 5H), 2.03 (s, 3H). LC-MS: m/z 439 [M+H]$^+$.

Synthesis of N-ethyl-4-(6-(4-(2-methyl-6,7-dihydropyrazolo[1,5-a]pyrimidin-4(5H)-yl)-4-oxobutanamido)pyridin-3-yl)piperazine-1-carboxamide, Compound 79

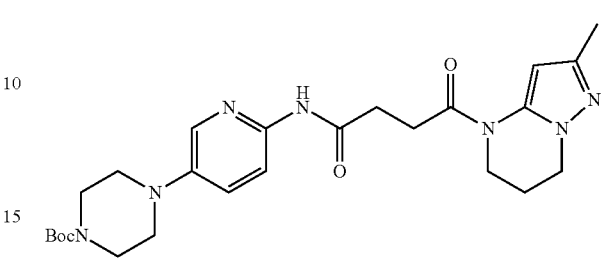

Step 1: Preparation of tert-butyl 4-(6-(4-(2-methyl-6,7-dihydropyrazolo[1,5-a]pyrimidin-4(5H)-yl)-4-oxobutanamido)pyridin-3-yl)piperazine-1-carboxylate LC-MS: m/z 498 [M+H]$^+$.

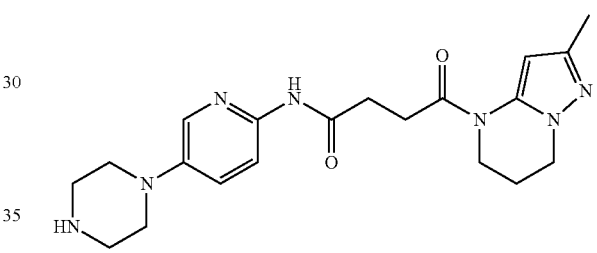

Step 2: Preparation of 4-(2-methyl-6,7-dihydropyrazolo[1,5-a]pyrimidin-4(5H)-yl)-4-oxo-N-(5-(piperazin-1-yl)pyridin-2-yl)butanamide To a stirred solution of tert-butyl 4-(6-(4-(2-methyl-6,7-dihydropyrazolo[1,5-c]pyrimidin-4(5H)-yl)-4-oxobutanamido)pyridin-3-yl)piperazine-1-carboxylate (1 equiv.) in dichloromethane (0.04M) was added TFA (5 equiv.) dropwise at 0° C. and stirred at room temperature for 1 h. The reaction mixture was diluted with water and basified with saturated sodium bicarbonate solution and then extracted with dichloromethane. The organic layer was dried over anhydrous sodium sulphate and concentrated under reduced pressure to afford the intermediate.

LC-MS: m/z 398 [M+H]$^+$.

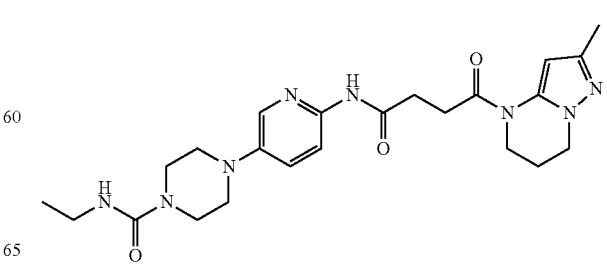

Step 3: Preparation of N-ethyl-4-(6-(4-(2-methyl-6,7-dihydropyrazolo[1,5-a]pyrimidin-4(5H)-yl)-4-oxobutanamido)pyridin-3-yl)piperazine-1-carboxamide To a stirred solution of 4-(2-methyl-6,7-dihydropyrazolo[1,5-a]pyrimidin-4(5H)-yl)-4-oxo-N-(5-(piperazin-1-yl)pyridin-2-yl)butanamide (1 equiv.) in THF (0.015 M) was added ethylisocyanate (4.5 equiv.) and the reaction mixture was stirred at 80° C. in sealed tube for 16 h. The reaction mixture was concentrated under reduced pressure to give crude product. The crude product was purified by preparative TLC to afford the product.

$^1$H NMR (400 MHz, DMSO-$d_6$): 10.25 (s, 1H), 8.01 (d, J=2.7 Hz, 1H), 7.92 (d, J=8.3 Hz, 1H), 7.41-7.39 (dd, J=2.7 Hz, 9.3 Hz, 1H), 6.53-6.55 (m, 1H), 6.32 (brs, 1H), 4.01 (t, J=5.7 Hz, 2H), 3.84 (brs, 2H), 3.39-3.41 (m, 4H), 3.05-3.07 (m, 6H), 2.82-2.84 (m, 2H), 2.64-2.66 (m, 2H), 2.07 (brs, 5H), 1.01 (t, J=7.5 Hz, 3H). MS (ESI) m/z 469.2 [M+H]$^+$.

Synthesis of 4-(2-methyl-6,7-dihydropyrazolo[1,5-a]pyrimidin-4(5H)-yl)-4-oxo-N-(4-phenylcyclohexyl)butanamide, Compound 80

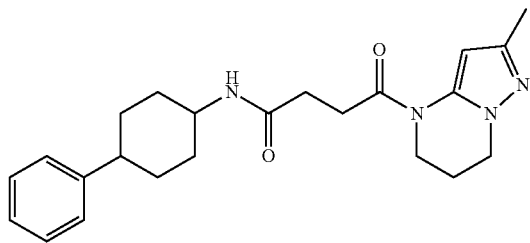 [SMILES: Cc1cc2n(n1)CCCN2C(=O)CCC(=O)NC1CCC(c2ccccc2)CC1]

$^1$H NMR (400 MHz, DMSO-$d_6$): 7.78 (d, J=7.6 Hz, 1H), 7.30-7.21 (m, 4H), 7.19-7.13 (m, 1H), 6.35 (bs, 1H), 4.01 (t, J=6.0 Hz, 2H), 3.83 (bs, 2H), 3.65-3.52 (m, 1H), 2.80-2.70 (m, 2H), 2.50-2.40 (m, 2H), 2.40-2.35 (m, 2H), 2.08 (m, 5H), 1.90-1.82 (m, 2H), 1.82-1.75 (m, 2H), 1.57-1.45 (m, 2H), 1.38-1.25 (m, 2H); MS (ESI) m/z 395 [M+H]$^+$.

Synthesis of 4-(2-methyl-6,7-dihydropyrazolo[1,5-a]pyrimidin-4(5H)-yl)-N-(4-(1-methylpiperidin-4-yl)phenyl)-4-oxobutanamide, Compound 82

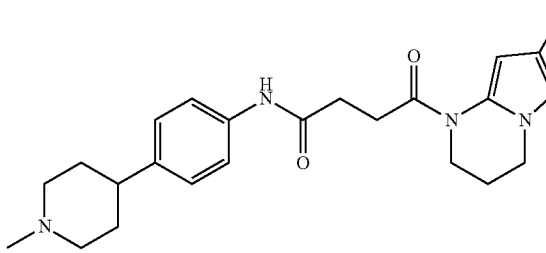

$^1$H NMR (400 MHz, DMSO-$d_6$): 9.90 (s, 1H), 7.49 (d, J=8.4 Hz, 2H), 7.14 (d, J=8.4 Hz, 2H), 6.33 (bs, 1H), 4.02 (t, J=6.0 Hz, 2H), 3.85 (bs, 2H), 2.88-2.86 (m, 5H), 2.61 (t, J=6.6 Hz, 2H), 2.20 (s, 3H), 2.08 (bs, 5H), 2.01-1.95 (m, 2H), 1.71-1.60 (m, 4H). LC-MS: m/z 410 [M+H]$^+$.

Synthesis of N-(6-(3-chlorophenyl)pyridin-3-yl)-4-(2-methyl-6,7-dihydropyrazolo[1,5-a]pyrimidin-4(5H)-yl)-4-oxobutanamide, Compound 83

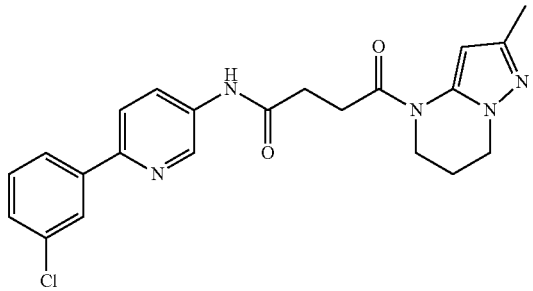 [SMILES: Cc1cc2n(n1)CCCN2C(=O)CCC(=O)Nc1ccc(-c2cccc(Cl)c2)nc1]

$^1$H NMR (400 MHz, Methanol-$d_4$): 8.80-8.81 (m, 1H), 8.18-8.20 (m, 1H), 7.97-7.98 (m, 1H), 7.82-7.87 (m, 2H), 7.38-7.47 (m, 2H), 4.55 (s, 1H), 4.19 (t, J=6.0 Hz, 2H), 3.94-3.96 (m, 2H), 2.99-3.01 (m, 2H), 2.82 (t, J=6.0 Hz, 2H), 2.22 (bs, 2H), 2.18 (s, 3H). LC-MS: m/z 424 [M+H]$^+$.

Synthesis of 4-(2-methyl-6,7-dihydropyrazolo[1,5-a]pyrimidin-4(5H)-yl)-4-oxo-N-(6-(m-tolyl)pyridin-3-yl)butanamide, Compound 85

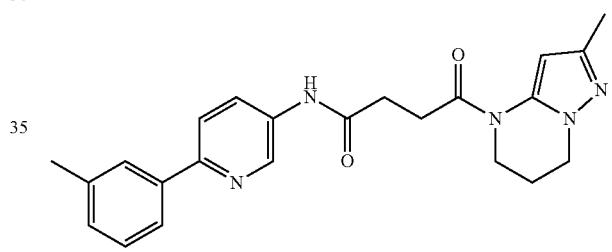

$^1$H NMR (400 MHz, DMSO-$d_6$): 10.31 (s, 1H), 8.81-8.80 (m, 1H), 8.14-8.11 (m, 1H), 7.91-7.87 (m, 2H), 7.82-7.80 (m, 1H), 7.34 (t, J=7.6 Hz, 1H), 7.21-7.19 (m, 1H), 6.35 (bs, 1H), 4.03 (t, J=6.0 Hz, 2H), 3.87 (bs, 2H), 2.92-2.89 (m, 2H), 2.71-2.68 (m, 2H), 2.38 (s, 3H), 2.08 (bs, 5H). LC-MS: m/z 404 [M+H]$^+$.

Synthesis of 4-(2-methyl-6,7-dihydropyrazolo[1,5-a]pyrimidin-4(5H)-yl)-N-(5-methyl-6-phenylpyridin-3-yl)-4-oxobutanamide, Compound 86

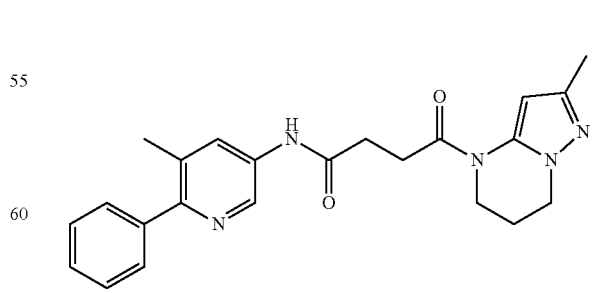

$^1$H NMR (400 MHz, DMSO-$d_6$): 10.24 (s, 1H), 8.64 (d, J=2.0 Hz, 1H), 7.97 (d, J=2.4 Hz, 1H), 7.52-7.48 (m, 2H), 7.48-7.40 (m, 2H), 7.40-7.35 (m, 1H), 6.35 (bs, 1H), 4.03 (t,

J=6.0 Hz, 2H), 3.87 (bs, 2H), 2.95-2.85 (m, 2H), 2.75-2.65 (m, 2H), 2.31 (s, 3H), 2.08 (bs, 5H). MS (ESI) m/z 404 [M+H]⁺.

Synthesis of N-(6-(4-fluorophenyl)pyridin-3-yl)-4-(2-methyl-6,7-dihydropyrazolo[1,5-a]pyrimidin-4(5H)-yl)-4-oxobutanamide, Compound 87

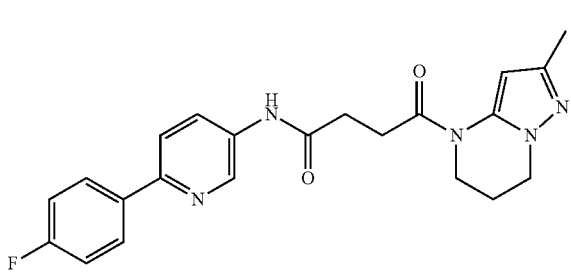 [SMILES: Cc1cc2n(n1)CCCN2C(=O)CCC(=O)Nc1ccc(-c2ccc(F)cc2)nc1]

¹H NMR (400 MHz, DMSO-d₆): 10.33 (s, 1H), 8.81-8.80 (m, 1H), 8.13-8.05 (m, 3H), 7.90 (d, J=8.4 Hz, 1H), 7.28 (t, 8.8 Hz, 2H), 6.34 (bs, 1H), 4.02 (t, J=6.0 Hz, 2H), 3.86 (bs, 2H), 2.92-2.88 (m, 2H), 2.70-2.67 (m, 2H), 2.08 (bs, 5H). LC-MS: m/z 408 [M+H]⁺.

Synthesis of N-(6-(3-fluorophenyl)pyridazin-3-yl)-4-(2-methyl-6,7-dihydropyrazolo[1,5-a]pyrimidin-4(5H)-yl)-4-oxobutanamide, Compound 88

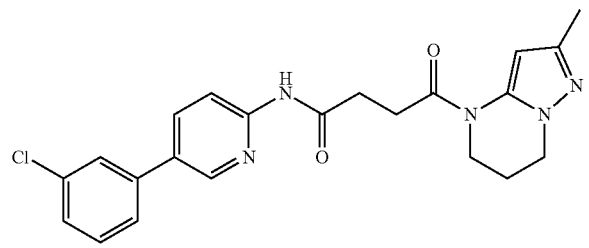 [SMILES: Cc1cc2n(n1)CCCN2C(=O)CCC(=O)Nc1ccc(-c2cccc(Cl)c2)cn1]

¹H NMR (400 MHz, DMSO-d₆): 10.67 (s, 1H), 8.68 (s, 1H), 8.13-8.10 (m, 2H), 7.80 (s, 1H), 7.70-7.68 (m, 1H), 7.52-7.48 (m, 1H), 7.44-7.42 (m, 1H), 6.33 (br s, 1H), 4.02 (t, J=6.0 Hz, 2H), 3.86 (s, 2H), 2.90-2.87 (m, 2H), 2.75-2.72 (m, 2H), 2.08 (s, 5H). LC-MS: m/z 424 [M+H]⁺.

Synthesis of N-(5-(3-fluorophenyl)pyridin-2-yl)-4-(2-methyl-6,7-dihydropyrazolo[1,5-a]pyrimidin-4(5H)-yl)-4-oxobutanamide, Compound 89

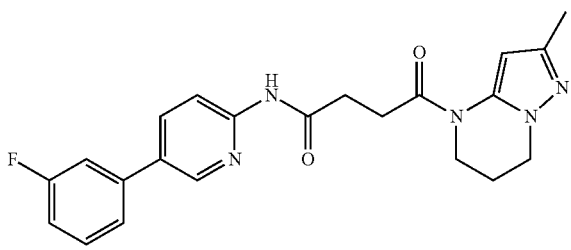

¹H NMR (400 MHz, DMSO-d₆): 10.67 (s, 1H), 8.69 (s, 1H), 8.13 (s, 2H), 7.61-7.48 (m, 3H), 7.23-7.18 (m, 1H), 6.33 (bs, 1H), 4.02 (t, J=5.8 Hz, 2H), 3.86 (bs, 2H), 2.91-2.87 (m, 2H), 2.76-2.72 (m, 2H), 2.08 (bs, 5H). LC-MS: m/z 408 [M+H]⁺.

Synthesis of N-(5-(4-fluorophenyl)pyridin-2-yl)-4-(2-methyl-6,7-dihydropyrazolo[1,5-a]pyrimidin-4(5H)-yl)-4-oxobutanamide, Compound 90

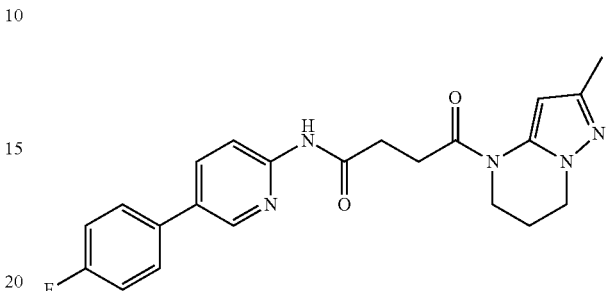

¹H NMR (400 MHz, DMSO-d₆): 10.62 (s, 1H), 8.62-8.63 (m, 1H), 8.12-8.14 (m, 1H), 8.04-8.07 (m, 1H), 7.73-7.77 (m, 2H), 7.28-7.32 (m, 2H), 6.34 (bs, 1H), 4.55 (s, 1H), 4.02 (t, J=6.0 Hz, 2H), 3.85-3.87 (m, 2H), 2.87-2.90 (m, 2H), 2.73 (t, J=6.0 Hz, 2H), 2.22 (bs, 2H), 2.08 (s, 3H). LC-MS: m/z 408 [M+H]⁺.

Synthesis of N-(3-methyl-5-phenylpyridin-2-yl)-4-(2-methyl-6,7-dihydropyrazolo[1,5-a]pyrimidin-4(5H)-yl)-4-oxobutanamide, Compound 91

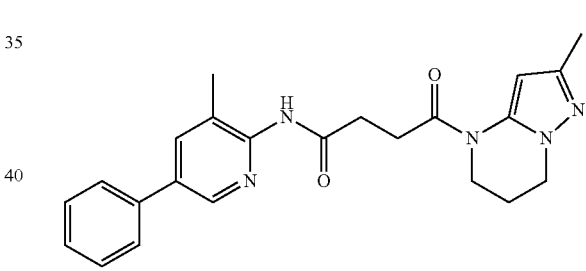

¹H NMR (400 MHz, DMSO-d₆): 10.07 (s, 1H), 8.53 (s, 1H), 7.94 (s, 1H), 7.72-7.70 (m, 2H), 7.51-7.47 (m, 2H), 7.42-7.38 (m, 1H), 6.35 (br s, 1H), 4.01 (t, J=6.0 Hz, 2H), 3.85 (s, 2H), 2.89-2.86 (m, 2H), 2.71-2.68 (m, 2H), 2.21 (s, 3H), 2.09 (s, 5H). LC-MS: m/z 404 [M+H]⁺.

Synthesis of N-(4-methyl-5-phenylpyridin-2-yl)-4-(2-methyl-6,7-dihydropyrazolo[1,5-a]pyrimidin-4(5H)-yl)-4-oxobutanamide, Compound 92

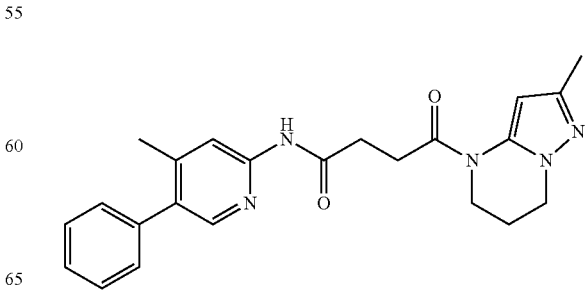

¹H NMR (400 MHz, DMSO-d₆): 10.55 (s, 1H), 8.61 (s, 2H), 8.16 (s, 1H), 8.05 (s, 1H), 7.85 (d, J=8.0 Hz, 1H), 7.51-7.47 (m, 1H), 6.33 (s, 1H), 4.02 (t, J=6.0 Hz, 2H), 3.86 (s, 2H), 2.88 (s, 2H), 2.73 (d, J=6.4 Hz, 2H), 2.24 (s, 3H), 2.08 (bs, 5H). MS (ESI) m/z 404.1 [M+H]⁺.

Synthesis of 4-(2-methyl-6,7-dihydropyrazolo[1,5-a]pyrimidin-4(5H)-yl)-4-oxo-N-(5-(m-tolyl)pyridin-2-yl)butanamide, Compound 93

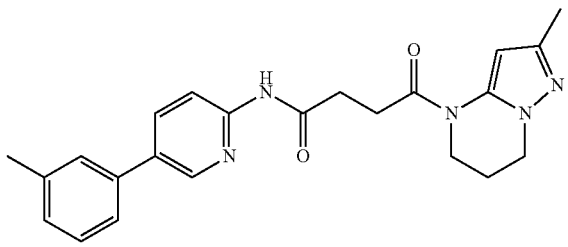

¹H NMR (400 MHz, DMSO-d₆): 10.63 (s, 1H), 8.63-8.622 (m, 1H), 8.14-8.12 (m, 1H), 8.07-8.04 (m, 1H), 7.53 (bs, 1H), 7.49 (d, J=8.0 Hz, 1H), 7.36 (t, J=7.6 Hz, 1H), 7.19 (d, J=7.6 Hz, 1H), 6.34 (bs, 1H), 4.02 (t, J=6.0 Hz, 2H), 3.87 (bs, 2H), 2.90-2.87 (m, 2H), 2.75-2.72 (m, 2H), 2.38 (s, 3H), 2.08 (bs, 5H). LC-MS: m/z 404 [M+H]⁺.

Synthesis of N-(5-fluoro-2,3'-bipyridin-6'-yl)-4-(2-methyl-6,7-dihydropyrazolo[1,5-a]pyrimidin-4(5H)-yl)-4-oxobutanamide, Compound 94

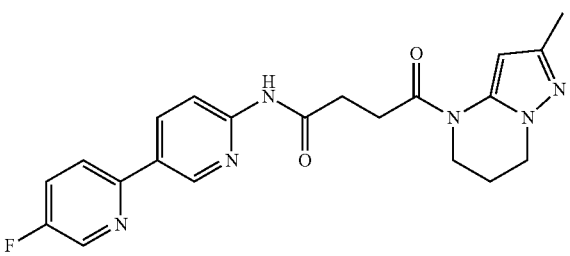

¹H NMR (400 MHz, DMSO-d₆): 10.72 (s, 1H), 8.99 (d, J=2.4 Hz, 1H), 8.66 (d, J=2.8 Hz, 1H), 8.43-8.38 (m, 1H), 8.19-8.14 (m, 1H), 8.12-8.07 (m, 1H), 7.84 (td, J=8.8, 3.2 Hz, 1H), 6.34 (bs, 1H), 4.02 (t, J=6.0 Hz, 2H), 3.86 (bs, 2H), 2.92-2.85 (m, 2H), 2.78-2.72 (m, 2H), 2.08 (bs, 5H). MS (ESI) m/z 409 [M+H]⁺.

Synthesis of N-(4-fluoro-2,3'-bipyridin-6'-yl)-4-(2-methyl-6,7-dihydropyrazolo[1,5-a]pyrimidin-4(5H)-yl)-4-oxobutanamide, Compound 95

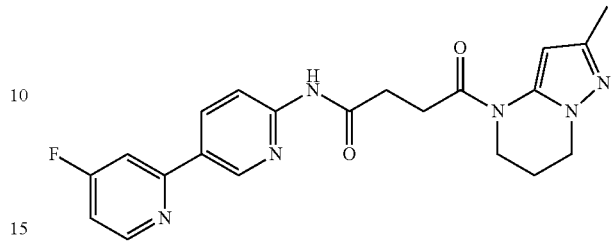

¹H NMR (400 MHz, DMSO-d₆): 10.75 (s, 1H), 9.07 (d, J=1.7 Hz, 1H), 8.70-8.67 (dd, J=5.7 Hz, 9.2 Hz, 1H), 8.48-8.46 (dd, J=2.2 Hz, 8.8 Hz, 1H), 8.18 (d, J=8.8 Hz, 1H), 7.99 (d, J=8.8 Hz, 1H), 7.31-7.28 (m, 1H), 6.33 (brs, 1H), 4.04-4.01 (t, J=5.7 Hz, 2H), 3.86 (brs, 2H), 2.89 (d, J=6.1 Hz, 2H), 2.76 (t, J=6.2 Hz, 2H), 2.08 (brs, 5H). MS (ESI) m/z 409.11 [M+H]⁺.

Synthesis of 4-(2-methyl-6,7-dihydropyrazolo[1,5-a]pyrimidin-4(5H)-yl)-N-(6-methyl-[2,3'-bipyridin]-6'-yl)-4-oxobutanamide, Compound 96

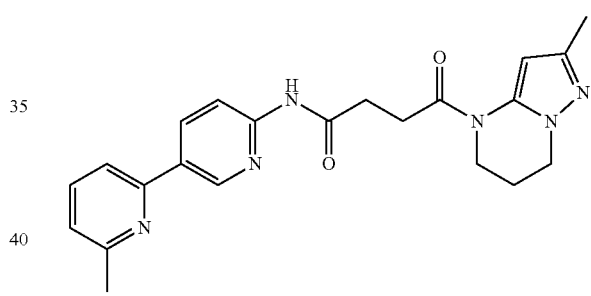

¹H NMR (400 MHz, DMSO-d₆): 10.71 (s, 1H), 9.01-9.00 (m, 1H), 8.42-8.40 (m, 1H), 8.17-8.15 (d, J=8.8 Hz, 1H), 7.80-7.75 (m, 2H), 7.23-7.21 (m, 1H), 6.33 (br, 1H), 4.02 (t, J=6.2 Hz, 2H), 3.86 (br, 2H), 2.89-2.87 (m, 2H), 2.75-2.72 (m, 2H), 2.54 (s, 3H), 2.08 (br, 5H). LC-MS: m/z 405 [M+H]⁺.

Synthesis of N-(6-(3-chlorophenyl)pyridazin-3-yl)-4-(2-methyl-6,7-dihydropyrazolo[1,5-a]pyrimidin-4(5H)-yl)-4-oxobutanamide, Compound 97

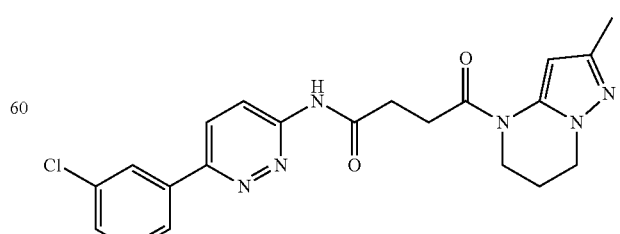

<sup>1</sup>H NMR (400 MHz, Methanol-d₄): 8.50-8.53 (m, 1H), 8.08-8.13 (m, 2H), 7.94-7.95 (m, 1H), 7.50-7.52 (m, 1H), 4.55 (s, 1H), 4.11 (t, J=6.0 Hz, 2H), 3.95-3.97 (m, 2H), 3.00-3.02 (m, 2H), 2.91 (t, J=6.0 Hz, 2H), 2.22 (bs, 2H), 2.18 (s, 3H). LC-MS: m/z 425 [M+H]⁺.

Synthesis of N-[6-(4-chlorophenyl)pyridazin-3-yl]-4-{2-methyl-5H,6H,7H-pyrazolo[1,5-a]pyrimidin-4-yl}-4-oxobutanamide, Compound 100

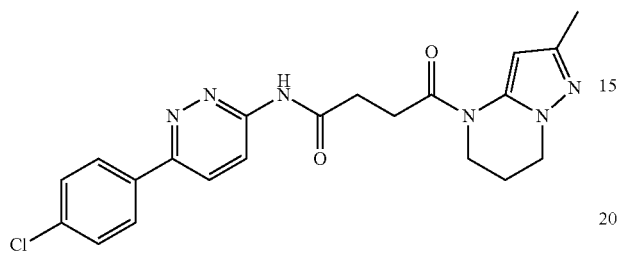

¹H NMR (400 MHz, DMSO-d₆): 11.29 (s, 1H), 8.37 (d, J=9.2 Hz, 1H), 8.24 (d, J=9.6 Hz, 1H), 8.13 (d, J=8.4 Hz, 2H), 7.60 (d, J=8.4 Hz, 2H), 4.02 (t, J=6.0 Hz, 2H), 3.86 (s, 2H), 2.91-2.89 (m, 2H), 2.81-2.78 (m, 2H), 2.07 (s, 5H). LC-MS: m/z 426 [M+H]⁺.

Synthesis of N-(6-(4-fluorophenyl)pyridazin-3-yl)-4-(2-methyl-6,7-dihydropyrazolo[1,5-a]pyrimidin-4(5H)-yl)-4-oxobutanamide, Compound 101

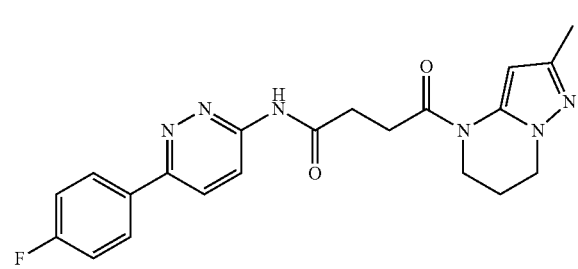

¹H NMR (400 MHz, Chloroform-d): 9.17 (1H, bs), 8.50 (1H, d, J=9.2 Hz), 8.00-8.04 (2H, m), 7.82 (1H, d, J=9.2 Hz), 7.19 (2H, t), 4.16 (2H, t), 3.94 (2H, bs), 2.96-3.06 (4H, m), 2.23 (5H, m). LC-MS: m/z 409.2 [M+H]⁺.

Synthesis of N-(6-(5-chloropyridin-3-yl)pyridazin-3-yl)-4-(2-methyl-6,7-dihydropyrazolo[1,5-a]pyrimidin-4(5H)-yl)-4-oxobutanamide, Compound 102

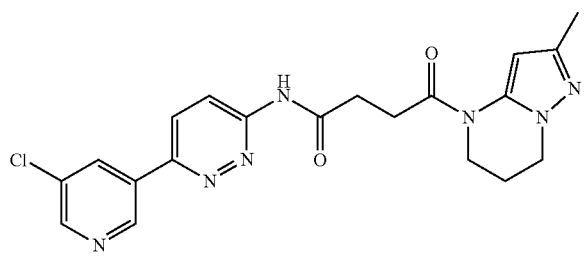

¹H NMR (400 MHz, DMSO-d₆): 11.36 (s, 1H), 9.24 (d, J=1.7 Hz, 1H), 8.75 (d, J=2.2 Hz, 1H), 8.59 (t, J=2.2 Hz, 1H), 8.38 (q, J=9.2 Hz, 17.1 Hz, 2H), 6.35 (br s, 1H), 4.03 (t, J=6.1 Hz, 2H), 3.86 (br s, 2H), 2.91-2.90 (m, 2H), 2.83-2.80 (m, 2H), 2.08 (br s, 5H). MS (ESI) m/z 426.24 [M+H]⁺.

Synthesis of N-(5'-chloro-[2,3'-bipyridin]-5-yl)-4-(2-methyl-6,7-dihydropyrazolo[1,5-a]pyrimidin-4(5H)-yl)-4-oxobutanamide, Compound 108

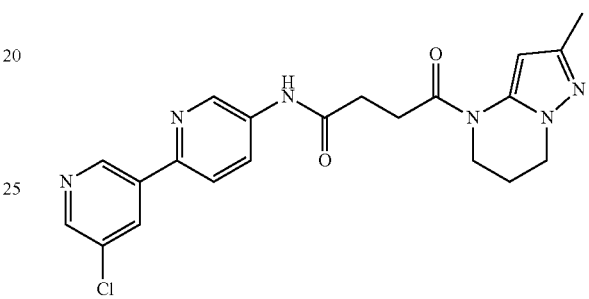

¹H NMR (400 MHz, Chloroform-d): 9.02 (1H, bs), 8.68 (1H, s), 8.57 (1H, d, J=2.4 Hz), 8.29-8.32 (3H, m), 7.73 (1H, d, J=8.8 Hz), 4.16 (2H, t), 3.94 (2H, bs), 2.97 (2H, m), 2.89 (2H, t), 2.24 (5H, m). LC-MS: m/z 425.1 [M+H]⁺.

Synthesis of N-(5'-fluoro-[2,3'-bipyridin]-5-yl)-4-(2-methyl-6,7-dihydropyrazolo[1,5-a]pyrimidin-4(5H)-yl)-4-oxobutanamide, Compound 109

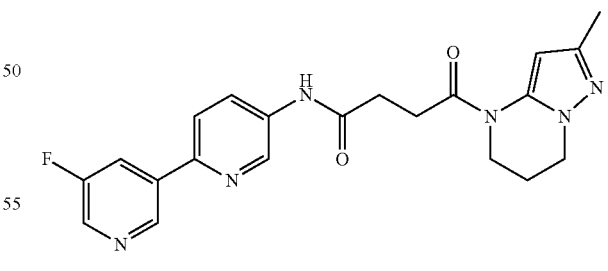

¹H NMR (400 MHz, DMSO-d₆): 10.43 (s, 1H), 9.12 (s, 1H), 8.87 (d, J=2.0 Hz, 1H), 8.59 (d, J=2.8 Hz, 1H), 8.29-8.25 (m, 1H), 8.21-8.18 (m, 1H), 8.10-8.08 (m, 1H), 6.34 (br s, 1H), 4.02 (t, J=6.4 Hz, 2H), 3.86 (s, 2H), 2.92-2.89 (m, 2H), 2.72-2.69 (m, 2H), 2.08 (s, 5H). LC-MS: m/z 409 [M+H]⁺.

Synthesis of N-(3-fluoro-2,3'-bipyridin-5-yl)-4-(2-methyl-6,7-dihydropyrazolo[1,5-a]pyrimidin-4(5H)-yl)-4-oxobutanamide, Compound 111

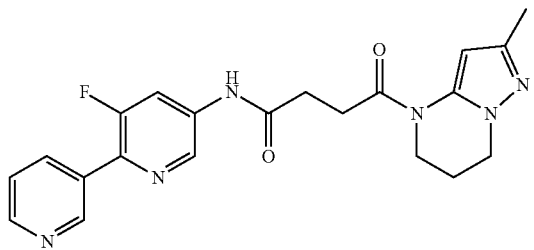 [SMILES: Cc1cc2n(n1)CCCN2C(=O)CCC(=O)Nc1cnc(-c2cccnc2)c(F)c1]

¹H NMR (400 MHz, DMSO-d₆): 10.68 (s, 1H), 9.05 (s, 1H), 8.68 (s, 1H), 8.70-8.65 (m, 1H), 8.30-8.15 (m, 2H), 7.55-7.50 (s, 1H), 6.35 (bs, 1H), 4.10-4.00 (m, 2H), 3.87 (bs, 2H), 3.00-2.85 (m, 2H), 2.80-2.65 (m, 2H), 2.08 (bs, 5H). MS (ESI) m/z 409 [M+H]⁺.

Synthesis of N-(5'-amino-2,3'-bipyridin-5-yl)-4-(2-methyl-6,7-dihydropyrazolo[1,5-a]pyrimidin-4(5H)-yl)-4-oxobutanamide, Compound 112

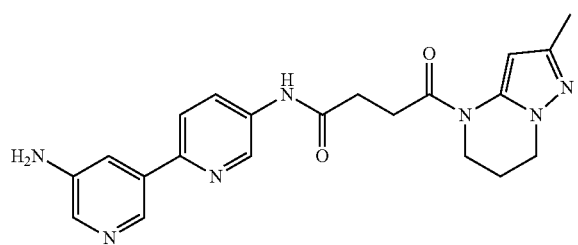 [SMILES: Cc1cc2n(n1)CCCN2C(=O)CCC(=O)Nc1ccc(-c2cncc(N)c2)nc1]

¹H NMR (400 MHz, DMSO-d₆): 10.38 (s, 1H), 8.83 (d, J=2.0 Hz, 1H), 8.35 (d, J=1.6 Hz, 1H), 8.12-8.09 (m, 1H), 7.93 (d, J=2.4 Hz, 1H), 7.88-7.82 (m, 1H), 7.58-7.52 (m, 1H), 6.35 (bs, 1H), 5.40 (s, 2H), 4.03 (t, J=6.0 Hz, 2H), 3.87 (bs, 2H), 2.95-2.85 (m, 2H), 2.75-2.65 (m, 2H), 2.08 (bs, 5H); MS (ESI) m/z 406 [M+H]⁺.

Synthesis of 4-(2-methyl-6,7-dihydropyrazolo[1,5-a]pyrimidin-4(5H)-yl)-N-(6'-methyl-[2,3'-bipyridin]-5-yl)-4-oxobutanamide, Compound 113

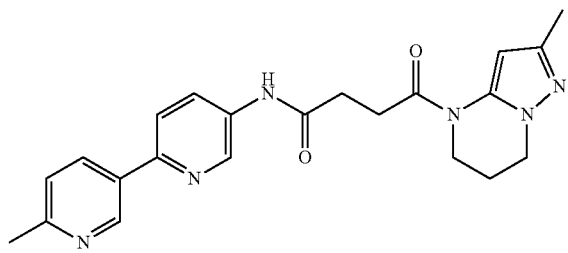

¹H NMR (400 MHz, DMSO-d₆): 10.36 (s, 1H), 9.08-9.07 (m, 1H), 8.83-8.82 (m, 1H), 8.27-8.25 (m, 1H), 8.16-8.13 (m, 1H), 7.96 (d, J=8.8 Hz, 1H), 7.34 (d, J=8.0 Hz, 1H), 6.34 (bs, 1H), 4.02 (t, J=5.6 Hz, 2H), 3.86 (bs, 2H), 2.92-2.89 (m, 2H), 2.69 (m, 2H), 2.08 (bs, 5H). LC-MS: m/z 405 [M+H]⁺.

Synthesis of N-(5'-chloro-[3,3'-bipyridin]-6-yl)-4-(2-methyl-6,7-dihydropyrazolo[1,5-a]pyrimidin-4(5H)-yl)-4-oxobutanamide, Compound 114

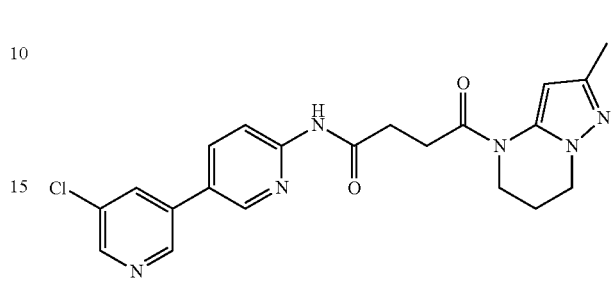

¹H NMR (400 MHz, DMSO-d₆): 10.73 (s, 1H), 8.92 (d, J=1.6 Hz, 1H), 8.78 (d, J=1.6 Hz, 1H), 8.62 (d, J=2.0 Hz, 1H), 8.34-8.33 (m, 1H), 8.23-8.15 (m, 2H), 6.33 (br s, 1H), 4.02 (t, J=6.0 Hz, 2H), 3.86 (s, 2H), 2.90-2.87 (m, 2H), 2.76-2.73 (m, 2H), 2.08 (s, 5H). LC-MS: m/z 425 [M+H]⁺.

Synthesis of N-(5'-fluoro-[3,3'-bipyridin]-6-yl)-4-(2-methyl-6,7-dihydropyrazolo[1,5-a]pyrimidin-4(5H)-yl)-4-oxobutanamide, Compound 115

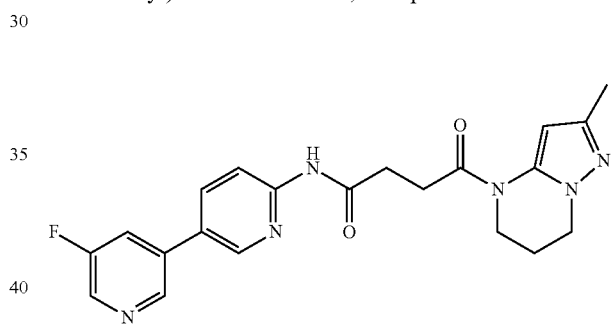

¹H NMR (400 MHz, DMSO-d₆): 10.73 (s, 1H), 8.86 (t, J=1.6 Hz, 1H), 8.78 (d, J=2.0 Hz, 1H), 8.58 (d, J=2.4 Hz, 1H), 8.24-8.13 (m, 3H), 6.30 (bs, 1H), 4.03 (t, J=5.8 Hz, 2H), 3.86 (bs, 2H), 2.91-2.88 (m, 2H), 2.76-2.73 (m, 2H), 2.08 (bs, 5H). LC-MS: m/z 409 [M+H]⁺.

Synthesis of 4-(2-methyl-6,7-dihydropyrazolo[1,5-a]pyrimidin-4(5H)-yl)-N-(5'-methyl-[3,3'-bipyridin]-6-yl)-4-oxobutanamide, Compound 116

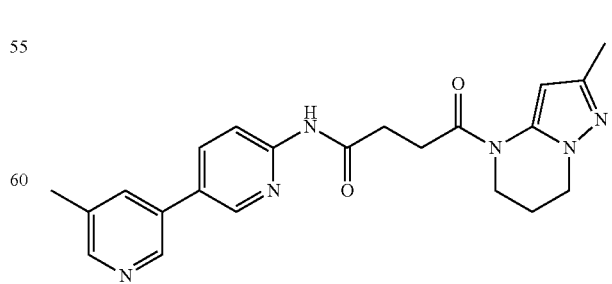

¹H NMR (400 MHz, DMSO-d₆): 10.68 (s, 1H), 8.74-8.70 (m, 2H), 8.42 (s, 1H), 8.18-8.12 (m, 2H), 7.96 (s, 1H), 6.34

(bs, 1H), 4.03 (t, J=5.8 Hz, 2H), 3.87 (bs, 2H), 2.90-2.87 (m, 2H), 2.76-2.73 (m, 2H), 2.37 (s, 3H), 2.08 (bs, 5H). LC-MS: m/z 405 [M+H]⁺.

Synthesis of 4-(2-methyl-6,7-dihydropyrazolo[1,5-a]pyrimidin-4(5H)-yl)-4-oxo-N-(4-(piperazin-1-yl)phenyl)butanamide, Compound 117

Step 1: Preparation of Boc-protected 4-(2-methyl-6,7-dihydropyrazolo[1,5-a]pyrimidin-4(5H)-yl)-4-oxo-N-(4-(piperazin-1-yl)phenyl)butanamide

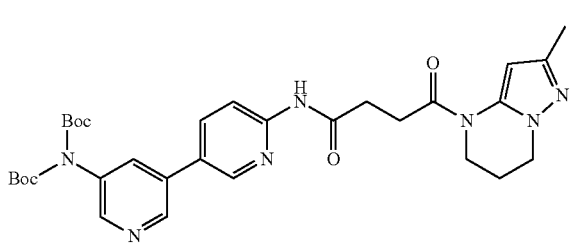 [SMILES: Cc1cc2n(n1)CCCN2C(=O)CCC(=O)Nc1ccc(-c2cncc(N(C(=O)OC(C)(C)C)C(=O)OC(C)(C)C)c2)cn1]

¹H NMR (400 MHz, DMSO-d₆): 10.71 (s, 1H), 8.90 (m, 1H), 8.75 (bs, 1H), 8.44-8.43 (d, J=2.4 Hz, 1H), 8.19-8.15 (m, 3H), 6.36 (bs, 1H), 4.02 (t, J=6.0 Hz, 2H), 3.86 (bs, 2H), 2.91-2.87 (m, 2H), 2.76-2.73 (m, 2H), 2.08 (bs, 5H), 1.40 (s, 18H). LC-MS: m/z 606 [M+H]⁺.

Step 2: Preparation of 4-(2-methyl-6,7-dihydropyrazolo[1,5-a]pyrimidin-4(5H)-yl)-4-oxo-N-(4-(piperazin-1-yl)phenyl)butanamide

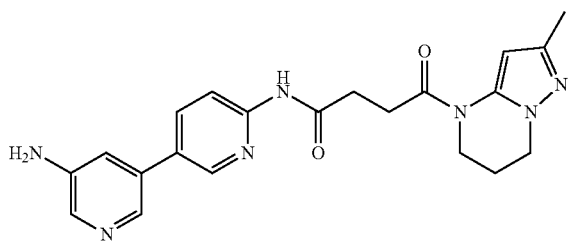 [SMILES: Cc1cc2n(n1)CCCN2C(=O)CCC(=O)Nc1ccc(-c2cncc(N)c2)cn1]

¹H NMR (400 MHz, DMSO-d₆): 10.64 (s, 1H), 8.56 (m, 1H), 8.14 (d, J=8.4 Hz, 1H), 8.06-8.05 (m, 1H), 8.01-7.99 (m, 1H), 7.94 (d, J=2.4 Hz, 1H), 7.16 (t, J=2.2 Hz, 1H), 6.33 (bs, 1H), 5.41 (s, 2H), 4.02 (t, J=6.0 Hz, 2H), 3.86 (bs, 2H), 2.90-2.87 (m, 2H), 2.75-2.72 (m, 2H), 2.08 (bs, 5H). LC-MS: m/z 406 [M+H]⁺.

Synthesis of 4-(2-methyl-6,7-dihydropyrazolo[1,5-a]pyrimidin-4(5H)-yl)-4-oxo-N-(5'-(trifluoromethyl)-[3,3'-bipyridin]-6-yl)butanamide, Compound 118

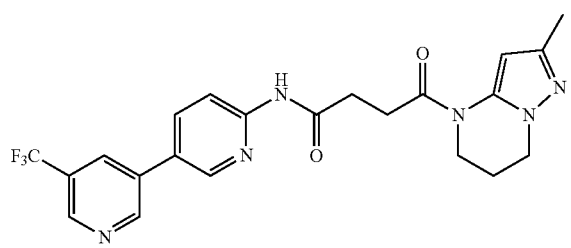

¹H NMR (400 MHz, DMSO-d₆): 10.77 (s, 1H), 9.27-9.26 (m, 1H), 8.97 (bs, 1H), 8.85-8.84 (m, 1H), 8.56 (bs, 1H), 8.31-8.28 (m, 1H), 8.20-8.18 (m, 1H), 6.34 (bs, 1H), 4.03 (t, J=6.0 Hz, 2H), 3.86 (bs, 2H), 2.91-2.88 (m, 2H), 2.77-2.74 (m, 2H), 2.08 (bs, 5H). LC-MS: m/z 459 [M+H]⁺.

Synthesis of N-(4-methyl-3,3'-bipyridin-6-yl)-4-(2-methyl-6,7-dihydropyrazolo[1,5-a]pyrimidin-4(5H)-yl)-4-oxobutanamide, Compound 119

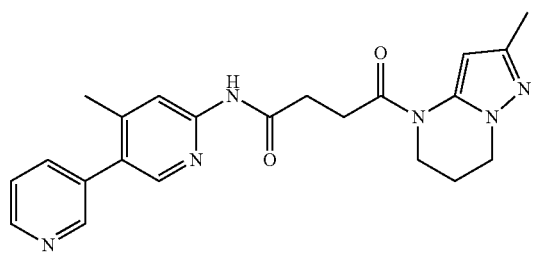

¹H NMR (400 MHz, DMSO-d₆): 10.56 (s, 1H), 8.61 (s, 2H), 8.16 (s, 1H), 8.05 (s, 1H), 7.85 (d, J=8.0 Hz, 1H), 7.51-7.47 (m, 1H), 6.33 (s, 1H), 4.02 (t, J=6.0 Hz, 2H), 3.86 (s, 2H), 2.87 (d, J=5.6 Hz, 2H), 2.73 (d, J=6.0 Hz, 2H), 2.25 (s, 3H), 2.08 (s, 5H); MS (ESI) m/z 405.39 [M+H]⁺.

Synthesis of N-(4,5'-dimethyl-3,3'-bipyridin-6-yl)-4-(2-methyl-6,7-dihydropyrazolo[1,5-a]pyrimidin-4(5H)-yl)-4-oxobutanamide, Compound 120

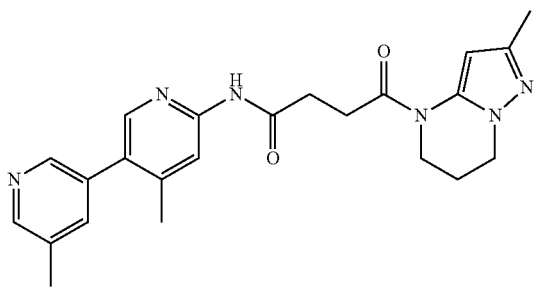 [SMILES: Cc1cncc(-c2cnc(NC(=O)CCC(=O)N3CCCn4nc(C)cc43)cc2C)c1]

¹H NMR (400 MHz, DMSO-d₆): 10.57 (s, 1H), 8.44 (d, J=1.2 Hz, 1H), 8.40 (d, J=1.2 Hz, 1H), 8.15 (s, 1H), 8.05 (s, 1H), 7.67 (s, 1H), 6.35 (bs, 1H), 4.03 (t, J=6.0 Hz, 2H), 3.87 (bs, 2H), 2.90-2.80 (m, 2H), 2.80-2.60 (m, 2H), 2.36 (s, 3H), 2.26 (s, 3H), 2.08 (bs, 5H). MS (ESI) m/z 419 [M+H]⁺.

Synthesis of N-(6'-methyl-3,3'-bipyridin-6-yl)-4-(2-methyl-6,7-dihydropyrazolo[1,5-a]pyrimidin-4(5H)-yl)-4-oxobutanamide, Compound 121

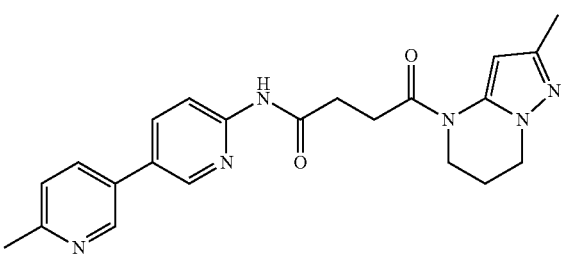

¹H NMR (400 MHz, Methanol-d₄): 8.68 (d, J=2.0 Hz, 1H), 8.58 (d, J=2.0 Hz, 1H), 8.22-8.18 (m, 1H), 8.08-7.98 (m, 2H), 7.41 (d, J=8.0 Hz, 1H), 4.56 (s, 1H), 4.11 (t, J=6.8 Hz, 2H), 3.96 (bs, 2H), 3.03-2.95 (m, 2H), 2.90-2.83 (m, 2H), 2.58 (s, 3H), 2.30-2.15 (m, 5H); MS (ESI) m/z 405 [M+H]⁺.

Synthesis of N-(5-(5-fluoropyridin-3-yl)pyrazin-2-yl)-4-(2-methyl-6,7-dihydropyrazolo[1,5-a]pyrimidin-4(5H)-yl)-4-oxobutanamide, Compound 122

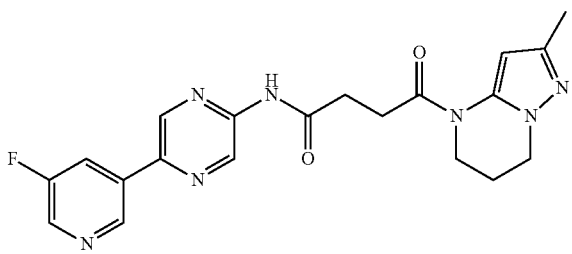

¹H NMR (400 MHz, DMSO-d₆): 11.06 (s, 1H), 9.42 (d, J=1.2 Hz, 1H), 9.18 (t, J=1.6 Hz, 1H), 9.14 (d, J=1.2 Hz, 1H), 8.66 (d, J=2.8 Hz, 1H), 8.40-8.30 (m, 1H), 6.33 (bs, 1H), 4.03 (t, J=6.0 Hz, 2H), 3.87 (bs, 2H), 2.95-2.85 (m, 2H), 2.85-2.75 (m, 2H), 2.08 (bs, 5H). MS (ESI) m/z 410 [M+H]⁺.

Synthesis of N-(5-(3-fluorophenyl)pyrazin-2-yl)-4-(2-methyl-6,7-dihydropyrazolo[1,5-a]pyrimidin-4(5H)-yl)-4-oxobutanamide, Compound 123

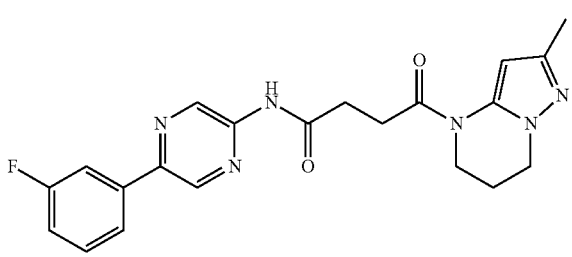

¹H NMR (400 MHz, DMSO-d₆) 10.98 (s, 1H), 9.37 (s, 1H), 9.05 (d, J=1.2 Hz, 1H), 7.97-7.89 (m, 2H), 7.58-7.52 (m, 1H), 7.30-7.28 (m, 1H), 6.33 (br s, 1H), 4.02 (t, J=6.0 Hz, 2H), 3.86 (s, 2H), 3.27 (s, 1H), 2.93-2.90 (m, 2H), 2.79-2.76 (m, 2H), 2.07 (s. 3H). LC-MS: m/z 409 [M+H]⁺.

Synthesis of 4-(2-methyl-6,7-dihydropyrazolo[1,5-a]pyrimidin-4(5H)-yl)-N-(5-(5-methylpyridin-3-yl)pyrazin-2-yl)-4-oxobutanamide, Compound 124

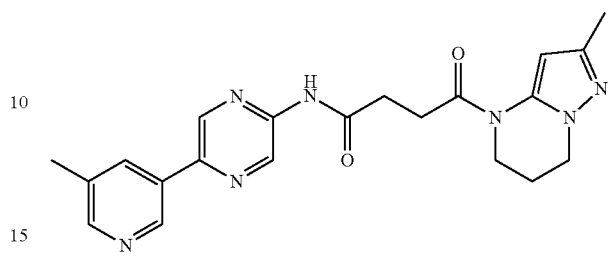

¹H NMR (400 MHz, DMSO-d₆): 10.98 (s, 1H), 9.39 (s, 2H), 9.06 (s, 2H), 8.48 (s, 1H), 8.27 (s, 1H), 6.33 (s, 1H), 4.02 (t, J=5.6 Hz, 2H), 3.86 (s, 2H), 2.91-2.88 (m, 2H), 2.50-2.75 (m, 2H), 2.39 (bs, 3H), 2.08 (bs, 5H); MS (ESI) m/z 404.10 [M+H]⁺.

Synthesis of N-(6-methyl-5-(pyridin-3-yl)pyrazin-2-yl)-4-(2-methyl-6,7-dihydropyrazolo[1,5-a]pyrimidin-4(5H)-yl)-4-oxobutanamide, Compound 125

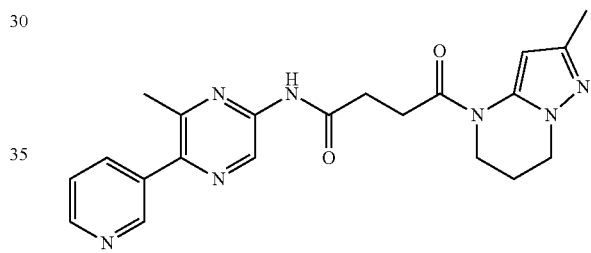

¹H NMR (400 MHz, DMSO-d₆): 10.95 (s, 1H), 9.24 (s, 1H), 8.83-8.82 (m, 1H), 8.65-8.63 (m, 1H), 8.07-8.04 (m, 1H), 7.54-7.51 (m, 1H), 6.34 (bs, 1H), 4.02 (t, J=6.0 z, 2H), 3.86 (bs, 2H), 2.92-2.89 (m, 2H), 2.78-2.75 (m, 2H), 2.54 (s, 3H), 2.08 (bs, 5H). LC-MS: m/z 406 [M+H]⁺.

Synthesis of 4-(2-methyl-6,7-dihydropyrazolo[1,5-a]pyrimidin-4(5H)-yl)-4-oxo-N-(5-(m-tolyl)pyrazin-2-yl)butanamide, Compound 126

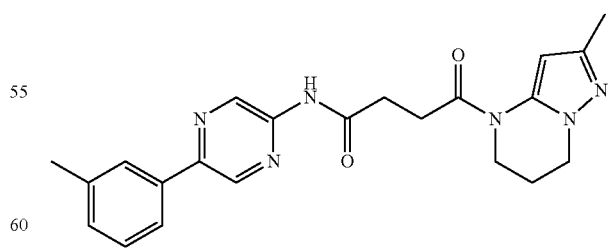

¹H NMR (400 MHz, DMSO-d₆): 10.91 (s, 1H), 9.35 (s, 1H),8.97 (s, 1H), 7.92-7.86 (m, 2H), 7.39 (t, J=7.6 Hz, 1H), 7.26 (d, J=6.8 Hz, 1H), 6.34 (br s, 1H), 4.02 (t, J=6.0 Hz, 2H), 3.86 (s, 2H), 2.91-2.89 (m, 2H), 2.78-2.75 (m, 2H), 2.39 (s, 3H), 2.08 (s, 5H). LC-MS: m/z 405 [M+H]⁺.

Synthesis of 4-(2-methyl-6,7-dihydropyrazolo[1,5-a]pyrimidin-4(5H)-yl)-N-(5-(6-methylpyridin-3-yl)pyrazin-2-yl)-4-oxobutanamide, Compound 127

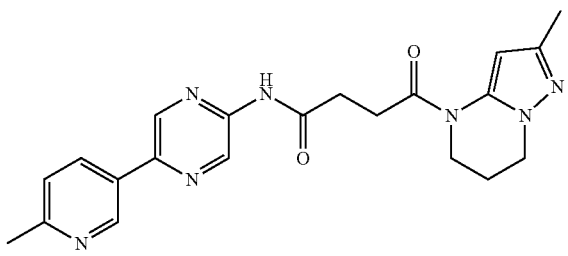

¹H NMR (400 MHz, DMSO-d₆): 10.97 (s, 1H), 9.38 (s, 1H), 9.13 (d, J=2.0 Hz, 1H), 9.04 (d, J=1.2 Hz, 1H), 8.33 (dd, J=8.0, 2.4 Hz, 1H), 7.39 (d, J=8.0 Hz, 1H), 6.35 (bs, 1H), 4.03 (t, J=6.0 Hz, 2H), 3.87 (bs, 2H), 2.95-2.85 (m, 2H), 2.80-2.70 (m, 2H), 2.53 (s, 3H), 2.08 (bs, 5H). MS (ESI) m/z 406 [M+H]⁺.

Synthesis of 4-(2-methyl-6,7-dihydropyrazolo[1,5-a]pyrimidin-4(5H)-yl)-N-(5-(6-methylpyrazin-2-yl)pyridin-2-yl)-4-oxobutanamide, Compound 128

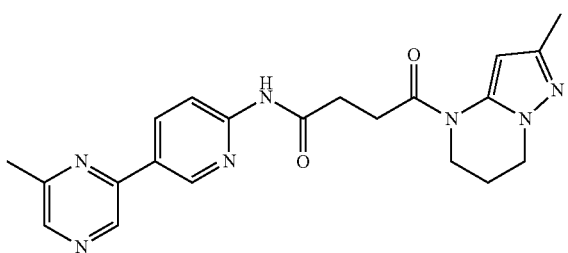

¹H NMR (400 MHz, DMSO-d₆): 10.79 (s, 1H), 9.08-9.06 (m, 2H), 8.51 (bs, 1H), 8.49-8.46 (m, 1H), 8.20 (d, J=8.8 Hz, 1H), 6.33 (bs, 1H), 4.02 (t, J=5.8 Hz, 2H), 3.86 (bs, 2H), 2.91-2.87 (m, 2H), 2.76-2.73 (m, 2H), 2.57 (s, 3H), 2.08 (bs, 5H). LC-MS: m/z 406 [M+H]⁺.

Synthesis of 4-(2-methyl-6,7-dihydropyrazolo[1,5-a]pyrimidin-4(5H)-yl)-4-oxo-N-(4-(pyrazin-2-yl)phenyl)butanamide, Compound 129

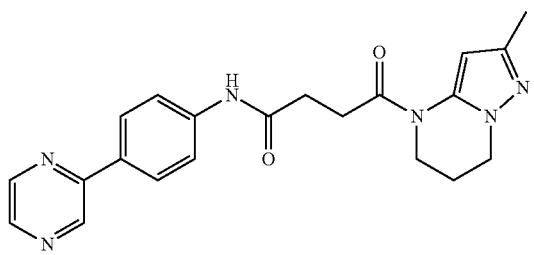 [SMILES: Cc1cc2n(n1)CCCN2C(=O)CCC(=O)Nc1ccc(-c2cnccn2)cc1]

¹H NMR (400 MHz, DMSO-d₆): 10.24 (s, 1H), 9.21 (d, J=1.6 Hz, 1H), 8.68-8.65 (m, 1H), 8.55 (d, J=2.4 Hz, 1H), 8.12-8.08 (m, 2H), 7.80-7.72 (m, 2H), 6.35 (bs, 1H), 4.03 (t, J=6.0 Hz, 2H), 3.87 (bs, 2H), 2.95-2.85 (m, 2H), 2.72-2.65 (m, 2H), 2.08 (bs, 5H). MS (ESI) m/z 391 [M+H]⁺.

Synthesis of N-(3-(3-chlorophenyl)isoxazol-5-yl)-N-methyl-4-(2-methyl-6,7-dihydropyrazolo[1,5-a]pyrimidin-4(5H)-yl)-4-oxobutanamide, Compound 130

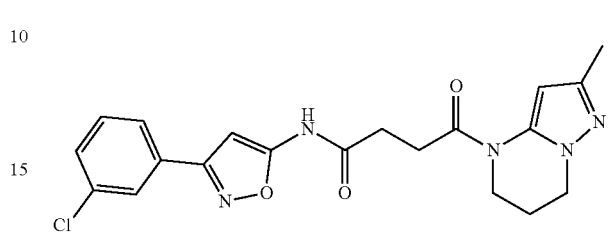

Step 1: Preparation of N-(3-(3-chlorophenyl)isoxazol-5-yl)-4-(2-methyl-6,7-dihydropyrazolo[1,5-a]pyrimidin-4(5H)-yl)-4-oxobutanamide ¹H NMR (400 MHz, Methanol-d₄): 7.66 (s, 1H), 7.60-7.58 (m, 1H), 7.33-7.29 (m, 2H), 6.53 (s, 1H), 6.13 (brs, 1H), 3.81 (brs, 2H), 3.64 (s, 1H), 2.70 (brs, 2H), 2.52-2.51 (m, 2H), 2.29 (s, 2H), 1.86 (brs, 5H). LC-MS: MS m/z 414 [M+H]⁺.

Step 2: Preparation of N-(3-(3-chlorophenyl)isoxazol-5-yl)-N-methyl-4-(2-methyl-6,7-dihydropyrazolo[1,5-a]pyrimidin-4(5H)-yl)-4-oxobutanamide

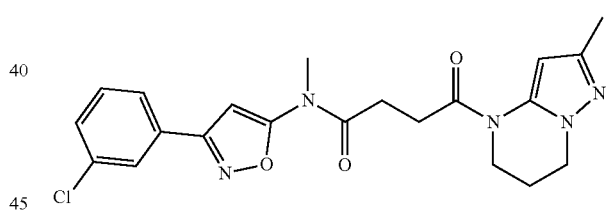

To a stirred solution of N-(3-(3-chlorophenyl)isoxazol-5-yl)-4-(2-methyl-6,7-dihydropyrazolo[1,5-a]pyrimidin-4(5H)-yl)-4-oxobutanamide (1 equiv.) in dry tetrahydrofuran was added K₂CO₃ (3 equiv.) at room temperature and stirring was continued for 15 minutes. CH₃I (5 equiv.) was added to reaction mixture drop wise at 0° C. followed by stirring at room temperature for 16 h. After completion, the reaction mixture was diluted with water and extracted with ethyl acetate. The combined organic layer was washed with water and brine solution. The organic solvent was dried over anhydrous sodium sulphate, filtered and concentrated under vacuum to give crude product. The crude product was purified by column chromatography.

¹H NMR (400 MHz, DMSO-d₆): 7.93 (s, 1H), 7.85 (d, J=7.1 Hz, 1H), 7.60-7.53 (m, 2H), 7.05 (s, 2H), 6.33 (bs, 1H), 4.02 (bs, 2H), 3.86 (bs, 2H), 3.40 (s, 3H), 2.87 (bs, 4H), 2.07 (bs, 5H); MS (ESI) m/z 428.20 [M+H]⁺.

155

Synthesis of 3-(3-chlorophenyl)-N-(4-(2-methyl-6,7-dihydropyrazolo[1,5-a]pyrimidin-4(5H)-yl)butyl)isoxazol-5-amine, Compound 131

Step 1: Preparation of N-(3-(3-chlorophenyl)isoxazol-5-yl)-4-(2-methyl-6,7-dihydropyrazolo[1,5-a]pyrimidin-4(5H)-yl)-4-oxobutanamide

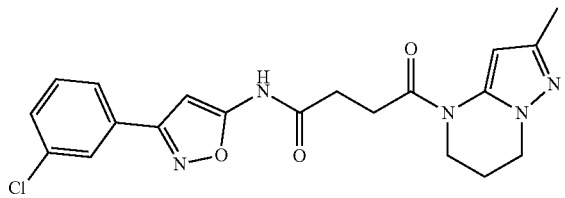 [SMILES: Cc1cc2n(n1)CCCN2C(=O)CCC(=O)Nc1cc(-c2cccc(Cl)c2)no1]

$^1$H NMR (400 MHz, DMSO-d$_6$): 11.88 (s, 1H), 7.91 (s, 1H), 7.82 (d, 1H), 7.58-7.51 (m, 2H), 6.89 (s, 1H), 6.36 (brs, 1H), 4.02 (t, 2H), 3.86 (brs, 2H), 2.92 (t, 2H), 2.71 (q, 2H), 2.07 (brs, 5H). LC-MS: MS m/z 414 [M+H]$^+$.

Step 2: Preparation of 3-(3-chlorophenyl)-N-(4-(2-methyl-6,7-dihydropyrazolo[1,5-a]pyrimidin-4(5H)-yl)butyl)isoxazol-5-amine

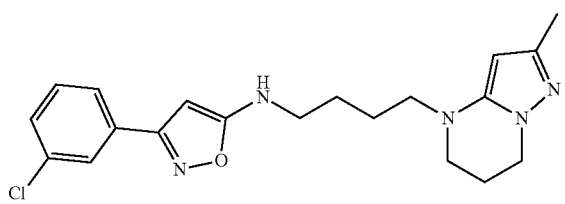 [SMILES: Cc1cc2n(n1)CCCN2CCCCNc1cc(-c2cccc(Cl)c2)no1]

A solution of N-(3-(3-chlorophenyl)isoxazol-5-yl)-4-(2-methyl-6,7-dihydropyrazolo[1,5-a]pyrimidin-4(5H)-yl)-4-oxobutanamide (1 equiv.) in THF (0.03 M) was treated with borane.DMS (5 equiv.) at 0° C. and the reaction mixture was heated to 40° C. for 10 h. After completion, the reaction mixture was quenched with methanol and concentrated under reduced pressure to obtain the crude product; water was added and extracted with ethyl acetate. The combined ethyl acetate layers were dried over sodium sulphate, filtered and concentrated under reduced pressure to obtain the crude product. The crude product was purified by preparative HPLC.

$^1$H NMR (400 MHz, Chloroform-d): 7.72 (brs, 1H), 7.62 (d, J=6.8 Hz, 1H), 7.37-7.33 (m, 2H), 5.26 (s, 1H), 5.16 (s, 1H), 4.61 (brs, 1H), 4.06 (t, J=6.0 Hz, 2H), 3.29 (d, J=5.6 Hz, 2H), 3.16 (brs, 4H), 2.20 (s, 3H), 2.16 (t, J=5.6 Hz, 2H), 1.69 (brs, 4H). LC-MS: MS m/z 386 [M+H]$^+$.

156

Synthesis of N-(3-(3-chlorophenyl)isoxazol-5-yl)-3-methyl-4-(2-methyl-6,7-dihydropyrazolo[1,5-a]pyrimidin-4(5H)-yl)-4-oxobutanamide, Compound 132

Step 1: Preparation of 4-methoxy-2-methyl-4-oxobutanoic acid

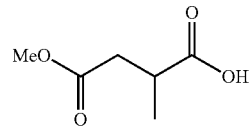

To a solution of 4-methoxy-2-methylene-4-oxobutanoic acid (1 equiv.) in methanol (0.3 M) was added a slurry of 10% Pd/C (0.1 equiv.) in methanol under nitrogen. The reaction mixture was hydrogenated under H$_2$ (balloon) at room temperature for 16 h. The reaction mixture was filtered through celite bed and washed with methanol. The filtrate was concentrated under reduced pressure to give crude product. The crude product was washed with n-pentane and diethyl ether to remove solid impurities. The solvent was evaporated under reduced pressure to afford the intermediate as a pale yellow liquid.

Step 2: Preparation of methyl 3-methyl-4-(2-methyl-6,7-dihydropyrazolo[1,5-a]pyrimidin-4(5H)-yl)-4-oxobutanoate

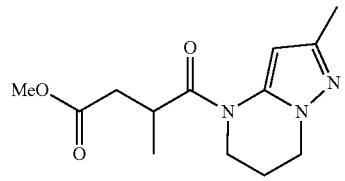 [SMILES: COC(=O)CC(C)C(=O)N1CCCn2nc(C)cc21]

To a stirred solution of 4-methoxy-2-methyl-4-oxobutanoic acid (1 equiv.), 2-methyl-4,5,6,7-tetrahydropyrazolo[1,5-a]pyrimidine (1 equiv.) in DMF (0.5 M) was added HATU (1.5 equiv.), TEA (3 equiv.) and the reaction mixture was stirred at rt for 12 h. Upon completion of reaction, the reaction mixture was added to the ice-water and extracted with ethyl acetate. The combined organic layer was washed with water, brine, dried over sodium sulphate, filtered and concentrated under reduced pressure to give the crude product. The crude product was purified by column chromatography to afford the intermediate. LC-MS: MS m/z 266 [M+H]$^+$.

Step 3: Preparation of 3-methyl-4-(2-methyl-6,7-dihydropyrazolo[1,5-a]pyrimidin-4(5H)-yl)-4-oxobutanoic acid

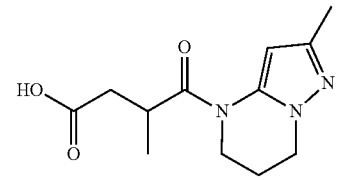 [SMILES: Cc1cc2n(n1)CCCN2C(=O)C(C)CC(=O)O]

To a stirred solution of methyl 3-methyl-4-(2-methyl-6,7-dihydropyrazolo[1,5-a]pyrimidin-4(5H)-yl)-4-oxobutanoate (1 equiv.) in THF—CH₃OH—H₂O (1:1:1) (0.2 M) was added LiOH.H₂O (2 equiv.) and the reaction mixture was stirred at room temperature for 2 h. After completion, the solvents were evaporated under reduced pressure and the residue was acidified with saturated KHSO₄ solution and extracted with 10% methanol in chloroform. The aqueous layer was evaporated under reduced pressure and stirred in 10% methanol in chloroform, filtered and concentrated under reduced pressure to afford the intermediate. LC-MS: MS m/z 266 [M+H]⁺.

Step 4: Preparation of N-(3-(3-chlorophenyl)isoxazol-5-yl)-3-methyl-4-(2-methyl-6,7-dihydropyrazolo[1,5-a]pyrimidin-4(5H)-yl)-4-oxobutanamide

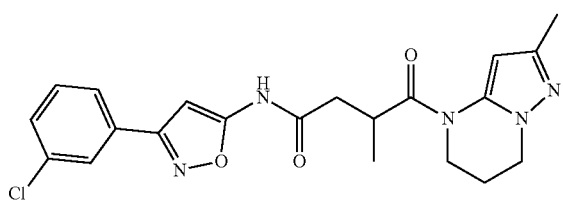 [SMILES: Cc1cc2n(n1)CCCN2C(=O)C(C)CC(=O)Nc1cc(-c2cccc(Cl)c2)no1]

¹H NMR (400 MHz, DMSO-d₆): 11.84 (s, 1H), 7.91 (s, 1H), 7.83 (d, J=7 Hz, 1H), 7.57-7.49 (m, 2H), 6.77 (s, 1H), 6.35 (bs, 1H), 4.06-4.03 (t, J=5.7 Hz, 2H), 3.96-3.92 (m, 2H), 2.89-2.86 (m, 1H), 2.60-2.55 (dd, J=4.8 Hz, 16.7 Hz, 1H), 2.13-2.07 (bs, 5H), 1.13 (d, J=6.6 Hz, 3H). MS (ESI) m/z 428.20 [M+H]⁺.

Synthesis of N-(3-(3-chlorophenyl)isoxazol-5-yl)-4-(6,7-dihydropyrazolo[1,5-a]pyrimidin-4(5H)-yl)-4-oxobutanamide, Compound 133

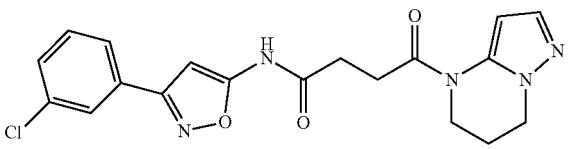 [SMILES: O=C(CCC(=O)N1CCCn2nccc21)Nc1cc(-c2cccc(Cl)c2)no1]

¹H NMR (400 MHz, DMSO-d₆): 11.86 (s, 1H), 7.90 (s, 1H), 7.83-7.82 (d, J=6.8 Hz, 1H), 7.58-7.53 (m, 2H), 7.29 (br s, 1H), 6.78 (s, 1H), 6.54 (br s, 1H), 4.14-4.11 (t, J=5.6 Hz, 2H), 3.92-3.90 (s, 2H), 2.95-2.91 (m, 2H), 2.74-2.71 (t, J=6 Hz, 2H), 2.16-2.12 (m, 2H). LC-MS: MS m/z 400.1 [M+H]⁺.

Synthesis of N-(3-(3-chlorophenyl)isoxazol-5-yl)-4-oxo-4-(2-(trifluoromethyl)-6,7-dihydropyrazolo[1,5-a]pyrimidin-4(5H)-yl)butanamide, Compound 134

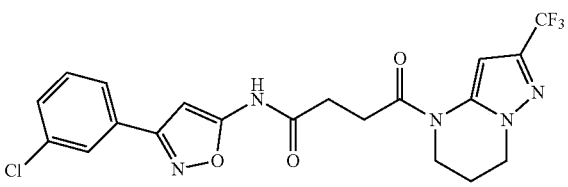 [SMILES: O=C(CCC(=O)N1CCCn2nc(C(F)(F)F)cc21)Nc1cc(-c2cccc(Cl)c2)no1]

¹H NMR (400 MHz, DMSO-d₆): 11.88 (s, 1H), 7.90 (s, 1H), 7.82 (d, J=7.6 Hz, 1H), 7.58-7.51 (m, 2H), 6.89 (brs, 1H), 6.77 (s, 1H), 4.22 (t, J=5.6 Hz, 2H), 3.95 (brs, 2H), 2.96 (m, 2H), 2.74 (t, J=6 Hz, 2H), 2.19 (brs, 2H). LC-MS: MS m/z 467 [M−H]⁺.

Synthesis of N-(3-(3-chlorophenyl)isoxazol-5-yl)-4-(2-methoxy-6,7-dihydropyrazolo[1,5-a]pyrimidin-4(5H)-yl)-4-oxobutanamide, Compound 135

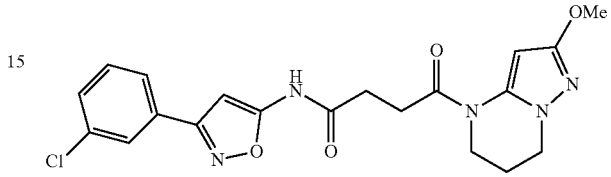

¹H NMR (400 MHz, DMSO-d₆): 7.87 (s, 1H), 7.79 (d, J=6.8 Hz, 1H), 7.56-7.50 (m, 2H), 6.70 (s, 1H), 5.96 (b s, 1H), 3.93 (t, J=6.2 Hz, 2H), 3.85 (b s, 2H), 3.71 (s, 3H), 2.90-2.88 (m, 2H), 2.67 (b s, 2H), 2.11 (b s, 2H). LC-MS: m/z 430 [M+H]⁺.

Synthesis of methyl 4-(4-(3-(3-chlorophenyl)isoxazol-5-ylamino)-4-oxobutanoyl)-4,5,6,7-tetrahydropyrazolo[1,5-a]pyrimidine-2-carboxylate, Compound 136

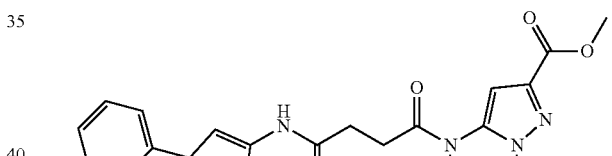

¹H NMR (400 MHz, DMSO-d₆): 9.3 (brs, 1H), 7.78 (s, 1H), 7.65 (d, J=7.2 Hz, 1H), 7.41-7.34 (m, 2H), 6.63 (s, 1H), 4.31 (t, J=6.4 Hz, 2H), 3.96 (brs, 2H), 3.92 (s, 3H), 3.03 (brs, 2H), 2.90 (brs, 2H), 2.28 (brs, 2H).

Synthesis of N-(3-(3-chlorophenyl)isoxazol-5-yl)-4-(2-ethyl-6,7-dihydropyrazolo[1,5-a]pyrimidin-4(5H)-yl)-4-oxobutanamide, Compound 137

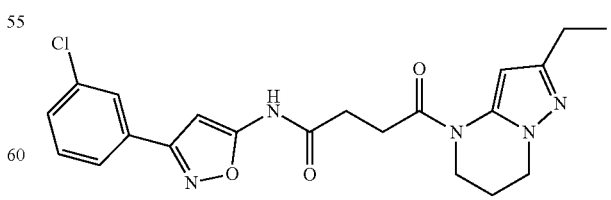

¹H NMR (400 MHz, Chloroform-d) 7.77 (1H, bs), 7.64 (1H, d, J=8.0 Hz), 7.33-7.40 (2H, m), 7.25 (1H, s), 6.64 (1H, s), 4.18 (2H, t), 4.00 (2H, m), 2.90 (2H, m), 2.88 (2H, m), 2.60 (2H, t), 2.19 (2H, m), 0.88 (3H, m).

Synthesis of N-(3-(3-chlorophenyl)isoxazol-5-yl)-4-(6-methyl-2,3-dihydro-1H-imidazo[1,2-b]pyrazol-1-yl)-4-oxobutanamide, Compound 138

Step 1: Preparation of 6-methyl-2,3-dihydro-1H-imidazo[1,2-b]pyrazole

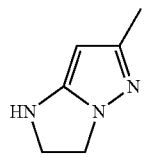

To a stirred solution of 3-methyl-1H-pyrazol-5-amine (1 equiv.) in 1,4-dioxane (0.5 M) was added triethylamine (5 equiv.) at room temperature. After 15 minutes, 1,2-dibromoethane (1.2 equiv.) was added to the reaction mixture at room temperature. The reaction mixture was stirred at 110° C. for 16 h. After completion, the reaction mixture was filtered and washed with ethyl acetate. The filtrate was concentrated under reduced pressure to give crude product. The crude product was purified by column chromatography to afford the product as an off-white solid. LC-MS: m/z 124 [M+H]$^+$.

Step 2: Preparation of 4-(6-methyl-2,3-dihydro-1H-imidazo[1,2-b]pyrazol-1-yl)-4-oxobutanoic acid

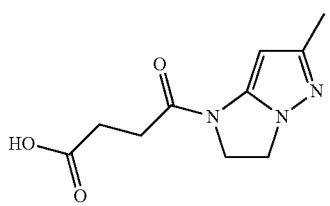 [SMILES: Cc1cc2n(n1)CCN2C(=O)CCC(=O)O]

To a stirred solution of 6-methyl-2,3-dihydro-1H-imidazo[1,2-b]pyrazole (1 equiv.) in chloroform (0.5 M) was added dihydrofuran-2,5-dione (1.3 equiv.). The reaction mixture was stirred at room temperature for 12 h. After completion, the solid thus precipitated was filtered and washed with n-pentane and dried to afford the product as an off-white solid. LC-MS: m/z 224 [M+H]$^+$.

Step 3: Preparation of N-(3-(3-chlorophenyl)isoxazol-5-yl)-4-(6-methyl-2,3-dihydro-1H-imidazo[1,2-b]pyrazol-1-yl)-4-oxobutanamide

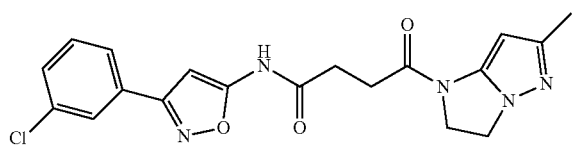 [SMILES: Cc1cc2n(n1)CCN2C(=O)CCC(=O)Nc1cc(-c2cccc(Cl)c2)no1]

$^1$H NMR (400 MHz, DMSO-d$_6$): 11.81 (brs, 1H), 7.89 (s, 1H), 7.82 (d, J=7.0 Hz, 1H), 7.57-7.54 (m, 2H), 6.77 (s, 1H), 5.71 (s, 1H), 4.55 (t, J=7.8 Hz, 1H), 4.32-4.24 (m, 2H), 4.20-4.16 (m, 1H), 2.84 (d, J=6.1 Hz, 1H), 2.75 (s, 3H), 2.15 (s, 2H), 2.11 (s, 1H). LC-MS: m/z 400.22 [M+H]$^+$.

Synthesis of 4-(2,6-dimethyl-6,7-dihydropyrazolo[1,5-a]pyrimidin-4(5H)-yl)-4-oxo-N-(6-phenylpyridazin-3-yl)butanamide, Compound 139

Step 1: Preparation of 2-methylpropane-1,3-diyl dimethanesulfonate

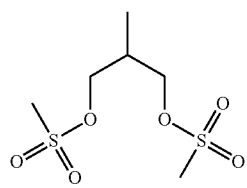

To a stirred solution of 2-methylpropane-1,3-diol (1 equiv.) in dichloromethane (0.45 M) was added methane sulfonyl chloride (2.7 equiv.), using triethylamine (2.7 equiv.) at 0° C. to room temperature for 16 h. Upon completion of reaction, the reaction mixture was washed with water and brine solution, dried over anhydrous Na$_2$SO$_4$, filtered and concentrated under reduced pressure to the product as a brown solid.

Step 2: Preparation of 2,6-dimethyl-4,5,6,7-tetrahydropyrazolo[1,5-a]pyrimidine

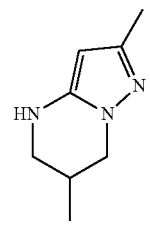

To a stirred solution of 2-methylpropane-1,3-diyl dimethanesulfonate (1.2 equiv.) in 1,4-dioxane (0.5 M) were added 3-methyl-M-pyrazol-5-amine (1 equiv.) and triethylamine (5 equiv.). The reaction mixture was heated at 100° C. for 48 h. Upon completion of reaction, the reaction mixture was filtered and concentrated under reduced pressure, purified by column chromatography to afford the product as a brown solid. LC-MS: m/z 152 [M+H]$^+$.

Step 3: Preparation of 4-(2,6-dimethyl-6,7-dihydropyrazolo[1,5-a]pyrimidin-4(5H)-yl)-4-oxobutanoic acid

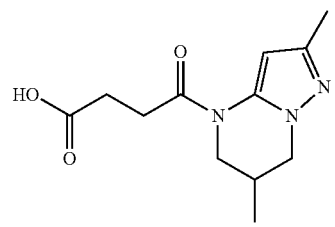 [SMILES: Cc1cc2n(n1)CC(C)CN2C(=O)CCC(=O)O]

To a stirred solution of 2,6-dimethyl-4,5,6,7-tetrahydropyrazolo[1,5-a]pyrimidine (1 equiv.) in chloroform (0.1 M) was added succinic anhydride (1 equiv.) and the reaction mixture was stirred at room temperature for 16 h. The reaction mixture was concentrated under reduced pressure to afford the product as an off-white solid. LC-MS: m/z 252 [M+H]$^+$.

Step 4: Preparation of 4-(2,6-dimethyl-6,7-dihydropyrazolo[1,5-a]pyrimidin-4(5H)-yl)-4-oxo-N-(6-phenylpyridazin-3-yl)butanamide

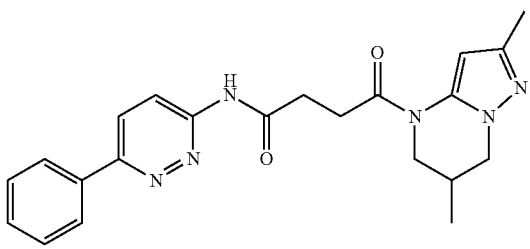 [SMILES: Cc1cc2n(n1)CC(C)CN2C(=O)CCC(=O)Nc1ccc(-c2ccccc2)nn1]

$^1$H NMR (400 MHz, DMSO-d$_6$): 8.37 (d, J=9.2 Hz, 1H), 8.23-8.17 (m, 1H), 8.09 (d, J=7.2 Hz, 2H), 7.60-7.47 (m, 5H), 4.32-3.97 (m, 3H), 3.65-3.60 (m, 1H), 2.95-2.75 (bs, 4H), 2.08 (s, 3H), 1.46 (s, 1H), 1.05 (s, 3H); LC-MS: m/z 405.0 [M+H]$^+$.

Synthesis of N-(2,3'-bipyridin-5-yl)-4-(2,6-dimethyl-6,7-dihydropyrazolo[1,5-a]pyrimidin-4(5H)-yl)-4-oxobutanamide, Compound 140

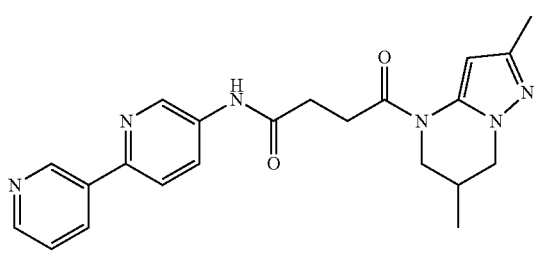 [SMILES: Cc1cc2n(n1)CC(C)CN2C(=O)CCC(=O)Nc1ccc(-c2cccnc2)nc1]

$^1$H NMR (400 MHz, DMSO-d$_6$): 10.40 (s, 1H), 9.22 (d, J=2.0 Hz, 1H), 8.86 (d, J=2.0 Hz, 1H), 8.62-8.57 (m, 1H), 8.40-8.35 (m, 1H), 8.20-8.15 (m, 1H), 8.05-7.99 (m, 1H), 7.52-7.47 (m, 1H), 6.35 (bs, 1H), 4.15-4.00 (m, 2H), 3.67-3.60 (m, 1H), 3.50-3.35 (m, 1H), 3.02-2.80 (m, 2H), 2.75-2.65 (m, 2H), 2.35-2.20 (m, 1H), 2.08 (bs, 3H), 1.05 (d, J=4.4 Hz, 3H). MS (ESI) m/z 405 [M+H]$^+$.

Synthesis of 4-(2,6-dimethyl-6,7-dihydropyrazolo[1,5-a]pyrimidin-4(5H)-yl)-4-oxo-N-(6-(pyridin-3-yl)pyridazin-3-yl)butanamide, Compound 141

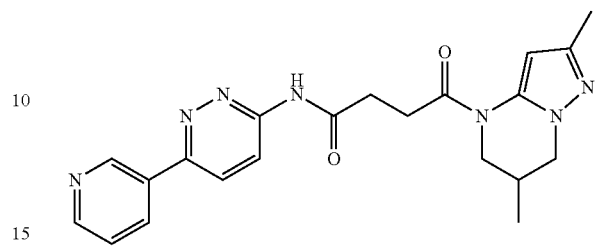

$^1$H NMR (400 MHz, DMSO-d$_6$): 11.33 (s, 1H), 9.27 (d, J=1.6 Hz, 1H), 8.69 (dd, J=4.8, 1.6 Hz, 1H), 8.50-8.43 (m, 1H), 8.43-8.37 (m, 1H), 8.34-8.19 (m, 1H), 7.70-7.55 (m, 1H), 6.35 (bs, 1H), 4.18-4.00 (m, 2H), 3.67-3.60 (m, 1H), 3.50-3.35 (m, 1H), 3.02-2.85 (m, 2H), 2.85-2.78 (m, 2H), 2.35-2.20 (m, 1H), 2.08 (bs, 3H), 1.05 (d, J=5.6 Hz, 3H). MS (ESI) m/z 406 [M+H]$^+$.

Synthesis of 4-(2,6-dimethyl-6,7-dihydropyrazolo[1,5-a]pyrimidin-4(5H)-yl)-N-(5'-methyl-[3,3'-bipyridin]-6-yl)-4-oxobutanamide, Compound 142

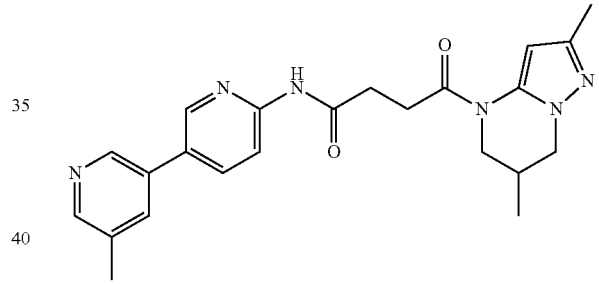

$^1$H NMR (400 MHz, DMSO-d$_6$): 10.69 (s, 1H), 8.74-8.70 (m, 2H), 8.42-8.42 (m, 1H), 8.16-8.14 (m, 2H), 7.97 (s, 1H), 6.34 (br, 1H), 4.14-4.04 (m, 2H), 3.66-3.60 (q, 1H), 2.97-2.87 (m, 2H), 2.76-2.73 (m, 2H), 2.37 (s, 3H), 2.08 (s, 3H), 1.06-1.04 (m, 3H). LC-MS: m/z 419 [M+H]$^+$.

Synthesis of 4-(2-methyl-6,7-dihydropyrazolo[1,5-a]pyrimidin-4(5H)-yl)-N-(6-methyl-[2,3'-bipyridin]-6'-yl)-4-oxobutanamide, Compound 143

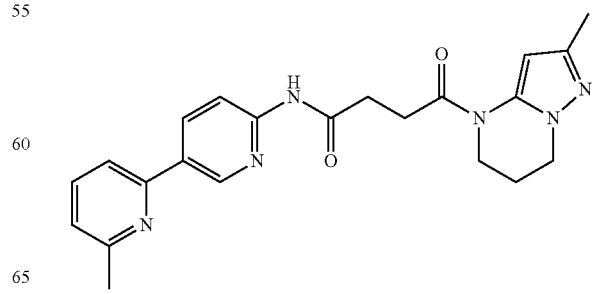

¹H NMR (400 MHz, DMSO-d₆): 10.71 (s, 1H), 9.01-9.00 (m, 1H), 8.42-8.40 (m, 1H), 8.17-8.15 (d, J=8.8 Hz, 1H), 7.80-7.75 (m, 2H), 7.23-7.21 (m, 1H), 6.33 (br, 1H), 4.02 (t, J=6.2 Hz, 2H), 3.86 (br, 2H), 2.89-2.87 (m, 2H), 2.75-2.72 (m, 2H), 2.54 (s, 3H), 2.08 (br, 5H). LC-MS: m/z 405 [M+H]⁺.

Synthesis of 4-(2,6-dimethyl-6,7-dihydropyrazolo[1,5-a]pyrimidin-4(5H)-yl)-N-(5'-methyl-[2,3'-bipyridin]-5-yl)-4-oxobutanamide, Compound 144

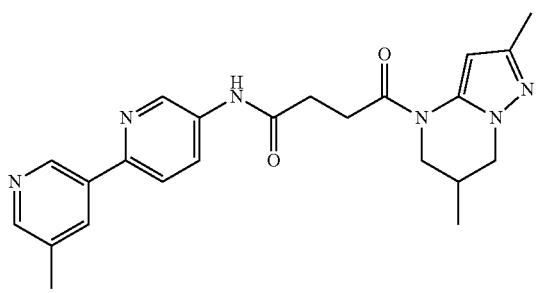 [SMILES: Cc1cncc(-c2ccc(NC(=O)CCC(=O)N3CC(C)Cn4nc(C)cc43)cn2)c1]

¹H NMR (400 MHz, DMSO-d₆): 10.39 (s, 1H), 9.01 (m, 1H), 8.85 (br, 1H), 8.43-8.42 (m, 1H), 8.21 (br, 1H), 8.18-8.15 (m, 1H), 8.00 (d, J=8.8 Hz, 1H), 6.33 (br, 1H), 4.14-4.10 (m, 2H), 3.66-3.61 (m, 1H), 2.99-2.89 (m, 2H), 2.72-2.67 (m, 2H), 2.38 (s, 3H), 2.08 (s, 3H), 1.06-1.05 (m, 3H). LC-MS: m/z 419 [M+H]⁺.

Synthesis of N-([2,3'-bipyridin]-5-yl)-2-methyl-4-(2-methyl-6,7-dihydropyrazolo[1,5-a]pyrimidin-4(5H)-yl)-4-oxobutanamide, Compound 145

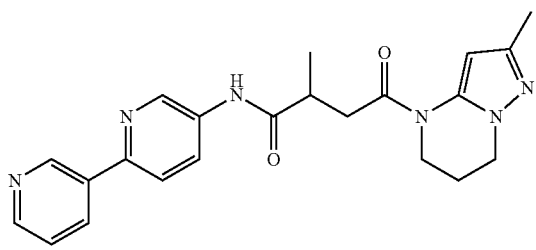 [SMILES: Cc1cc2n(n1)CCCN2C(=O)CC(C)C(=O)Nc1ccc(-c2cccnc2)nc1]

¹H NMR (400 MHz, DMSO-d₆): 10.38 (s, 1H), 9.22 (d, J=1.6 Hz, 1H), 8.88 (d, J=2.4 Hz, 1H), 8.59 (dd, J=4.8, 1.6 Hz, 1H), 8.38 (dt, J=8.0, 2.0 Hz, 1H), 8.22-8.18 (m, 1H), 8.03-8.00 (m, 1H), 7.53-7.48 (m, 1H), 6.35 (bs, 1H), 4.05-4.00 (m, 2H), 3.90-3.84 (m, 2H), 3.10-3.00 (m, 2H), 2.75-2.60 (m, 1H), 2.07 (bs, 5H), 1.21 (d, J=6.4 Hz, 3H). MS (ESI) m/z 405 [M+H]⁺.

Synthesis of N-([3,3'-bipyridin]-6-yl)-2-methyl-4-(2-methyl-6,7-dihydropyrazolo[1,5-a]pyrimidin-4(5H)-yl)-4-oxobutanamide, Compound 147

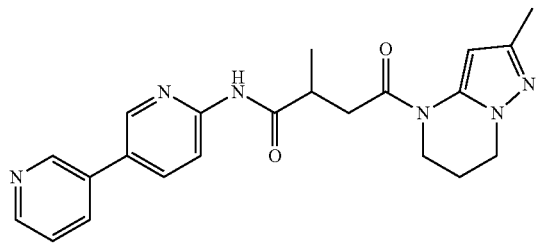 [SMILES: Cc1cc2n(n1)CCCN2C(=O)CC(C)C(=O)Nc1ccc(-c2cccnc2)cn1]

¹H NMR (400 MHz, DMSO-d₆): 10.68 (s, 1H), 8.94 (s, 1H), 8.72 (s, 1H), 8.58-8.57 (m, 1H), 8.19-8.12 (m, 3H), 7.51-7.48 (m, 1H), 6.27 (br, 1H), 4.02 (t, J=6.0 Hz, 2H), 3.86 (br, 2H), 3.06-2.99 (m, 1H), 2.06 (br, 5H), 1.19 (d, J=7.2 Hz, 3H). LC-MS: m/z 405 [M+H]⁺.

Synthesis of N-(4-methyl-2,3'-bipyridin-6'-yl)-4-(2-methyl-6,7-dihydropyrazolo[1,5-a]pyrimidin-4(5H)-yl)-4-oxobutanamide, Compound 148

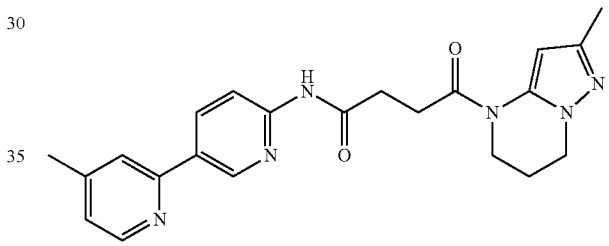

¹H NMR (400 MHz, DMSO-d₆): 10.70 (s, 1H), 9.01 (d, J=2.1 Hz, 1H), 8.51 (d, J=4.8 Hz, 1H), 8.43-8.40 (dd, J=2.6 Hz, 8.7 Hz, 1H), 8.15 (d, J=8.8 Hz, 1H), 7.85 (s, 1H), 7.19 (d, J=4.8 Hz, 1H), 6.33 (brs, 1H), 4.02 (t, J=5.7 Hz, 2H), 3.86 (brs, 2H), 2.89 (t, J=5.7 Hz, 2H), 2.74 (t, J=6.1 Hz, 2H), 2.39 (s, 3H), 2.08 (brs, 5H); MS (ESI) m/z 405.18 [M+H]⁺.

Synthesis of 4-(2-methyl-6,7-dihydropyrazolo[1,5-a]pyrimidin-4(5H)-yl)-N-(5-(5-methylpyrazin-2-yl)pyridin-2-yl)-4-oxobutanamide, Compound 149

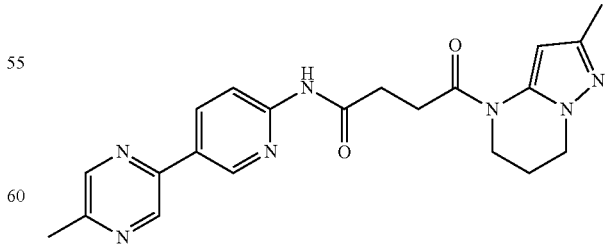

¹H NMR (400 MHz, DMSO-d₆): 10.75 (s, 1H), 9.14 (d, J=0.8 Hz, 1H), 9.04 (d, J=2.2 Hz, 1H), 8.60 (s, 1H), 8.46-8.43 (dd, J=2.2 Hz, 2.2 Hz, 1H), 8.19 (d, J=8.7 Hz, 1H), 6.33 (brs, 1H), 4.02 (t, J=5.7 Hz, 2H), 3.86 (brs, 2H), 2.89

(t, J=6.1 Hz, 2H), 2.75 (t, J=6.6 Hz, 2H), 2.53 (s, 3H), 2.07 (brs, 5H). MS (ESI) m/z 406.16 [M+H]⁺.

Synthesis of 2-methyl-4-(2-methyl-6,7-dihydropyrazolo[1,5-a]pyrimidin-4(5H)-yl)-N-(5'-methyl-[2,3'-bipyridin]-5-yl)-4-oxobutanamide, Compound 150

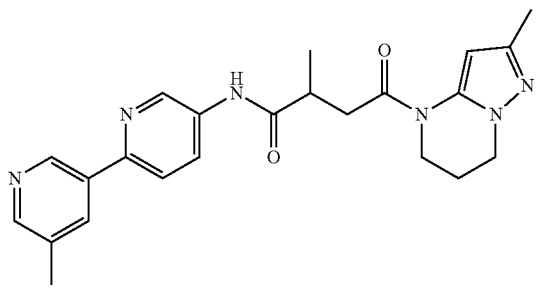 [SMILES: Cc1cncc(-c2ccc(NC(=O)C(C)CC(=O)N3CCCn4nc(C)cc43)cn2)c1]

¹H NMR (400 MHz, DMSO-d₆): 10.37 (s, 1H), 9.01 (s, 1H), 8.87 (s, 1H), 8.42 (s, 1H), 8.21-8.17 (m, 2H), 7.99 (d, J=8.8 Hz, 1H), 6.32 (br, 1H), 4.03-4.00 (m, 2H), 3.86 (br, 2H), 3.04-3.01 (m, 2H), 2.69-2.66 (m, 1H), 2.38 (s, 3H), 2.07 (br, 5H), 1.21 (d, J=6.0 Hz, 3H). LC-MS: m/z 419 [M+H]⁺.

Synthesis of 2-methyl-4-(2-methyl-6,7-dihydropyrazolo[1,5-a]pyrimidin-4(5H)-yl)-N-(5-(6-methylpyrazin-2-yl)pyridin-2-yl)-4-oxobutanamide, Compound 151

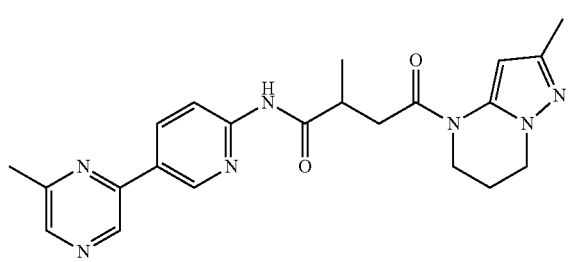

¹H NMR (400 MHz, DMSO-d₆): 10.78 (s, 1H), 9.08 (s, 2H), 8.56-8.46 (m, 2H), 8.21 (d, J=8.4 Hz, 1H), 6.29 (br, 1H), 4.02 (m, 2H), 3.86 (br, 2H), 3.18 (br, 2H), 3.05-2.99 (m, 1H), 2.57 (s, 3H), 2.06 (br, 5H), 1.19 (d, J=6.8 Hz, 3H). LC-MS: m/z 420 [M+H]⁺.

Synthesis of 2-methyl-4-(2-methyl-6,7-dihydropyrazolo[1,5-a]pyrimidin-4(5H)-yl)-N-(5'-methyl-[3,3'-bipyridin]-6-yl)-4-oxobutanamide, Compound 152

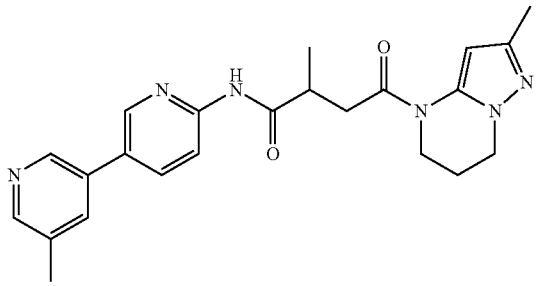 [SMILES: Cc1cncc(-c2ccc(NC(=O)C(C)CC(=O)N3CCCn4nc(C)cc43)nc2)c1]

¹H NMR (400 MHz, DMSO-d₆): 10.67 (s, 1H), 8.75-8.69 (m, 2H), 8.42 (s, 1H), 8.20-8.10 (m, 2H), 7.96 (s, 1H), 6.35 (bs, 1H), 4.05-4.00 (m, 2H), 3.90-3.80 (m, 2H), 3.20-3.10 (m, 2H), 3.10-2.95 (m, 1H), 2.37 (s, 3H), 2.07 (bs, 5H), 1.19 (d, J=6.8 Hz, 3H). MS (ESI) m/z 419 [M+H]⁺.

Synthesis of 4-(2-methyl-6,7-dihydropyrazolo[1,5-a]pyrimidin-4(5H)-yl)-4-oxo-N-(5-(pyrimidin-5-yl)pyridin-2-yl)butanamide, Compound 153

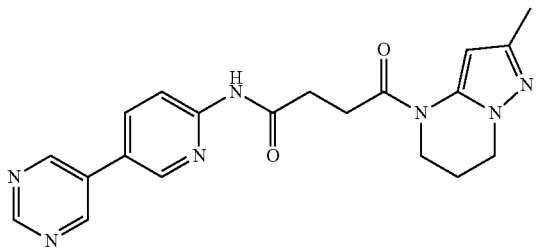

¹H NMR (400 MHz, DMSO-d₆): 10.73 (s, 1H), 9.19 (d, J=2.2 Hz, 3H), 8.79 (d, J=2.2 Hz, 1H), 8.25-8.18 (m, 2H), 6.32 (brs, 1H), 4.03 (t, J=5.7 Hz, 2H), 3.86 (s, 2H), 2.89 (t, J=6.2 Hz, 2H), 2.75 (t, J=6.6 Hz, 2H), 2.08 (s, 5H). MS (ESI) m/z 392.15 [M+H]⁺.

Synthesis of 4-(2-methyl-6,7-dihydropyrazolo[1,5-a]pyrimidin-4(5H)-yl)-4-oxo-N-(6-(pyrimidin-5-yl)pyridin-3-yl)butanamide, Compound 154

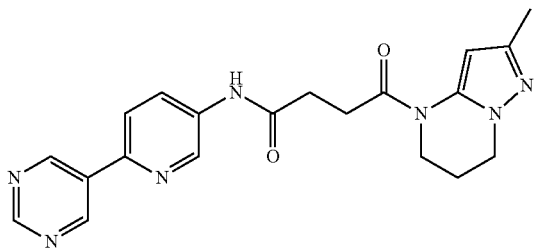

¹H NMR (400 MHz, DMSO-d₆): 10.44 (s, 1H), 9.39 (s, 2H), 9.20 (s, 1H), 8.89 (s, 1H), 8.22-8.20 (dd, J=2.2 Hz, 8.8 Hz, 1H), 8.10 (d, J=8.4 Hz, 1H), 6.33 (brs, 1H), 4.02 (t, J=5.7 Hz, 2H), 3.86 (s, 2H), 2.90 (d, J=6.2 Hz, 2H), 2.71 (t, J=6.2 Hz, 2H), 2.08 (s, 5H). MS (ESI) m/z 392.15 [M+H]⁺.

Synthesis of N-(5-fluoro-6-phenylpyridin-3-yl)-4-(2-methyl-6,7-dihydropyrazolo[1,5-a]pyrimidin-4(5H)-yl)-4-oxobutanamide, Compound 156

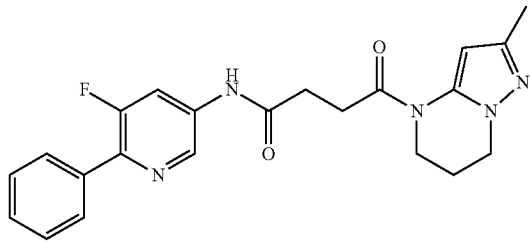

¹H NMR (400 MHz, DMSO-d₆): 10.62 (s, 1H), 8.64 (s, 1H), 8.15 (dd, J=13.6, 2.0 Hz, 1H), 7.92-7.85 (m, 2H), 7.55-7.56 (m, 2H), 7.56-7.40 (m, 1H), 6.35 (bs, 1H), 4.03 (t, J=5.6 Hz, 2H), 3.87 (bs, 2H), 2.95-2.85 (m, 2H), 2.75-2.65 (m, 2H), 2.08 (bs, 5H); MS (ESI) m/z 408 [M+H]⁺.

Synthesis of 4-(2,6-dimethyl-6,7-dihydropyrazolo[1,5-a]pyrimidin-4(5H)-yl)-N-(5-(6-methylpyrazin-2-yl)pyridin-2-yl)-4-oxobutanamide, Compound 157

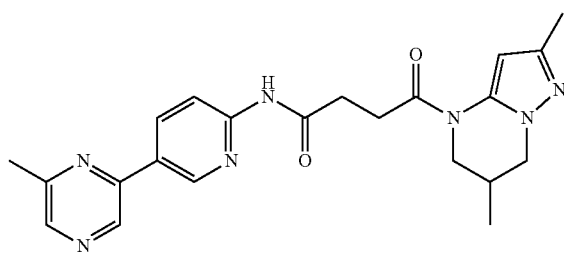

¹H NMR (400 MHz, DMSO-d₆): 10.80 (s, 1H), 9.08-9.07 (m, 2H), 8.54-8.47 (m, 2H), 8.21-8.19 (m, 1H), 6.34 (br, 1H), 4.13-4.04 (m, 3H), 3.66-3.61 (m, 2H), 2.95-2.86 (m, 2H), 2.77-2.75 (m, 2H), 2.57 (s, 3H), 2.08 (s, 3H), 1.06-1.05 (m, 3H). LC-MS: m/z 420 [M+H]⁺.

Synthesis of N-(3-fluoro-5'-methyl-[2,3'-bipyridin]-5-yl)-4-(2-methyl-6,7-dihydropyrazolo[1,5-a]pyrimidin-4(5H)-yl)-4-oxobutanamide, Compound 158

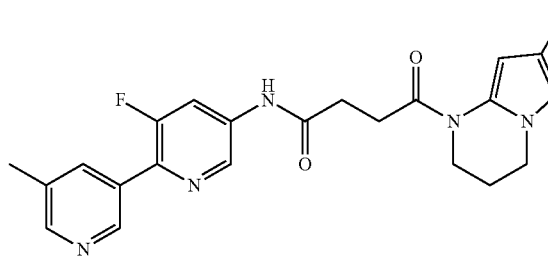

¹H NMR (400 MHz, DMSO-d₆): 10.69 (s, 1H), 8.85 (s, 1H), 8.67 (s, 1H), 8.47 (m, 1H), 8.20-8.17 (m, 1H), 8.07 (s, 1H), 6.32 (br, 1H), 4.03 (t, J=5.6 Hz, 2H), 3.87 (br, 2H), 2.93-2.90 (m, 2H), 2.73-2.70 (m, 2H), 2.38 (s, 3H), 2.08 (br, 5H). LC-MS: m/z 423 [M+H]⁺.

Synthesis of N-(3-(3-chlorophenyl)isoxazol-5-yl)-2-methyl-4-(2-methyl-6,7-dihydropyrazolo[1,5-a]pyrimidin-4(5H)-yl)-4-oxobutanamide, Compound 159

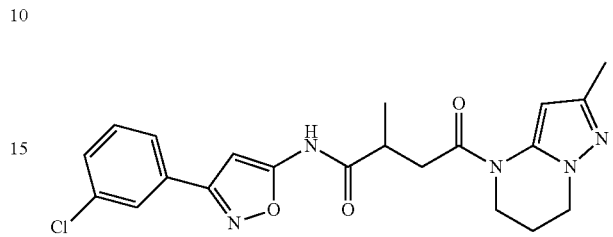

¹H NMR (400 MHz, DMSO-d₆): 11.86 (br, 1H), 7.84-7.77 (m, 2H), 7.53-7.51 (m, 2H), 6.66 (br, 1H), 6.34 (br, 1H), 4.03-4.00 (m, 2H), 3.84 (br, 2H), 3.07-2.95 (m, 2H), 2.07 (br, 5H), 1.74 (br, 1H), 1.18-1.16 (d, J=4.8 Hz, 3H). LC-MS: m/z 428 [M+H]⁺.

Synthesis of 4-(2,6-dimethyl-6,7-dihydropyrazolo[1,5-a]pyrimidin-4(5H)-yl)-N-(4-methyl-2,3'-bipyridin-6'-yl)-4-oxobutanamide, Compound 160 and Compound 161

The product was subjected to chiral chromatography to afford enantiomeric pure compound 160 and compound 161.

¹H NMR (400 MHz, DMSO-d₆): 10.66 (s, 1H), 8.73 (s, 1H), 8.69 (s, 1H), 8.42 (s, 1H), 8.17-8.14 (m, 2H), 7.95 (s, 1H), 6.33 (brs, 1H), 4.14-4.07 (m, 2H), 3.65-3.60 (dd, J=9.2 Hz, 11.8 Hz 1H), 3.4 (s, 1H) 2.97-2.86 (m, 2H), 2.74 (t, J=6.1 Hz, 2H), 2.37 (s, 3H), 2.32-2.28 (m, 1H), 2.08 (brs, 3H), 1.05 (d, J=5.7 Hz, 3H). MS (ESI) m/z 419.15 [M+H]⁺.

Synthesis of 4-(2,6-dimethyl-6,7-dihydropyrazolo[1,5-a]pyrimidin-4(5H)-yl)-N-(5'-fluoro-[2,3'-bipyridin]-5-yl)-4-oxobutanamide, Compound 162

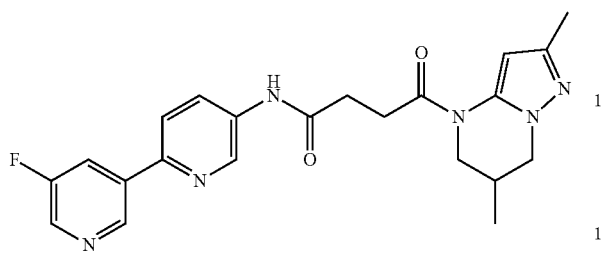

$^1$H NMR (400 MHz, DMSO-d$_6$): 10.46 (s, 1H), 9.13 (s, 1H), 8.88 (br, 1H), 8.60-8.59 (m, 1H), 8.30-8.26 (m, 1H), 8.21-8.18 (m, 1H), 8.11-8.08 (m, 1H), 6.34 (br, 1H), 4.13-4.04 (m, 2H), 3.66-3.61 (m, 1H), 3.36 (br, 1H), 3.00-2.80 (m, 2H), 2.73-2.66 (m, 2H), 2.28 (br, 1H), 2.08 (s, 3H), 1.06-1.05 (m, 3H). LC-MS: m/z 423 [M+H]$^+$.

Synthesis of 4-(2,6-dimethyl-6,7-dihydropyrazolo[1,5-a]pyrimidin-4(5H)-yl)-N-(5'-fluoro-[3,3'-bipyridin]-6-yl)-4-oxobutanamide, Compound 163

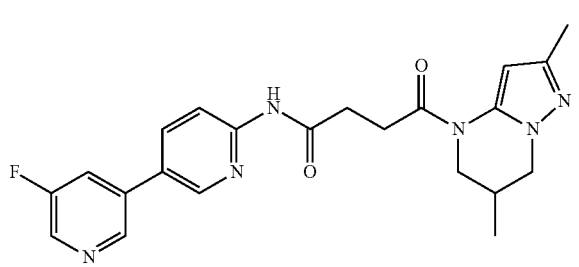

$^1$H NMR (400 MHz, DMSO-d$_6$): 10.74 (s, 1H), 8.86 (s, 1H), 8.79-8.78 (m, 1H), 8.59-8.58 (m, 1H), 8.24-8.21 (m, 1H), 8.18-8.14 (m, 2H), 6.34 (br, 1H), 4.13-4.05 (m, 2H), 3.66-3.60 (m, 1H), 3.40 (br, 1H), 2.95-2.86 (m, 2H), 2.76-2.73 (m, 2H), 2.28 (br, 1H), 2.08 (s, 3H), 1.06-1.04 (m, 3H). LC-MS: m/z 423 [M+H]$^+$.

Synthesis of 4-(2,6-dimethyl-6,7-dihydropyrazolo[1,5-a]pyrimidin-4(5H)-yl)-N-(5-fluoro-[2,3'-bipyridin]-6'-yl)-4-oxobutanamide, Compound 164

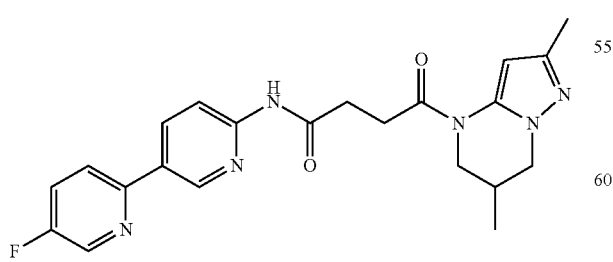

$^1$H NMR (400 MHz, DMSO-d$_6$): 10.73 (s, 1H), 8.99 (d, J=2.0 Hz, 1H), 8.66 (d, J=2.8 Hz, 1H), 8.42-8.38 (m, 1H), 8.20-8.12 (m, 1H), 8.12-8.06 (m, 1H), 7.89-7.80 (m, 1H), 6.33 (bs, 1H), 4.15-4.00 (m, 2H), 3.67-3.60 (m, 1H), 3.55-3.35 (m, 1H), 3.00-2.80 (m, 2H), 2.80-2.70 (m, 2H), 2.30-2.20 (m, 1H), 2.08 (bs, 3H), 1.05 (d, J=5.6 Hz, 3H). MS (ESI) m/z 423 [M+H]$^+$.

Synthesis of 4-(2,6-dimethyl-6,7-dihydropyrazolo[1,5-a]pyrimidin-4(5H)-yl)-N-(4-fluoro-[3,3'-bipyridin]-6-yl)-4-oxobutanamide, Compound 165

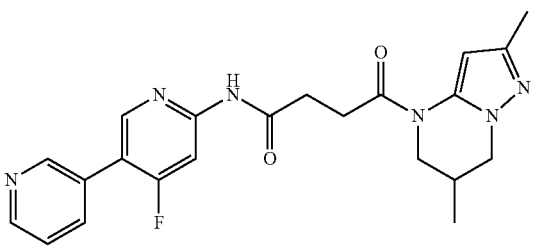 [SMILES: Cc1cc2n(n1)CC(C)CN2C(=O)CCC(=O)Nc1cc(F)c(-c2cccnc2)cn1]

$^1$H NMR (400 MHz, DMSO-d$_6$): 10.99 (s, 1H), 8.80 (s, 1H), 8.65-8.55 (m, 2H), 8.06-7.98 (m, 2H), 7.56-7.50 (m, 1H), 6.33 (bs, 1H), 4.15-4.00 (m, 2H), 3.67-3.60 (m, 1H), 3.50-3.35 (m, 1H), 3.00-2.80 (m, 2H), 2.80-2.70 (m, 2H), 2.35-2.20 (m, 1H), 2.08 (bs, 3H), 1.05 (d, J=4.8 Hz, 3H). MS (ESI) m/z 423 [M+H]$^+$.

Synthesis of N-(3,5'-dimethyl-[2,3'-bipyridin]-5-yl)-4-(2-methyl-6,7-dihydropyrazolo[1,5-a]pyrimidin-4(5H)-yl)-4-oxobutanamide, Compound 168

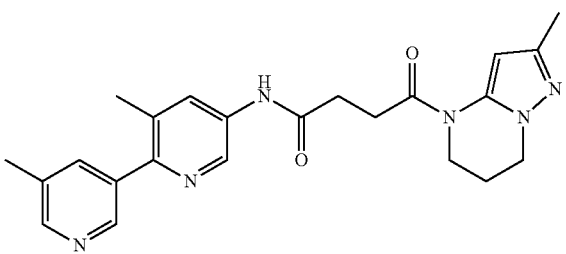

$^1$H NMR (400 MHz, DMSO-d$_6$): 10.29 (s, 1H), 8.68 (s, 1H), 8.53 (d, J=2.0 Hz, 1H), 8.43 (d, J=1.6 Hz, 1H), 8.01 (d, J=2.0 Hz, 1H), 7.76 (s, 1H), 6.35 (bs, 1H), 4.03 (t, J=5.6 Hz, 2H), 3.87 (bs, 2H), 2.95-2.85 (m, 2H), 2.72-2.65 (m, 2H), 2.36 (s, 3H), 2.33 (s, 3H), 2.08 (bs, 5H); MS (ESI) m/z 419 [M+H]$^+$.

Synthesis of N-(3,3'-bipyridin-6-yl)-4-(2,6-dimethyl-6,7-dihydropyrazolo[1,5-a]pyrimidin-4(5H)-yl)-4-oxobutanamide, Compound 169 and Compound 170

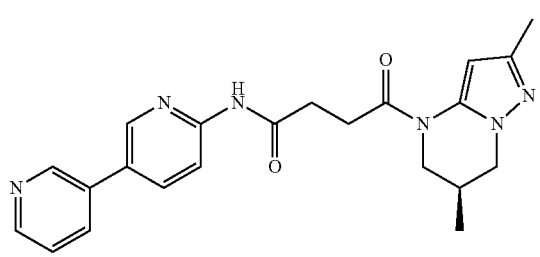

-continued

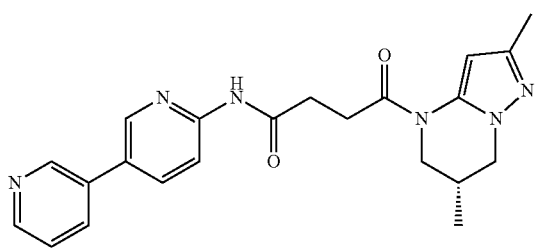

The product was subjected to chiral chromatography to afford enantiomeric pure compound 169 and compound 170.

$^1$H NMR (400 MHz, DMSO-d$_6$): 10.67 (s, 1H), 8.94 (d, J=2.0 Hz, 1H), 8.71 (s, 1H), 8.58 (d, J=4.0 Hz, 1H), 8.16-8.11 (m, 3H), 7.50-7.47 (dd, J=4.4 Hz, 7.6 Hz, 1H), 6.3 (brs, 1H), 4.14-4.06 (m, 2H), 3.65-3.60 (m, 1H), 3.4 (s, 1H), 2.97-2.87 (m, 2H), 2.75 (t, J=12.8 Hz, 2H), 2.30 (d, J=14.8 Hz, 1H), 2.08 (s, 3H), 1.05 (d, J=6.4 Hz, 3H); MS (ESI) m/z 405.18 [M+H]$^+$.

Synthesis of N-([2,3'-bipyridin]-6'-yl)-4-(2,6-dimethyl-6,7-dihydropyrazolo[1,5-a]pyrimidin-4(5H)-yl)-4-oxobutanamide, Compound 171

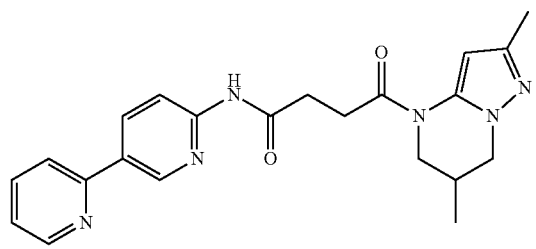 [SMILES: Cc1cc2n(n1)CC(C)CN2C(=O)CCC(=O)Nc1ccc(-c2ccccn2)cn1]

$^1$H NMR (400 MHz, DMSO-d$_6$): 10.72 (s, 1H), 9.03 (m, 1H), 8.67-8.66 (m, 1H), 8.45-8.42 (m, 1H), 8.17 (d, J=8.4 Hz, 1H), 8.01-7.99 (m, 1H), 7.91-7.87 (m, 1H), 7.38-7.35 (m, 1H), 6.34 (br, 1H), 4.14-4.06 (m, 2H), 3.66-3.60 (m, 1H), 2.97-2.86 (m, 2H), 2.76-2.73 (m, 2H), 2.29 (br, 1H), 2.08 (s, 3H), 1.05 (m, 3H). MS (ESI) m/z 405 [M+H]$^+$.

Amide Coupling Method B:

Triethylamine (1.3 eq) and isobutyl chloroformate (1.0 equiv.) were added dropwise to a stirred solution of acid (1.1 equiv.) in dichloromethane (0.05 M) at 0° C. and stirred for 15 minutes before adding the respective amine (1.0 equiv.). The reaction was stirred from 0° C. to room temperature for 3 hours. Upon completion the reaction was diluted with dichloromethane and basified to pH 9.0 with saturated sodium carbonate solution. The aqueous layer was extracted with dichloromethane, organic phase combined, washed with brine, dried over sodium sulphate, filtered and concentrated in vacuo. Crude was purified with reversed phase HPLC to afford the pure product.

Synthesis of 4-(2-methyl-6,7-dihydropyrazolo[1,5-a]pyrimidin-4(5H)-yl)-4-oxo-N-(6-(pyridin-3-yl)pyridazin-3-yl)butanamide, Compound 51

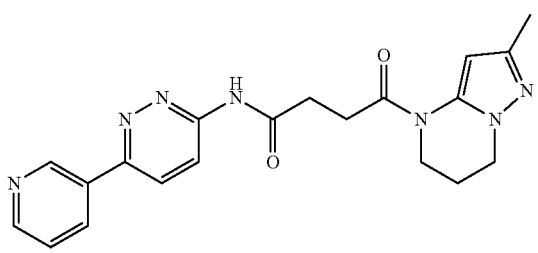 [SMILES: Cc1cc2n(n1)CCCN2C(=O)CCC(=O)Nc1ccc(-c2cccnc2)nn1]

$^1$H NMR (400 MHz, DMSO-d$_6$): 11.32 (S, 1H), 9.26 (d, J=2 Hz, 1H), 8.70-8.68 (m, 1H), 8.48-8.46 (m, 1H), 8.40 (d, J=9.2 Hz, 1H), 8.30 (d, J=9.6 Hz, 1H), 7.59-7.56 (m, 1H), 6.33 (bs, 1H), 4.02 (t, J=5.8 Hz, 2H), 3.86 (bs, 2H), 2.91-2.90 (m, 2H), 2.83-2.80 (m, 2H), 2.08 (bs, 5H). LC-MS: m/z 392 [M+H]$^+$.

Synthesis of N-(6-(3-fluorophenyl)pyridin-3-yl)-4-(2-methyl-6,7-dihydropyrazolo[1,5-a]pyrimidin-4(5H)-yl)-4-oxobutanamide, Compound 84

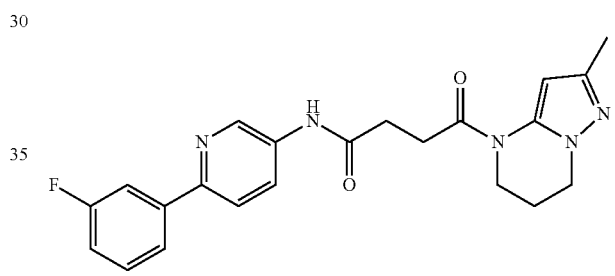

$^1$H NMR (400 MHz, DMSO-d$_6$): 10.73 (s, 1H), 8.83 (d, J=2.4 Hz, 1H), 8.16-8.14 (m, 1H), 7.99-7.97 (m, 1H), 7.90-7.88 (m, 1H), 7.85-7.82 (m, 1H), 7.53-7.47 (m, 1H), 7.24-7.19 (m, 1H), 6.34 (br s, 1H), 4.02 (t, J=6.0 Hz, 2H), 3.87 (s, 2H), 2.92-2.89 (m, 2H), 2.71-2.68 (m, 2H), 2.08 (s, 5H). LC-MS: m/z 408 [M+H]$^+$.

Synthesis of N-(6-(3-fluorophenyl)pyridazin-3-yl)-4-(2-methyl-6,7-dihydropyrazolo[1,5-a]pyrimidin-4(5H)-yl)-4-oxobutanamide, Compound 98

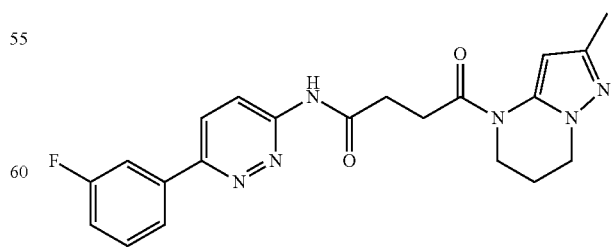

$^1$H NMR (400 MHz, DMSO-d$_6$): 11.30 (s, 1H), 8.39-8.37 (m, 1H), 8.28-8.26 (m, 1H), 7.97-7.91 (m, 2H), 7.61-7.56 (m, 1H), 7.36-7.31 (m, 1H), 6.34 (br s, 1H), 4.02 (t, J=6.0

Hz, 2H), 3.86 (s, 2H), 2.91-2.90 (m, 2H), 2.82-2.79 (m, 2H), 2.08 (s, 5H). LC-MS: m/z 409 [M+H]⁺.

Synthesis of 4-(2-methyl-6,7-dihydropyrazolo[1,5-a]pyrimidin-4(5H)-yl)-N-(6-(5-methylpyridin-3-yl)pyridazin-3-yl)-4-oxobutanamide, Compound 104

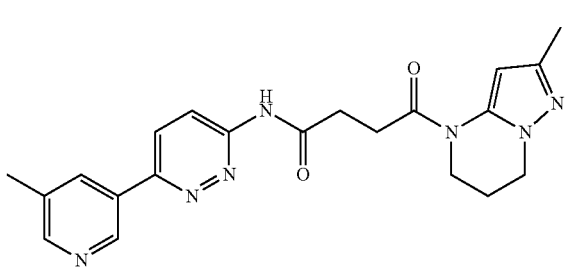

¹H NMR (400 MHz, DMSO-d₆): 11.31 (s, 1H), 9.06 (s, 1H), 8.53 (s, 1H), 8.40-8.38 (m, 1H), 8.30-8.27 (m, 2H), 6.33 (br s, 1H), 4.02 (t, J=6.0 Hz, 2H), 3.86 (s, 2H), 2.91-2.90 (m, 2H), 2.82-2.79 (m, 2H), 2.41 (s, 3H), 2.08 (s, 5H). LC-MS: m/z 406 [M+H]⁺.

Amide Coupling Method C:

Amine (1.1 equiv.) was added to a stirred solution of acid, N,N-diisopropylethylamine (3.0 equiv.) and HATU (1.5 equiv.) in DMF (0.2 M) after 5 minutes. Solution is left to stir at room temperature for 3 h. Upon completion the reaction was diluted with water and extracted with dichloromethane. The organic phase was combined, washed with brine, dried over sodium sulphate, filtered and concentrated in vacuo. Crude was purified by Shimadzu semi-prep and lyophilized to afford a white solid.

Synthesis of N-(2'-fluoro-[1,1'-biphenyl]-4-yl)-4-(2-methyl-6,7-dihydropyrazolo[1,5-a]pyrimidin-4(5H)-yl)-4-oxobutanamide, Compound 64

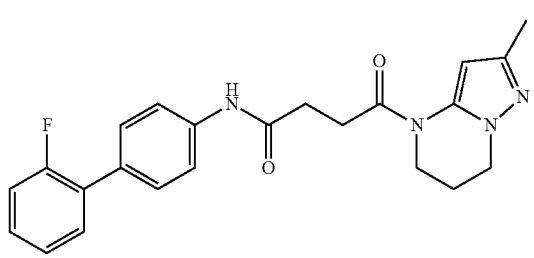 [SMILES: Cc1cc2n(n1)CCCN2C(=O)CCC(=O)Nc1ccc(-c2ccccc2F)cc1]

¹H NMR (400 MHz, DMSO-d₆): 10.14 (s, 1H), 7.70 (d, J=8.4 Hz, 2H), 7.53-7.48 (m, 3H), 7.39-7.35 (m, 1H), 7.31-7.26 (m, 2H), 6.35 (br, 1H), 4.02 (t, J=6.0 Hz, 2H), 3.87 (br, 2H), 2.91-2.88 (m, 2H), 2.68-2.65 (m, 2H), 2.08 (br, 5H). LC-MS: m/z 407 [M+H]⁺.

Synthesis of N,N-dimethyl-4'-(4-(2-methyl-6,7-dihydropyrazolo[1,5-a]pyrimidin-4(5H)-yl)-4-oxobutanamido)-[1,1'-biphenyl]-3-carboxamide, Compound 68

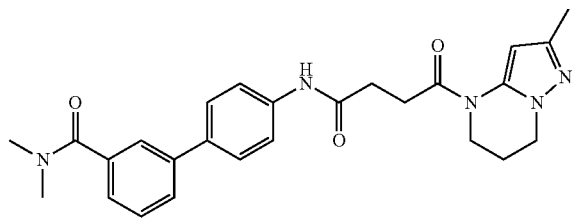

¹H NMR (400 MHz, DMSO-d₆): 10.11 (s, 1H), 7.72-7.62 (m, 6H), 7.49 (t, J=7.6 Hz, 1H), 7.34-7.32 (m, 1H), 6.33 (bs, 1H), 4.02 (t, J=6.0 Hz, 2H), 3.87 (bs, 2H), 2.97 (d, J=23.6 Hz, 6H), 2.91-2.87 (m, 2H), 2.68-2.65 (m, 2H), 2.08 (bs, 5H). LC-MS: m/z 460 [M+H]⁺.

Synthesis of 4-(2-methyl-6,7-dihydropyrazolo[1,5-a]pyrimidin-4(5H)-yl)-N-(3'-morpholinobiphenyl-4-yl)-4-oxobutanamide, Compound 73

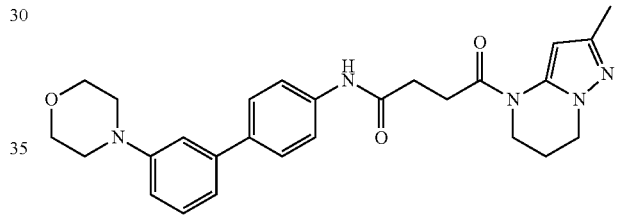

¹H NMR (400 MHz, DMSO-d₆): 10.05 (s, 1H), 7.66 (d, J=8.8 Hz, 2H), 7.59 (d, J=8.8 Hz, 2H), 7.27 (t, J=8.0 Hz, 1H), 7.13 (s, 1H), 7.06 (d, J=7.6 Hz, 1H), 6.90 (d, J=6.4 Hz, 1H), 6.32 (bs, 1H), 4.02 (t, J=6.4 Hz, 2H), 3.86 (bs, 2H), 3.75 (t, J=4.8 Hz, 4H), 3.17 (t, J=4.8 Hz, 4H), 2.88 (t, J=6.4 Hz, 2H), 2.65 (t, J=6.4 Hz, 2H), 2.08 (bs, 5H). MS (ESI) m/z 474.33 [M+H]⁺.

Synthesis of 4-(2-methyl-6,7-dihydropyrazolo[1,5-a]pyrimidin-4(5H)-yl)-4-oxo-N-(1-phenylpiperidin-4-yl)butanamide, Compound 81

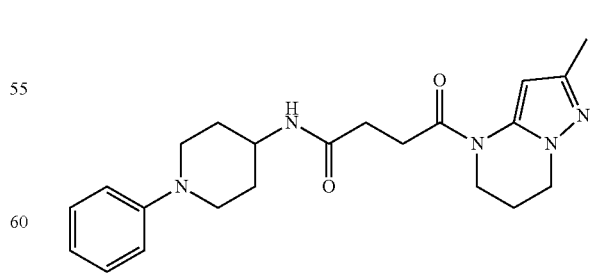

¹H NMR (400 MHz, DMSO-d₆): 7.82 (d, J=7.6 Hz, 1H), 7.18 (t, J=6.8 Hz, 2H), 6.92 (d, J=8.0 Hz, 2H), 6.73 (t, J=7.6 Hz, 1H), 6.20 (s, 1H), 4.00 (t, J=6.0 Hz, 2H), 3.82 (s, 2H), 3.80-3.61 (m, 3H), 2.80-2.74 (m, 4H), 2.38 (t, J=6.8 Hz,

2H), 2.08 (bs, 5H), 1.79 (d, J=9.6 Hz, 2H), 1.55-1.44 (m, 2H). MS (ESI) m/z 396.40 [M+H]⁺.

Synthesis of 4-(2-methyl-6,7-dihydropyrazolo[1,5-a]pyrimidin-4(5H)-yl)-4-oxo-N-(6-(m-tolyl)pyridazin-3-yl)butanamide, Compound 99

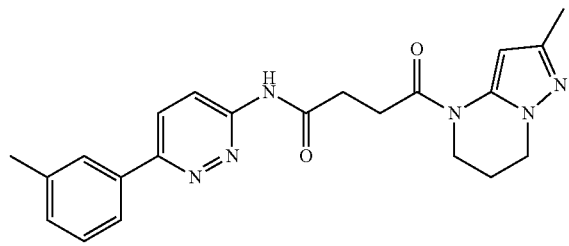

¹H NMR (400 MHz, DMSO-d₆): 11.25 (s, 1H), 8.35 (d, J=9.6 Hz, 1H), 8.19 (d, J=9.6 Hz, 1H), 7.93 (bs, 1H), 7.87 (d, J=7.6 Hz, 1H), 7.42 (t, J=7.6 Hz, 1H), 7.32-7.30 (m, 1H), 6.30 (bs, 1H), 4.04-4.01 (t, J=5.8 Hz, 2H), 3.87 (bs, 2H), 2.91-2.90 (m, 2H), 2.82-2.79 (m, 2H), 2.41 (s, 3H), 2.08 (bs, 5H). LC-MS: m/z 405 [M+H]⁺.

Synthesis of N-(6-(5-fluoropyridin-3-yl)pyridazin-3-yl)-4-(2-methyl-6,7-dihydropyrazolo[1,5-a]pyrimidin-4(5H)-yl)-4-oxobutanamide, Compound 103

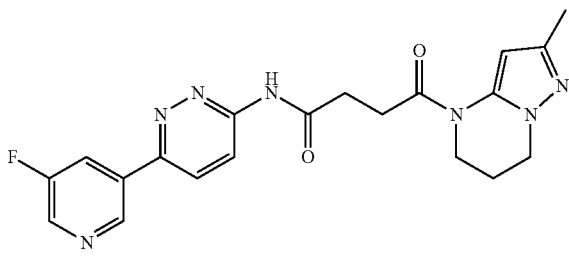 [SMILES: Cc1cc2n(n1)CCCN2C(=O)CCC(=O)Nc1ccc(-c2cncc(F)c2)nn1]

¹H NMR (400 MHz, DMSO-d₆): 11.38 (s, 1H), 9.18 (s, 1H), 8.71 (d, J=2.8 Hz, 1H), 7.45-7.33 (m, 3H), 6.34 (bs, 1H), 4.03 (t, J=6.0 Hz, 2H), 3.87 (bs, 2H), 2.95-2.85 (m, 2H), 2.85-2.75 (m, 2H), 2.08 (bs, 5H). MS (ESI) m/z 410 [M+H]⁺.

Synthesis of 4-(2-methyl-6,7-dihydropyrazolo[1,5-a]pyrimidin-4(5H)-yl)-4-oxo-N-(6-(5-(trifluoromethyl)pyridin-3-yl)pyridazin-3-yl)butanamide, Compound 105

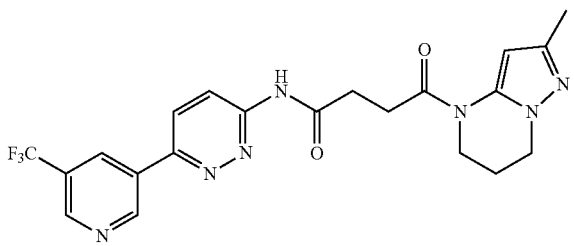 [SMILES: Cc1cc2n(n1)CCCN2C(=O)CCC(=O)Nc1ccc(-c2cncc(C(F)(F)F)c2)nn1]

¹H NMR (400 MHz, DMSO-d₆): 11.41 (s, 1H), 9.58 (m, 1H), 9.10 (m, 1H), 8.83 (m, 1H), 8.46 (m, 2H), 6.33 (bs, 1H), 4.03 (t, J=6.0 Hz, 2H), 3.87 (bs, 2H), 2.93-2.91 (m, 2H), 2.84-2.81 (m, 2H), 2.08 (bs, 5H). LC-MS: m/z 460 [M+H]⁺.

Synthesis of 4-(2-methyl-6,7-dihydropyrazolo[1,5-a]pyrimidin-4(5H)-yl)-N-(5-methyl-6-(pyridin-3-yl)pyridazin-3-yl)-4-oxobutanamide, Compound 106

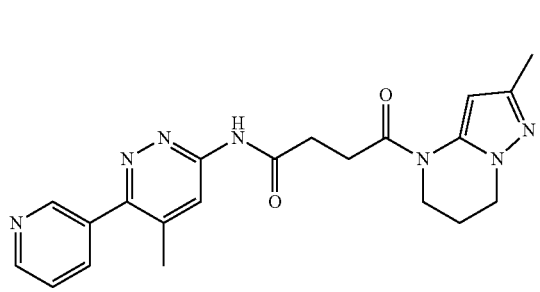 [SMILES: Cc1cc2n(n1)CCCN2C(=O)CCC(=O)Nc1cc(C)c(-c2cccnc2)nn1]

¹H NMR (400 MHz, DMSO-d₆): 11.21 (s, 1H), 8.81-8.80 (m, 1H), 8.69-8.68 (m, 1H), 8.28 (s, 1H), 8.07-8.04 (m, 1H), 7.57-7.54 (m, 1H), 6.33 (s, 1H), 4.03 (t, J=5.8 Hz, 2H), 3.87 (bs, 2H), 2.93-2.89 (m, 2H), 2.81-2.78 (m, 2H), 2.34 (s, 3H), 2.08 (bs, 5H). LC-MS: m/z 406 [M+H]⁺.

Synthesis of 4-(2-methyl-6,7-dihydropyrazolo[1,5-a]pyrimidin-4(5H)-yl)-N-(6-(6-methylpyridin-3-yl)pyridazin-3-yl)-4-oxobutanamide, Compound 107

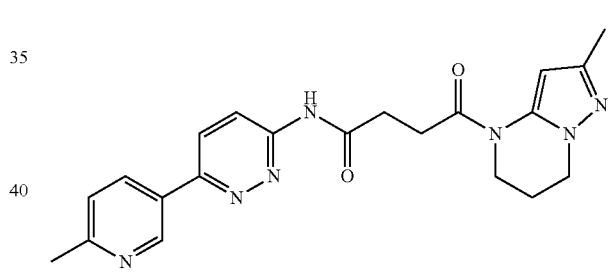

¹H NMR (400 MHz, DMSO-d₆): 11.29 (s, 1H), 9.14-9.13 (m, 1H), 8.39-8.34 (m, 2H), 8.28-8.25 (m, 1H), 7.42 (d, J=8.0 Hz, 1H), 6.33 (bs, 1H), 4.03 (t, J=6.0 Hz, 2H), 3.87 (bs, 2H), 2.93-2.90 (m, 2H), 2.82-2.79 (m, 2H), 2.55 (s, 3H), 2.08 (bs, 5H). LC-MS: m/z 406 [M+H]⁺.

Synthesis of N-(5'-methyl-2,3'-bipyridin-5-yl)-4-(2-methyl-6,7-dihydropyrazolo[1,5-a]pyrimidin-4(5H)-yl)-4-oxobutanamide, Compound 110

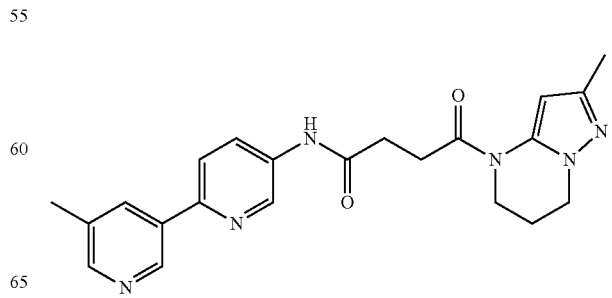

¹H NMR (400 MHz, DMSO-d₆): 10.35 (s, 1H), 9.01 (s, 1H), 8.85 (d, J=2.0 Hz, 1H), 8.42 (s, 1H), 8.21 (s, 1H), 8.16 (d, J=10.8 Hz, 1H), 7.99 (d, J=8.8 Hz, 1H), 6.34 (s, 1H), 4.02 (t, J=5.6 Hz, 2H), 3.86 (bs, 2H), 2.93-2.88 (m, 2H), 2.73-2.67 (m, 2H), 2.37 (s, 3H), 2.08 (bs, 5H). MS (ESI) m/z 405.33 [M+H]⁺.

Synthesis of 2-methyl-4-(2-methyl-6,7-dihydropyrazolo[1,5-a]pyrimidin-4(5H)-yl)-4-oxo-N-(6-phenylpyridazin-3-yl)butanamide, Compound 146

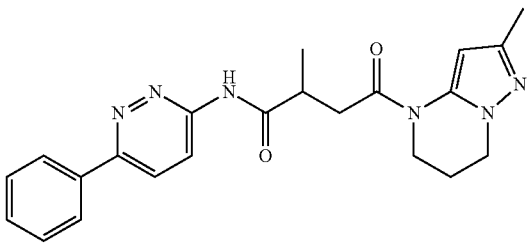 [SMILES: Cc1cc2n(n1)CCCN2C(=O)CC(C)C(=O)Nc1ccc(-c2ccccc2)nn1]

¹H NMR (400 MHz, DMSO-d₆): 11.25 (s, 1H), 8.37 (d, J=9.6 Hz, 1H), 8.21 (d, J=9.6 Hz, 1H), 8.11-8.09 (m, 2H), 7.55-7.50 (m, 3H), 6.31 (s, 1H), 4.02 (t, J=6.0 Hz, 2H), 3.86 (br, 2H), 3.25-3.21 (m, 1H), 3.07-3.00 (m, 1H), 2.06 (br, 5H), 1.22 (d, J=7.2 Hz, 3H). LC-MS: m/z 405 [M+H]⁺.

Synthesis of N-(2-fluorobiphenyl-4-yl)-4-(2-methyl-6,7-dihydropyrazolo[1,5-a]pyrimidin-4(5H)-yl)-4-oxobutanamide, Compound 155

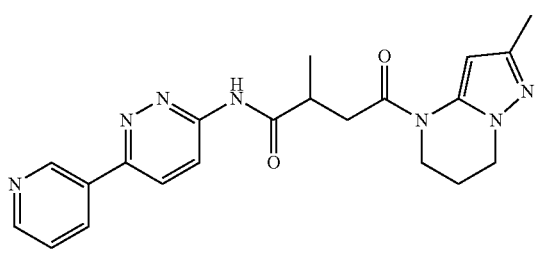 [SMILES: Cc1cc2n(n1)CCCN2C(=O)CC(C)C(=O)Nc1ccc(-c2cccnc2)nn1]

¹H NMR (400 MHz, DMSO-d₆): 11.32 (s, 1H), 9.27 (d, J=2.0 Hz, 1H), 8.69 (dd, J=4.8, 1.6 Hz, 1H), 8.47 (dt, J=8.4, 1.6 Hz, 1H), 8.45-8.38 (m, 1H), 8.32-8.28 (m, 1H), 7.53-7.60 (m, 1H), 6.35 (bs, 1H), 4.05-4.00 (m, 1H), 3.95-3.80 (m, 2H), 3.25-3.15 (m, 2H), 3.10-2.95 (m, 1H), 2.75-2.55 (m, 1H), 2.06 (bs, 5H), 1.22 (d, J=7.2 Hz, 3H). MS (ESI) m/z 406 [M+H]⁺.

Synthesis of 4-(2-methyl-6,7-dihydropyrazolo[1,5-a]pyrimidin-4(5H)-yl)-4-oxo-N-(6-(pyrazin-2-yl)pyridin-3-yl)butanamide, Compound 166

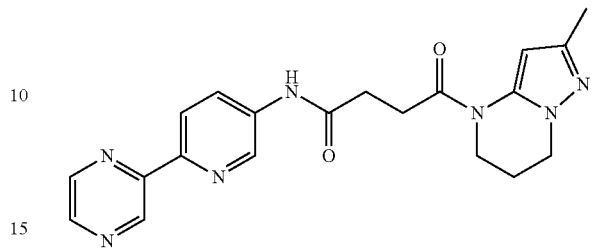

¹H NMR (400 MHz, DMSO-d₆): 10.46 (s, 1H), 9.47 (d, J=1.6 Hz, 1H), 8.89 (s, 1H), 8.70 (t, J=2.8 Hz, 1H), 8.65 (d, J=2.4 Hz, 1H), 8.31-8.29 (m, 1H), 8.26-8.23 (dd, J=2.4 Hz, 8.8 Hz, 1H), 6.3 (brs, 1H), 4.06-4.01 (m, 2H), 3.87 (brs, 1H), 3.17 (d, J=5.2 Hz, 1H), 2.92 (t, J=6.4 Hz, 2H), 2.73-2.70 (t, J=6.4 Hz, 2H), 2.08 (s, 5H); MS (ESI) m/z 392.2 [M+H]⁺.

Synthesis of 4-(2,6-dimethyl-6,7-dihydropyrazolo[1,5-a]pyrimidin-4(5H)-yl)-N-(6-(5-fluoropyridin-3-yl)pyridazin-3-yl)-4-oxobutanamide, Compound 167

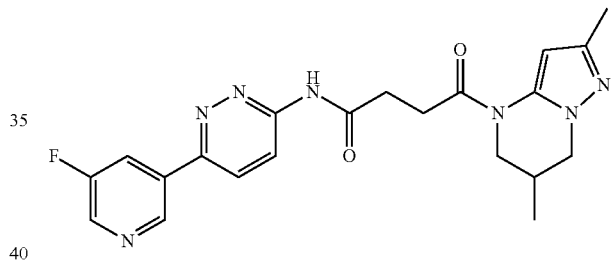

¹H NMR (400 MHz, DMSO-d₆): 11.38 (s, 1H), 9.18 (s, 1H), 8.71 (d, J=2.8 Hz, 1H), 8.55-8.45 (m, 3H), 6.34 (bs, 1H), 4.15-4.00 (m, 2H), 3.68-3.60 (m, 1H), 3.45-3.30 (m, 1H), 3.00-2.85 (m, 2H), 2.85-2.80 (m, 2H), 2.35-2.20 (m, 1H), 2.07 (bs, 3H), 1.05 (d, J=4.8 Hz, 3H); MS (ESI) m/z 424 [M+H]⁺.

Materials and Methods

Cell Lines and Culture Conditions:

HEK293-STF cell line was modified from Human embryonic kidney cell line HEK293 transfected with the STF reporter. HEK293-STF3A cell line was further modified from HEK293-STF cell line to express Wnt3A. This cell line was used to identify compounds that regulate either early or late signaling components of the Wnt pathway. These two cell lines were obtained from David Virshup's laboratory, Duke-NUS. L-Wnt3A (ATCC, #CRL-2647) cell line was used for providing Wnt3A conditioned media. The three cell lines were grown in DMEM with 10% FBS incubated in 37° C. with 5% CO₂.

Cell Viability Assay:

5000 cells in 75 μl culture media were seeded in each well of black 96 well plates (Greiner #655090) and incubated overnight at 37° C. 25 μl of serially diluted compound was added to the cells giving final concentration of 50 μM to 1.5 nM. After 1 day of treatment, 100 μl of CellTiter-Glo Luminescent Cell Viability Assay reagent (#G7571, Promega) was added to each well and incubated for 10 minutes at room temperature. Luminescence was measured using Tecan Safire2 microplate reader.

STF3A Assay:

$2 \times 10^4$ HEK293-STF3A cells in 75 µl culture media were seeded in each well of white 96 well plates (Greiner #655098) and incubated overnight at 37° C. 25 µl serially diluted compound was added to the cells to give final concentration of 50 µM to 1.5 nM. After 1 day of treatment, 100 µl of Steady-Glo Luciferase Assay reagent (#E2520, Promega) was added to each well and incubated for 10 minutes at room temperature. Luminescence was measured using Tecan Safire2 plate reader.

STF/WNT3A Conditioned Medium (STF/WNT3A CM) Assay:

L-Wnt3A cells were cultured in three T-175 flasks at $3 \times 10^4$ cells/ml in 30 ml culture medium per flask. After 4 days of incubation, the Wnt3A conditioned media were harvested and then centrifuged at 2000 rpm for 10 minutes to remove the debris. The Wnt3A conditioned media were stored at −20° C. if not used immediately.

$2 \times 10^4$ HEK293-STF cells in 25 µl culture media were added in each well of white 96 well plates (Greiner #655098). 25 µl serially diluted compound was added to the cells. After 4 hours of incubation, 100 µl Wnt-3A conditioned medium was added to the cells. The final concentration of compound ranged from 33 µM to 1 nM. After incubation for 1 day at 37° C., 100 µl of Steady-Glo® Luciferase Assay reagent (#E2520, Promega) was added to each well and incubated for 10 minutes at room temperature. Luminescence was measured using Tecan Safire2 microplate reader.

Western Blot:

$8.0 \times 10^5$ cells in 2.5 ml media were seeded in T-25 flasks. Compounds were diluted to 600 nM in 1 ml medium and 0.5 ml was added to the T-25 flask to give a final concentration of 100 nM. After incubation in 37° C. for two days, the culture media were collected and centrifuged at 2000 rpm for 10 min. The supernatants were collected and 32 µl from each sample was used for SDS PAGE gel electrophoresis. After transferring the separated proteins to the membrane it was incubated with the primary Wnt3A antibody (1:1000, #09-162, Millipore) overnight. After washing with Tris-Buffered Saline containing 0.05% Tween 20 (TBST), the membrane was incubated with polyclonal Goat anti-Rabbit IgG HRP-conjugated secondary antibody (1:3000, #P0448) for 1 hour at room temperature. After washing with TBST, the membrane was developed with Amersham™ ECL™ Select Western Blotting Detection Reagent (#RPN2235, GE Healthcare Life Sciences) and documented with Bio-Rad Molecular Imager VersaDoc MP.

MMTV-Wnt1 Mouse Model 1:

8-10 weeks old Female BALBc mice were anaesthetized with 150 mg/kg Ketamine +75 mg/kg Xylazine. Under aseptic conditions, skin near the $4^{th}$ mammary fat pad was incised. Mammary fat pad was tweaked with forceps and tumor fragment ~2 mm³ was implanted. The incision was closed using a tissue adhesive. Animals were randomised into groups of eight and treated daily with the test compounds for 14 days. Tumors were measured in two dimensions using calipers, and volume was calculated using the formula: Tumor Volume (mm³)=w²×½. Maximum tumor volume limit was 2000 mm³.

Wnt3A Palmitoylation Assay:

The assay used to determine the inhibition of the palmitoylation of Wnts by compound was described by Yap et al, (Yap M C, Kostiuk M A, Martin D D, Perinpanayagam M A, Hak P G, Siddam A, Majjigapu J R, Rajaiah G, Keller B O, Prescher J A, Wu P, Bertozzi C R, Falck J R, Berthiaume L G. 2010. Rapid and selective detection of fatty acylated proteins using omega-alkynyl-fatty acids and click chemistry. J Lipid Res. 51(6):1566-1580) with some modification. $3 \times 10^6$ HeLa cells were seeded in 10 cm culture dish and incubated at 37° C. overnight. The cells were transfected with 5 µg pCDNA3.2/V5-Wnt3a vector (Najdi R, Proffitt K, Sprowl S, Kaur S, Yu J, Covey T M, Virshup D M, Waterman M L. 2012. A uniform human Wnt expression library reveals a shared secretory pathway and unique signaling activities. Differentiation, 84(2), 203-213. doi:10.1016/j.diff.2012.06.004) to over-express V5-tagged Wnt3a. After six hours, the cells were washed with PBS and treated with 100 µM alkyne palmitate in medium with 5% BSA. 100 nM compound or DMSO was added and the cells were incubated overnight at 37° C. The cells were lyzed and 600 µg cell lysate was collected and incubated with anti-V5 antibody (Invitrogen) followed by the pull down of V5-Wnt3a with the addition of Protein A/G agarose beads (Thermo scientific). The pulled down lysates containing V5-Wnt3a was click-reacted with biotin-azide (Invitrogen). The biotin-labelled protein lysate was then separated on SDS-PAGE and transferred to a nitrocellulose membrane. The membrane was incubated with primary anti-V5 antibody, followed by secondary anti-mouse Dylight 680 (Thermo scientific) to detect V5-Wnt3a. The membrane was then incubated with streptavidin-Dylight 800 (Thermo scientific) to detect biotin labelled Wnt3a. The signals were captured on the Odyssey CLx Infrared Imaging System (LI-COR Bioscience).

Soft Agar Assay:

AsPC-1 cells were maintained in RPMI164 supplemented with 10% FBS, 2 mM L-glutamine and P/S (100 units/ml penicillin and 100 µg/ml streptomycin). HPAF-II cells were maintained in MEM (Eagles') supplemented with 10% FBS, 2 mM L-glutamine and P/S (100 units/ml penicillin and 100 µg/ml streptomycin). CFPAC-1 cells were maintained in Iscove MEM supplemented with 10% FBS, 2 mM L-glutamine and P/S (100 units/ml penicillin and 100 µg/ml streptomycin).

600 µl of 0.6% agar was added to 24-well plate to form the base layer. Then a middle layer of 0.36% agar (containing 5000 cells and serially diluted compound) was added on to the base layer. Finally 500 µl of fresh growth medium was added to the top of the middle layer. The plates were incubated at 37° C. with 5% carbon dioxide in a humidified incubator for 2 weeks. Formation of colonies was observed using a light microscope. When the colony size was larger than 500 µm, 70 µl MTT (5 mg/ml) was added to each well and the plates were incubated at 37° C. for at least 2 hours. Colonies were counted with GelCount® instrument. The colony counts were plotted against compound concentrations using the GraphPad Prism software. The software was also used to perform non-linear curve fitting and calculation of compound concentration that inhibited 50% colony formation.

Results:

Compounds of the present invention specifically inhibit mammalian PORCN.

PORCN-null HT1080 cells were transfected with mammalian or Xenopus PORCN expression plasmids, along with WNT3A, STF reporter and mCherry as transfection control. 6 hours after transfection, cells were treated with the compounds or DMSO as indicated, and the following day assayed for luciferase. Xenopus PORCN was resistant to the inhibitory effects of compounds. The two compounds, Compound 51 and Compound 110 inhibit the activity of mammalian porcupine (FIG. 1).

Figure 2:
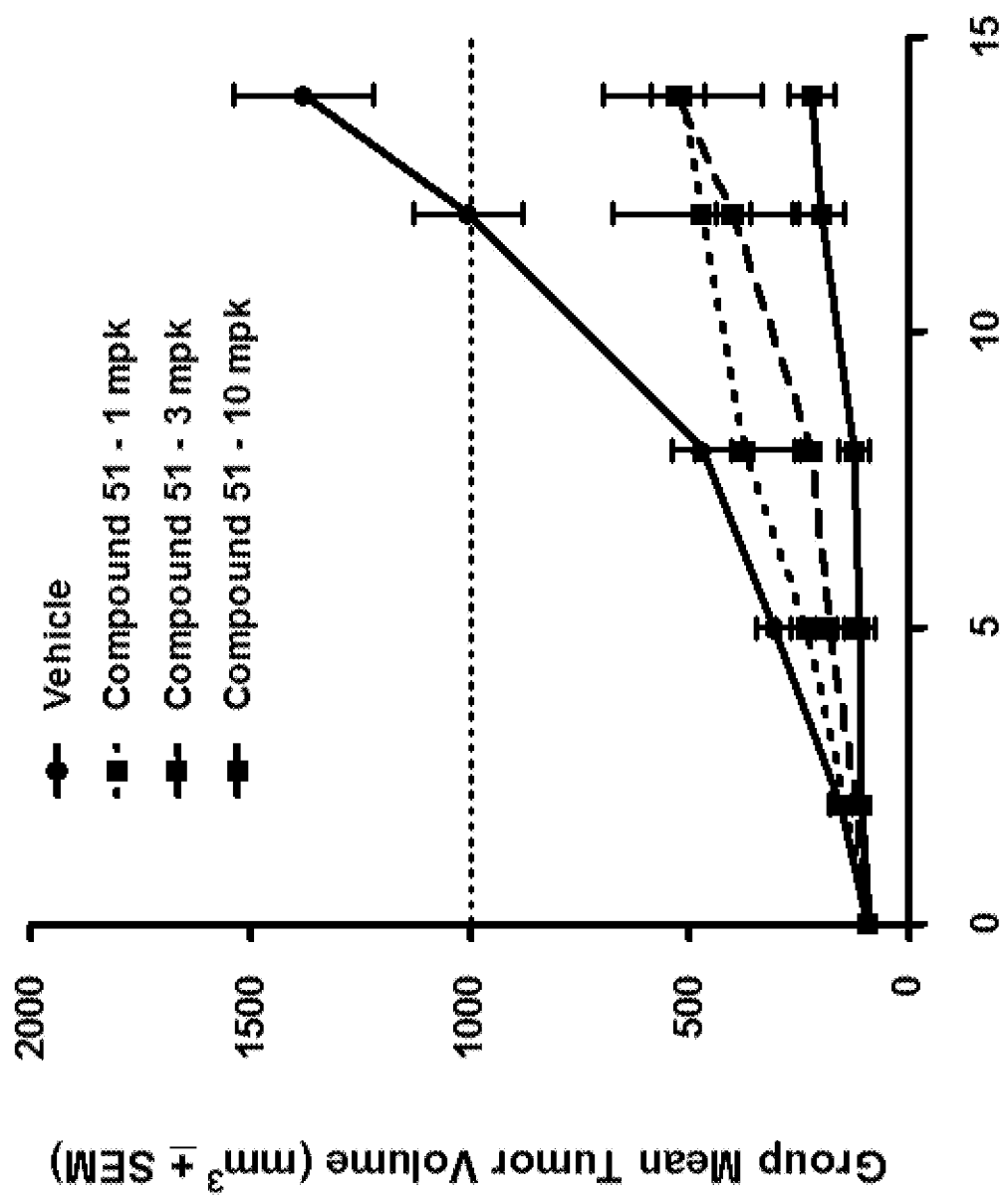
FIG. 2: A graph illustrating efficacy of Compound 51 on the MMTV-Wnt1 mouse model.
Figure 3:
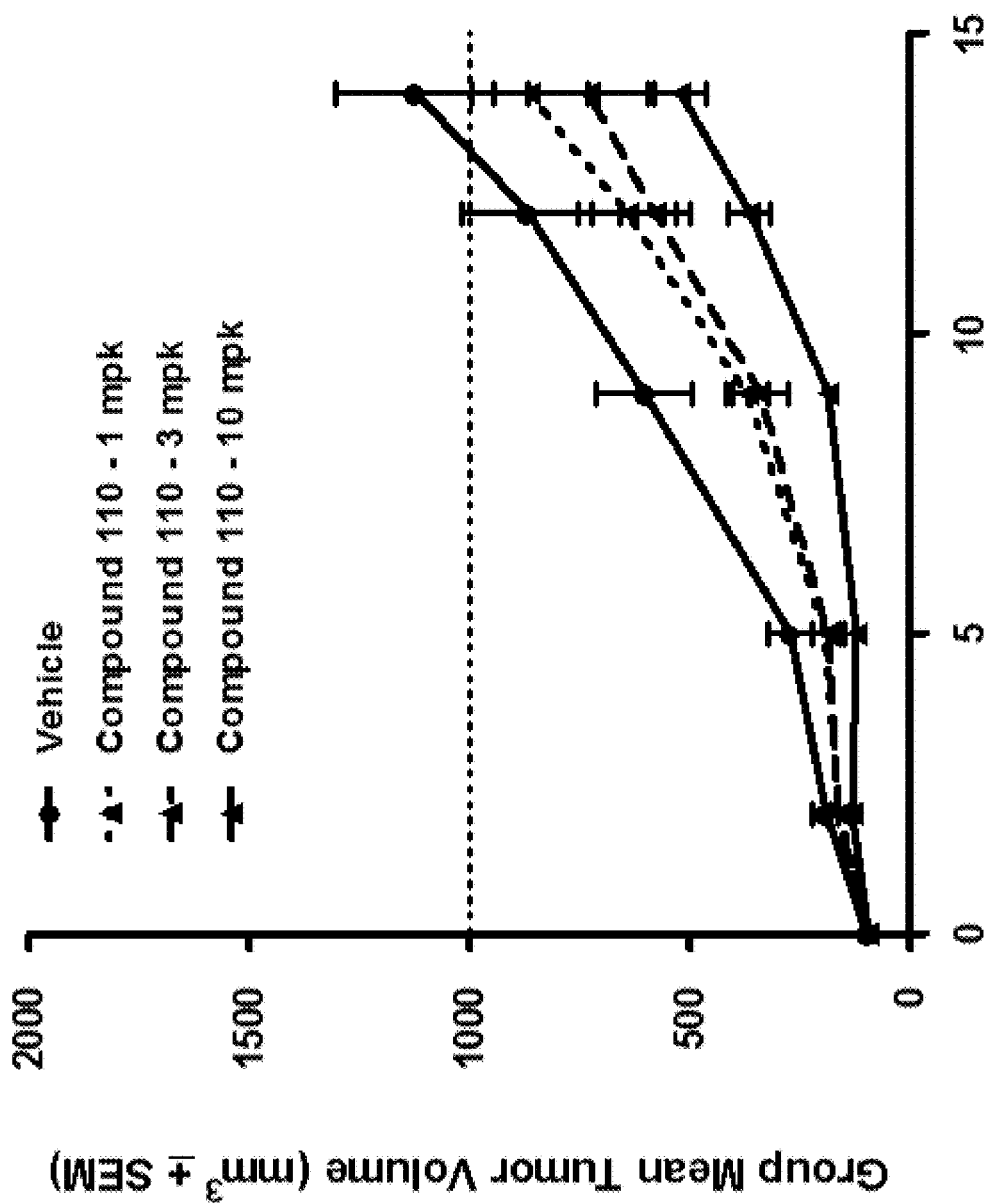
FIG. 3: A graph illustrating efficacy data of Compound 110 in the MMTV-Wnt1 mouse model.

Treatment with Compounds 51 and 110 decreased tumor growth in all the treated mice (FIG. 2 and FIG. 3).

Figure 4:
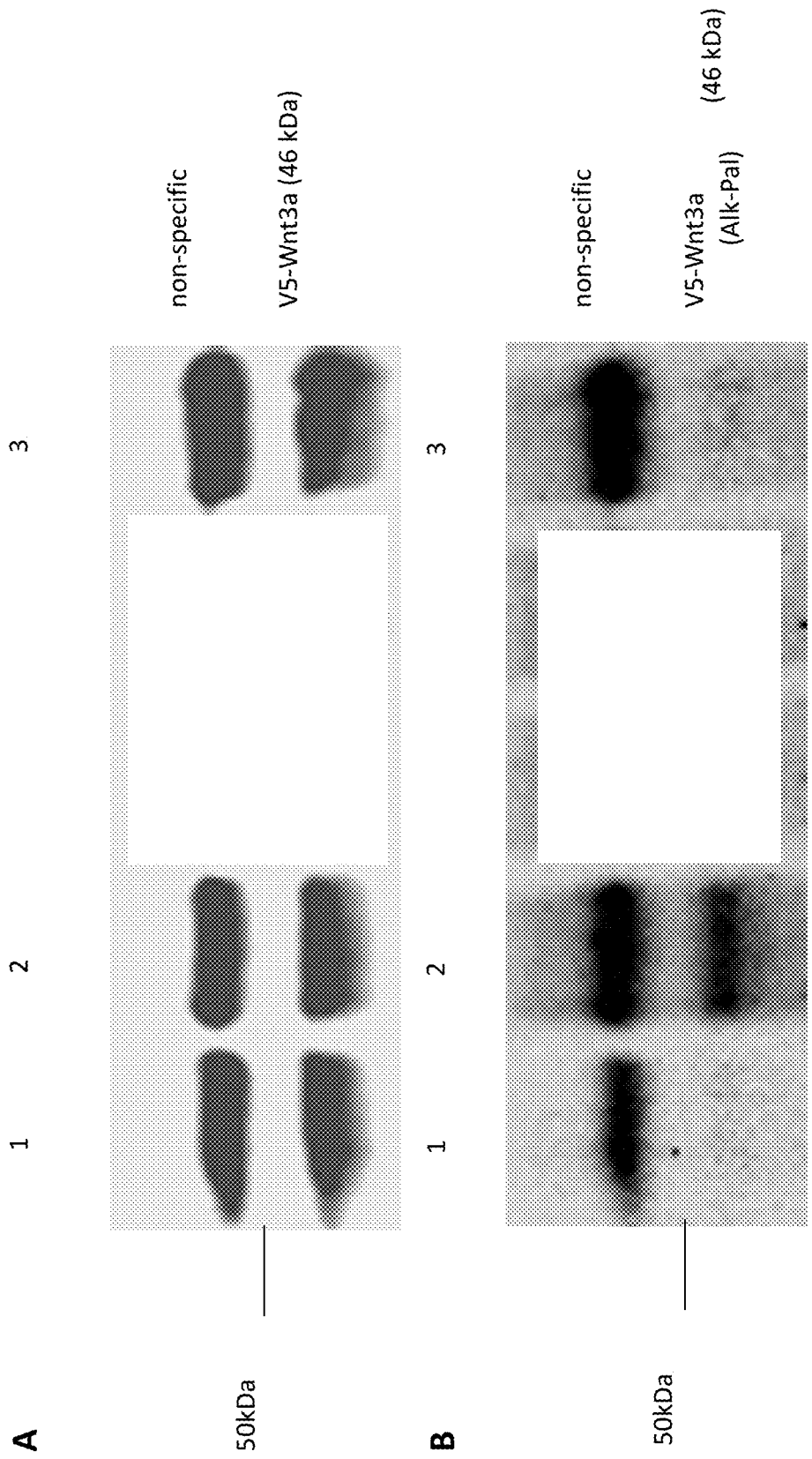
FIG. 4: Images illustrating inhibition of Palmitoylation of Wnt3a by Compound 51.

Palmitoylation of Wnt3a is inhibited by Compound 51 (FIG. 4). The Wnt3a-V5 was visualized using anti-V5 antibody, followed by anti-mouse Dylight 680. B. Biotin-azide clicked palmitate in V5-Wnt3a was detected with streptavidin-Dylight 800. A non-specific band was observed above the Wnt3a-V5 protein. Biotin-azide clicked palmitate was detected with streptavidin-Dylight 800 (lower band). DMSO was used as negative control. Lane 1: Without Alkyne palmitate; Lane 2: untreated control, DMSO+ Alkyne palmitate; Lane 3: 100 nM Compound 51+Alkyne palmitate.

Figure 5:
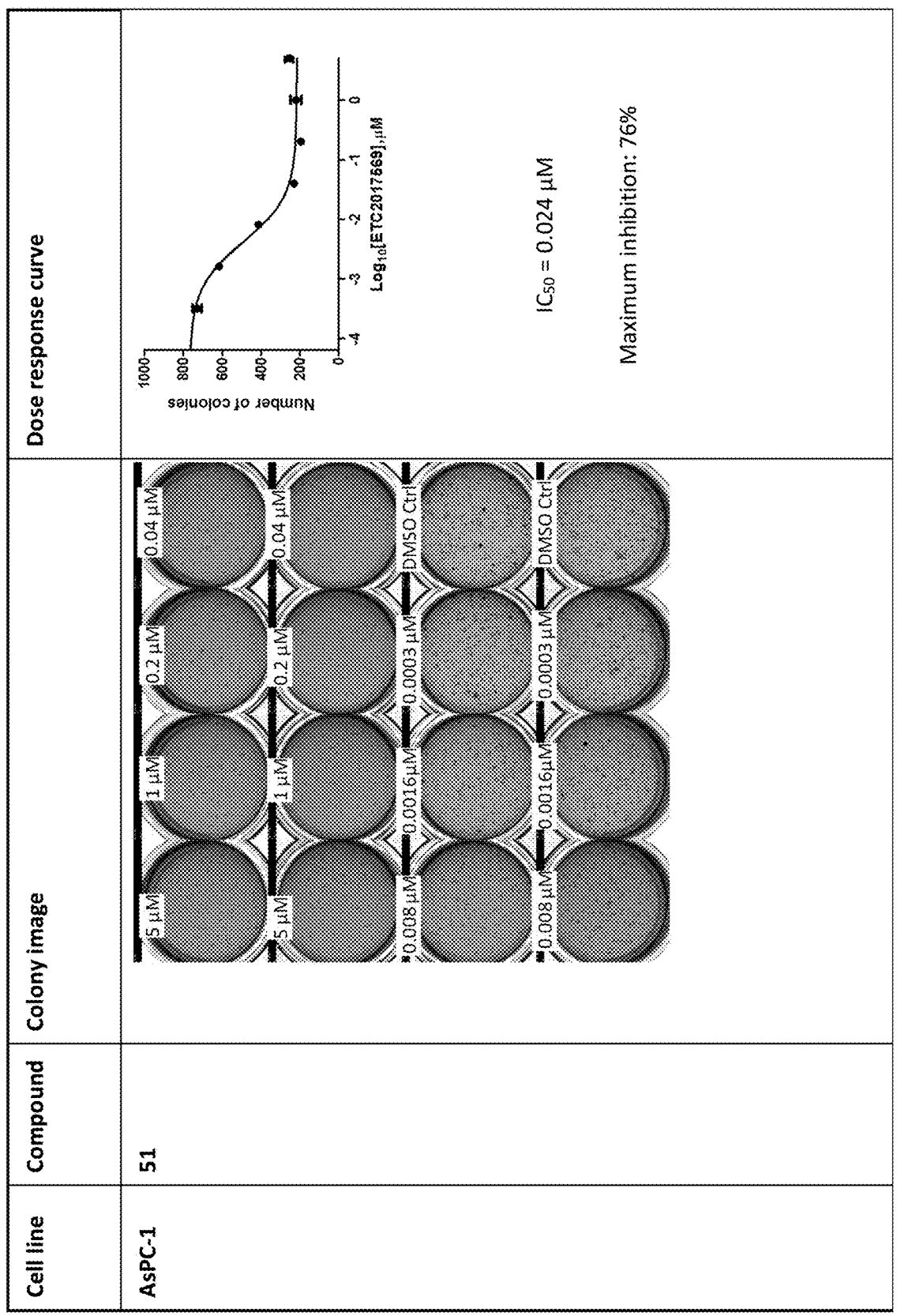
FIGS. 5 to 7: Images and graphs showing results of the Soft Agar Assay.
Figure 6:
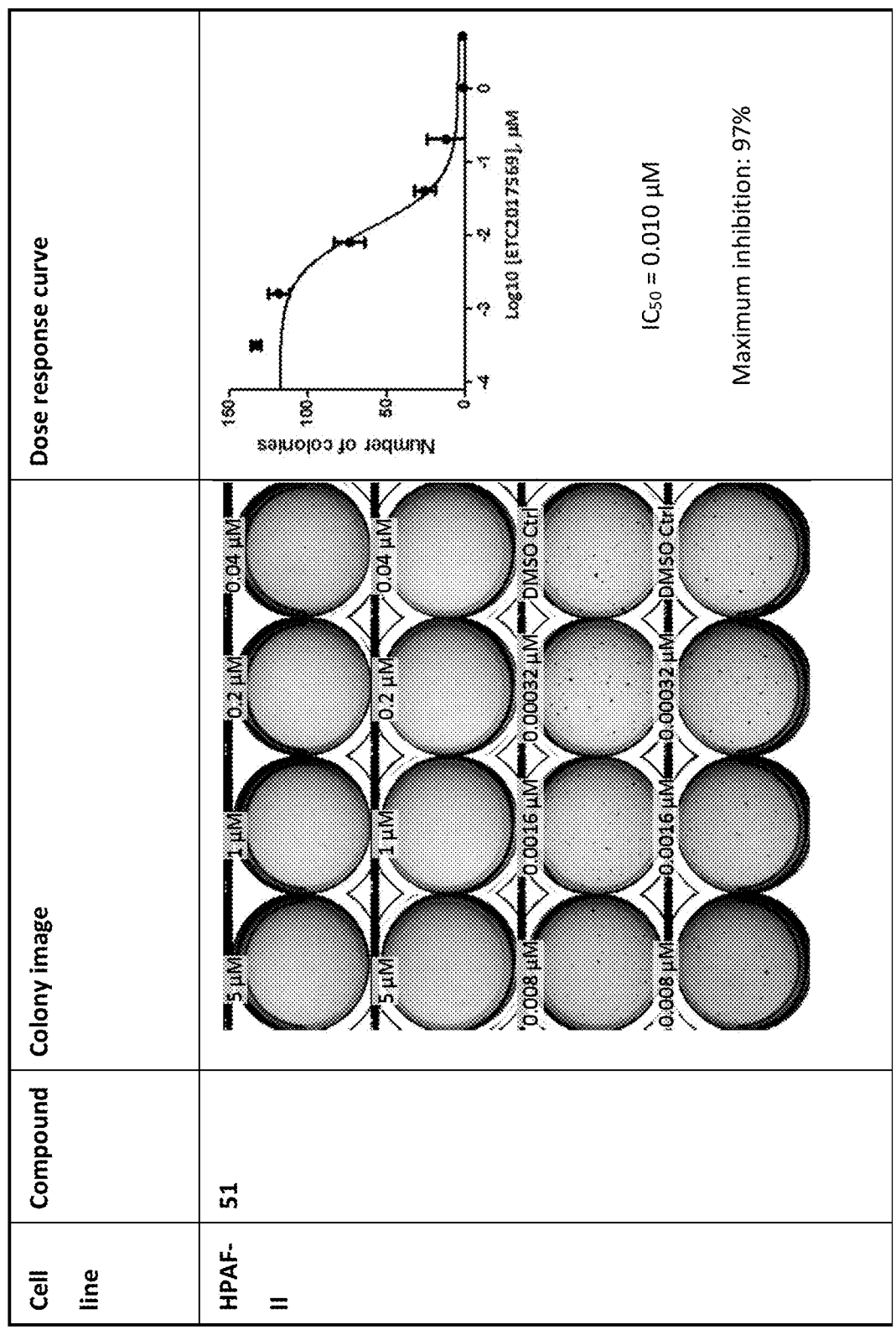
Figure 7:
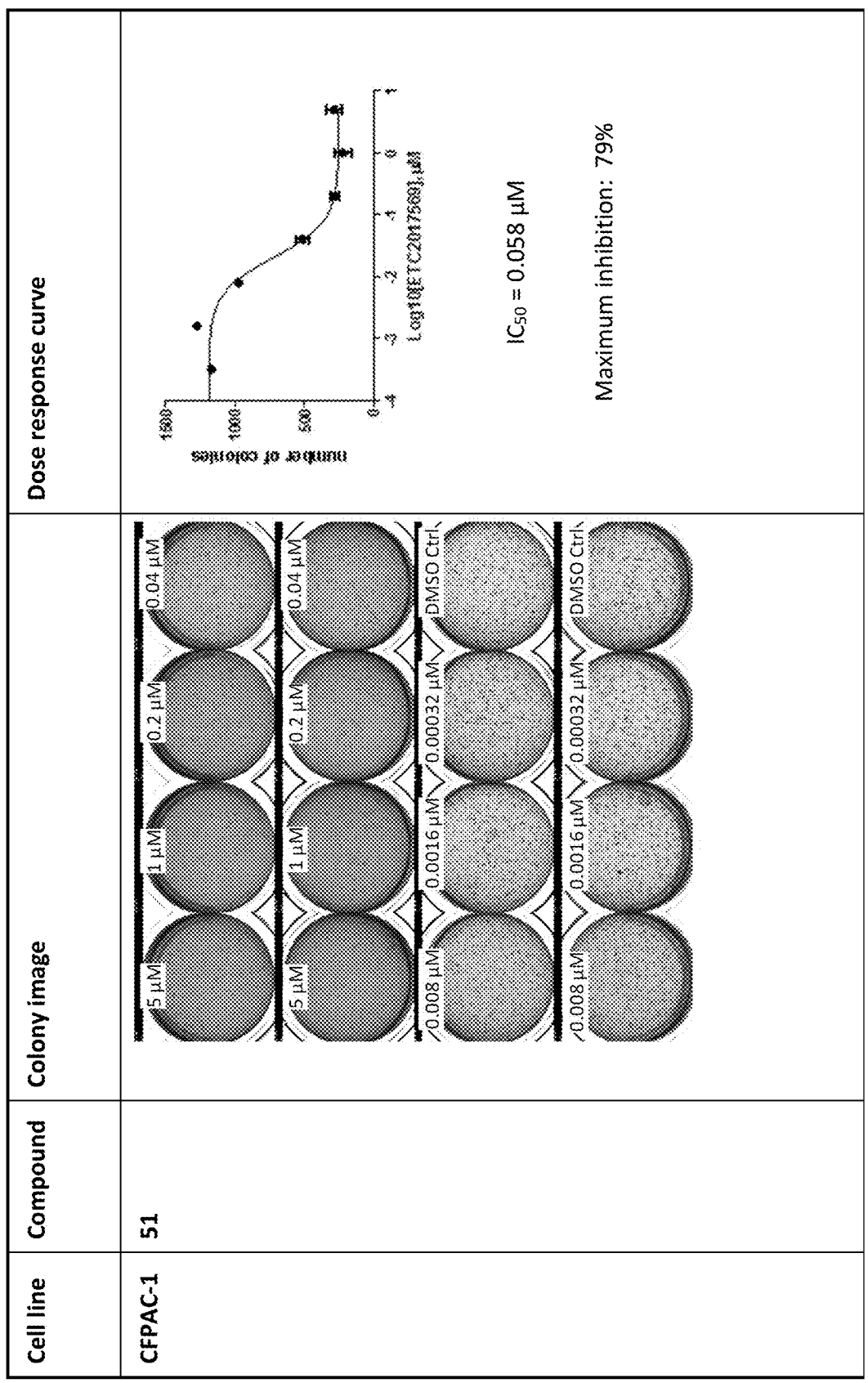

Results of the Soft Agar Assay are shown in Table 1 and FIGS. 5 to 7.

TABLE 1

Fifty percent colony growth inhibitory concentration ($IC_{50}$, µM) of Compound 51 on pancreatic cell lines AsPC-1 and HPAF-II. Results shown below are mean ± standard deviation (SD) from two independent experiments.

| Compound | Cell line | Test 1 $IC_{50}$ (µM) | Test 2 $IC_{50}$ (µM) | Mean $IC_{50}$ (µM) | Standard deviation (SD) | Maximum inhibition |
|---|---|---|---|---|---|---|
| 51 | AsPC-1 | 0.024 | 0.010 | 0.017 | 0.010 | 76% |
| | HPAF-II | 0.008 | 0.010 | 0.009 | 0.001 | 97% |
| | CFPAC-1 | 0.058 | 0.039 | 0.049 | 0.013 | 79% |

The results of the MMTV-Wnt1 Mouse Model are shown in FIG. 2 and Table 2:

TABLE 2

| | | Day 14 | | | | |
|---|---|---|---|---|---|---|
| Compound - dose | % TGI | % T/C | T/C | Significance | TRD | NTRD |
| Vehicle | — | — | — | — | 0/8 | 0/8 |
| Compound 51-1 mg/Kg | 68 | 0.375 | 37.5 | *** | 0/8 | 1/8 |
| Compound 51-3 mg/Kg | 67 | 0.383 | 38.3 | *** | 0/8 | 0/8 |
| Compound 51-10 mg/Kg | 91 | 0.160 | 16.0 | *** | 0/8 | 0/8 |

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

All patents and patent applications mentioned throughout the specification of the present invention are herein incorporated in their entirety by reference.

The invention embraces all combinations of preferred and more preferred groups and embodiments of groups recited above.

The invention claimed is:

1. A method of modulating WNT activity comprising exposing a WNT protein or a WNT receptor to an effective amount of a compound of formula (I)

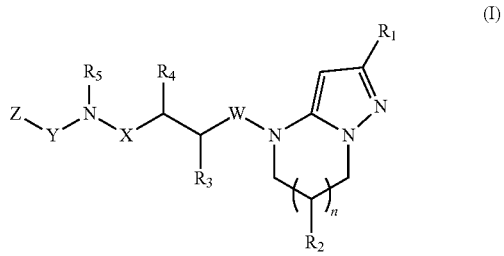

or a pharmaceutically acceptable salt, solvate, polymorph, tautomer, or stereoisomer thereof wherein:
$R_1$ represents H; alkyl optionally substituted with one or more substituents each independently selected from the group consisting of $C_{1-6}$alkoxy, $NH_2$, —$NHC_{1-3}$alkyl, and —$N(C_{1-3}$alkyl$)_2$; —C(O)Oalkyl; haloalkyl; haloalkoxy; or -alkylaryl;
each $R_2$ independently represents H; alkyl optionally substituted with one or more substituents each independently selected from the group consisting of $C_{1-6}$alkoxy, $NH_2$, —$NHC_{1-3}$alkyl, and —$N(C_{1-3}$alkyl$)_2$; -alkylaryl; carbocyclyl optionally substituted with one or more substituents each independently selected from the group consisting of $C_{1-6}$alkyl, $C_{1-6}$alkoxy, $C_{1-6}$haloalkyl, $C_{1-6}$haloalkoxy and halo; heterocyclyl optionally substituted with one or more substituents each independently selected from the group consisting of $C_{1-6}$alkyl, $C_{1-6}$alkoxy, —C(O)O$C_{1-6}$alkyl, —C(O)$C_{1-6}$alkyl, and —C(O)NH$C_{1-6}$alkyl; —NHalkyl; —N(alkyl)$_2$; amino; hydroxyl; alkoxy; or halo;
n represents 0, 1, or 2;
$R_3$ represents H or alkyl;
$R_4$ represents H or alkyl;
$R_5$ represents H or alkyl;
W and X each independently represent C=O; C=S; or $CH_2$;
Y represents aryl; heteroaryl; carbocyclyl optionally substituted with one or more substituents each independently selected from the group consisting of $C_{1-6}$alkyl, $C_{1-6}$alkoxy, $C_{1-6}$haloalkyl, $C_{1-6}$haloalkoxy, and halo; or heterocyclyl optionally substituted with one or more substituents each independently selected from the group consisting of $C_{1-6}$alkyl, $C_{1-6}$alkoxy, —C(O)O$C_{1-6}$alkyl, —C(O)$C_{1-6}$alkyl, and —C(O)NH$C_{1-6}$alkyl; and
Z represents alkyl optionally substituted with one or more substituents each independently selected from the group consisting of $C_{1-6}$alkoxy, $NH_2$, —$NHC_{1-3}$alkyl, and —$N(C_{1-3}$alkyl$)_2$; aryl; heteroaryl; -alkylaryl; -alkylheteroaryl; carbocyclyl optionally substituted with one or more substituents each independently selected from the group consisting of $C_{1-6}$alkyl, $C_{1-6}$alkoxy, $C_{1-6}$haloalkyl, $C_{1-6}$haloalkoxy, and halo; heterocyclyl optionally substituted with one or more substituents each independently selected from the group consisting of $C_{1-6}$alkyl, $C_{1-6}$alkoxy, —C(O)O$C_{1-6}$alkyl, —C(O)$C_{1-6}$alkyl, and —C(O)NH$C_{1-6}$alkyl; -alkylcarbocyclyl, wherein carbocyclyl is optionally substituted with one or more substituents each independently selected from the group consisting of $C_{1-6}$alkyl, $C_{1-6}$alkoxy, $C_{1-6}$haloalkoxy and halo; -alkylheterocyclyl wherein heterocyclyl is optionally substituted with one or more substituents each independently selected from the group consisting of $C_{1-6}$alkyl, —C(O)O$C_{1-6}$alkyl, —C(O)$C_{1-6}$alkyl, and —C(O)NH$C_{1-6}$alkyl; -arylcarbocyclyl wherein carbocyclyl is optionally substituted with one or more substituents each independently selected from the group consisting of $C_{1-6}$alkyl, $C_{1-6}$alkoxy, $C_{1-6}$haloalkoxy, and halo; or -arylheterocyclyl wherein heterocyclyl of the -arylheterocyclyl is optionally substituted with one or more substituents each independently selected from the group consisting of $C_{1-6}$alkyl, —C(O)O$C_{1-6}$alkyl, —C(O)$C_{1-6}$alkyl, and —C(O)NH$C_{1-6}$alkyl.

2. A method according to claim 1 wherein the method is an in vivo method.

3. A method of treating a tumor comprising administering to a subject in need thereof a therapeutically effective amount of a compound of formula (I)

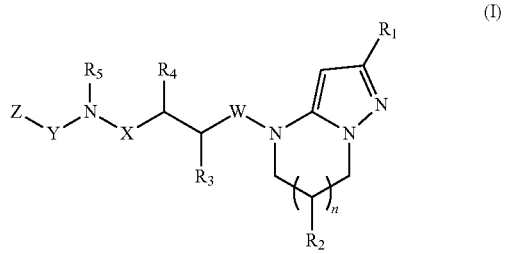

(I)

or a pharmaceutically acceptable salt, solvate, polymorph, tautomer, or stereoisomer thereof wherein, $R_1$ represents H; alkyl optionally substituted with one or more substituents each independently selected from the group consisting of $C_{1-6}$alkoxy, $NH_2$, —NH$C_{1-3}$alkyl, and —N($C_{1-3}$alkyl)$_2$; —C(O)Oalkyl; haloalkyl; haloalkoxy; or -alkylaryl;

each $R_2$ independently represents H; alkyl optionally substituted with one or more substituents each independently selected from the group consisting of $C_{1-6}$alkoxy, $NH_2$, —NH$C_{1-3}$alkyl, and —N($C_{1-3}$alkyl)$_2$; -alkylaryl; carbocyclyl optionally substituted with one or more substituents each independently selected from the group consisting of $C_{1-6}$alkyl, $C_{1-6}$alkoxy, $C_{1-6}$haloalkyl, $C_{1-6}$haloalkoxy and halo; heterocyclyl optionally substituted with one or more substituents each independently selected from the group consisting of $C_{1-6}$alkyl, $C_{1-6}$alkoxy, —C(O)O$C_{1-6}$alkyl, —C(O)$C_{1-6}$alkyl, and —C(O)NH$C_{1-6}$alkyl; -NHalkyl; —N(alkyl)$_2$; amino; hydroxyl; alkoxy; or halo;

n represents 1;

$R_3$ represents H or alkyl;

$R_4$ represents H or alkyl;

$R_5$ represents H or alkyl;

W and X each independently represent C=O; C=S; or $CH_2$;

Y represents optionally substituted phenyl or optionally substituted 6-membered heteroaryl; and Z represents optionally substituted aryl or optionally substituted heteroaryl.

4. The method of claim 3, wherein the tumor is selected from the group consisting of cervical cancer, colon cancer, breast cancer, bladder cancer, head and neck cancer, gastric cancer, lung cancer, ovarian cancer, prostate cancer, thyroid cancer, non-small-cell lung cancer, mesothelioma, melanoma, pancreatic adenocarcinoma, basal cell carcinoma, osteosarcoma, hepatocellular carcinoma, Wilm's tumor, and medulloblastoma.

5. The method of claim 3, wherein the compound of formula (I), is selected from the group consisting of:

| Compound ID | Structure | IUPAC Name |
|---|---|---|
| 14 | 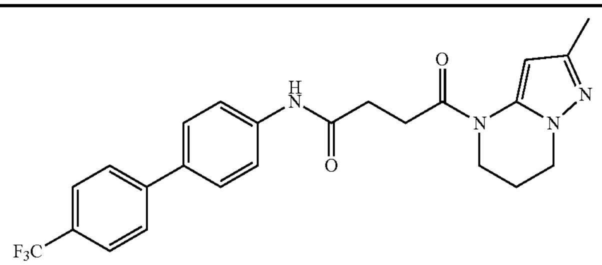 | 4-(2-methyl-6,7-dihydropyrazolo[1,5-a]pyrimidin-4(5H)-yl)-4-oxo-N-(4'-(trifluoromethyl)-[1,1'-biphenyl]-4-yl)butanamide |
| 24 | 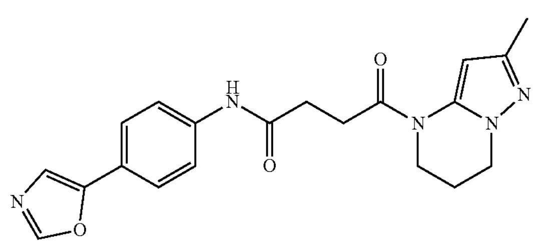 [SMILES: Cc1cc2n(n1)CCCN2C(=O)CCC(=O)Nc1ccc(-c2cnco2)cc1] | 4-(2-methyl-6,7-dihydropyrazolo[1,5-a]pyrimidin-4(5H)-yl)-N-(4-(oxazol-5-yl)phenyl)-4-oxobutanamide |
| 25 | 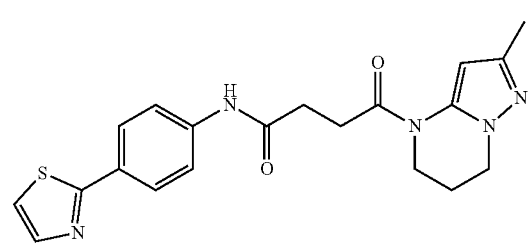 | 4-(2-methyl-6,7-dihydropyrazolo[1,5-a]pyrimidin-4(5H)-yl)-N-(4-(oxazol-5-yl)phenyl)-4-oxobutanamide |

| Compound ID | Structure | IUPAC Name |
|---|---|---|
| 26 | 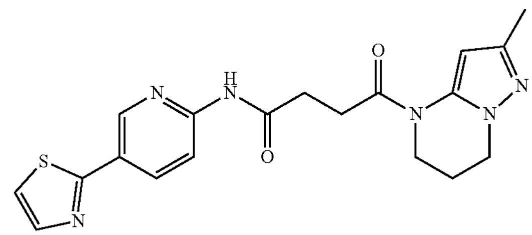 [SMILES: Cc1cc2n(n1)CCCN2C(=O)CCC(=O)Nc1ccc(-c2nccs2)cn1] | 4-(2-methyl-6,7-dihydropyrazolo[1,5-a]pyrimidin-4(5H)-yl)-4-oxo-N-(5-(thiazol-2-yl)pyridin-2-yl)butanamide |
| 27 | 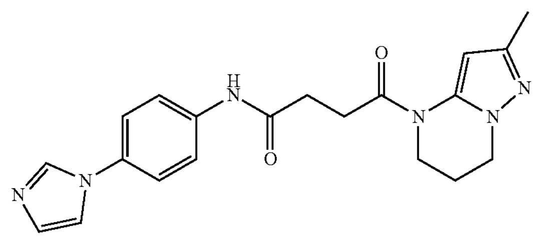 [SMILES: Cc1cc2n(n1)CCCN2C(=O)CCC(=O)Nc1ccc(-n2ccnc2)cc1] | N-(4-(1H-imidazol-1-yl)phenyl)-4-(2-methyl-6,7-dihydropyrazolo[1,5-a]pyrimidin-4(5H)-yl)-4-oxobutanamide |
| 28 | 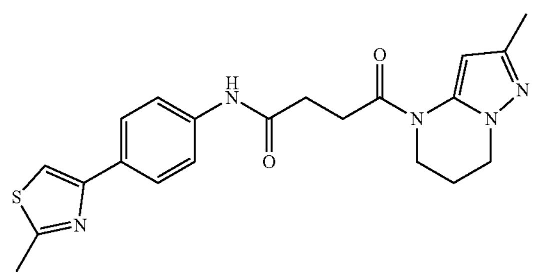 [SMILES: Cc1cc2n(n1)CCCN2C(=O)CCC(=O)Nc1ccc(-c2csc(C)n2)cc1] | 4-(2-methyl-6,7-dihydropyrazolo[1,5-a]pyrimidin-4(5H)-yl)-N-(4-(2-methylthiazol-4-yl)phenyl)-4-oxobutanamide |
| 29 | 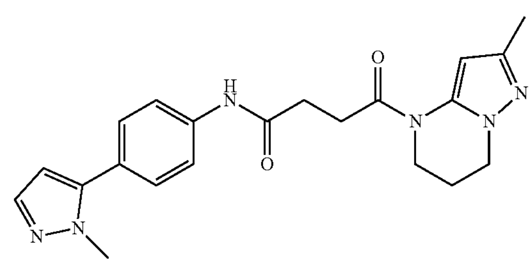 [SMILES: Cc1cc2n(n1)CCCN2C(=O)CCC(=O)Nc1ccc(-c2ccnn2C)cc1] | N-(4-(1-methyl-1H-pyrazol-5-yl)phenyl)-4-(2-methyl-6,7-dihydropyrazolo[1,5-a]pyrimidin-4(5H)-yl)-4-oxobutanamide |
| 32 | 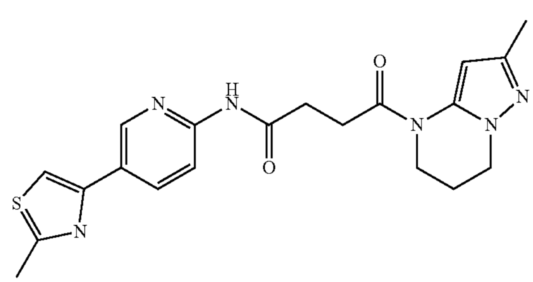 | 4-(2-methyl-6,7-dihydropyrazolo[1,5-a]pyrimidin-4(5H)-yl)-N-(4-(2-methylthiazol-4-yl)phenyl)-4-oxobutanamide |
| 33 | 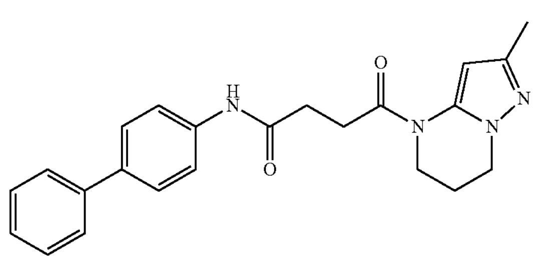 [SMILES: Cc1cc2n(n1)CCCN2C(=O)CCC(=O)Nc1ccc(-c2ccccc2)cc1] | N-([1,1'-biphenyl]-4-yl)-4-(2-methyl-6,7-dihydropyrazolo[1,5-a]pyrimidin-4(5H)-yl)-4-oxobutanamide |

| Compound ID | Structure | IUPAC Name |
|---|---|---|
| 34 | 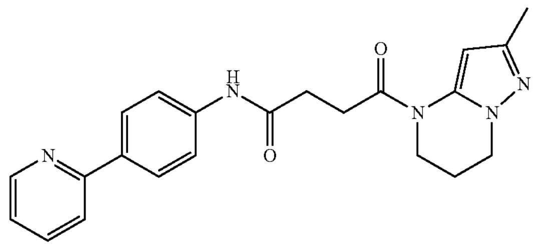 [SMILES: Cc1cc2n(n1)CCCN2C(=O)CCC(=O)Nc1ccc(-c2ccccn2)cc1] | 4-(2-methyl-6,7-dihydropyrazolo[1,5-a]pyrimidin-4(5H)-yl)-4-oxo-N-(4-(pyridin-2-yl)phenyl)butanamide |
| 35 | 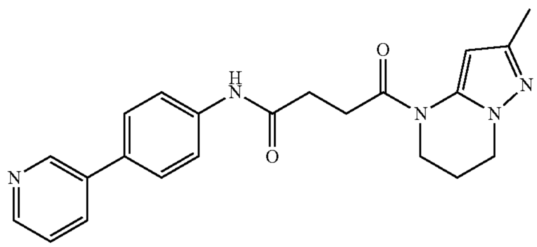 [SMILES: Cc1cc2n(n1)CCCN2C(=O)CCC(=O)Nc1ccc(-c2cccnc2)cc1] | 4-(2-methyl-6,7-dihydropyrazolo[1,5-a]pyrimidin-4(5H)-yl)-4-oxo-N-(4-(pyridin-3-yl)phenyl)butanamide |
| 36 | 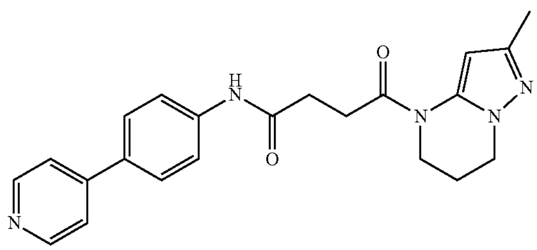 [SMILES: Cc1cc2n(n1)CCCN2C(=O)CCC(=O)Nc1ccc(-c2ccncc2)cc1] | 4-(2-methyl-6,7-dihydropyrazolo[1,5-a]pyrimidin-4(5H)-yl)-4-oxo-N-(4-(pyridin-4-yl)phenyl)butanamide |
| 37 | 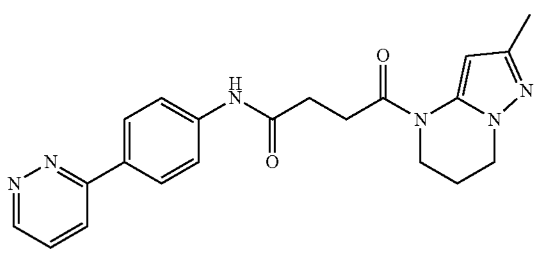 | 4-{2-methyl-5H,6H,7H-pyrazolo[1,5-a]pyrimidin-4-yl}-4-oxo-N-[4-(pyridazin-3-yl)phenyl]butanamide |
| 38 | 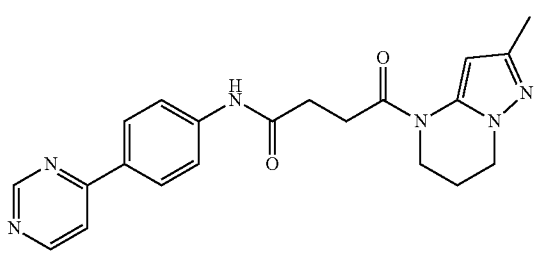 [SMILES: Cc1cc2n(n1)CCCN2C(=O)CCC(=O)Nc1ccc(-c2ccncn2)cc1] | 4-(2-methyl-6,7-dihydropyrazolo[1,5-a]pyrimidin-4(5H)-yl)-4-oxo-N-(4-(pyrimidin-4-yl)phenyl)butanamide |
| 39 | 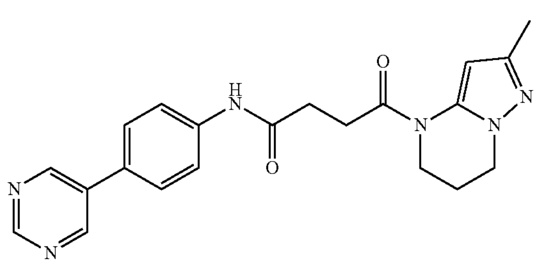 [SMILES: Cc1cc2n(n1)CCCN2C(=O)CCC(=O)Nc1ccc(-c2cncnc2)cc1] | 4-{2-methyl-5H,6H,7H-pyrazolo[1,5-a]pyrimidin-4-yl}-4-oxo-N-[4-(pyrimidin-5-yl)phenyl]butanamide |

| Compound ID | Structure | IUPAC Name |
|---|---|---|
| 40 | 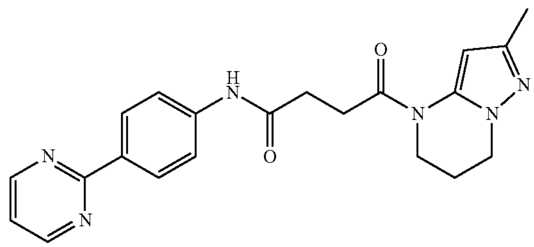 [SMILES: Cc1cc2n(n1)CCCN2C(=O)CCC(=O)Nc1ccc(-c2ncccn2)cc1] | 4-{2-methyl-5H,6H,7H-pyrazolo[1,5-a]pyrimidin-4-yl}-4-oxo-N-[4-(pyrimidin-2-yl)phenyl]butanamide |
| 41 | 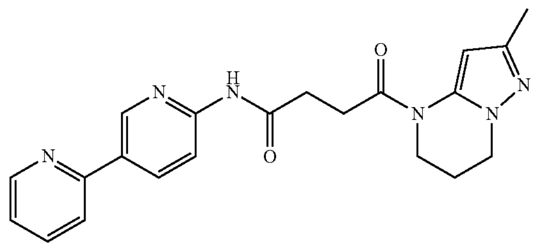 [SMILES: Cc1cc2n(n1)CCCN2C(=O)CCC(=O)Nc1ccc(-c2ccccn2)cn1] | N-([2,3'-bipyridin]-6'-yl)-4-(2-methyl-6,7-dihydropyrazolo[1,5-a]pyrimidin-4(5H)-yl)-4-oxobutanamide |
| 42 | 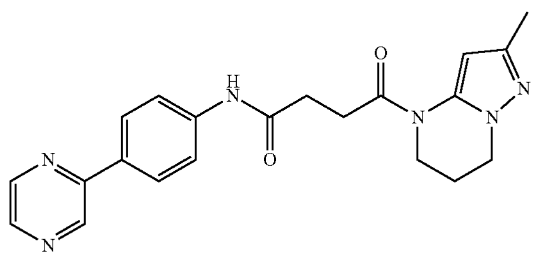 [SMILES: Cc1cc2n(n1)CCCN2C(=O)CCC(=O)Nc1ccc(-c2cnccn2)cc1] | 4-(2-methyl-6,7-dihydropyrazolo[1,5-a]pyrimidin-4(5H)-yl)-4-oxo-N-(4-(pyrazin-2-yl)phenyl)butanamide |
| 43 | 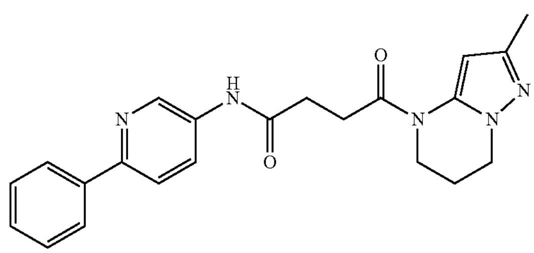 [SMILES: Cc1cc2n(n1)CCCN2C(=O)CCC(=O)Nc1ccc(-c2ccccc2)nc1] | 4-(2-methyl-6,7-dihydropyrazolo[1,5-a]pyrimidin-4(5H)-yl)-4-oxo-N-(6-phenylpyridin-3-yl)butanamide |
| 44 | 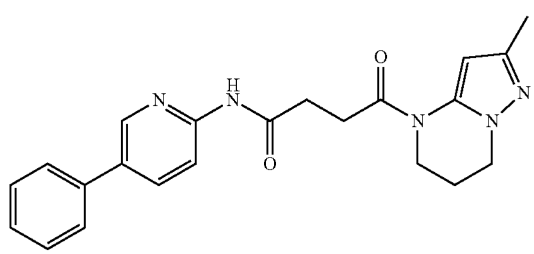 [SMILES: Cc1cc2n(n1)CCCN2C(=O)CCC(=O)Nc1ccc(-c2ccccc2)cn1] | 44Synthesis of 4-(2-methyl-6,7-dihydropyrazolo[1,5-a]pyrimidin-4(5H)-yl)-4-oxo-N-(5-phenylpyridin-2-yl)butanamide |
| 45 | 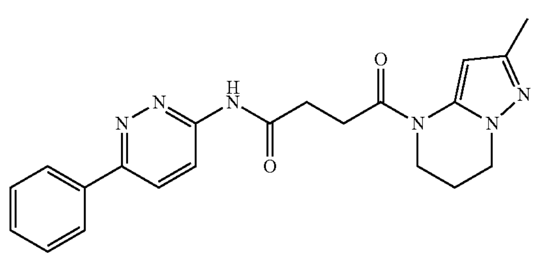 [SMILES: Cc1cc2n(n1)CCCN2C(=O)CCC(=O)Nc1ccc(-c2ccccc2)nn1] | 4-(2-methyl-6,7-dihydropyrazolo[1,5-a]pyrimidin-4(5H)-yl)-4-oxo-N-(6-phenylpyridazin-3-yl)butanamide |

-continued

| Compound ID | Structure | IUPAC Name |
|---|---|---|
| 46 | 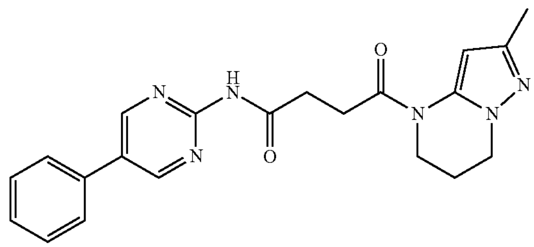 [SMILES: Cc1cc2n(n1)CCCN2C(=O)CCC(=O)Nc1ncc(-c2ccccc2)cn1] | 4-{2-methyl-5H,6H,7H-pyrazolo[1,5-a]pyrimidin-4-yl}-4-oxo-N-(5-phenylpyrimidin-2-yl)butanamide |
| 47 | 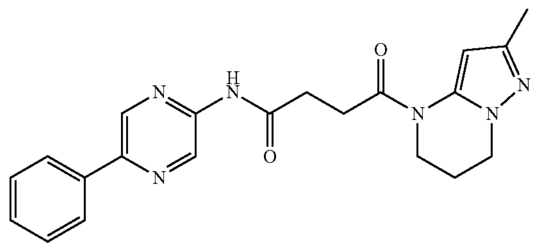 [SMILES: Cc1cc2n(n1)CCCN2C(=O)CCC(=O)Nc1cnc(-c2ccccc2)cn1] | 4-(2-methyl-6,7-dihydropyrazolo[1,5-a]pyrimidin-4(5H)-yl)-4-oxo-N-(5-phenylpyrazin-2-yl)butanamide |
| 48 | 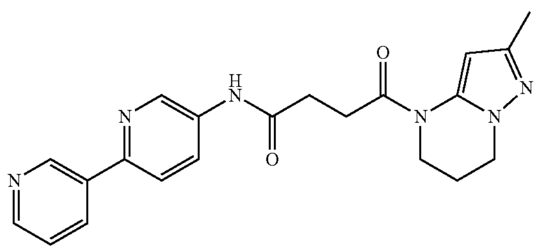 [SMILES: Cc1cc2n(n1)CCCN2C(=O)CCC(=O)Nc1ccc(-c2cccnc2)nc1] | N-([2,3'-bipyridin]-5-yl)-4-(2-methyl-6,7-dihydropyrazolo[1,5-a]pyrimidin-4(5H)-yl)-4-oxobutanamide |
| 49 | 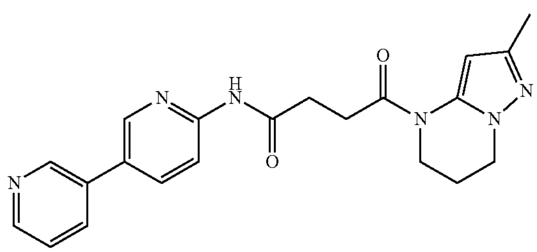 | 4-{2-methyl-5H,6H,7H-pyrazolo[1,5-a]pyrimidin-4-yl}-4-oxo-N-[5-(pyridin-3-yl)pyridin-2-yl]butanamide |
| 50 | 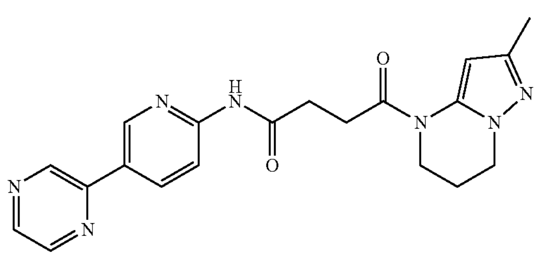 | 4-(2-methyl-6,7-dihydropyrazolo[1,5-a]pyrimidin-4(5H)-yl)-4-oxo-N-(5-(pyrazin-2-yl)pyridin-2-yl)butanamide |
| 51 | 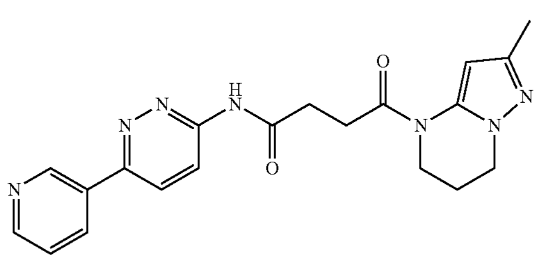 | 4-(2-methyl-6,7-dihydropyrazolo[1,5-a]pyrimidin-4(5H)-yl)-4-oxo-N-(6-(pyridin-3-yl)pyridazin-3-yl)butanamide |

-continued

| Compound ID | Structure | IUPAC Name |
|---|---|---|
| 52 | 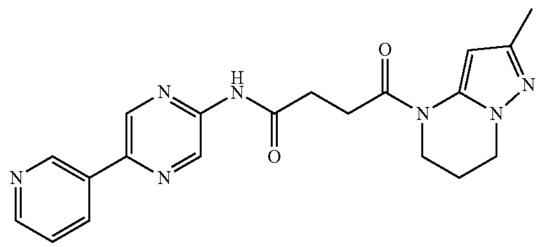 [SMILES: Cc1cc2n(n1)CCCN2C(=O)CCC(=O)Nc1cnc(-c2cccnc2)cn1] | 4-(2-methyl-6,7-dihydropyrazolo[1,5-a]pyrimidin-4(5H)-yl)-4-oxo-N-(5-(pyridin-3-yl)pyrazin-2-yl)butanamide |
| 53 | 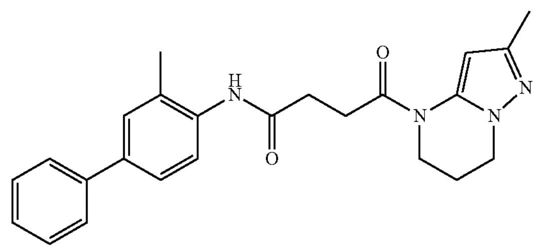 [SMILES: Cc1cc2n(n1)CCCN2C(=O)CCC(=O)Nc1ccc(-c2ccccc2)cc1C] | 4-(2-methyl-6,7-dihydropyrazolo[1,5-a]pyrimidin-4(5H)-yl)-N-(3-methyl-[1,1'-biphenyl]-4-yl)-4-oxobutanamide |
| 54 | 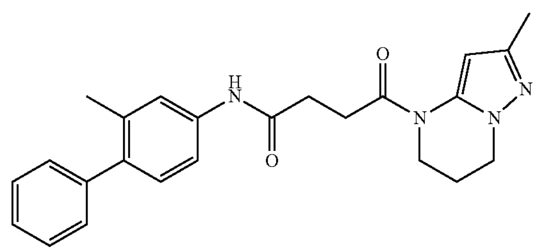 [SMILES: Cc1cc2n(n1)CCCN2C(=O)CCC(=O)Nc1ccc(-c2ccccc2)c(C)c1] | 4-(2-methyl-6,7-dihydropyrazolo[1,5-a]pyrimidin-4(5H)-yl)-N-(2-methyl-[1,1'-biphenyl]-4-yl)-4-oxobutanamide |
| 55 | 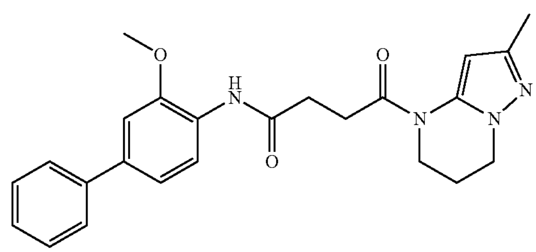 [SMILES: COc1cc(-c2ccccc2)ccc1NC(=O)CCC(=O)N1CCCn2nc(C)cc21] | N-(3-methoxy-[1,1'-biphenyl]-4-yl)-4-(2-methyl 6,7-dihydropyrazolo[1,5-a]pyrimidin-4(5H)-yl)-4-oxobutanamide |
| 56 | 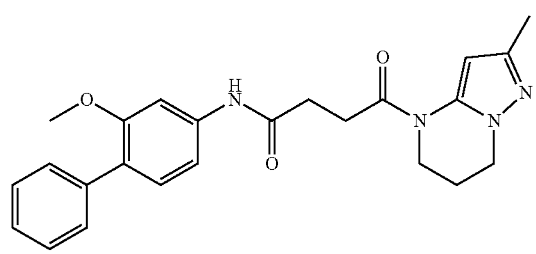 [SMILES: COc1cc(NC(=O)CCC(=O)N2CCCn3nc(C)cc32)ccc1-c1ccccc1] | N-(2-methoxy-[1,1'-biphenyl]-4-yl)-4-(2-methyl-6,7-dihydropyrazolo[1,5-a]pyrimidin-4(5H)-yl)-4-oxobutanamide |
| 57 | 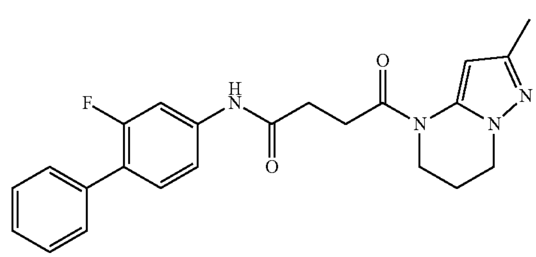 [SMILES: Cc1cc2n(n1)CCCN2C(=O)CCC(=O)Nc1ccc(-c2ccccc2)c(F)c1] | N-(2-fluorobiphenyl-4-yl)-4-(2-methyl-6,7-dihydropyrazolo[1,5-a]pyrimidin-4(5H)-yl)-4-oxobutanamide |

| Compound ID | Structure | IUPAC Name |
|---|---|---|
| 58 | 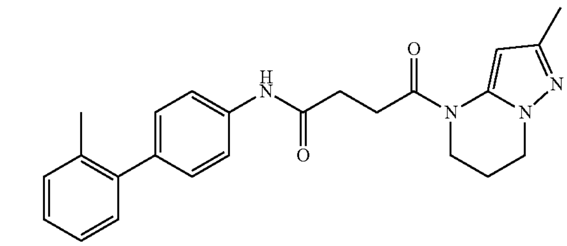 [SMILES: Cc1cc2n(n1)CCCN2C(=O)CCC(=O)Nc1ccc(-c2ccccc2C)cc1] | 4-(2-methyl-6,7-dihydropyrazolo[1,5-a]pyrimidin-4(5H)-yl)-N-(2'-methyl-[1,1'-biphenyl]-4-yl)-4-oxobutanamide |
| 59 | 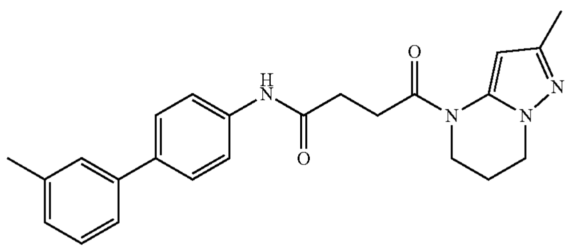 | 4-(2-methyl-6,7-dihydropyrazolo[1,5-a]pyrimidin-4(5H)-yl)-N-(3'-methyl-[1,1'-biphenyl]-4-yl)-4-oxobutanamide |
| 60 | 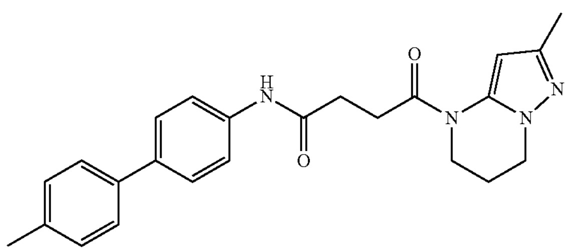 | 4-(2-methyl-6,7-dihydropyrazolo[1,5-a]pyrimidin-4(5H)-yl)-N-(4'-methyl-[1,1'-biphenyl]-4-yl)-4-oxobutanamide |
| 61 | 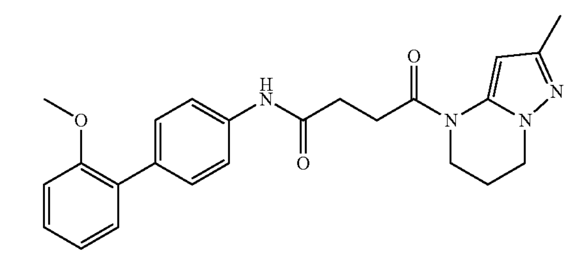 [SMILES: COc1ccccc1-c1ccc(NC(=O)CCC(=O)N2CCCn3nc(C)cc32)cc1] | N-(2'-methoxy-[1,1'-biphenyl]-4-yl)-4-(2-methyl 6,7-dihydropyrazolo[1,5-a]pyrimidin-4(5H)-yl)-4-oxobutanamide |
| 62 | 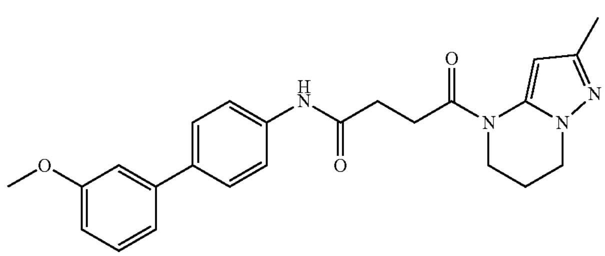 | N-(3'-methoxy-[1,1'-biphenyl]-4-yl)-4-(2-methyl-6,7-dihydropyrazolo[1,5-a]pyrimidin-4(5H)-yl)-4-oxobutanamide |
| 63 | 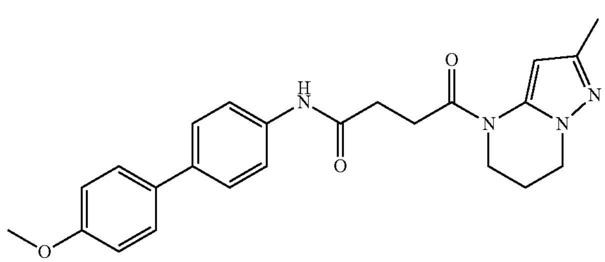 | N-(4'-methoxy-[1,1'-biphenyl]-4-yl)-4-(2-methyl-6,7-dihydropyrazolo[1,5-a]pyrimidin-4(5H)-yl)-4-oxobutanamide |

-continued

| Compound ID | Structure | IUPAC Name |
|---|---|---|
| 64 | 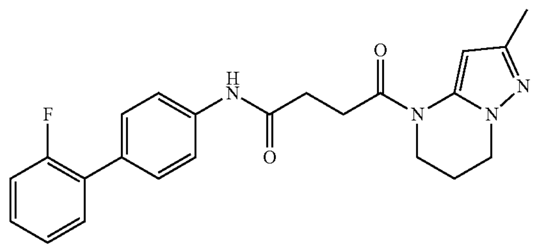 [SMILES: Cc1cc2n(n1)CCCN2C(=O)CCC(=O)Nc1ccc(-c2ccccc2F)cc1] | N-(2'-fluoro-[1,1'-biphenyl]-4-yl)-4-(2-methyl-6,7-dihydropyrazolo[1,5-a]pyrimidin-4(5H)-yl)-4-oxobutanamide |
| 65 | 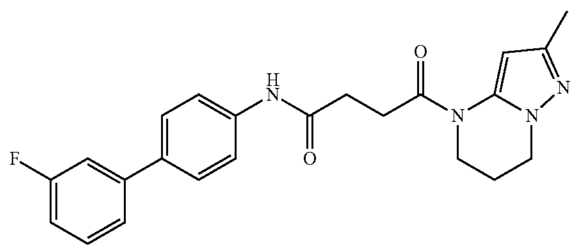 [SMILES: Cc1cc2n(n1)CCCN2C(=O)CCC(=O)Nc1ccc(-c2cccc(F)c2)cc1] | N-(3'-fluoro-[1,1'-biphenyl]-4-yl)-4-(2-methyl-6,7-dihydropyrazolo[1,5-a]pyrimidin-4(5H)-yl)-4-oxobutanamide |
| 66 | 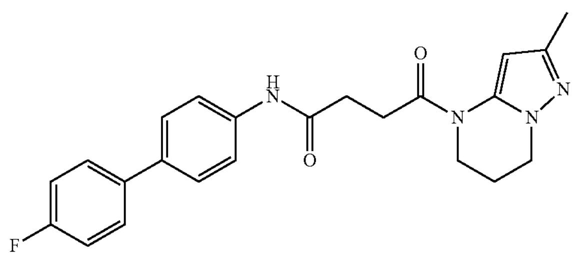 [SMILES: Cc1cc2n(n1)CCCN2C(=O)CCC(=O)Nc1ccc(-c2ccc(F)cc2)cc1] | N-(4'-fluorobiphenyl-4-yl)-4-(2-methyl-6,7-dihydropyrazolo[1,5-a]pyrimidin-4(5H)-yl)-4-oxobutanamide |
| 67 | 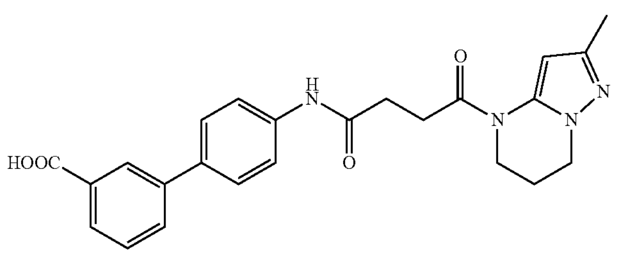 [SMILES: Cc1cc2n(n1)CCCN2C(=O)CCC(=O)Nc1ccc(-c2cccc(C(=O)O)c2)cc1] | 4'-(4-(2-methyl-6,7-dihydropyrazolo[1,5-a]pyrimidin-4(5H)-yl)-4-oxobutanamido)-[1,1'-biphenyl]-3-carboxylic acid |
| 68 | 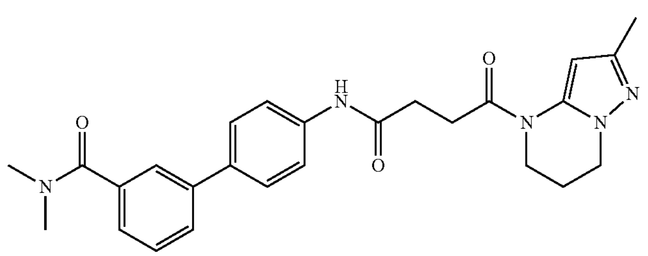 | N,N-dimethyl-4'-(4-(2-methyl-6,7-dihydropyrazolo[1,5-a]pyrimidin-4(5H)-yl)-4-oxobutanamido)-[1,1'-biphenyl]-3-carboxamide |
| 69 | 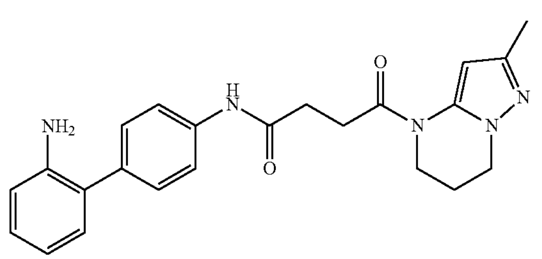 [SMILES: Cc1cc2n(n1)CCCN2C(=O)CCC(=O)Nc1ccc(-c2ccccc2N)cc1] | N-(2'-amino-[1,1'-biphenyl]-4-yl)-4-(2-methyl-6,7-dihydropyrazolo[1,5-a]pyrimidin-4(5H)-yl)-4-oxobutanamide |

| Compound ID | Structure | IUPAC Name |
|---|---|---|
| 70 | 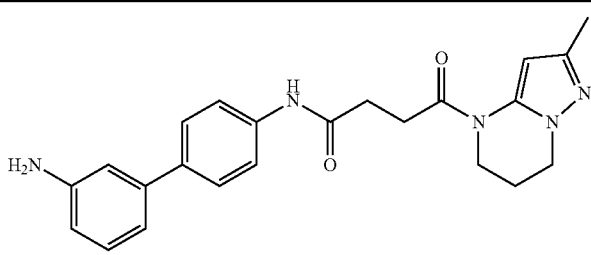 | N-(3'-amino-[1,1'-biphenyl]-4-yl)-4-(2-methyl-6,7-dihydropyrazolo[1,5-a]pyrimidin-4(5H)-yl)-4-oxobutanamide |
| 71 | 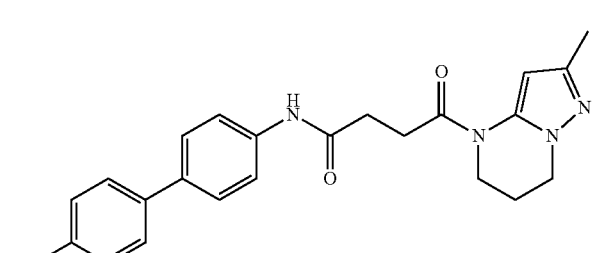 | N-(4'-amino-[1,1'-biphenyl]-4-yl)-4-(2-methyl-6,7-dihydropyrazolo[1,5-a]pyrimidin-4(5H)-yl)-4-oxobutanamide |
| 72 | 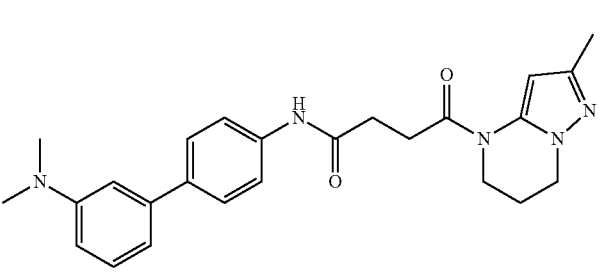 | N-(3'-(dimethylamino)-[1,1'-biphenyl]-4-yl)-4-(2-methyl-6,7-dihydropyrazolo[1,5-a]pyrimidin-4(5H)-yl)-4-oxobutanamide |
| 73 | 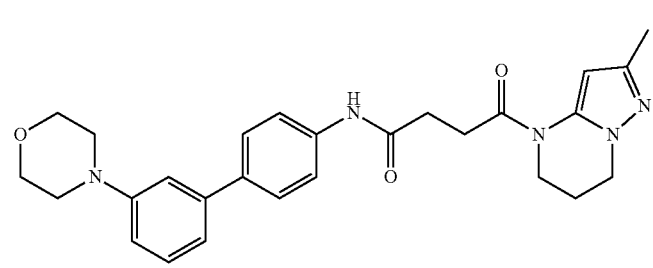 [SMILES: Cc1cc2n(n1)CCCN2C(=O)CCC(=O)Nc1ccc(-c2cccc(N3CCOCC3)c2)cc1] | 4-(2-methyl-6,7-dihydropyrazolo[1,5-a]pyrimidin-4(5H)-yl)-N-(3'-morpholinobiphenyl-4-yl)-4-oxobutanamide |
| 74 | 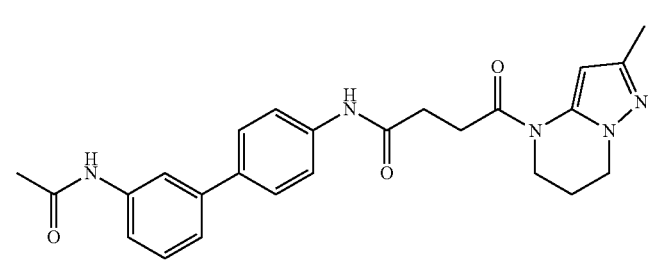 [SMILES: CC(=O)Nc1cccc(-c2ccc(NC(=O)CCC(=O)N3CCCn4nc(C)cc43)cc2)c1] | N-(3'-acetamido-[1,1'-biphenyl]-4-yl)-4-(2-methyl-6,7-dihydropyrazolo[1,5-a]pyrimidin-4(5H)-yl)-4-oxobutanamide |
| 83 | 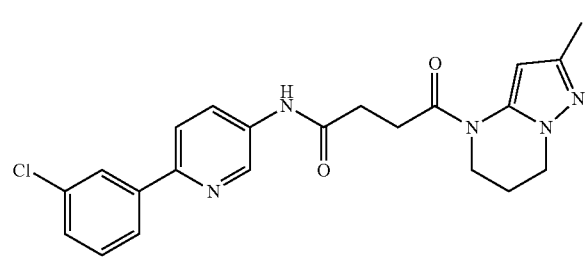 | N-(6-(3-chlorophenyl)pyridin-3-yl)-4-(2-methyl-6,7-dihydropyrazolo[1,5-a]pyrimidin-4(5H)-yl)-4-oxobutanamide |

| Compound ID | Structure | IUPAC Name |
|---|---|---|
| 84 | 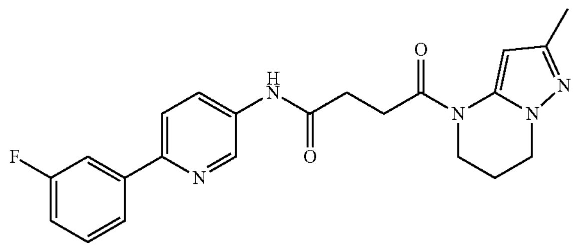 [SMILES: Cc1cc2n(n1)CCCN2C(=O)CCC(=O)Nc1ccc(-c2cccc(F)c2)nc1] | N-(6-(3-fluorophenyl)pyridin-3-yl)-4-(2-methyl-6,7-dihydropyrazolo[1,5-a]pyrimidin-4(5H)-yl)-4-oxobutanamide |
| 85 | 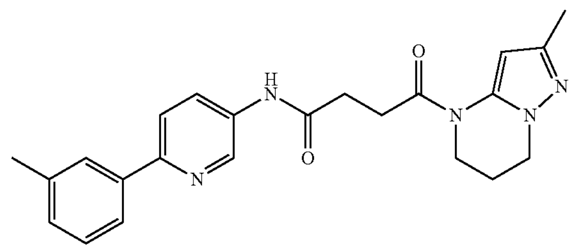 | 4-(2-methyl-6,7-dihydropyrazolo[1,5-a]pyrimidin-4(5H)-yl)-4-oxo-N-(6-(m-tolyl)pyridin-3-yl)butanamide |
| 86 | 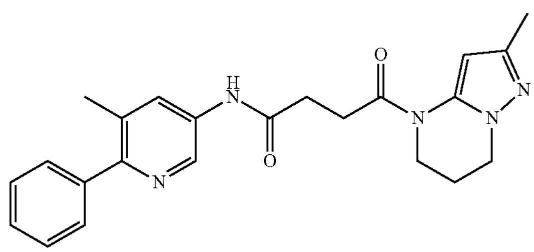 | 4-(2-methyl-6,7-dihydropyrazolo[1,5-a]pyrimidin-4(5H)-yl)-N-(5-methyl-6-phenylpyridin-3-yl)-4-oxobutanamide |
| 87 | 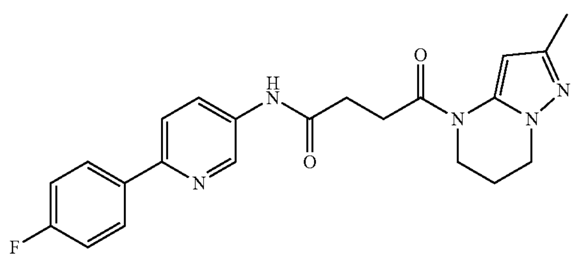 [SMILES: Cc1cc2n(n1)CCCN2C(=O)CCC(=O)Nc1ccc(-c2ccc(F)cc2)nc1] | N-(6-(4-fluorophenyl)pyridin-3-yl)-4-(2-methyl-6,7-dihydropyrazolo[1,5-a]pyrimidin-4(5H)-yl)-4-oxobutanamide |
| 88 | 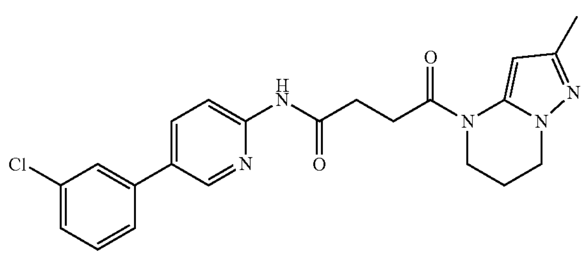 [SMILES: Cc1cc2n(n1)CCCN2C(=O)CCC(=O)Nc1ccc(-c2cccc(Cl)c2)cn1] | N-(6-(3-fluorophenyl)pyridazin-3-yl)-4-(2-methyl-6,7-dihydropyrazolo[1,5-a]pyrimidin-4(5H)-yl)-4-oxobutanamide |
| 89 | 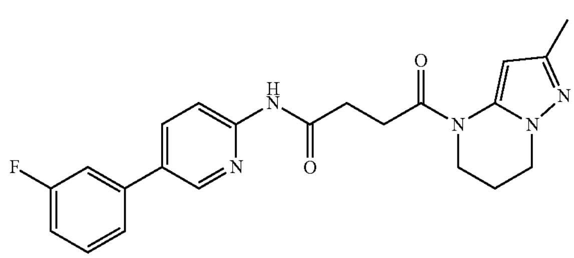 [SMILES: Cc1cc2n(n1)CCCN2C(=O)CCC(=O)Nc1ccc(-c2cccc(F)c2)cn1] | N-(5-(3-fluorophenyl)pyridin-2-yl)-4-(2-methyl-6,7-dihydropyrazolo[1,5-a]pyrimidin-4(5H)-yl)-4-oxobutanamide |

-continued

| Compound ID | Structure | IUPAC Name |
|---|---|---|
| 90 | 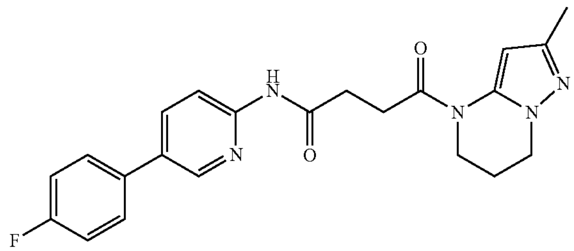 [SMILES: Cc1cc2n(n1)CCCN2C(=O)CCC(=O)Nc1ccc(-c2ccc(F)cc2)cn1] | N-(5-(4-fluorophenyl)pyridin-2-yl)-4-(2-methyl-6,7-dihydropyrazolo[1,5-a]pyrimidin-4(5H)-yl)-4-oxobutanamide |
| 91 | 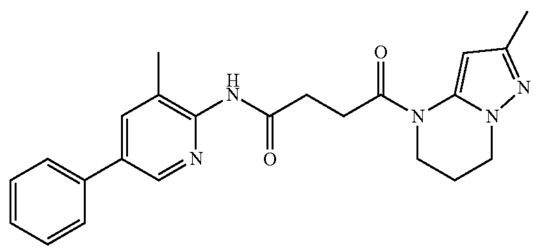 [SMILES: Cc1cc2n(n1)CCCN2C(=O)CCC(=O)Nc1ncc(-c2ccccc2)cc1C] | N-(3-methyl-5-phenylpyridin-2-yl)-4-(2-methyl-6,7-dihydropyrazolo[1,5-a]pyrimidin-4(5H)-yl)-4-oxobutana |
| 92 | 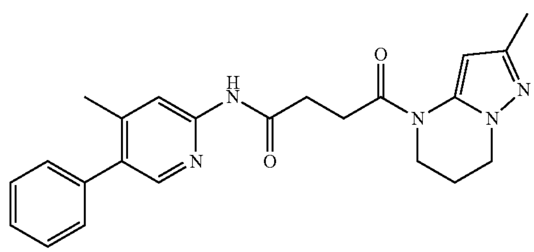 [SMILES: Cc1cc2n(n1)CCCN2C(=O)CCC(=O)Nc1cc(C)c(-c2ccccc2)cn1] | N-(4-methyl-5-phenylpyridin-2-yl)-4-(2-methyl-6,7-dihydropyrazolo[1,5-a]pyrimidin-4(5H)-yl)-4-oxobutanamide |
| 93 | 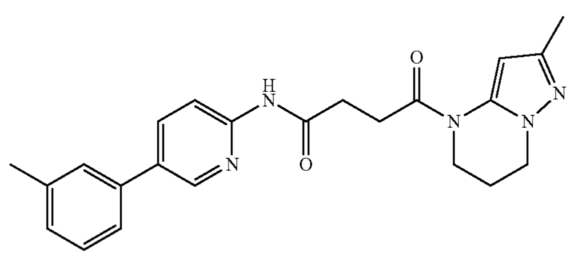 | 4-(2-methyl-6,7-dihydropyrazolo[1,5-a]pyrimidin-4(5H)-yl)-4-oxo-N-(5-(m-tolyl)pyridin-2-yl)butanamide |
| 94 | 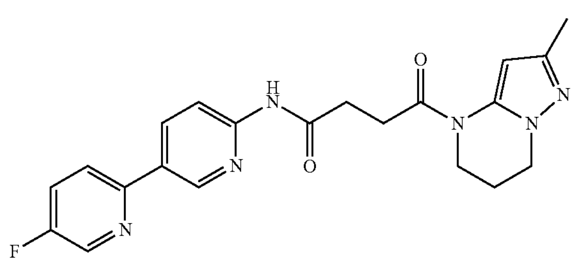 [SMILES: Cc1cc2n(n1)CCCN2C(=O)CCC(=O)Nc1ccc(-c2ccc(F)cn2)cn1] | N-(5-fluoro-2,3'-bipyridin-6'-yl)-4-(2-methyl-6,7-dihydropyrazolo[1,5-a]pyrimidin-4(5H)-yl)-4-oxobutanamide |
| 95 | 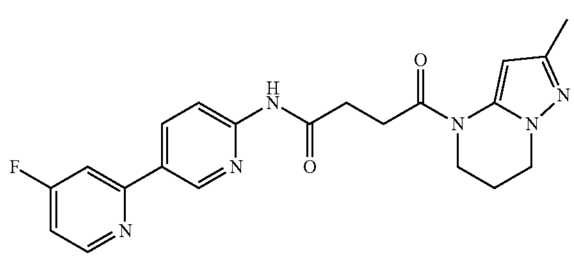 [SMILES: Cc1cc2n(n1)CCCN2C(=O)CCC(=O)Nc1ccc(-c2cc(F)ccn2)cn1] | N-(4-fluoro-2,3'-bipyridin-6'-yl)-4-(2-methyl-6,7-dihydropyrazolo[1,5-a]pyrimidin-4(5H)-yl)-4-oxobutanamide |

| Compound ID | Structure | IUPAC Name |
|---|---|---|
| 96 | 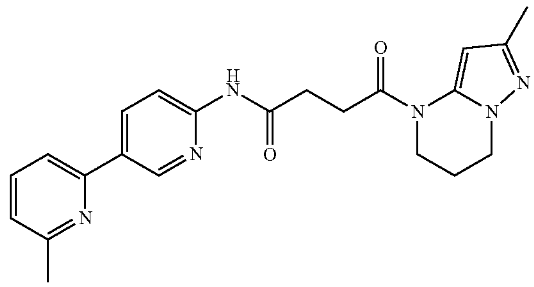 [SMILES: Cc1cccc(-c2ccc(NC(=O)CCC(=O)N3CCCn4nc(C)cc43)nc2)n1] | 4-(2-methyl-6,7-dihydropyrazolo[1,5-a]pyrimidin-4(5H)-yl)-N-(6-methyl-[2,3'-bipyridin]-6'-yl)-4-oxobutanamide |
| 97 | 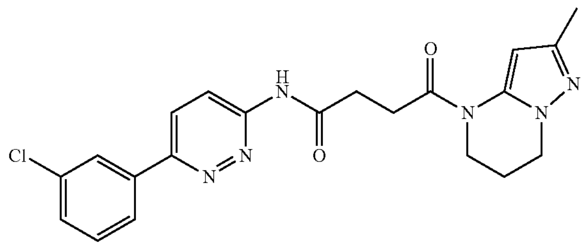 [SMILES: Cc1cc2n(n1)CCCN2C(=O)CCC(=O)Nc1ccc(-c2cccc(Cl)c2)nn1] | N-(6-(3-chlorophenyl)pyridazin-3-yl)-4-(2-methyl-6,7-dihydropyrazolo[1,5-a]pyrimidin-4(5H)-yl)-4-oxobutanamide |
| 98 | 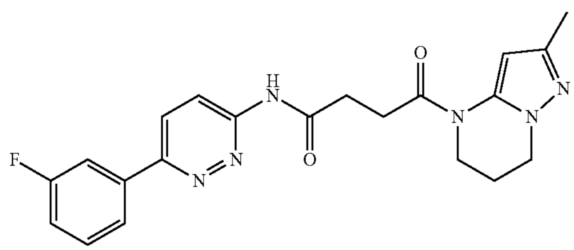 [SMILES: Cc1cc2n(n1)CCCN2C(=O)CCC(=O)Nc1ccc(-c2cccc(F)c2)nn1] | N-(6-(3-fluorophenyl)pyridazin-3-yl)-4-(2-methyl-6,7-dihydropyrazolo[1,5-a]pyrimidin-4(5H)-yl)-4-oxobutanamide |
| 99 | 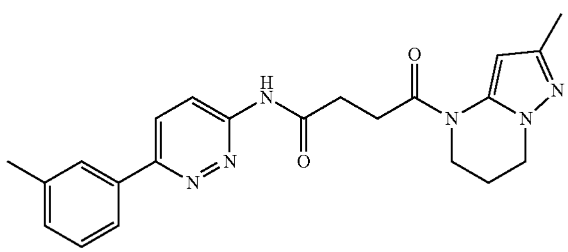 | 4-(2-methyl-6,7-dihydropyrazolo[1,5-a]pyrimidin-4(5H)-yl)-4-oxo-N-(6-(m-tolyl)pyridazin-3-yl)butanamide |
| 100 | 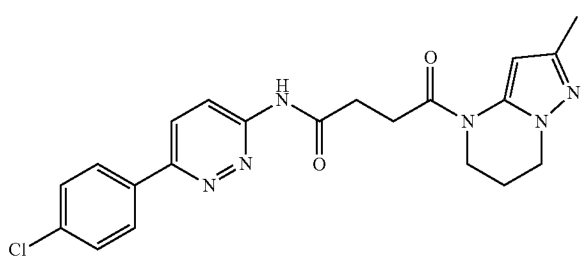 [SMILES: Cc1cc2n(n1)CCCN2C(=O)CCC(=O)Nc1ccc(-c2ccc(Cl)cc2)nn1] | N-[6-(4-chlorophenyl)pyridazin-3-yl]-4-{2-methyl-5H,6H,7H-pyrazolo[1,5-a]pyrimidin-4-yl}-4-oxobutanamide |
| 101 | 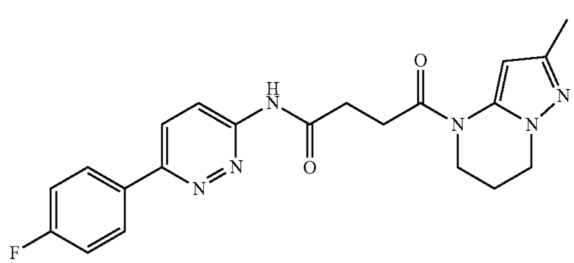 [SMILES: Cc1cc2n(n1)CCCN2C(=O)CCC(=O)Nc1ccc(-c2ccc(F)cc2)nn1] | N-(6-(4-fluorophenyl)pyridazin-3-yl)-4-(2-methyl-6,7-dihydropyrazolo[1,5-a]pyrimidin-4(5H)-yl)-4-oxobutanamide |

| Compound ID | Structure | IUPAC Name |
|---|---|---|
| 102 | 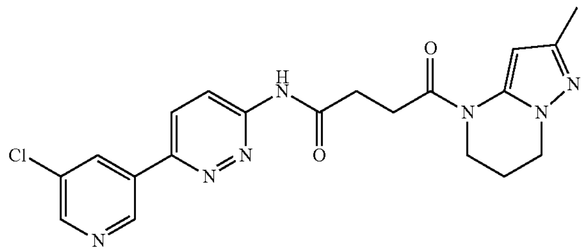 [SMILES: Cc1cc2n(n1)CCCN2C(=O)CCC(=O)Nc1ccc(-c2cncc(Cl)c2)nn1] | N-(6-(5-chloropyridin-3-yl)pyridazin-3-yl)-4-(2-methyl-6,7-dihydropyrazolo[1,5-a]pyrimidin-4(5H)-yl)-4-oxobutanamide |
| 103 | 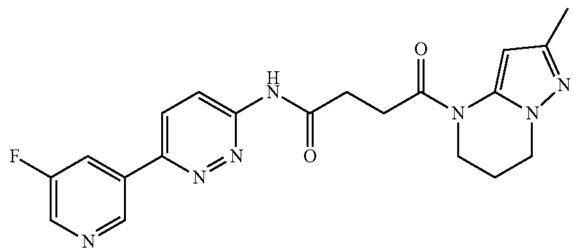 [SMILES: Cc1cc2n(n1)CCCN2C(=O)CCC(=O)Nc1ccc(-c2cncc(F)c2)nn1] | N-(6-(5-fluoropyridin-3-yl)pyridazin-3-yl)-4-(2-methyl-6,7-dihydropyrazolo[1,5-a]pyrimidin-4(5H)-yl)-4-oxobutanamide |
| 104 | 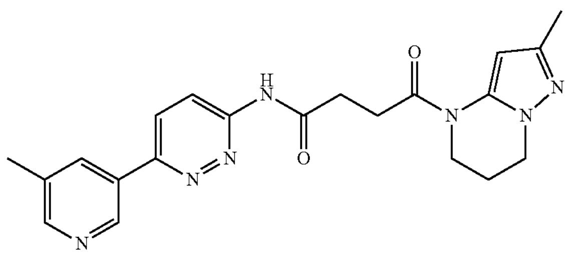 | 4-(2-methyl-6,7-dihydropyrazolo[1,5-a]pyrimidin-4(5H)-yl)-N-(6-(5-methylpyridin-3-yl)pyridazin-3-yl)-4-oxobutanamide |
| 105 | 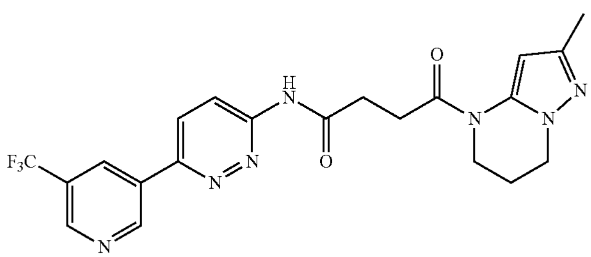 | 4-(2-methyl-6,7-dihydropyrazolo[1,5-a]pyrimidin-4(5H)-yl)-4-oxo-N-(6-(5-(trifluoromethyl)pyridin-3-yl)pyridazin-3-yl)butanamide |
| 106 | 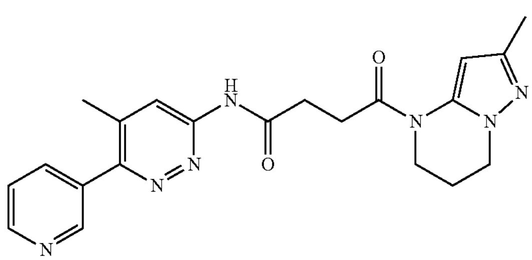 [SMILES: Cc1cc2n(n1)CCCN2C(=O)CCC(=O)Nc1cc(C)c(-c2cccnc2)nn1] | 4-(2-methyl-6,7-dihydropyrazolo[1,5-a]pyrimidin-4(5H)-yl)-N-(5-methyl-6-(pyridin-3-yl)pyridazin-3-yl)-4-oxobutanamide |
| 107 | 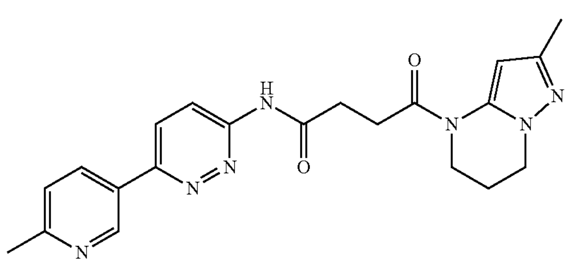 | 4-(2-methyl-6,7-dihydropyrazolo[1,5-a]pyrimidin-4(5H)-yl)-N-(6-(6-methylpyridin-3-yl)pyridazin-3-yl)-4-oxobutanamide |

| Compound ID | Structure | IUPAC Name |
|---|---|---|
| 108 | 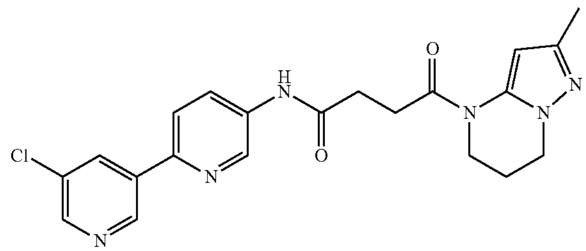 [SMILES: Cc1cc2n(n1)CCCN2C(=O)CCC(=O)Nc1ccc(-c2cncc(Cl)c2)nc1] | N-(5'-chloro-[2,3'-bipyridin]-5-yl)-4-(2-methyl-6,7-dihydropyrazolo[1,5-a]pyrimidin-4(5H)-yl)-4-oxobutanamide |
| 109 | 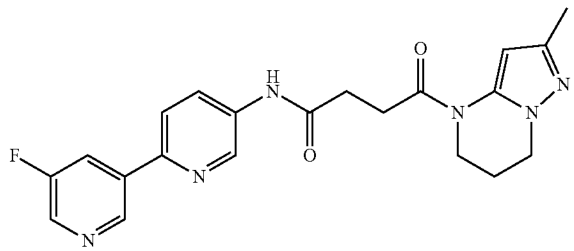 [SMILES: Cc1cc2n(n1)CCCN2C(=O)CCC(=O)Nc1ccc(-c2cncc(F)c2)nc1] | N-(5'-fluoro-[2,3'-bipyridin]-5-yl)-4-(2-methyl-6,7-dihydropyrazolo[1,5-a]pyrimidin-4(5H)-yl)-4-oxobutanamide |
| 110 | 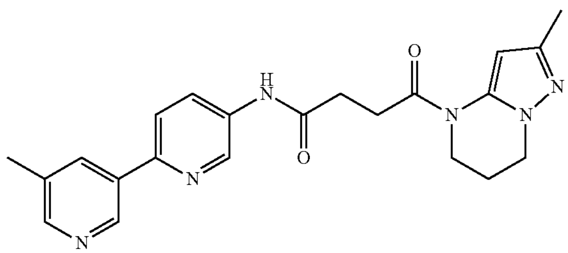 | N-(5'-methyl-2,3'-bipyridin-5-yl)-4-(2-methyl-6,7-dihydropyrazolo[1,5-a]pyrimidin-4(5H)-yl)-4-oxobutanamide |
| 111 | 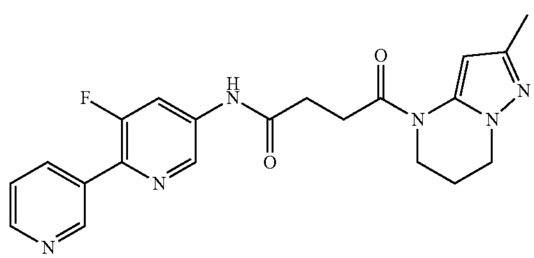 [SMILES: Cc1cc2n(n1)CCCN2C(=O)CCC(=O)Nc1cnc(-c2cccnc2)c(F)c1] | N-(3-fluoro-2,3'-bipyridin-5-yl)-4-(2-methyl-6,7-dihydropyrazolo[1,5-a]pyrimidin-4(5H)-yl)-4-oxobutanamide |
| 112 | 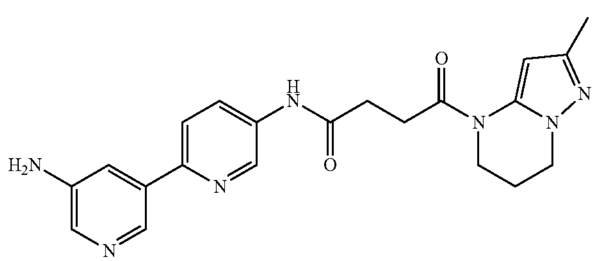 [SMILES: Cc1cc2n(n1)CCCN2C(=O)CCC(=O)Nc1ccc(-c2cncc(N)c2)nc1] | N-(5'-amino-2,3'-bipyridin-5-yl)-4-(2-methyl-6,7-dihydropyrazolo[1,5-a]pyrimidin-4(5H)-yl)-4-oxobutanamide |
| 113 | 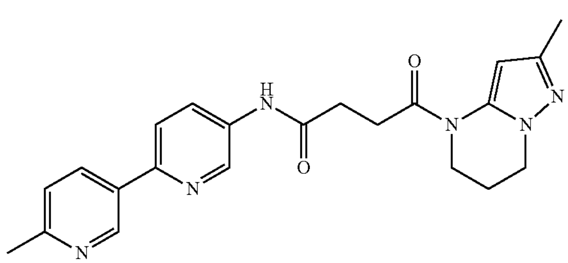 | 4-(2-methyl-6,7-dihydropyrazolo[1,5-a]pyrimidin-4(5H)-yl)-N-(6'-methyl-[2,3'-bipyridin]-5-yl)-4-oxobutanamide |

| Compound ID | Structure | IUPAC Name |
|---|---|---|
| 114 | 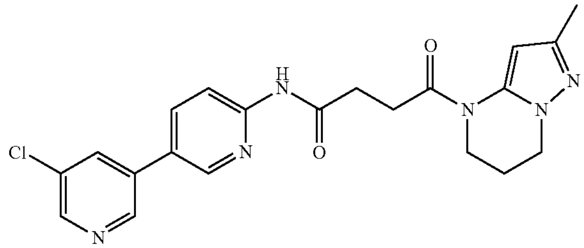 [SMILES: Cc1cc2n(n1)CCCN2C(=O)CCC(=O)Nc1ccc(-c2cncc(Cl)c2)cn1] | N-(5'-chloro-[3,3'-bipyridin]-6-yl)-4-(2-methyl-6,7-dihydropyrazolo[1,5-a]pyrimidin-4(5H)-yl)-4-oxobutanamide |
| 115 | 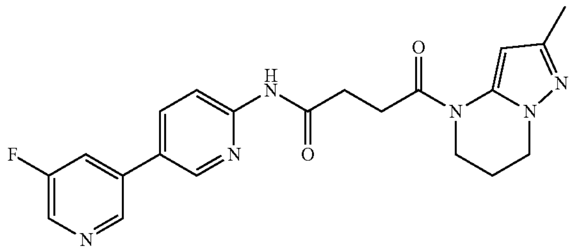 [SMILES: Cc1cc2n(n1)CCCN2C(=O)CCC(=O)Nc1ccc(-c2cncc(F)c2)cn1] | N-(5'-fluoro-[3,3'-bipyridin]-6-yl)-4-(2-methyl-6,7-dihydropyrazolo[1,5-a]pyrimidin-4(5H)-yl)-4-oxobutanamide |
| 116 | 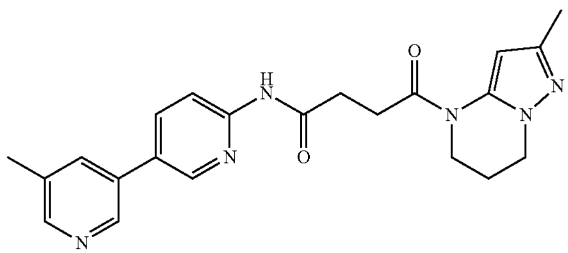 | 4-(2-methyl-6,7-dihydropyrazolo[1,5-a]pyrimidin-4(5H)-yl)-N-(5'-methyl-[3,3'-bipyridin]-6-yl)-4-oxobutanamide |
| 117 | 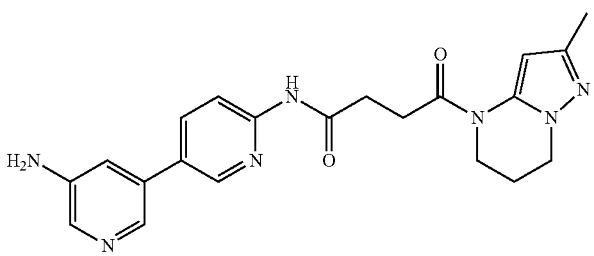 | 4-(2-methyl-6,7-dihydropyrazolo[1,5-a]pyrimidin-4(5H)-yl)-4-oxo-N-(4-(piperazin-1-yl)phenyl)butanamide |
| 118 | 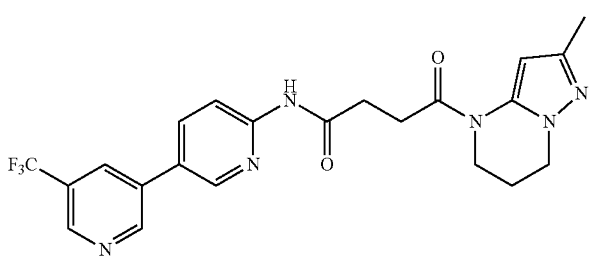 [SMILES: Cc1cc2n(n1)CCCN2C(=O)CCC(=O)Nc1ccc(-c2cncc(C(F)(F)F)c2)cn1] | 4-(2-methyl-6,7-dihydropyrazolo[1,5-a]pyrimidin-4(5H)-yl)-4-oxo-N-(5'-(trifluoromethyl)-[3,3'-bipyridin]-6-yl)butanamide |
| 119 | 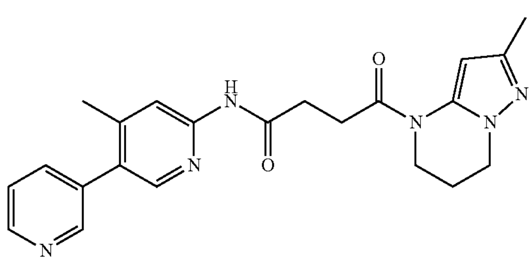 [SMILES: Cc1cc2n(n1)CCCN2C(=O)CCC(=O)Nc1cc(C)c(-c2cccnc2)cn1] | N-(4-methyl-3,3'-bipyridin-6-yl)-4-(2-methyl-6,7-dihydropyrazolo[1,5-a]pyrimidin-4(5H)-yl)-4-oxobutanamide |

| Compound ID | Structure | IUPAC Name |
|---|---|---|
| 120 | 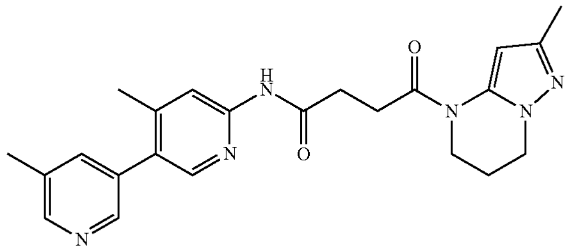 | N-(4,5'-dimethyl-3,3'-bipyridin-6-yl)-4-(2-methyl-6,7-dihydropyrazolo[1,5-a]pyrimidin-4(5H)-yl)-4-oxobutanamide |
| 121 | 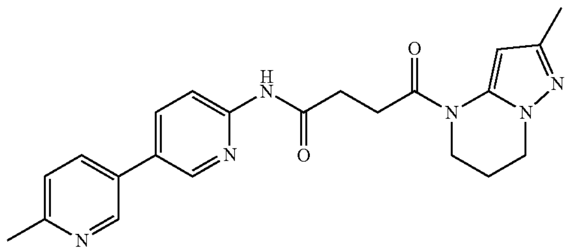 | N-(6'-methyl-3,3'-bipyridin-6-yl)-4-(2-methyl-6,7-dihydropyrazolo[1,5-a]pyrimidin-4(5H)-yl)-4-oxobutanamide |
| 122 | 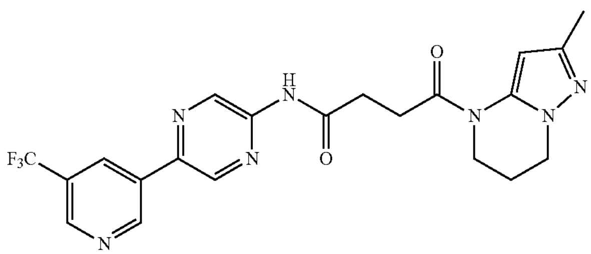 | N-(5-(5-fluoropyridin-3-yl)pyrazin-2-yl)-4-(2-methyl-6,7-dihydropyrazolo[1,5-a]pyrimidin-4(5H)-yl)-4-oxobutanamide |
| 123 | 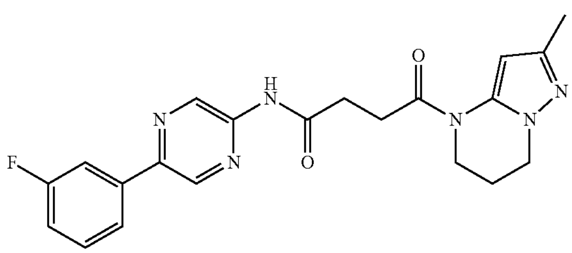 [SMILES: Cc1cc2n(n1)CCCN2C(=O)CCC(=O)Nc1cnc(-c2cccc(F)c2)cn1] | N-(5-(3-fluorophenyl)pyrazin-2-yl)-4-(2-methyl-6,7-dihydropyrazolo[1,5-a]pyrimidin-4(5H)-yl)-4-oxobutanamide |
| 124 | 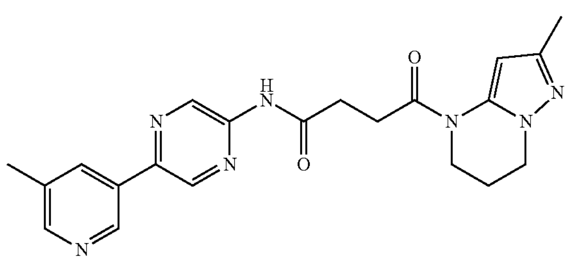 | 4-(2-methyl-6,7-dihydropyrazolo[1,5-a]pyrimidin-4(5H)-yl)-N-(5-(5-methylpyridin-3-yl)pyrazin-2-yl)-4-oxobutanamide |
| 125 | 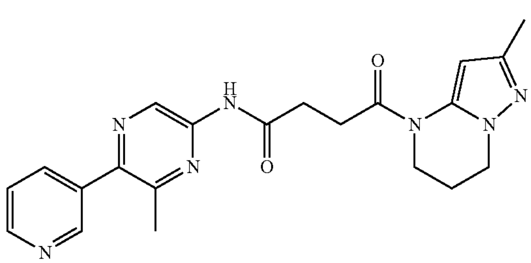 [SMILES: Cc1cc2n(n1)CCCN2C(=O)CCC(=O)Nc1cnc(-c2cccnc2)c(C)n1] | N-(6-methyl-5-(pyridin-3-yl)pyrazin-2-yl)-4-(2-methyl-6,7-dihydropyrazolo[1,5-a]pyrimidin-4(5H)-yl)-4-oxobutanamide |

| Compound ID | Structure | IUPAC Name |
|---|---|---|
| 126 | 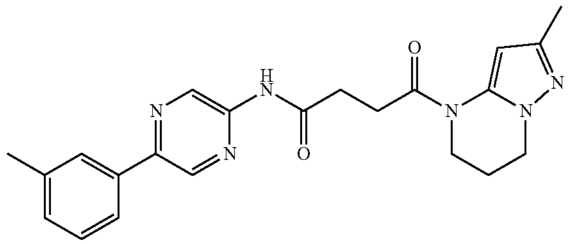 | 4-(2-methyl-6,7-dihydropyrazolo[1,5-a]pyrimidin-4(5H)-yl)-4-oxo-N-(5-(m-tolyl)pyrazin-2-yl)butanamide |
| 127 | 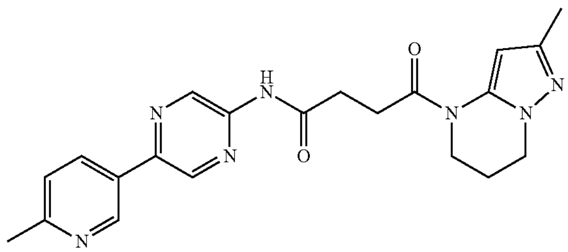 | 4-(2-methyl-6,7-dihydropyrazolo[1,5-a]pyrimidin-4(5H)-yl)-N-(5-(6-methylpyridin-3-yl)pyrazin-2-yl)-4-oxobutanamide |
| 128 | 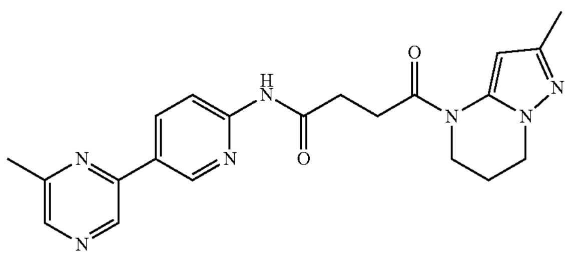 | 4-(2-methyl-6,7-dihydropyrazolo[1,5-a]pyrimidin-4(5H)-yl)-N-(5-(6-methylpyrazin-2-yl)pyridin-2-yl)-4-oxobutanamide |
| 129 | 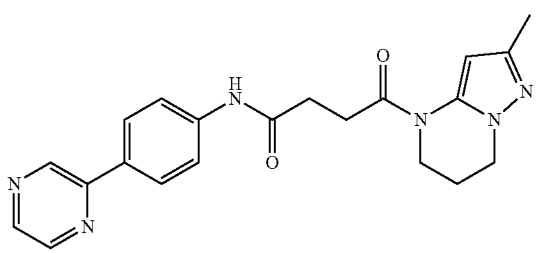 | 4-(2-methyl-6,7-dihydropyrazolo[1,5-a]pyrimidin-4(5H)-yl)-4-oxo-N-(4-(pyrazin-2-yl)phenyl)butanamide |
| 139 | 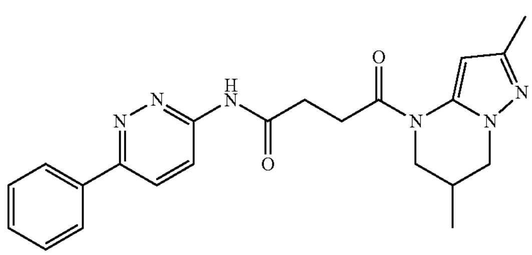 [SMILES: Cc1cc2n(n1)CC(C)CN2C(=O)CCC(=O)Nc1ccc(-c2ccccc2)nn1] | 4-(2,6-dimethyl-6,7-dihydropyrazolo[1,5-a]pyrimidin-4(5H)-yl)-4-oxo-N-(6-phenylpyridazin-3-yl)butanamide |
| 140 | 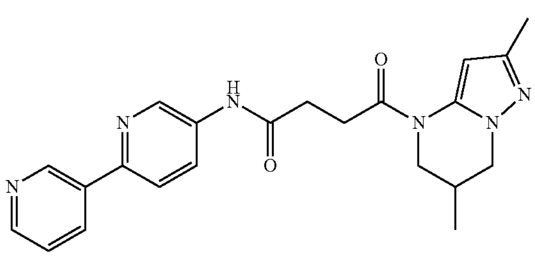 | N-(2,3'-bipyridin-5-yl)-4-(2,6-dimethyl-6,7-dihydropyrazolo[1,5-a]pyrimidin-4(5H)-yl)-4-oxobutanamide |

| Compound ID | Structure | IUPAC Name |
|---|---|---|
| 141 | 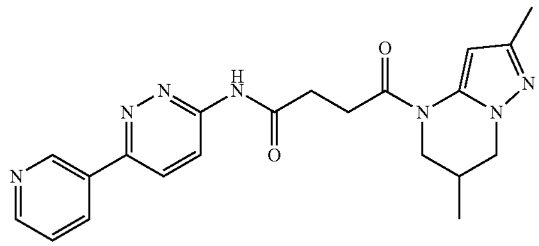 [SMILES: Cc1cc2n(n1)CC(C)CN2C(=O)CCC(=O)Nc1ccc(-c2cccnc2)nn1] | 4-(2,6-dimethyl-6,7-dihydropyrazolo[1,5-a]pyrimidin-4(5H)-yl)-4-oxo-N-(6-(pyridin-3-yl)pyridazin-3-yl)butanamide |
| 142 | 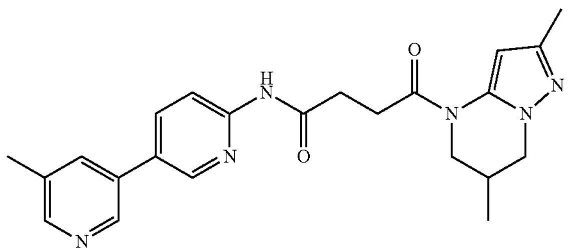 | 4-(2,6-dimethyl-6,7-dihydropyrazolo[1,5-a]pyrimidin-4(5H)-yl)-N-(5'-methyl-[3,3'-bipyridin]-6-yl)-4-oxobutanamide |
| 143 | 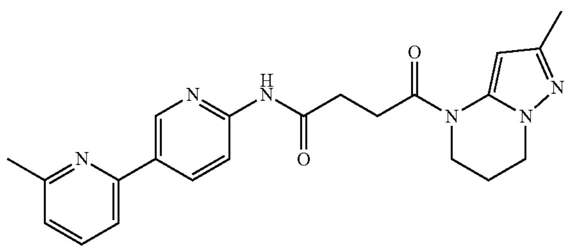 | 4-(2-methyl-6,7-dihydropyrazolo[1,5-a]pyrimidin-4(5H)-yl)-N-(6-methyl-[2,3'-bipyridin]-6'-yl)-4-oxobutanamide |
| 144 | 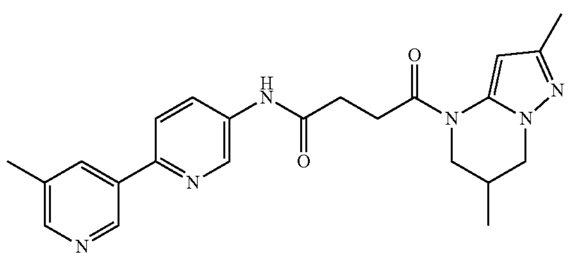 | 4-(2,6-dimethyl-6,7-dihydropyrazolo[1,5-a]pyrimidin-4(5H)-yl)-N-(5'-methyl-[2,3'-bipyridin]-5-yl)-4-oxobutanamide |
| 145 | 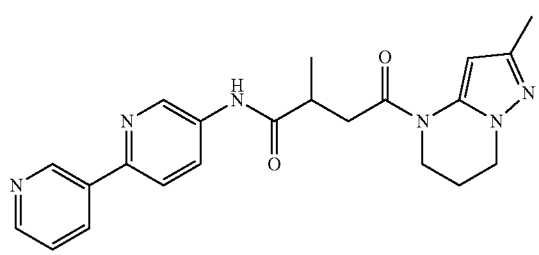 [SMILES: Cc1cc2n(n1)CCCN2C(=O)CC(C)C(=O)Nc1ccc(-c2cccnc2)nc1] | N-([2,3'-bipyridin]-5-yl)-2-methyl-4-(2-methyl-6,7-dihydropyrazolo[1,5-a]pyrimidin-4(5H)-yl)-4-oxobutanamide |
| 146 | 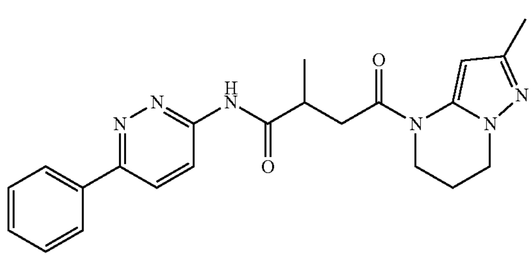 [SMILES: Cc1cc2n(n1)CCCN2C(=O)CC(C)C(=O)Nc1ccc(-c2ccccc2)nn1] | 2-methyl-4-(2-methyl-6,7-dihydropyrazolo[1,5-a]pyrimidin-4(5H)-yl)-4-oxo-N-(6-phenylpyridazin-3-yl)butanamide |

| Compound ID | Structure | IUPAC Name |
|---|---|---|
| 147 | 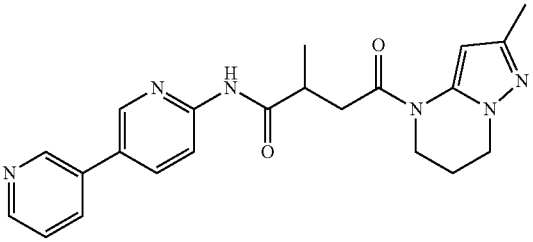 | N-([3,3'-bipyridin]-6-yl)-2-methyl-4-(2-methyl-6,7-dihydropyrazolo[1,5-a]pyrimidin-4(5H)-yl)-4-oxobutanamide |
| 148 | 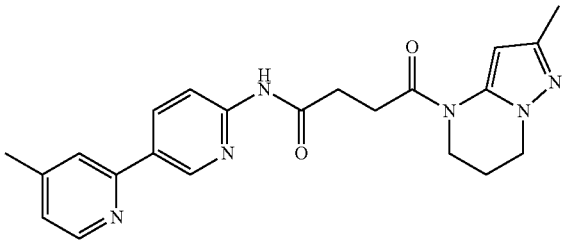 | N-(4-methyl-2,3'-bipyridin-6'-yl)-4-(2-methyl-6,7-dihydropyrazolo[1,5-a]pyrimidin-4(5H)-yl)-4-oxobutanamide |
| 149 | 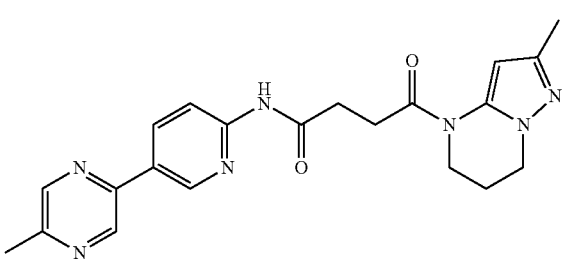 | 4-(2-methyl-6,7-dihydropyrazolo[1,5-a]pyrimidin-4(5H)-yl)-N-(5-(5-methylpyrazin-2-yl)pyridin-2-yl)-4-oxobutanamide |
| 150 | 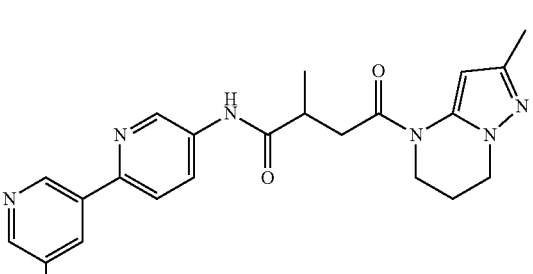 | 2-methyl-4-(2-methyl-6,7-dihydropyrazolo[1,5-a]pyrimidin-4(5H)-yl)-N-(5'-methyl-[2,3'-bipyridin]-5-yl)-4-oxobutanamide |
| 151 | 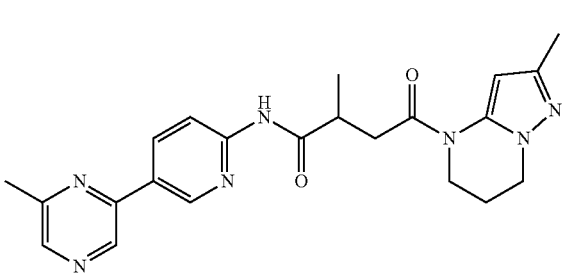 | 2-methyl-4-(2-methyl-6,7-dihydropyrazolo[1,5-a]pyrimidin-4(5H)-yl)-N-(5-(6-methylpyrazin-2-yl)pyridin-2-yl)-4-oxobutanamide |

-continued

| Compound ID | Structure | IUPAC Name |
|---|---|---|
| 152 | 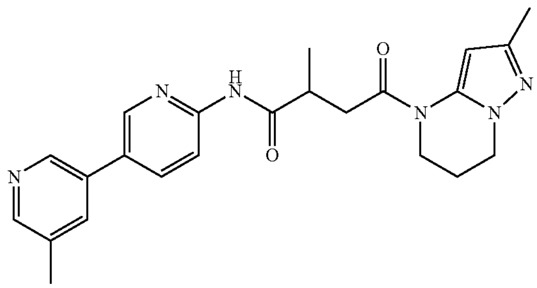 [SMILES: Cc1cncc(-c2ccc(NC(=O)C(C)CC(=O)N3CCCn4nc(C)cc43)nc2)c1] | 2-methyl-4-(2-methyl-6,7-dihydropyrazolo[1,5-a]pyrimidin-4(5H)-yl)-N-(5'-methyl-[3,3'-bipyridin]-6-yl)-4-oxobutanamide |
| 153 | 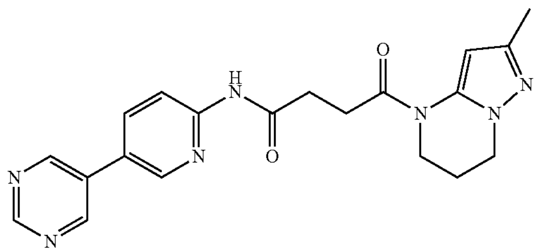 [SMILES: Cc1cc2n(n1)CCCN2C(=O)CCC(=O)Nc1ccc(-c2cncnc2)cn1] | 4-(2-methyl-6,7-dihydropyrazolo[1,5-a]pyrimidin-4(5H)-yl)-4-oxo-N-(5-(pyrimidin-5-yl)pyridin-2-yl)butanamide |
| 154 | 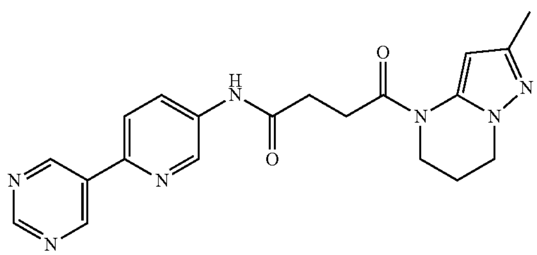 [SMILES: Cc1cc2n(n1)CCCN2C(=O)CCC(=O)Nc1ccc(-c2cncnc2)nc1] | 4-(2-methyl-6,7-dihydropyrazolo[1,5-a]pyrimidin-4(5H)-yl)-4-oxo-N-(6-(pyrimidin-5-yl)pyridin-3-yl)butanamide |
| 155 | 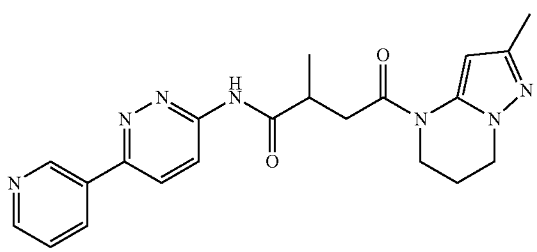 | N-(2-fluorobiphenyl-4-yl)-4-(2-methyl-6,7-dihydropyrazolo[1,5-a]pyrimidin-4(5H)-yl)-4-oxobutanamide |
| 156 | 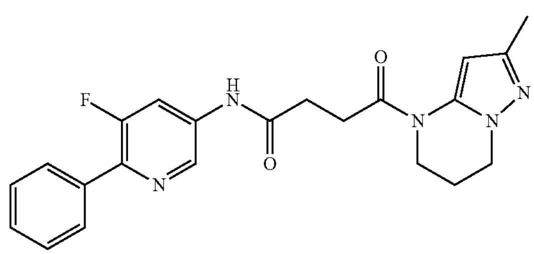 [SMILES: Cc1cc2n(n1)CCCN2C(=O)CCC(=O)Nc1cnc(-c2ccccc2)c(F)c1] | N-(5-fluoro-6-phenylpyridin-3-yl)-4-(2-methyl-6,7-dihydropyrazolo[1,5-a]pyrimidin-4(5H)-yl)-4-oxobutanamide |
| 157 | 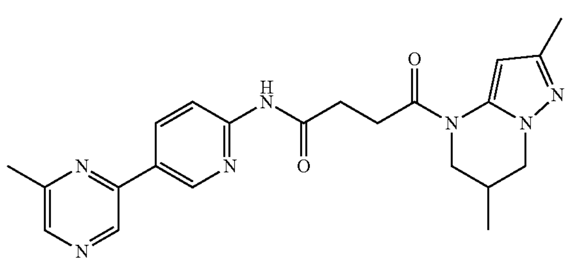 | 4-(2,6-dimethyl-6,7-dihydropyrazolo[1,5-a]pyrimidin-4(5H)-yl)-N-(5-(6-methylpyrazin-2-yl)pyridin-2-yl)-4-oxobutanamide |

| Compound ID | Structure | IUPAC Name |
|---|---|---|
| 158 | 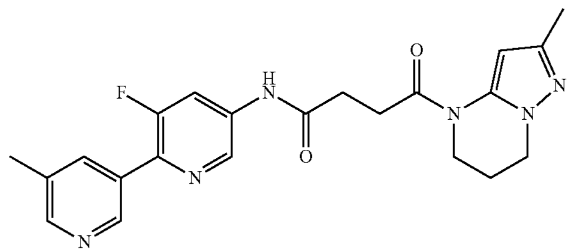 | N-(3-fluoro-5'-methyl-[2,3'-bipyridin]-5-yl)-4-(2-methyl-6,7-dihydropyrazolo[1,5-a]pyrimidin-4(5H)-yl)-4-oxobutanamide |
| 160 | 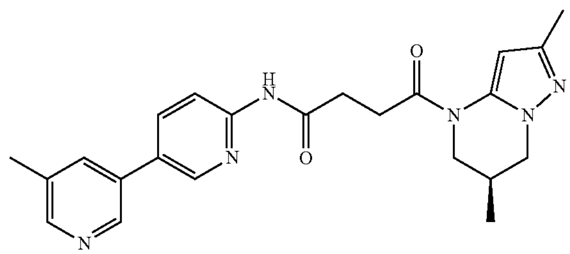 | (S)-4-(2,6-dimethyl-6,7-dihydropyrazolo[1,5-a]pyrimidin-4(5H)-yl)-N-(5'-methyl-[3,3'-bipyridin]-6-yl)-4-oxobutanamide |
| 161 | 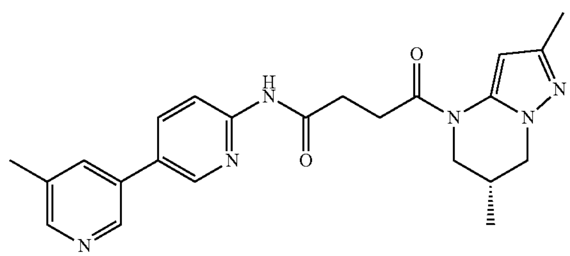 | (R)-4-(2,6-dimethyl-6,7-dihydropyrazolo[1,5-a]pyrimidin-4(5H)-yl)-N-(5'-methyl-[3,3'-bipyridin]-6-yl)-4-oxobutanamide |
| 162 | 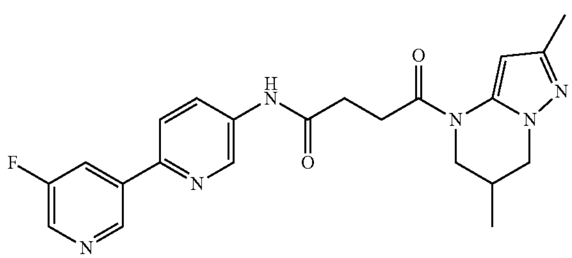 [SMILES: Cc1cc2n(n1)CC(C)CN2C(=O)CCC(=O)Nc1ccc(-c2cncc(F)c2)nc1] | 4-(2,6-dimethyl-6,7-dihydropyrazolo[1,5-a]pyrimidin-4(5H)-yl)-N-(5'-fluoro-[2,3'-bipyridin]-5-yl)-4-oxobutanamide |
| 163 | 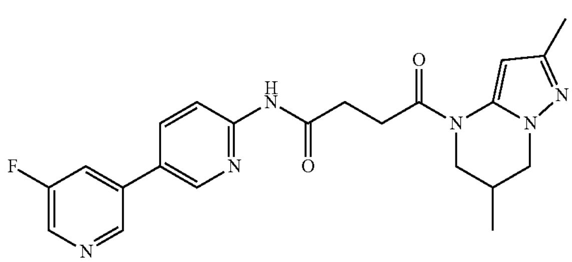 [SMILES: Cc1cc2n(n1)CC(C)CN2C(=O)CCC(=O)Nc1ccc(-c2cncc(F)c2)cn1] | 4-(2,6-dimethyl-6,7-dihydropyrazolo[1,5-a]pyrimidin-4(5H)-yl)-N-(5'-fluoro-[3,3'-bipyridin]-6-yl)-4-oxobutanamide |
| 164 | 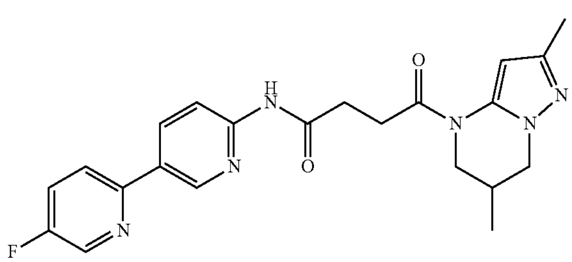 [SMILES: Cc1cc2n(n1)CC(C)CN2C(=O)CCC(=O)Nc1ccc(-c2ccc(F)cn2)cn1] | 4-(2,6-dimethyl-6,7-dihydropyrazolo[1,5-a]pyrimidin-4(5H)-yl)-N-(5-fluoro-[2,3'-bipyridin]-6'-yl)-4-oxobutanamide |

-continued

| Compound ID | Structure | IUPAC Name |
|---|---|---|
| 165 | 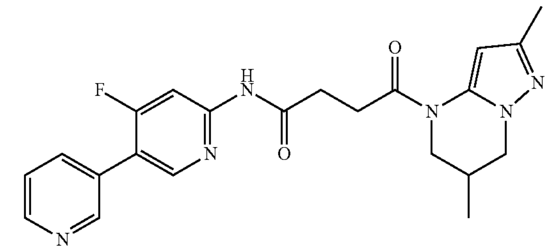 [SMILES: Cc1cc2n(n1)CC(C)CN2C(=O)CCC(=O)Nc1cc(F)c(-c2cccnc2)cn1] | 4-(2,6-dimethyl-6,7-dihydropyrazolo[1,5-a]pyrimidin-4(5H)-yl)-N-(4-fluoro-[3,3'-bipyridin]-6-yl)-4-oxobutanamide |
| 166 | 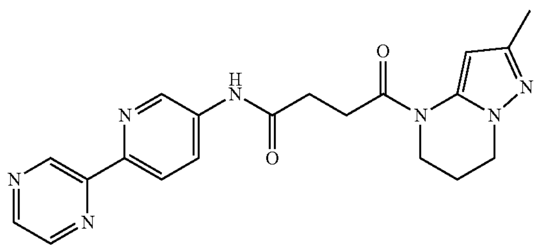 [SMILES: Cc1cc2n(n1)CCCN2C(=O)CCC(=O)Nc1ccc(-c2cnccn2)nc1] | 4-(2-methyl-6,7-dihydropyrazolo[1,5-a]pyrimidin-4(5H)-yl)-4-oxo-N-(6-(pyrazin-2-yl)pyridin-3-yl)butanamide |
| 167 | 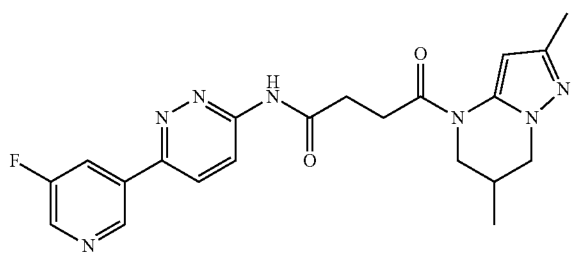 [SMILES: Cc1cc2n(n1)CC(C)CN2C(=O)CCC(=O)Nc1ccc(-c2cncc(F)c2)nn1] | 4-(2,6-dimethyl-6,7-dihydropyrazolo[1,5-a]pyrimidin-4(5H)-yl)-N-(6-(5-fluoropyridin-3-yl)pyridazin-3-yl)-4-oxobutanamide |
| 168 | 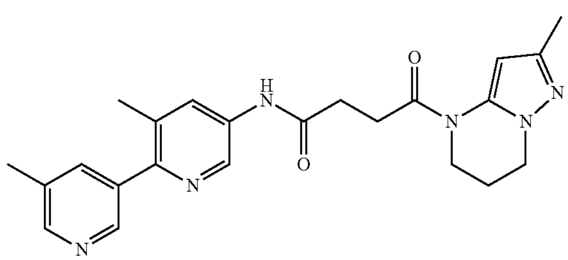 | N-(3,5'-dimethyl-[2,3'-bipyridin]-5-yl)-4-(2-methyl-6,7-dihydropyrazolo[1,5-a]pyrimidin-4(5H)-yl)-4-oxobutanamide |
| 169 | 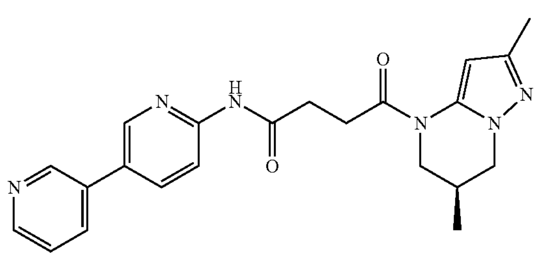 [SMILES: Cc1cc2n(n1)C[C@@H](C)CN2C(=O)CCC(=O)Nc1ccc(-c2cccnc2)cn1] | (S)-N-([3,3'-bipyridin]-6-yl)-4-(2,6-dimethyl-6,7-dihydropyrazolo[1,5-a]pyrimidin-4(5H)-yl)-4-oxobutanamide |
| 170 | 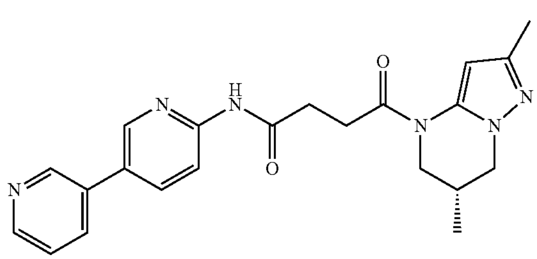 [SMILES: Cc1cc2n(n1)C[C@H](C)CN2C(=O)CCC(=O)Nc1ccc(-c2cccnc2)cn1] | (R)-N-([3,3'-bipyridin]-6-yl)-4-(2,6-dimethyl-6,7-dihydropyrazolo[1,5-a]pyrimidin-4(5H)-yl)-4-oxobutanamide |

| Compound ID | Structure | IUPAC Name |
|---|---|---|
| 171 | | N-([2,3'-bipyridin]-6'-yl)-4-(2,6-dimethyl-6,7-dihydropyrazolo[1,5-a]pyrimidin-4(5H)-yl)-4-oxobutanamide | or a pharmaceutically acceptable salt, polymorph, tautomer, or stereoisomer thereof.

6. The method of claim 3, wherein $R_1$ represents H, methyl, ethyl, —C(O)OMe, or $CF_3$.

7. The method of claim 3, wherein each $R_2$ independently represents H or alkyl.

8. The method of claim 3, wherein each $R_2$ independently represents H.

9. The method of claim 3, wherein $R_3$ represents H.

10. The method of claim 3, wherein $R_4$ represents H.

11. The method of claim 3, wherein $R_5$ represents H.

12. The method of claim 3, wherein W and X each represent C═O.

13. The method of claim 3, wherein Y represents phenyl.

14. The method of claim 3, wherein Y is substituted by one or more substituents each independently selected from the group consisting of $C_{1-6}$ alkyl, $C_{1-6}$alkoxy, halo, and $C_{1-6}$haloalkyl.

15. The method of claim 3, wherein the tumor is pancreatic adenocarcinoma.

16. The method of claim 3, wherein the tumor is osteosarcoma.

17. The method of claim 3, wherein the tumor is hepatocellular carcinoma.

18. The method of claim 3, wherein the tumor is Wilm's tumor.

19. The method of claim 3, wherein the tumor is medulloblastoma.

* * * * *

UNITED STATES PATENT AND TRADEMARK OFFICE
CERTIFICATE OF CORRECTION

PATENT NO. : 10,870,653 B2
APPLICATION NO. : 16/226398
DATED : December 22, 2020
INVENTOR(S) : Jenefer Alam et al.

Page 1 of 2

It is certified that error appears in the above-identified patent and that said Letters Patent is hereby corrected as shown below:

In the Claims

In Claim 5, in Columns 185-186, the formula for compound ID 32:

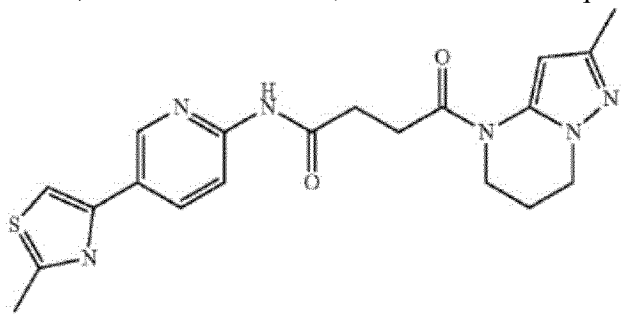

, should be replaced with the formula:

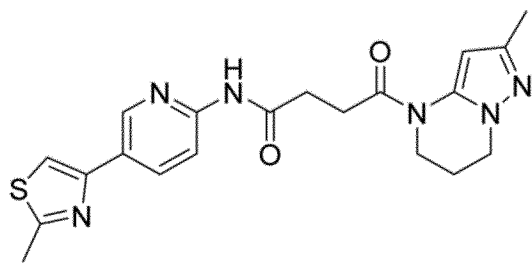

.

Signed and Sealed this
First Day of June, 2021

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 10,870,653 B2

In Claim 5, in Columns 213-214, the formula for compound ID 122:

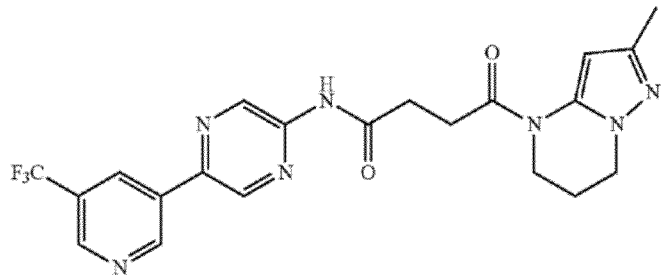

, should replaced with the formula:

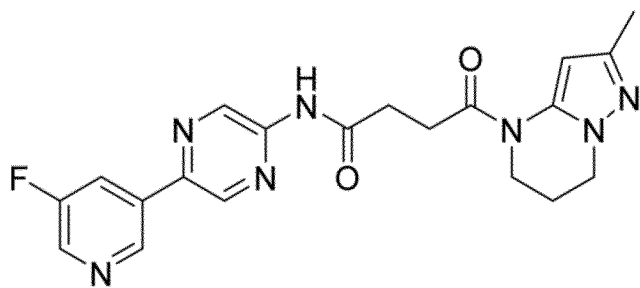

.